US007256296B2

(12) United States Patent
Diamond et al.

(10) Patent No.: US 7,256,296 B2
(45) Date of Patent: Aug. 14, 2007

(54) HETEROCYCLE-AMINE LIGANDS, COMPOSITIONS, COMPLEXES, AND CATALYSTS

(75) Inventors: Gary M. Diamond, Santa Clara, CA (US); Anne M. LaPointe, Sunnyvale, CA (US); Margarete K. Leclerc, Mt. View, CA (US); James Longmire, San Jose, CA (US); Victor Nava-Salgado, San Jose, CA (US); James A. W. Shoemaker, Gilroy, CA (US); Pu Sun, Mt. View, CA (US)

(73) Assignee: Symyx Technologies, Inc., Sunnyvale, CA (US)

( * ) Notice: Subject to any disclaimer, the term of this patent is extended or adjusted under 35 U.S.C. 154(b) by 0 days.

(21) Appl. No.: 11/232,982

(22) Filed: Sep. 21, 2005

(65) Prior Publication Data

US 2006/0094867 A1    May 4, 2006

Related U.S. Application Data

(60) Provisional application No. 60/611,943, filed on Sep. 22, 2004.

(51) Int. Cl.
*C07F 7/00*  (2006.01)
*C07F 9/00*  (2006.01)
*C07F 11/00* (2006.01)
*C07F 5/00*  (2006.01)
*B01J 31/00* (2006.01)

(52) U.S. Cl. .................. 548/101; 548/108; 502/162
(58) Field of Classification Search ................ 548/101, 548/108; 502/162
See application file for complete search history.

(56) References Cited

U.S. PATENT DOCUMENTS

| 4,297,465 | A | 10/1981 | Smith |
| 4,971,936 | A | 11/1990 | Wilson et al. |
| 5,064,802 | A | 11/1991 | Stevens et al. |
| 5,093,415 | A | 3/1992 | Brady, III et al. |
| 5,153,157 | A | 10/1992 | Hlatky et al. |
| 5,318,935 | A | 6/1994 | Canich et al. |
| 5,385,993 | A | 1/1995 | Fujita |
| 5,453,410 | A | 9/1995 | Kolthammer et al. |
| 5,599,761 | A | 2/1997 | Turner |

(Continued)

FOREIGN PATENT DOCUMENTS

EP        0 292 134       5/1987

(Continued)

OTHER PUBLICATIONS

Barron, Andrew, "Alkylalumoxanes: Synthesis, Structure and Reactivity", Metallocene-Based Polyolefins-Preparation, Properties and Technology, Chap. 2, pp. 33-67, vol. 1, 2000, Scheirs and Kaminsky (Eds.), John Wiley & Sons.

(Continued)

*Primary Examiner*—Porfirio Nazario-Gonzalez

(57) ABSTRACT

Ligands, compositions, and metal-ligand complexes that incorporate heterocycle-amine compounds are disclosed that are useful in the catalysis of transformations such as the polymerization of monomers into polymers. The catalysts have high performance characteristics, including higher comonomer incorporation into ethylene/olefin copolymers, where such olefins are for example, 1-octene, propylene or styrene. The catalysts also polymerize propylene to form isotactic polypropylene.

36 Claims, 4 Drawing Sheets

U.S. PATENT DOCUMENTS

| | | | |
|---|---|---|---|
| 5,616,664 | A | 4/1997 | Timmers et al. |
| 5,985,356 | A | 11/1999 | Schultz et al. |
| 6,030,917 | A | 2/2000 | Weinberg et al. |
| 6,034,240 | A | 3/2000 | La Pointe |
| 6,043,363 | A | 3/2000 | La Pointe et al. |
| 6,103,657 | A | 8/2000 | Murray |
| 6,175,409 | B1 | 1/2001 | Nielsen et al. |
| 6,214,939 | B1 | 4/2001 | Shinozaki et al. |
| 6,239,236 | B1 | 5/2001 | Morini et al. |
| 6,260,407 | B1 | 7/2001 | Petro et al. |
| 6,294,388 | B1 | 9/2001 | Petro |
| 6,306,658 | B1 | 10/2001 | Turner et al. |
| 6,406,632 | B1 | 6/2002 | Safir et al. |
| 6,436,292 | B1 | 8/2002 | Petro |
| 6,454,947 | B1 | 9/2002 | Safir et al. |
| 6,455,316 | B1 | 9/2002 | Turner et al. |
| 6,461,515 | B1 | 10/2002 | Safir et al. |
| 6,475,391 | B2 | 11/2002 | Safir et al. |
| 6,489,168 | B1 | 12/2002 | Wang et al. |
| 6,491,816 | B2 | 12/2002 | Petro |
| 6,491,823 | B1 | 12/2002 | Safir et al. |
| 6,508,984 | B1 | 1/2003 | Turner et al. |
| 6,548,026 | B1 | 4/2003 | Dales et al. |
| 6,706,829 | B2 | 3/2004 | Boussie et al. |
| 6,713,577 | B2 | 3/2004 | Boussie et al. |
| 6,727,361 | B2 | 4/2004 | La Pointe et al. |
| 6,750,345 | B2 | 6/2004 | Boussie et al. |
| 6,828,397 | B2 | 12/2004 | Boussie et al. |
| 2003/0232717 | A1 | 12/2003 | Brummer et al. |

FOREIGN PATENT DOCUMENTS

| | | |
|---|---|---|
| EP | 0 277 004 | 8/1988 |
| EP | 0 622 380 | 9/1998 |
| WO | WO 98/03521 | 1/1998 |
| WO | WO 99/01460 | 1/1999 |
| WO | WO 99/05186 | 2/1999 |
| WO | WO 99/06413 | 2/1999 |
| WO | WO 99/42467 | 8/1999 |
| WO | WO 00/09255 | 2/2000 |
| WO | WO 01/98371 | 12/2001 |
| WO | WO 02/38628 | 5/2002 |
| WO | WO 02/065820 | 10/2002 |
| WO | WO 03/040201 | 5/2003 |
| WO | WO 2004/083263 A1 * | 9/2004 |

OTHER PUBLICATIONS

Beesley and Scott (Eds.), Chiral Chromatography, John Wiley & Sons, Chichester, 1998.

Begue et al., "Facile Ring Opening of Oxiranes with Aromatic Amines in Fluoro Alcohols", J. Org. Chem., vol. 65, 2000, pp. 6749-6751.

Blaser et al., "3.3 Special Products, 3.3.1 Enantioselective Synthesis", Applied Homogeneous Catalysis with Organometallic Compounds, 2nd ed, vol. 3, pp. 1131-1149, Cornils and Herrmann (Eds.), Wiley-VCH, Weinheim, Germany.

Bochmann et al., "Base-Free Cationic Zirconium Benzyl Complexes as Highly Active Polymerization Catalysts", Organometallics, vol. 12, 1993, pp. 633-640.

Boussie et al., "A Fully Integrated High-Throughput Screening Methodology for the Discovery of New Polyolefin Catalysts: Discovery of a New Class of High Temperature Single-Site Group (IV) Copolymerization Catalysts", J Am Chem Soc, vol. 125, 2003, pp. 4306-4317.

Brintzinger et al., "Stereospecific Olefin Polymerization with Chiral Metallocene Catalysts", Angew Chem Int Ed Engl, vol. 34, 1995, pp. 1143-1170.

Buchi et al., "A Two-Step Synthesis of Imidazoles from Aldehydes via 4-Tosyloxazolines", Heterocycles, vol. 39, No. 1, 1994, pp. 139-153.

Carreira et al., "A Novel, General Method for the Synthesis of Nitrile Oxides: Dehydration of O-Silylated Hydroxamic Acids", Organic Letters, vol. 2, No. 4, 2000, pp. 539-541.

Chan et al., "Observation of Intramolecular C-H**F-C Contacts in Non-Metallocene Polyolefin Catalysts: Model for Weak Attractive Interactions between Polymer Chain and Noninnocent Ligand". Angew Chem Int Ed. vol. 42. 2003. pp. 1628-1632.

Coates, Geoffrey, "Precise Control of Polyolefin Stereochemistry Using Single-Site Metal Catalysts", Chem Rev., vol. 100, 2000, pp. 1223-1252.

Comprehensive Heterocyclic Chemistry—The Structure, Reactions, Synthesis and Uses of Heterocyclic Compounds, Katritzky et al (Eds), vol. 1, 1st. Ed., Pergammon Press Ltd., New York, 1984.

Comprehensive Heterocyclic Chemistry II—A Review of the Literature 1982-1995, Katritzky et al (Eds), vol. 1A, 1st Ed., Elsevier Science Ltd, New York, 1996.

Diamond et al., "Efficient Synthesis of Chiral ansa-Metallocenes by Amine Elimination. Synthesis, Structure, and Reactivity of . . . ", J Am Chem Soc., vol. 118, 1996, pp. 8024-8033.

Fink et al., "Propene Polymerization with Silica-Supported Metallocene/MAO Catalysts", Chem Rev., vol. 100, 2000, pp. 1377-1390.

Gibson et al., "The Search for New-Generation Olefin Polymerization Catalysts: Life Beyond Metallocenes", Angew Chem Int Ed., vol. 38, 1999, pp. 428-447.

Gibson et al., "Advances in Non-Metallocene Olefin Polymerization Catalysis", Chem Rev., vol. 103, 2003, pp. 283-315.

Groger, Harald, "Catalytic Enantioselective Strecker Reactions and Analogous Syntheses", Chem Rev., vol. 103, 2003, pp. 2795-2827.

Katritzky, Alan (Ed.), Handbook of Heterocyclic Chemistry, Pergamon Press, 1985, Oxford, England.

Hanson, James (Ed.), Protecting Groups in Organic Synthesis, Sheffield Academic Press, Sheffield, England, 1999.

Hernandez et al., "Synthesis of Various 3-Substituted 1,2,4-Oxadiazole-Containing Chiral beta-3 and alpha-Amino Acids from Fmoc-Protected Aspartic Acid", J Org Chem., vol. 68, 2003, pp. 7316-7321.

Hlatky, Gregory, "Heterogeneous Single-Site Catalysts for Olefin Polymerization", Chem Rev., vol. 100, 2000, pp. 1347-1376.

Hoveyda, Amir, "Chiral Zirconium Catalysts for Enantioselective Synthesis", Titanium and Zirconium in Organic Synthesis, Chap. 6, pp. 180-229, 2002, Ilan Marek (Ed.), Wiley-VCH, Weinheim, Germany.

Huang et al., "Syntheses of Some New Group 4 non-Cp Complexes Bearing Schiff-base, Thiophene Diamide Ligands Respectively and Their Catalytic Activities for beta-Olefin Polymerization", Chinese Journal of Chemistry, vol. 22, 2004, pp. 577-584.

Jacques et al. (Eds.), Enantiomers, Racemates, and Resolutions, Krieger Publishing Company, Florida, Original Edition 1981, Reissue 1994 with corrections.

Jager et al., "Nitride Oxide", The Chemistry of Heterocyclic Compounds: Synthetic Applications of 1,3-Dipolar Cycloaddition Chemistry Toward Heterocycles and Natural Products, vol. 59, Chap. 6, 2002, pp. 361-472.

Jones et al., "Quinazoline Antifolates Inhibiting Thymidylate Synthase: Variation of the . . . Substituent", J Med Chem., vol. 28, 1985, pp. 1468-1476.

Jordan, Richard, "Chemistry of Cationic Dicyclopentadienyl Group 4 Metal—Alkyl Complexes", Advances in Organometallic Chemistry, vol. 32, 1991, pp. 325-387.

Kilenyi, S. Nicholas, "Oxidation of Carbon-Halogen Bonds", Comprehensive Organic Synthesis, vol. 7, 1991, pp. 653-670.

Kobayashi et al., "Aldehydes vs Aldimines. Unprecedented Aldimine-Selective Nucleophilic Additions in the Coexistence of Aldehydes Using a Lanthanide Salt as a Lewis Acid Catalyst", J Am Chem Soc., vol. 119, 1997, pp. 10049-10053.

Kuber, Frank, "Metallocenes as a Source of Fine Chemicals", Applied Homogeneous Catalysis with Organometallic Compounds, vol. 2, Cornilis and Herrmann (Eds.), VCH, Weinheim, Germany, pp. 893-902.

LaPointe et al., "New Family of Weakly Coordinating Anions", J Am Chem Soc., vol. 122, 2000, pp. 9560-9561.

Liu et al., "A Particularly Convenient Preparation of Benzohydroximinoyl Chlorides (Nitrile Oxide Precursors)", J Org Chem., vol. 45, 1980, pp. 3916-3918.

Luongo, J.P., "Infrared Study of Polypropylene", Journal of Applied Polymer Science, vol. III, Issue No. 9, 1960, pp. 302-309.

March, Jerry (Ed.), Advanced Organic Chemistry—Reactions, Mechanisms, and Structure, Fourth Edition, 1992, John Wiley & Sons, New York.

Smith and March (Eds.), March's Advanced Organic Chemistry—Reactions, Mechanisms, and Structure, Fifth Edition, 2001, John Wiley & Sons, New York.

Marek, Ilan (Ed.), Titanium and Zirconium in Organic Synthesis, 2002, Wiley-VCH Verlag GmbH, Weinheim, Germany.

Marks et al., "Cocatalysts for Metal-Catalyzed Olefin Polymerization: Activators, Activation Processes, and Structure-Activity Relationships", Chem Rev., vol. 100, 2000, pp. 1391-1434.

Maruoka et al., "Asymmetric Reactions with Chiral Lewis Acid Catalsts", Catalytic Asymmetric Synthesis, Chap. 9, pp. 413-440, Ojima (ed.), 1993, VCH Publishers, Inc., New York.

McEwen et al., "Synthetic Uses of Open-Chain Analogues of Reissert Compounds", J Org Chem., vol. 45, 1980, pp. 1301-1308.

Murphy et al., "Low-Coordinate (Arylimido)vanadium(V) Alkyls: Synthesis and Reactivity of . . . " Organometallics, vol. 16, 1997, pp. 2495-2497.

Mylari et al., "Potent, Orally Active Aldose Reductase Inhibitors Related to Zopolrestat: Surrogates for Benzothiazole Side Chain", J Med Chem., vol. 35, 1992, pp. 457-465.

Naim et al., "A Novel Synthesis of N-Substituted Amino Acids", Indian Journal of Chemistry, vol. 198, Jul. 1980, pp. 622-624.

Negishi, Ei-ichi, "Some Newer Aspects of Organoziroconium Chemistry of Relevance to Organic Synthesis. Zr-Ca'alyzed Enantioselective Carbometallation", Pure Appl Chem., vol. 73, No. 2, 2001, pp. 239-242.

Ojima, Iwao (Ed.), Catalytic Asymmetric Synthesis, 1993, VCH Publishers, Inc., New York.

Padwa and Pearson (Eds)., Synthetic Applications of 1,3-Dipolar Cycloaddition Chemistry Toward Heterocycles and Natural Products, 2002, John Wiley & Sons, New York.

Pellecchia et al., "Single Insertion of beta-Olefins into the Cationic Complex . . . Adducts: A Model for the Insertion Mechanism in Ziegler-Natta Polymerization", Organometallics, vol. 13, 1994, pp. 298-302.

Pellecchia et al., "A Novel . . . Coordination Mode of a Benzyl Ligand in a Cationic Zirconium Complex", Organometallics, vol. 13, 1994, pp. 3773-3775.

Pellecchia et al., "Synthesis, Crystal Structure, and Olefin Polymerization Activity of a Zwitterionic . . . ", J Am Chem Soc., vol. 115, 1993, pp. 1160-1162.

Piers et al., "New Bifunctional Perfluoroaryl Boranes. Synthesis and Reactivity of the ortho-Phenylene-Bridged Diboranes . . . ", J Am Chem Soc., vol. 121, 1999, pp. 3244-3245.

Resconi et al., "Selectivity in Propene Polymerization with Metallocene Catalysts", Chem Rev., vol. 100, 2000, pp. 1253-1345.

Rickborn et al., "Benzyne-Oxazole Cycloadducts: Isolation and Retro-Diels-Alder Reactions", J Org Chem., vol. 55, 1990, pp. 929-935.

Rickborn et al., "Substituted Oxazoles: Syntheses via Lithio Intermediates", J Org Chem., vol. 56, 1991, pp. 3058-3063.

Ringwald et al., "Asymmetric Thermal Transformation, a New Way to Enantiopure Biphenyl-Bridged Titanocene and Ziroconocene Complexes: Efficient Catalysts for Asymmetric Imine Hydrogenation", J Am Chem Soc., vol. 121, 1999, pp. 1524-1527.

Schrock et al., "Preparation and Activation of Complexes of the Type . . . ", Organometallics, vol. 19, 2000, pp. 5325-5341.

Schrock et al., "Synthesis of Titanium, Zirconium, and Hafnium Complexes that Contain Diamido Donor Ligands of the Type . . . ", Organometallics, vol. 18, 1999, pp. 3649-3670.

Scott et al., "Zirconium Catalyzed Enantioselective Hydroamination/cyclisation", Chem Commun., 2004, pp. 894-895.

Sibi et al., "Chiral Lewis Acid Catalysis in Nitrile Oxide Cycloadditions", J Am Chem Soc., vol. 126, 2004, pp. 5366-5367.

Sita et al., "Stereospecific Living Ziegler-Natta Polymerization of 1-Hexene", J Am Chem Soc, vol. 122, 2000, pp. 958-959.

Sundell et al., "Isotacticity Determination of Polypropylene Using FT-Raman Spectroscopy", Polymer, vol. 37, No. 15, 1996, pp. 3227-3231.

Thompson et al., "Novel Polypyrazolylborate Ligands: Coordination Control through 3-Substituents of the Pyrazole Ring", Inorg. Chem., vol. 26, 1987, pp. 1507-1514.

Torssell, "The Nitride Oxides", Nitrile Oxides, Nitrones, and Nitronates in Organic Synthesis, Chap. 2, pp. 55-74, 1988, VCH, New York.

Vedejs et al., "A Method for Iodination of Oxazoles at C-4 via 2-Lithiooxazoles", J Org Chem., vol. 64, 1999, pp. 1011-1014.

Youssef et al., "Synthesis of Pyrazolo[4,3-d]oxazoles", J Heterocyclic Chem., vol. 21, Nov.-Dec. 1984, pp. 1747-1752.

* cited by examiner

HETEROCYCLE-AMINE LIGANDS, COMPOSITIONS, COMPLEXES, AND CATALYSTS

CROSS-REFERENCE TO RELATED APPLICATION

This application claims the benefit of U.S. Provisional Application 60/611,943, filed Sep. 22, 2004, which is incorporated herein by reference.

TECHNICAL FIELD

The present invention relates to ligands, ligand-metal compositions, complexes, and catalysts useful in the polymerization of olefins and other transformations.

BACKGROUND

Ancillary (or spectator) ligand-metal coordination complexes (including organometallic complexes) and compositions are useful as catalysts, additives, stoichiometric reagents, solid-state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, Diels-Alder reactions and other transformations.

One example of the use of these types of ancillary ligand-metal complexes and compositions is in the field of polymerization catalysis. In connection with single site catalysis, the ancillary ligand typically offers opportunities to modify the electronic and/or steric environment surrounding an active metal center. This allows the ancillary ligand to assist in the creation of possibly different polymers. Group 4 metallocene based single site catalysts are generally known for polymerization reactions. See, generally, "Chemistry of Cationic Dicyclopentadienyl Group 4 Metal-Alkyl Complexes", Jordan, *Adv. Organometallic Chem.* 1991, 32, 325-153, and the references therein, all of which is incorporated herein by reference.

One application for metallocene catalysts is producing isotactic polypropylene. An extensive body of scientific literature examines catalyst structures, mechanism and polymers prepared by metallocene catalysts. See, e.g., Resconi et al., "Selectivity in Propene Polymerization with Metallocene Catalysts," *Chem. Rev.* 2000, 100, 1253-1345 and G. W. Coates, "Precise Control of Polyolefin Stereochemistry Using Single-Site Metal Catalysts," *Chem. Rev.* 2000, 100, 1223-1252 and the references cited in these review articles. Isotactic polypropylene has historically been produced with heterogeneous catalysts that may be described as a catalyst on a solid support (e.g., titanium tetrachloride and aluminum alkyls and additional modifiers or "donors" on magnesium dichloride). This process typically uses hydrogen to control the molecular weight and electron-donor compounds to control the isotacticity. See also EP 0 622 380, EP 0 292 134 and U.S. Pat. Nos. 4,971,936, 5,093,415, 4,297,465, 5,385,993 and 6,239,236.

Given the extensive research activities with respect to metallocene catalysts, there is continued interested in the next generation of non-cyclopentadienyl ligands for olefin polymerization catalysts providing attractive alternatives. See, e.g., "The Search for New-Generation Olefin Polymerization Catalysts: Life beyond Metallocenes", Gibson, et al., *Angew. Chem. Int. Ed.* 1999, 38, 428-447; *Organometallics* 1999, 18, 3649-3670 and "Advances in Non-Metallocene Olefin Polymerization Catalysts", Gibson, et al., *Chem Rev.* 2003, 103, 283-315. See also U.S. Pat. No. 6,750,345 and International Application No. WO 02/38628. Recently, for isotactic polypropylene, bis-amide catalysts have been disclosed in U.S. Pat. No. 5,318,935 and amidinate catalysts have been disclosed in WO 99/05186. See also U.S. Pat. Nos. 6,214,939 and 6,713,577, and International Application No. WO 03/040201 for non-metallocene isotactic polypropylene catalysts.

SUMMARY

The invention features ligands, compositions and metal complexes that are useful in catalysts for olefin polymerization and other transformations, as well as methods for preparing the ligands and for using the compositions or complexes in catalytic transformations such as olefin polymerization. In general, the ligands have a heterocycle-amine structure, as will be discussed in more detail below. Catalysts according to the invention can be provided by compositions including a ligand, a metal precursor, and optionally an activator, combination of activators, or an activator package. Alternatively, catalysts can be provided by metal-ligand complexes and optionally may additionally include an activator, combination of activators or activator package.

In general, in one aspect, the invention provides compositions of matter, including ligands, compositions and metal-ligand complexes, that include a compound characterized by the formula:

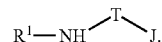

$R^1$ is optionally substituted alkyl, heteroalkyl, aryl, or heteroaryl. T is a bridging group of the general formula $-(T'R^2R^3)_n-$. Each T' is independently selected from the group consisting of carbon and silicon. $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof. n is 1 or 2. Two or more $R^2$ and/or $R^3$ groups may be joined together to form one or more optionally substituted ring systems. One or more T' atoms may be involved in a double bond to a neighboring group and correspondingly be bonded to only a single $R^2$ or $R^3$ substituent. J is an optionally substituted heterocyclic group containing a five-membered heterocycle, provided that the five-membered heterocycle contains at least two but no more than four heteroatoms. At least one of the heteroatoms is a nitrogen, phosphorus, oxygen, or sulfur in in a ring position adjacent to the ring atom bonded to T.

Particular embodiments can include one or more of the following features. The compound can be characterized by the formula:

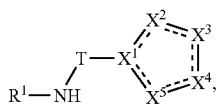

where $X^1$ is nitrogen, phosphorus, or —C($R^4$)$_{n''}$—, $X^2$, $X^3$, and $X^4$ are selected from the group consisting of oxygen, sulfur, —C($R^4$)$_{n'}$—, —N($R^4$)$_{n''}$—, and —P($R^4$)$_{n''}$—, and $X^5$ is —N($R^4$)$_{n''}$— provided that at least one, but no more than three, of $X^1$, or $X^2$, $X^3$, and $X^4$ is carbon or —C($R^4$)$_{n'}$—, respectively, each n' is 1 or 2, and each n" is 0 or 1, where each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof; provided that optionally any combination of two or more $R^1$, $R^2$, $R^3$, and/or $R^4$ groups may be joined together to form one or more optionally substituted fused ring systems. $X^4$ can be selected from the group consisting of —C($R^4$)$_{n''}$ $R^{4'}$—, —NR$^{4'}$—, and —PR$^{4'}$, and $R^{4'}$ can be optionally substituted cyclic hydrocarbyl or heteroatom-containing hydrocarbyl, including bicyclic and polycyclic hydrocarbyls and heteroatom-containing hydrocarbyls, such as optionally substituted aryl or heteroaryl. J can be a five-membered heterocycle selected from the group consisting of optionally substituted imidazole, oxazole, isoxazole, thiazole, isothiazole, pyrazole, oxadiazole, thiadiazole, indazole, benzimidazole, benzthiazole, triazole, oxadiazole, thiadiazole, tetrazole, and thiatriazole, and isomers thereof. $R^1$ can be optionally substituted ary, such as 2,6-disubtituted aryl. $R^2$ can be different from $R^3$.

In general, in another aspect, the invention provides compositions of matter, including ligands, compositions and metal-ligand complexes, that include a compound characterized by the formula:

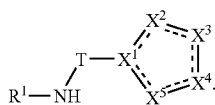

$R^1$ is optionally substituted hydrocarbyl or heteroatom containing hydrocarbyl. T is a bridging group of the general formula -(T'$R^2R^3$)$_n$—, wherein each T' is independently selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, and n is 1 or 2, provided that two or more $R^2$ and/or $R^3$ groups may be joined together to form one or more optionally substituted ring systems, and that one or more T' atoms may be involved in a double bond to a neighboring group and correspondingly be bonded to only a single $R^2$ or $R^3$ substituent. $X^1$ is nitrogen, phosphorus, or —C($R^4$)$_{n'}$—. $X^2$ and $X^3$ are independently selected from the group consisting of oxygen, sulfur, —C($R^4$)$_{n'}$—, —N($R^4$)$_{n''}$—, and —P($R^4$)$_{n''}$—. $X^4$ is —N($R^{4'}$)—, —P($R^{4'}$)—, or —C($R^{4'}$)($R^4$)$_{n''}$—. Each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Each $R^{4'}$ is selected from the group consisting of optionally substituted aryl and heteroaryl. $X^5$ is oxygen or sulfur. Each n' is 1 or 2, and each n" is 0 or 1. Optionally, two or more $R^1$, $R^2$, $R^3$, $R^4$ or $R^{4'}$ groups may be joined to form one or more optionally substituted fused ring systems.

In general, in another aspect, the invention provides compositions of matter, including ligands, compositions and metal-ligand complexes, that include a compound characterized by the formula:

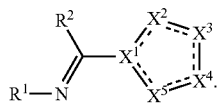

$R^1$ is optionally substituted hydrocarbyl or heteroatom containing hydrocarbyl. $R^2$ is selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof. n is 1 or 2. $X^1$ is nitrogen, phosphorus, or —C($R^4$)$_{n'}$—. $X^2$, $X^3$, and $X^4$ are independently selected from the group consisting of oxygen, sulfur, —C($R^4$)$_{n'}$—, —N($R^4$)$_{n''}$—, and —P($R^4$)$_{n''}$—. $X^5$ is —N($R^4$)$_{n''}$—. Alternatively, $X^2$ and $X^3$ are independently selected from the group consisting of oxygen, sulfur, —C($R^4$)$_{n'}$—, —N($R^4$)$_{n''}$—, and —P($R^4$)$_{n''}$—, $X^4$ is —N($R^{4'}$)—, —P($R^{4'}$)—, or —C($R^{4'}$)($R^4$)$_{n''}$—, and $X^5$ is oxygen or sulfur. At least one, but no more than three, of $X^1$, or $X^2$, $X^3$, and $X^4$ is carbon or —C($R^4$)$_{n'}$—, respectively. Each n' is 1 or 2. Each n" is 0 or 1. Each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Each $R^{4'}$ is selected from the group consisting of optionally substituted aryl and heteroaryl. Optionally any combination of two or more $R^1$, $R^2$, $R^4$ and/or $R^{4'}$ groups may be joined together to form one or more optionally substituted fused ring systems.

In any of the preceding aspects, compositions according to the invention can include a metal precursor or activated metal precursor including a metal selected from groups 3-6 and the lanthanide series of the periodic table of elements, and one or more optional activators. In particular embodiments, the metal precursor can be a compound characterized by the general formula M(L)$_m$, where M is a metal selected from the group consisting of groups 3-6 and lanthanides of the periodic table of elements, and each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups can be joined into a ring structure, Optionally, one or more of the ligands L can be ionically bonded to the metal M. m is 1, 2, 3, 4, 5, or 6. In more particular embodiments, M can be Ti, Zr, and Hf.

In general, in another aspect, the invention features metal-ligand complexes be characterized by the formula:

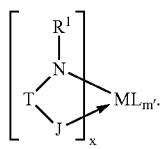

M is a metal selected from the group consisting of groups 3-6 and lanthanides of the periodic table of elements. $R^1$ is an optionally substituted hydrocarbyl or heteroatom containing hydrocarbyl. T is a bridging group of the general formula -$(T'R^2R^3)_n$—. Each T' is independently selected from the group consisting of carbon and silicon. $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof. n is 1 or 2. Two or more $R^2$ and/or $R^3$ groups may optionally be joined together to form one or more optionally substituted ring systems. One or more T' atoms may be involved in a double bond to a neighboring group and correspondingly be bonded to only a single $R^2$ or $R^3$ substituent. J is an optionally substituted heterocyclic group containing a five-membered heterocycle that includes at least one but no more than four heteroatoms and includes a nitrogen, phosphorus, oxygen, sulfur, or carbene in a ring position adjacent to the ring atom bonded to T. The nitrogen, phosphorus, oxygen, sulfur, or carbene in the ring position adjacent to the ring atom bonded to T is bonded to M via a dative bond. If the five-membered heterocycle includes a nitrogen, phosphorus, oxygen, or sulfur in the ring position adjacent to the bond to T, the five-membered heterocycle contains at least two heteroatoms. x is 1 or 2. Each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups are joined into a ring structure. Optionally, one or more of the ligands L may be ionically bonded to the metal M. m' is 1, 2, 3, or 4.

Particular embodiments can include one or more of the following features. In particular embodiments, the complex can be characterized by the formula:

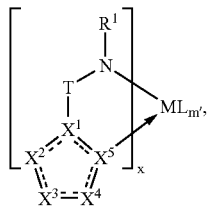

where M, L, m', T and $R^1$ are defined above, $X^1$ is nitrogen, phosphorus, or —$C(R^4)_{n'}$—, $X^2$, $X^3$, and $X^4$ are independently selected from the group consisting of oxygen, sulfur, —$C(R^4)_{n'}$—, —$N(R^4)_{n''}$—, and —$P(R^4)_{n''}$—, and $X^5$ is nitrogen, phosphorus, oxygen, sulfur or a carbine. In such embodiments, each n' is 1 or 2, each n" is 0 or 1, and each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that optionally any combination of two or more $R^1$, $R^2$, $R^3$, and/or $R^4$ groups may be joined together to form one or more optionally substituted fused ring systems. $X^4$ can be selected from the group consisting of —$C(R^4)_{n''}R^{4'}$—, —$NR^{4'}$—, and —$PR^{4'}$—, and $R^{4'}$ can be optionally substituted cyclic hydrocarbyl or heteroatom-containing hydrocarbyl. $R^{4'}$ can be optionally substituted aryl or heteroaryl. $R^{4'}$ and M can be optionally joined to form a metallocycle, such as a 5- or 6-membered metallocycle. M can be selected from the group consisting of Ti, Zr, and Hf, and x can be 1. The five-membered heterocycle can be optionally substituted imidazole, oxazole, isoxazole, thiazole, isothiazole, pyrazole, oxadiazole, thiadiazole, indazole, benzimidazole, benzthiazole, triazole, oxadiazole, thiadiazole, tetrazole, and thiatriazole, and isomers thereof. $R^1$ can be optionally substituted aryl, such as 2,6-disubtituted aryl. $R^2$ can be different than $R^3$.

In general, in another aspect, the invention provides metal-ligand complexes characterized by the formula:

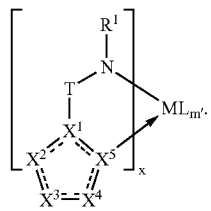

M is a metal selected from the group consisting of groups 3-6 and lanthanides of the periodic table of elements. $R^1$ is an optionally substituted hydrocarbyl or heteroatom containing hydrocarbyl. T is a bridging group of the general formula -$(T'R^2R^3)_n$—. Each T' is independently selected from the group consisting of carbon and silicon. $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof. n is 1 or 2. Two or more $R^2$ and/or $R^3$ groups may be joined together to form one or more optionally substituted ring systems. One or more T' atoms may be involved in a double bond to a neighboring group and correspondingly be bonded to only a single $R^2$ or $R^3$ substituent. $X^1$ is nitrogen, phosphorus, or —$C(R^4)_{n'}$—. $X^2$ and $X^3$ are independently selected from the group consisting of oxygen, sulfur, —$C(R^4)_{n'}$—, —$N(R^4)_{n''}$—, and —$P(R^4)_{n''}$—. $X^4$ is —$N(R^{4'})$—, —$P(R^{4'})$—, or —$C(R^{4'})(R^4)_{n''}$—. Each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Each $R^{4'}$ is selected from the group consisting of optionally substituted aryl and heteroaryl. $X^{5'}$ is oxygen or sulfur. Each n' is 1 or 2. Each n" is 0 or 1. Optionally, two or more $R^1$, $R^2$, $R^3$, $R^4$ or $R^{4'}$ groups may be joined to form one or more optionally substituted fused ring systems. x is 1 or 2. Each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups are joined into a ring structure. Optionally, one or more of the ligands L may be ionically bonded to the metal M. m' is 1, 2, 3, or 4.

In general, in another aspect, the invention provides metal-ligand complexes characterized by the formula:

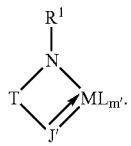

M is a metal selected from the group consisting of groups 3-6 and lanthanides of the periodic table of elements. $R^1$ is an optionally substituted hydrocarbyl or heteroatom containing hydrocarbyl. T is a bridging group of the general formula $-(T'R^2R^3)_n-$. Each T' is independently selected from the group consisting of carbon and silicon. $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof. n is 1 or 2. Two or more $R^2$ and/or $R^3$ groups may be joined together to form one or more optionally substituted ring systems. One or more T' atoms may be involved in a double bond to a neighboring group and correspondingly be bonded to only a single $R^2$ or $R^3$ substituent. J' is an optionally substituted heterocyclic group containing a five-membered heterocycle that includes at least one but no more than four heteroatoms and including a nitrogen, phosphorus, oxygen, sulfur, or carbene in a ring position adjacent to the ring atom bonded to T. J' includes 2 atoms bonded to the metal M. One of the 2 atoms is the nitrogen, phosphorus, oxygen, sulfuer, or carbene in the ring position adjacent to the ring atom bonded to T, and is bonded to M via a dative bond. The other of the 2 atoms is bonded to the metal M through a covalent bond. Each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof, provided that optionally, two or more L groups are joined into a ring structure and that one or more of the ligands L may be ionically bonded to the metal M. m' is 1, 2 3, or 4.

Particular embodiments can include one or more of the following features. The complex can be characterized by the formula:

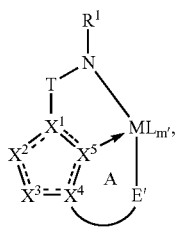

where M, L, m', T, $R^1$ are defined above, $X^1$ and $X^4$ are independently selected from the group consisting of nitrogen, phosphorus, or $-C(R^4)_{n''}-$, $X^2$ and $X^3$ are independently selected from the group consisting of oxygen, sulfur, $-C(R^4)_{n'}-$, $-N(R^4)_{n'}-$, and $-P(R^4)_{n''}-$, and $X^5$ is nitrogen, phosphorus, oxygen, sulfur or a carbene, where each n' is 1 or 2, each n'' is 0 or 1, and each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof; provided that optionally any combination of two or more $R^1$, $R^2$, $R^3$, and/or $R^4$ groups may be joined together to form one or more optionally substituted fused ring systems; and E' is selected from the group consisting of oxygen, sulfur, $-N(R^{21})_{n'''}-$, $-C(R^{21})_{n'}-$, $-P(R^{21})_{n''}-$, and $-Si(R^{21})_{n'}-$, each $R^{21}$ is independently selected from the group consisting of hydrogen, halogen, and optionally substituted alkyl, heteroalkyl, aryl and heteroaryl, and E' is connected to $X^4$ through an optionally substituted divalent hydrocarbyl or heteroatom-containing hydrocarbyl group to form a metallocycle containing five, six or seven members, including M, provided that $R^{21}$ can be joined to the divalent hydrocarbyl or heteroatom-containing hydrocarbyl group connecting E' to $X^4$ as part of an aromatic ring, each n' is 1 or 2, and each n'' is 0 or 1, depending on the bond order of the adjacent bonds, and provided that optionally two or more $R^4$ and/or $R^{21}$ groups are joined to form one or more optionally substituted ring structures having from 3 to 50 atoms each. ach $R^{19}$ and $R^{20}$ is independently selected from the group consisting of hydrogen, halogen and optionally substituted alkyl, heteroalkyl, aryl and heteroaryl, and each n''' is 1 or 2, depending on the bond order of the adjacent bonds, provided that optionally two or more $R^4$, $R^{19}$, $R^{20}$ and $R^{21}$ groups are joined to form one or more optionally substituted ring structures having from 3 to 50 atoms each. M can be selected from the group consisting of Ti, Zr, and Hf. The five-membered heterocycle includes at least two heteroatoms, and can be selected from optionally substituted imidazole, oxazole, isoxazole, thiazole, isothiazole, pyrazole, oxadiazole, thiadiazole, indazole, benzimidazole, benzthiazole, triazole, oxadiazole, thiadiazole, tetrazole, and thiatriazole, and isomers thereof. The five-membered heterocycle can be furan or thiophene. $X^5$ can be nitrogen. $X^1$ and $X^4$ can be $-C(R^4)_{n''}-$, one of $X^2$ and $X^3$ can be sulfur and the other of $X^2$ and $X^3$ can be $-C(R^4)_{n'}-$. n can be 1, T can be C, $R_2$ can be optionally substituted aryl, and $R_3$ can be hydrogen or alkyl. $R_2$ can be optionally substituted aryl, and $R_3$ can be hydrogen or alkyl. $R^1$ can be an optionally substituted aryl, such as 2,6-di-substituted aryl. $R^2$ can be different than $R^3$.

In general, in another aspect, the invention provides metal-ligand complexes characterized by the formula:

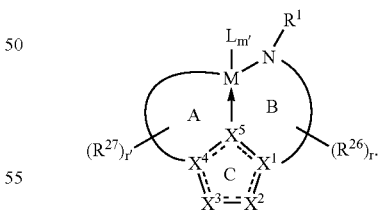

M is a metal selected from the group consisting of groups 3-6 and lanthanides of the periodic table of elements. A is an optionally substituted metallocycle containing five, six or seven atoms in the ring, including M. B is an optionally substituted metallocycle containing five or six atoms in the ring, including M. C is an optionally substituted five-membered heterocycle. $X^1$ and $X^4$ are selected from the group consisting of nitrogen, phosphorus, and $-C(R^4)_{n''}-$. $X^2$ and $X^3$ are selected from the group consisting of oxygen, sulfur, $-C(R^4)_{n'}-$, $N(R^4)_{n''}-$, and $-P(R^4)_{n''}-$. $X^5$ is nitrogen, carbon, oxygen, phosphorus, or sulfur. n' is 1 or 2. n" is 0 or 1. $R^1$ is an optionally substituted hydrocarbyl or heteroatom containing hydrocarbyl. Each $R^4$, $R^{26}$ and $R^{27}$ is independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof. r is 1, 2, 3 or 4. r' is 1, 2, 3, or 4. Optionally any combination of two or more $R^4$, $R^{26}$ and/or $R^{27}$ groups may be joined together to form one or more optionally substituted fused ring systems. Each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups are joined into a ring structure. One or more of the ligands L may be ionically bonded to the metal M. m' is 1, 2, 3 or 4.

Particular embodiments can include one or more of the following featuers one of A or B can be a 5-membered ring and the other of A or B can be a 6-membered ring. Ring A can include a carbon-metal bond. M can be selected from the group consisting of Ti, Zr, and Hf.

In general, in still another aspect, the invention provides arrays of materials. The arrays include a substrate having at least 8 members associated with regions of the substrate. Each array member is different from the other members of the array. Each array member includes a compound, composition or complex according to one of the aspects described above.

In general, in another aspect, the invention provides catalytic methods. In the methods, one or more reagents is reacted in the presence of a catalyst comprising a composition or complex as described above, and optionally one or more activators, under conditions sufficient to yield one or more reaction products.

Particular embodiments can include one or more of the following features. The selectivity of the reaction, including stereoselectivity, enantioselectivity or diastereoselectivity, can be influenced by the catalyst. The composition or the complex can be substantially enantiomerically or diastereomerically pure. The product can be substantially enantiomerically or diastereomerically pure.

In general, in another aspect, the invention provides polymerization processes that employ the composition or complexes of the invention, optionally in the presence of at least one activator. In particular embodiments, the activator can include an ion forming activator and, optionally, a group 13 reagent. The activator can include an alumoxane.

In general, in another aspect, the invention provides a process for the polymerization of an alpha-olefin. According to the process, at least one alpha-olefin is polymerized in the presence of a catalyst formed from a composition or complex of the invention, optionally in the presence of one or more activators, under polymerization conditions sufficient to form a substantially stereoregular polymer.

Particular embodiments can include one or more of the following features. The at least one alpha-olefin can include propylene. The substantially steroregular polymer can be isotactic polypropylene. The process can be a solution process operated under polymerization conditions that comprise a temperature of at least 100° C., or at least 125° C. The stereoregular polymer can be characterized as having $^{13}C$ NMR peaks corresponding to a regioerror at about 14.6 and 15.7 ppm, the peaks being of about equal intensity. M can be Hf or Zr.

In general, in another aspect, the invention provides a process for polymerizing ethylene and at least one alpha-olefin. According to the process, ethylene is polymerized in the presence of at least one alpha-olefin in the presence of a catalyst formed from a composition or complex of the invention, optionally in the presence of one or more activators.

Particular embodiments can include one or more of the following features. The at least one alpha-olefin can include propylene, 1-hexene, 1-octene or styrene. The process can be a solution process, and can be operated under polymerization conditions that include a temperature of at least 100° C., or at least 125° C.

In general, in another aspect, the invention provides a process for polymerizing at least one monomer. The process includes providing a reactor with reactor contents including at least one polymerizable monomer and a composition or complex of the invention, and subjecting the reactor contents to polymerization conditions. In particular embodiments, the at least one polymerizable monomer can include ethylene and propylene, ethylene and 1-hexene, ethylene and 1-octene, ethylene and styrene, ethylene and a cyclic alkene, ethylene and a diene, or ethylene, propylene, and a diene selected from the group consisting of ethylidenenorbornene, dicyclopentadiene, and 1,4-hexadiene.

In general, in another aspect, the invention provides a process for the polymerization of a polymerizable monomer. According to the process, a composition or complex of the invention is provided, the composition or complex is optionally activated, and at least one polymerizable monomer is polymerized in the presence of the activated composition or complex to produce a distribution of product polymers that is at least bimodal by one or more of molecular weight or composition.

In general, in another aspect, the invention provides a polypropylene characterized as having $^{13}C$ NMR peaks corresponding to a regioerror at about 14.6 and 15.7 ppm, the peaks being of about equal intensity.

The invention and its various aspects can be implemented to provide one or more of the following advantages. The ligands, compositions, complexes and polymerization methods of the invention can be used to provide catalysts exhibiting enhanced activity. Catalysts incorporating the ligands, compositions and/or complexes can be used to catalyze a variety of transformations, such as olefin oligomerization or polymerization. By selecting an appropriate ligand and metal, compositions and/or complexes can be obtained to provide for desired properties in the resulting product. Thus, polymers produced using the ligands, compositions, complexes, and methods of the invention can exhibit higher (or lower) melting points, higher (or lower) molecular weights, and/or higher (or lower) polydispersities, than polymers produced using prior known catalysts. In some embodiments, products having high stereoregularity or other desirable product properties can be obtained by selecting ligand precursors that will provide specific chelate ring sizes when combined with an appropriate transition metal. In some embodiments, polymer products having bi- or multi-modal distributions of product composition and/or molecular weight can be obtained by selecting a single catalyst precursor and activating it under certain conditions. Catalysts incorporating the ligands, compositions and/or complexes can be used according to the polymerization methods of the invention to produce polymers under commercially desirable polymerization conditions. Catalysts incorporating the ligands, compositions and complexes of the invention can exhibit catalytic activity at higher temperatures than prior known catalysts. Copolymerization processes (e.g., ethylene/α-olefin copolymerizations) using the ligands, compositions and complexes of the invention can exhibit higher (or lower) comonomer incorporation than processes involving prior known catalysts. Chiral compositions and/or complexes according to the inveniton can be used to catalyze stereoselective, enantioselective or diastereoselective transformations.

The details of one or more embodiments of the invention are set forth in the description below. Other features, objects and advantages of the invention will be apparent from the drawings, the following detailed description and from the claims.

DETAILED DESCRIPTION

Figure 1A:
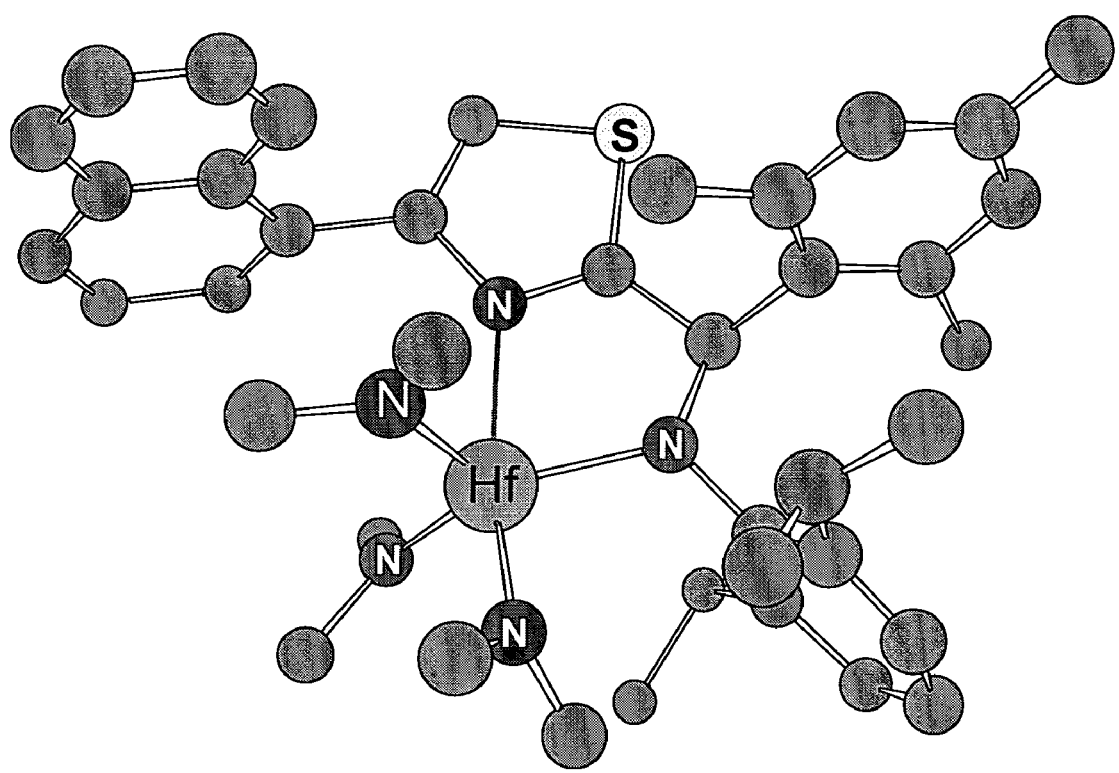
FIGS. 1A and B are X-ray structure determination of two thiazole-amine (2,1) complexes according to one aspect of the invention

The invention provides ligands, compositions and complexes that are useful as catalysts for a variety of transformations, including olefin polymerization reactions.

As used herein, the phrase "characterized by the formula" is not intended to be limiting and is used in the same way that "comprising" is commonly used. The term "independently selected" is used herein to indicate that the groups in question—e.g., $R^1$, $R^2$, $R^3$, and $R^5$—can be identical or different (e.g., $R^1$, $R^2$, $R^3$, $R^4$, and $R^5$ may all be substituted alkyls, or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where the event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "substituted" as in "substituted hydrocarbyl," "substituted aryl," "substituted alkyl," and the like, means that in the group in question (i.e., the hydrocarbyl, alkyl, aryl or other moiety that follows the term), at least one hydrogen atom bound to a carbon atom is replaced with one or more substituent groups such as hydroxy, alkoxy, alkylthio, phosphino, amino, halo, silyl, and the like. When the term "substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, napthyl, pyrrolyl, fliryl, thiophenyl, imidazolyl, and the like. In particular embodiments, cyclic moieties include between 3 and 200 atoms other than hydrogen, between 3 and 50 atoms other than hydrogen or between 3 and 20 atoms other than hydrogen.

The term "hydrocarbyl" refers to hydrocarbyl radicals containing 1 to about 50 carbon atoms, specifically 1 to about 24 carbon atoms, most specifically 1 to about 16 carbon atoms, including branched or unbranched, cyclic or acyclic, saturated or unsaturated species, such as alkyl groups, alkenyl groups, aryl groups, and the like.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms.

The term "alkenyl" as used herein refers to a branched or unbranched, cyclic or acyclic hydrocarbon group typically although not necessarily containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 20 carbon atoms.

The term "alkynyl" as used herein refers to a branched or unbranched, cyclic or acyclic hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 20 carbon atoms.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "alkoxy" as used herein intends an alkyl group bound through a single, terminal ether linkage; that is, an "alkoxy" group may be represented as —O-alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. The term "arylthio" is used similarly, and may be represented as —S-aryl, with aryl as defined below. The term "mercapto" refers to —SH.

The terms "halo" and "halogen" are used in the conventional sense to refer to a chloro, bromo, fluoro or iodo radical.

The terms "heterocycle" and "heterocyclic" refer to a cyclic radical, including ring-fused systems, including heteroaryl groups as defined below, in which one or more carbon atoms in a ring is replaced with a heteroatom—that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyrrolidine, pyrroline, furan, tetrahydrofuran, thiophene, imidazole, oxazole, thiazole, indole, and the like, including any isomers of these. Additional heterocycles are described, for example, in Alan R. Katritzky, Handbook of Heterocyclic Chemistry, Pergammon Press, 1985, and in Comprehensive Heterocyclic Chemistry, A. R. Katritzky et al., eds, Elsevier, 2d. ed., 1996. The term "metallocycle" refers to a heterocycle in which one or more of the heteroatoms in the ring or rings is a metal.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene and the like.

More generally, the modifiers "hetero" and "heteroatom-containing", as in "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. When the term "heteroatom-containing" introduces a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds.

As used herein the term "silyl" refers to the —SiZ$^1$Z$^2$Z$^3$ radical, where each of Z$^1$, Z$^2$, and Z$^3$ is independently selected from the group consisting of hydrogen and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —BZ$^1$Z$^2$ group, where each of Z$^1$ and Z$^2$ is as defined above. As used herein, the term "phosphino" refers to the group —PZ$^1$Z$^2$ where each of Z$^1$ and Z$^2$ is as defined above. As used herein, the term "phosphine" refers to the group :PZ$^1$Z$^2$Z$^3$, where each of Z$^1$, Z$^3$ and Z$^2$ is as defined above. The term "amino" is used herein to refer to the group —NZ$^1$Z$^2$, where each of Z$^1$ and Z$^2$ is as defined above. The term "amine" is used herein to refer to the group :NZ$^1$Z$^2$Z$^3$, where each of Z$^1$, Z$^2$ and Z$^3$ is as defined above.

In this specification, the metal-ligand complexes of the invention are sometimes referred to as as (2,1) complexes or (3,2) complexes, with the first number representing the number of coordinating atoms and second number representing the number of anionic sites on the heterocycle-amine ligand, when the metal-ligand bonding is considered from an ionic bonding model perspective, with the metal considered to be cationic and the ligand considered to be anionic. From a covalent bonding model perspective, a (2,1) complex may be considered to be a complex in which the heterocycle-amine ligand is bound to the metal center via one covalent bond and one dative bond, while a (3,2) complex may be considered to be a complex in which the heterocycle-amine ligand is bound to the metal center via two covalent bonds and one dative bond. Examples of (2,1) complexes include the complex examples labeled M1-M12, M14-M16, M18-M21, M23-M25, and M32-M60, as listed below. Examples of (3,2) complexes include the complex examples labeled below as M13, M17, M22, M26, and M28-M31. Other coordination modes are also possible, for example in the complex example labeled M27 below, the heterocycle-amine ligand is bound to the metal center via one covalent bond and two dative bonds, and may thus be described as a (3,1) complex.

Other abbreviations used herein include: ""Pr" to refer to isopropyl; "Bu" to refer to tert-butyl; "Me" to refer to methyl; "Et" to refer to ethyl; "Ph" to refer to phenyl; "Mes" to refer to mesityl (2,4,6-trimethyl phenyl); "TFA" to refer to trifluoroacetate and "THF" to refer to tetrahydrofuran.

The ligands according to the invention can be characterized broadly as monoanionic ligands having an amine and a heterocyclic or substituted heterocyclic group. Preferred ligand substituents for some particular monomers are described in more detail below. In some embodiments, the ligands of the invention can be characterized by the following formula:

(I)

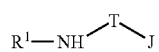

where R$^1$ is generally selected from the group consisting of optionally substituted hydrocarbyl or heteroatom containing hydrocarbyl. In some embodiments, R$^1$ is selected from optionally substituted alkyl, heteroalkyl, aryl, heteroaryl and combinations thereof. In more particular embodiments, R$^1$ is a ring having from 4-8 atoms in the ring generally selected from the group consisting of substituted cycloalkyl, heterocycloalkyl, aryl and heteroaryl.

T is a bridging group, typically of the general formula -(T'R$^2$R$^3$)$_n$—, where each T' is independently selected from the group consisting of carbon and silicon, R$^2$ and R$^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, and n is 1 or 2, provided that two or more R$^2$ and/or R$^3$ groups may be joined together to form one or more optionally substituted ring systems, such as saturated, unsaturated or aromatic ring systems having from 3-50 non-hydrogen atoms (e.g., cyclopropyl, where T'=C, n=1, and $R^2$ and $R^3$ together form —$CH_2$—$CH_2$—; or cyclohexyl, where T'=C, n=2 and the two $R^2$ groups together form —$CH_2$—$CH_2$—$CH_2$—$CH_2$—), and that one or more T' atoms may be involved in a double bond to a neighboring group (e.g., to an $R^2$, an $R^3$, or T') and correspondingly be bonded to only a single R substituent (i.e., just an $R^2$ or just an $R^3$)— for example, where -(T'$R^2R^3$)$_n$— is a phenyl group bonded to N and J through adjacent ring carbon atoms.

J is an optionally substituted containing a five-membered heterocycle. In particular embodiments, the five-membered heterocycle contains at least two but no more than four heteroatoms. In more particular embodiments, at least one of the heteroatoms is a nitrogen, phosphorus, oxygen, or sulfur in a ring position adjacent to the ring atom that is bonded to T.

In more specific embodiments, suitable ligands according to the invention are characterized by the following formula:

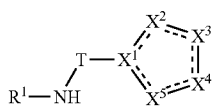

(II)

where $R^1$ and T are as defined above. In structure II (and throughout this specification), the presence of one solid line and one dashed line between any pair of atoms is intended to indicate that the bond in question may be a single bond or a double bond, or a bond with bond order intermediate between single and double, such as the delocalized bonding in an aromatic ring. In some embodiments of the structure of formula II, $X^1$ is nitrogen, phosphorus, or —C($R^4$)$_{n''}$—, $X^2$, $X^3$, and $X^4$ are selected from the group consisting of oxygen, sulfur, —C($R^4$)$_{n'}$—, —N($R^4$)$_{n''}$—, and —P($R^4$)$_{n''}$—, and $X^5$ is —N($R^4$)$_{n''}$— provided that at least one of $X^1$, or $X^2$, $X^3$, and $X^4$ is carbon or —C($R^4$)$_{n''}$—, respectively, each n' is 1 or 2 and each n'' is 0 or 1 (depending, e.g., on the degree of saturation of the ring). In some embodiments, no more than three of $X^1$, $X^2$, $X^3$, and $X^4$ are carbon (in the case of $X^1$) or —C($R^4$)$_{n''}$— (in the case of $X^2$, $X^3$, and/or $X^4$), respectively. Each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more $R^1$, $R^2$, $R^3$, and/or $R^4$ groups may be joined together to form one or more optionally substituted fused ring systems, such as ring systems having from 3-50 non-hydrogen atoms.

In certain more specific embodiments, $X^4$ is selected from the group consisting of —C($R^4$)$_{n''}R^{4'}$—, —N$R^{4'}$—, and —P$R^{4'}$—, where n'' is 0 or 1 as noted above, and $R^{4'}$ is optionally substituted cyclic hydrocarbyl or heteroatom-containing hydrocarbyl. In some such embodiments, $R^{4'}$ is optionally substituted bicyclic or polycyclic hydrocarbyl or heteroatom-containing hydrocarbyl, or optionally substituted aryl or heteroaryl, including optionally substituted bicyclic or polycyclic aryl or heteroaryl. Moreover, in some embodiments, at least one of the bonds between $X^1$, $X^2$, $X^3$, $X^4$ and $X^5$ is a double bond (as in, e.g., a five-membered aromatic heterocycle).

In other embodiments of the structure of formula II, $X^1$ is nitrogen, phosphorus, or —C($R^4$)$_{n''}$—, $X^2$, $X^3$, and $X^4$ are independently selected from the group consisting of oxygen, sulfur, —C($R^4$)$_{n'}$—, —N($R^4$)$_{n''}$—, and —P($R^4$)$_{n''}$—, provided that at least one of $X^3$ and $X^4$ is —N($R^4$)—, —P($R^4$)—, or —C($R^4$)($R^4$)$_{n''}$—, where each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and each $R^{4'}$ is selected from the group consisting of optionally substituted aryl and heteroaryl, and $X^5$ is oxygen or sulfur, each n' is 1 or 2, and each n'' is 0 or 1, provided that optionally, two or more $R^1$, $R^2$, $R^3$, $R^4$ or $R^{4'}$ groups may be joined to form one or more optionally substituted fused ring systems.

In some embodiments, the ligands can be characterized by the following formula:

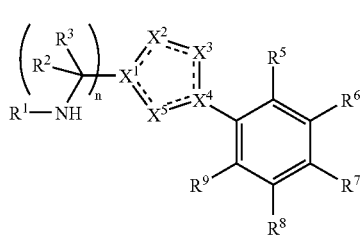

(III)

where $X^4$ is nitrogen, phosphorus, or —C($R^4$)$_{n''}$—, where n'' is 0 or 1, and $R^5$, $R^6$, $R^7$, $R^8$ and $R^9$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more of $R^4$, $R^5$, $R^6$, $R^7$, $R^8$ and $R^9$ may be joined to form one or more optionally substituted fused ring systems, such as ring systems having from 3-50 non-hydrogen atoms.

In some embodiments, $R^{4'}$ is bicyclic or polycyclic aryl or heteroaryl, such as napthyl, benzofuranyl, benzothiophenyl, benzimidazolyl, benzthiazolyl, or the like. In some such embodiments, the ligands can thus be characterized by the formula:

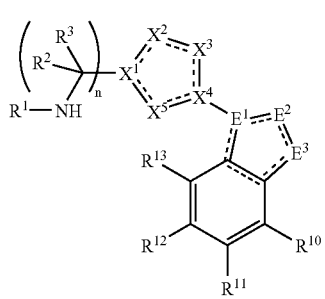

(IV)

where $X^4$ is nitrogen, phosphorus, or —C($R^4$)$_{n''}$—, $E^1$ is selected from the group consisting of carbon, nitrogen and phosphorus, —C($R^{14}$)$_{n''}$—, and —Si($R^{14}$)$_{n''}$—, and $E^2$ and $E^3$ are selected from the group consisting of oxygen, sulfur, —N($R^{14}$)$_{n''}$—, —C($R^{14}$)$_{n'}$—, —P($R^{14}$)$_{n''}$—, and —Si($R^{14}$)$_{n'}$—, where each n' is 1 or 2 and each n'' is 0 or 1 (depending, e.g., on the degree of saturation of the bonds between $X^4$, $E^2$ and/or $E^3$ and their adjacent atoms). In particular embodiments, at least one of $E^1$, $E^2$ and $E^3$ is not carbon (in the case of $E^1$) or —C($R^{14}$)$_{n''}$— (in the case of $E^2$ and/or $E^3$). Each $R^{10}$, $R^{11}$, $R^{12}$, $R^{13}$, and $R^{14}$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. In some embodiments, where $E^2$ and/or $E^3$ is —N($R^{14}$)$_{n''}$—, —P($R^{14}$)$_{n''}$—, or —Si($R^{14}$)$_{n'}$—, the corresponding $R^{14}$ is selected from the group consisting of hydrogen, halogen, and optionally substituted alkyl, heteroalkyl, aryl, heteroaryl, alkoxy, aryloxy, silyl. Optionally, two or more $R^4$, $R^{10}$, $R^{11}$, $R^{12}$, $R^{13}$, and $R^{14}$ groups may be joined to form one or more optionally substituted fused ring systems, such as ring systems having from 3-50 non-hydrogen atoms.

In other embodiments, the ligands are characterized by the formula:

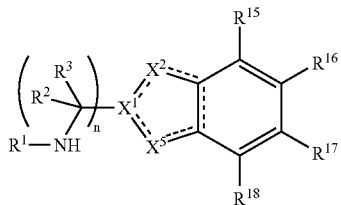

(V)

where $R^{15}$, $R^{16}$, $R^{17}$ and $R^{18}$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more of $R^4$, $R^{15}$, $R^{16}$, $R^{17}$ and $R^{18}$ may be joined to form one or more optionally substituted fused ring systems, such as ring systems having from 3-50 non-hydrogen atoms. In particular embodiments, $X^2$ is oxygen, sulfur, —N($R^4$)$_{n''}$—, or —P($R^4$)$_{n''}$—, where n" is 0 or 1.

In certain other embodiments, ligands according to the invention can be characterized by the formula:

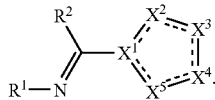

(VI)

In the structure of formula VI, $R^1$ is optionally substituted hydrocarbyl or heteroatom containing hydrocarbyl, $R^2$ is hydrogen, halogen, or optionally substituted alkyl, heteroalkyl, aryl, heteroaryl, alkoxy, aryloxy, silyl, boryl, phosphino, amino, alkylthio, arylthio, or combinations thereof, and n is 1 or 2. $X^1$ is nitrogen, phosphorus, or —C($R^4$)$_{n''}$—, $X^2$, $X^3$, and $X^4$ are independently selected from the group consisting of oxygen, sulfur, —C($R^4$)$_{n''}$—, —N($R^4$)$_{n''}$—, and —P($R^4$)$_{n''}$—. Each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof; provided that optionally any combination of two or more $R^1$, $R^2$, and/or $R^4$ groups may be joined together to form one or more optionally substituted fused ring systems. Each n' is 1 or 2, and each n" is 0 or 1. In some embodiments, at least one but no more than three of $X^1$, or $X^2$, $X^3$, and $X^4$ is carbon or —C($R^4$)$_{n'}$—, respectively, and $X^5$ is —N($R^4$)$_{n''}$—. In other embodiments, at least one of $X^3$ and $X^4$ is —N($R^{4'}$)—, —P($R^{4'}$)—, or —C($R^{4'}$)($R^{4'}$)$_{n''}$—, where each $R^{4'}$ is optionally substituted aryl or heteroaryl, and $X^5$ is oxygen or sulfur. Optionally, two or more $R^1$, $R^2$, $R^4$ or $R^{4'}$ groups may be joined to form one or more optionally substituted fused ring systems.

In certain embodiments, $R^1$ is optionally substituted alkyl or aryl. In certain more specific embodiments, $R^1$ is selected from the group consisting of n-butyl, cyclohexyl, benzyl, mesityl, 4-isopropylphenyl (4-$^i$Pr—$C_6H_4$—), napthyl, 3,5-di-trifluoromethylpheny (3,5-($CF_3$)$_2$—$C_6H_3$—), 2-methyl-napthyl, 2,6-diisoproylphenyl (2,6-($^i$Pr)$_2$—$C_6H_3$—), 2,4,6-tri-isopropylphenyl (2,4,6-($^i$Pr)$_3$—$C_6H_2$—), 2-biphenyl, 2-methyl-4-methoxyphenyl (2Me-4-MeO—$C_6H_3$—), 2-tert-butylphenyl (2-$^t$Bu-$C_6H_4$—), 2,6-di-tert-butylphenyl (2,6-($^t$Bu)$_2$-$C_6H_3$—), 2-isopropyl-6-methylphenyl (2-$^i$Pr-6-Me-$C_6H_3$—), 2-tert-butyl-6-methylphenyl (2-$^t$Bu-6-Me-$C_6H_3$—), 2,6-diethylphenyl (2,6-$Et_2$-$C_6H_3$—) 2-sec-butyl-6-ethylphenyl, 4-n-butylphenyl, 2,6,-diphenylphenyl, and 2,6-ditolylphenyl.

In some embodiments, T is —$CR^2R^3$—, and $R^2$ is different from $R^3$ such that T contains a chiral center. Thus, for example, in some embodiments $R^2$ is hydrogen and $R^3$ is selected from the group consisting of methyl, isopropyl, cyclohexyl, benzyl, phenyl, 2-cyclohexylphenyl, naphthyl, 2-biphenyl, t-butyl, 2-N,N-dimethylanilinyl (2-($NMe_2$)—$C_6H_4$—), 2-methoxyphenyl (2-MeO—$C_6H_4$—), anthracenyl, mesityl, 2,4,6-($^i$Pr)$_3$—$C_6H_2$—, 2-pyridyl, 2,6-($^i$Pr)$_2$—$C_6H_3$—, 3,5-dimethylphenyl, o-tolyl, phenanthrenyl, mesityl, 2,6-diphenylphenyl and 2,6-ditolylphenyl. In other embodiments, T is —($CR^2R^3$)$_2$—, where the $R^2$ groups can be the same or different, and the $R^3$ groups can be the same or different and can be as defined above. Thus, for example, in particular embodiments both $R^2$ groups are hydrogen, while both $R^3$ groups are phenyl (where the $R^3$ substituents can be arranged in any relative configuration (i.e., R,R, S,S, R,S, or S,R)), or both $R^3$ groups together form a three- or four-carbon bridge, such that T forms a divalent cyclopentyl or cyclohexyl ring.

In particular embodiments, the heterocyclic J group, which can be saturated or unsaturated (e.g., a heteroaryl group) includes two, three or four heteroatoms selected from nitrogen, oxygen, phosphorus and sulfur. Particular J groups in such embodiments include imidazole, oxazole, isoxazole, thiazole, isothiazole, pyrazole, oxadiazole, thiadiazole, indazole, benzimidazole, benzthiazole, triazole, oxadiazole, thiadiazole, tetrazole, and thiatriazole, including the various isomeric and/or substituted variants of these.

In some embodiments, the $R^{4'}$ substituents (i.e., the substitutents at ring position $X^3$ or $X^4$) are selected from the group consisting of hydrogen, methyl, benzyl, phenyl, o-tolyl, 4-ethylphenyl, 3,5-dimethylphenyl, mesityl, 2-hydroxyphenyl, 2-methoxyphenyl, 3-methoxyphenyl, 4-methoxyphenyl, napthyl, 2-methylnapthyl, anthracenyl, phenanthrenyl, N-methyl-4-indolyl, 3-benzofuranyl, 2-methyl-3-benzofuranyl, 2-ethyl-3-benzofuranyl, 3-benzothiophenyl, 2-methyl-3-benzothiophenyl, carbazolyl, 3,5-($CF_3$)$_2$—$C_6H_3$—, 2-trifluoromethylphenyl, 4-trifluoromethylphenyl, 4-chlorophenyl, 3,5-dichlorophenyl, 2,4-dichlorophenyl, 2,6-dichlorophenyl, 4-fluorophenyl, 3,5-difluorophenyl, 2,4-difluorophenyl, 2,6-difluorophenyl, and 4-N,N-dimethylanilinyl.

In particular embodiments in which the ligand is characterized by formula V, $R^{18}$ is selected from the group consisting of optionally substituted aryl and heteroaryl. In more particular embodiments, $R^{18}$ is phenyl or napthyl.

Specific examples of ligands within the scope of these formulas include those set out in Table 1.

TABLE 1
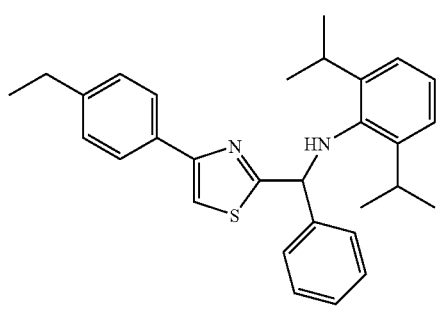 A1
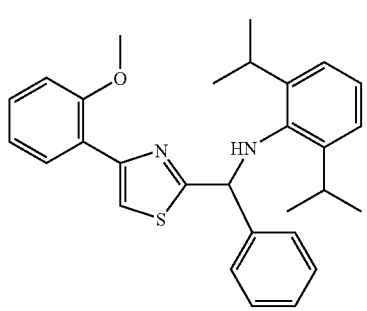 A2
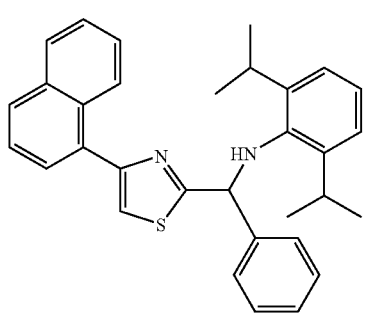 A3
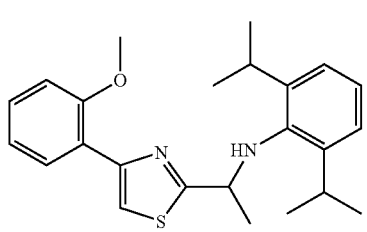 A4
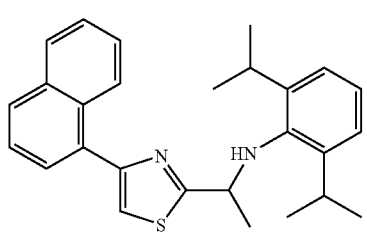 A5

TABLE 1-continued
| | |
|---|---|
| 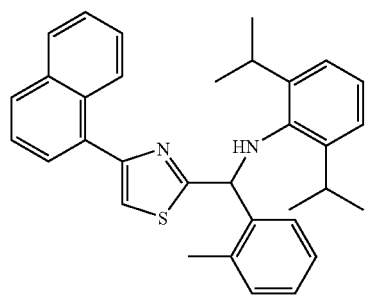 | A6 |
| 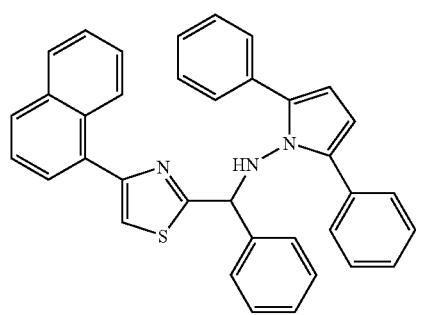 | A7 |
| 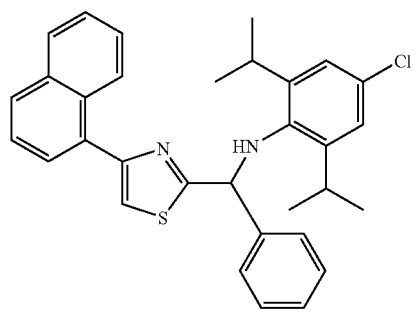 | A8 |
| 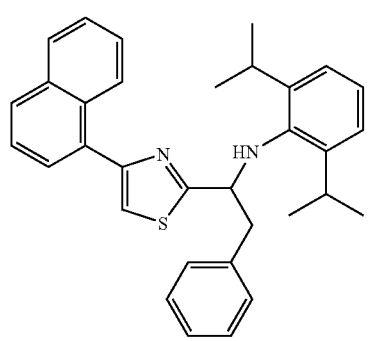 | A9 |
| 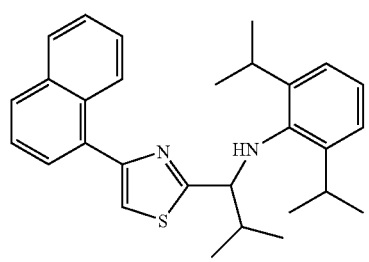 | A10 |

TABLE 1-continued
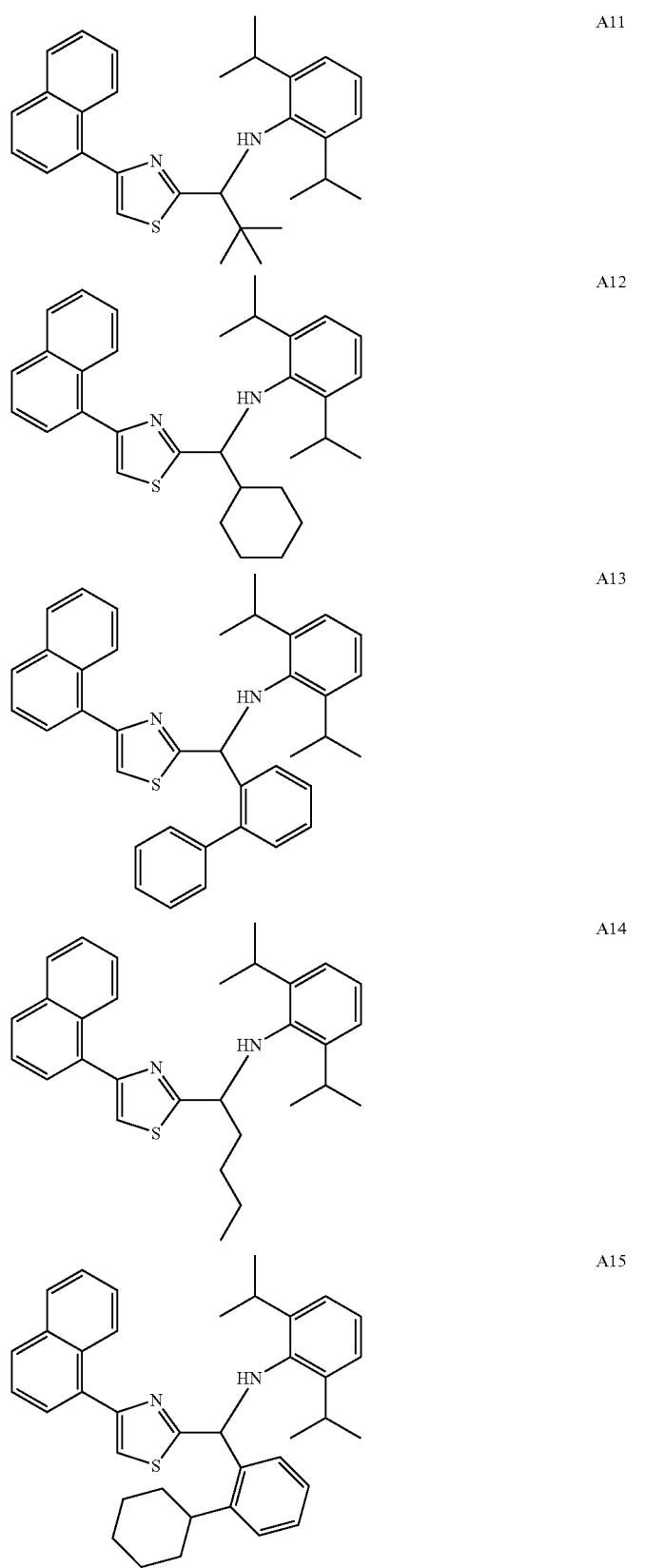
A11
A12
A13
A14
A15

TABLE 1-continued
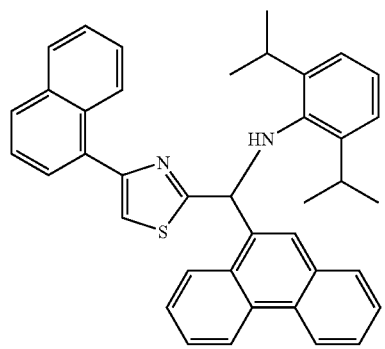 A16
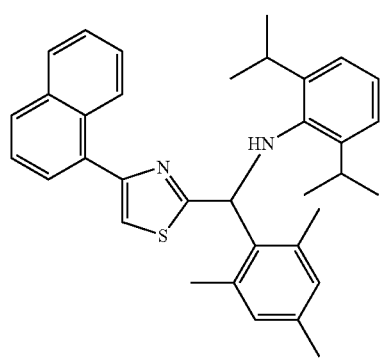 A17
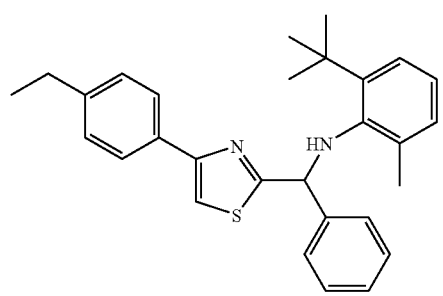 A18
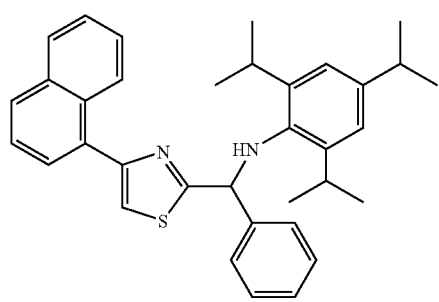 A19
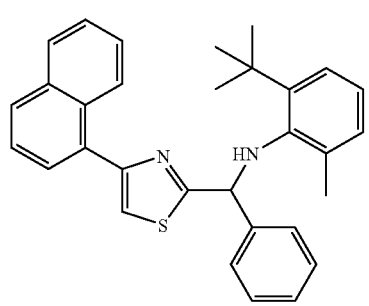 A20

TABLE 1-continued
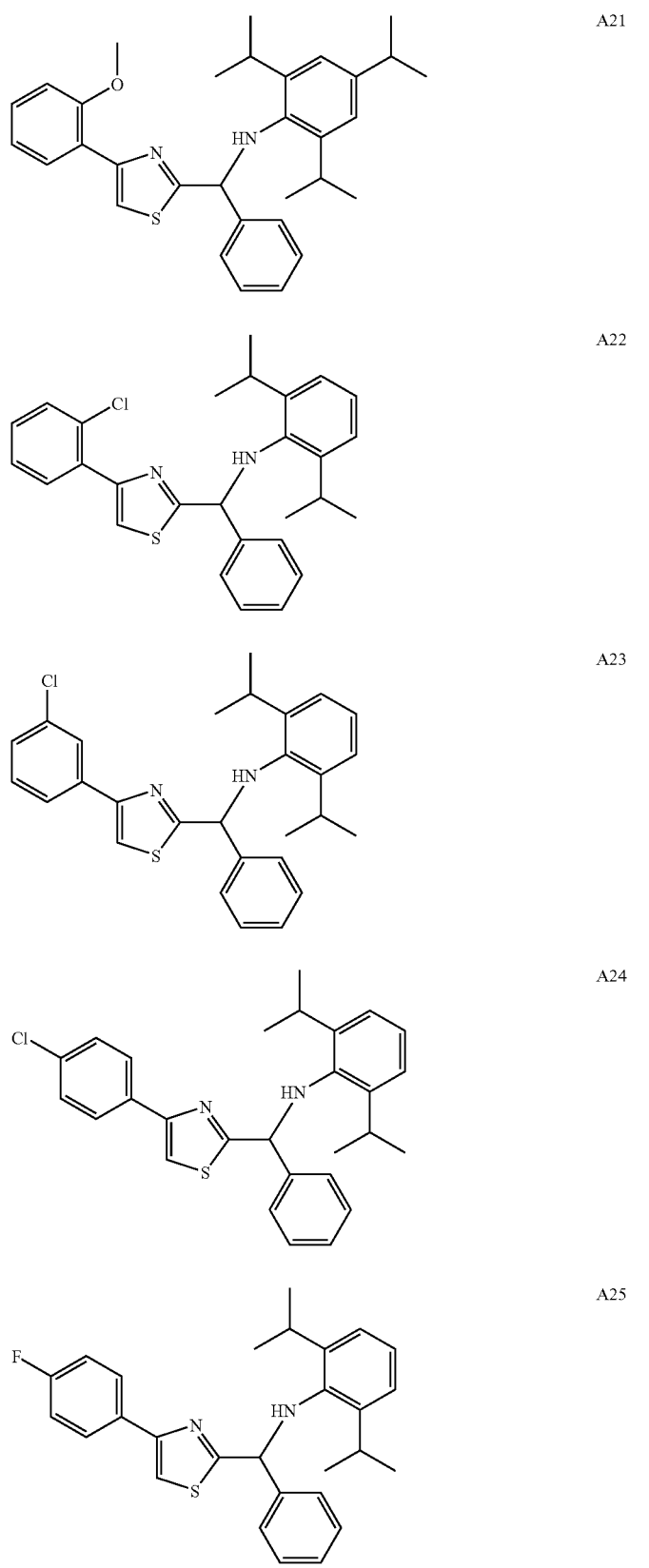

TABLE 1-continued
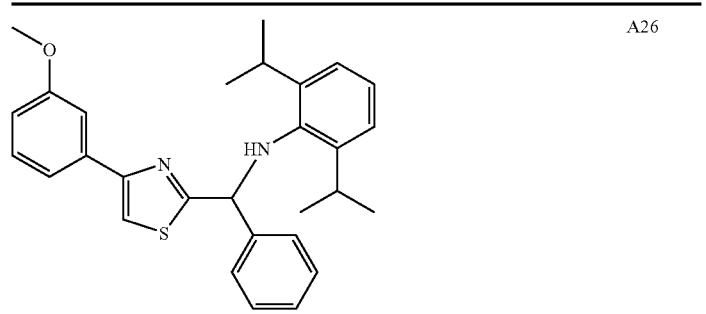
A26
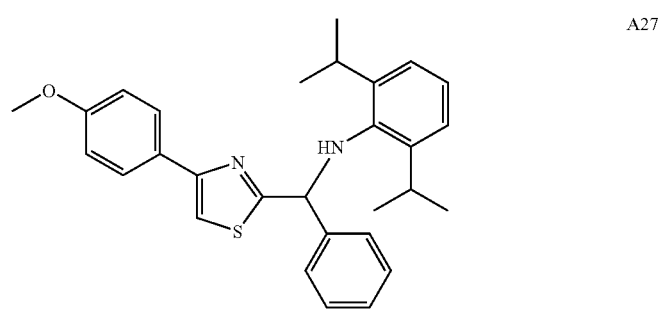
A27
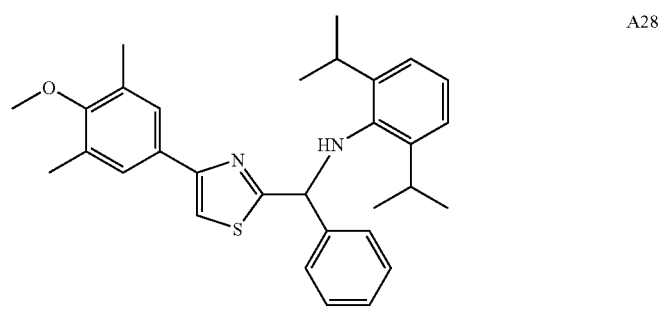
A28
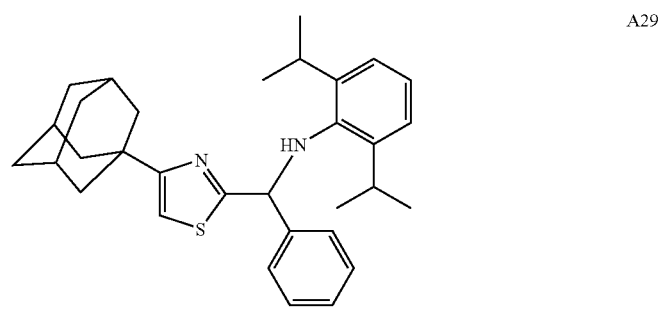
A29
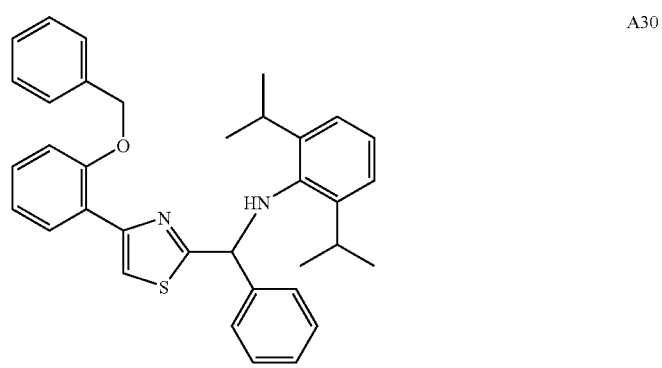
A30

TABLE 1-continued
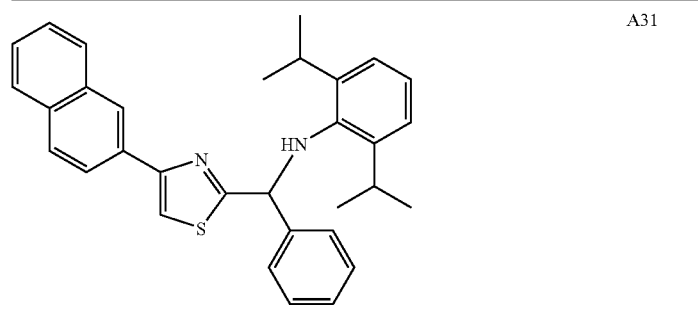
A31
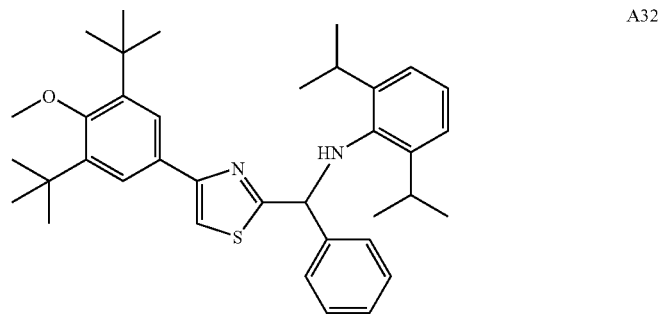
A32
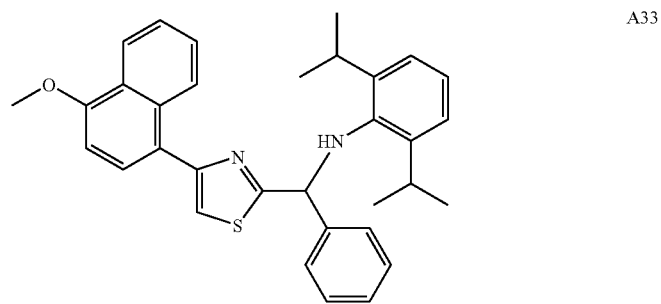
A33
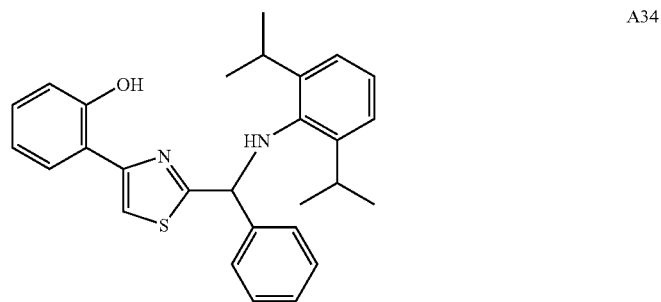
A34
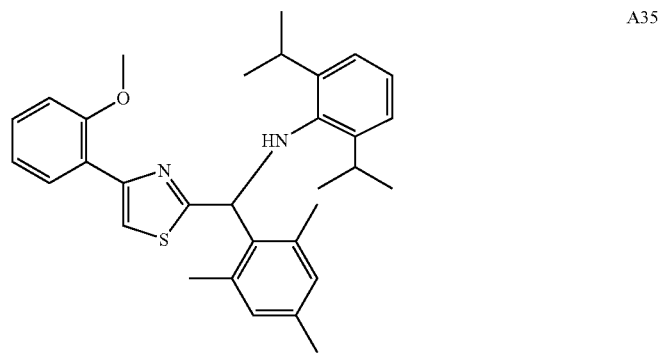
A35

TABLE 1-continued
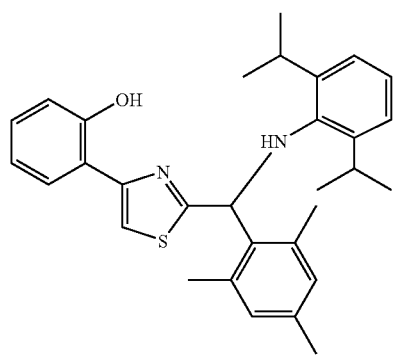 A36
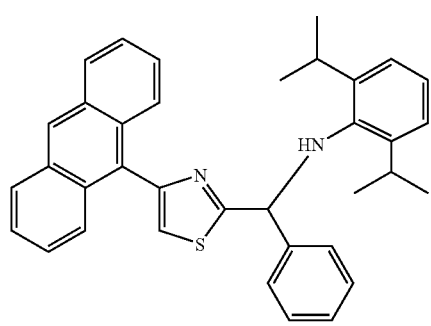 A37
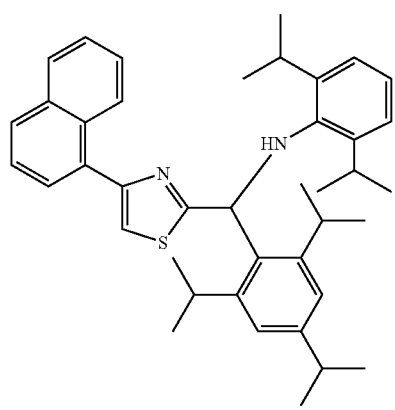 A38
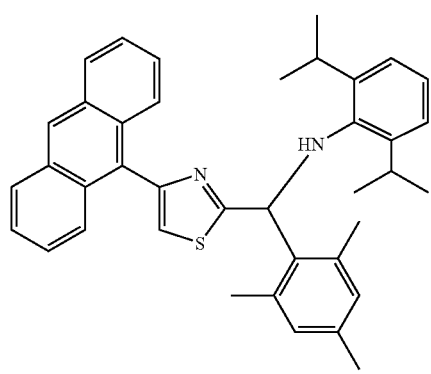 A39

TABLE 1-continued
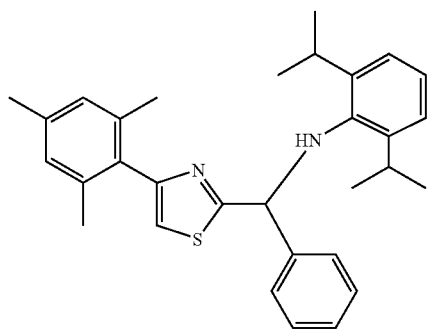 A40
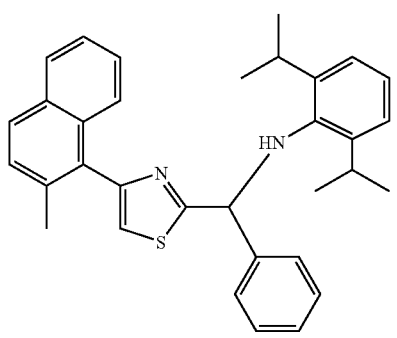 A41
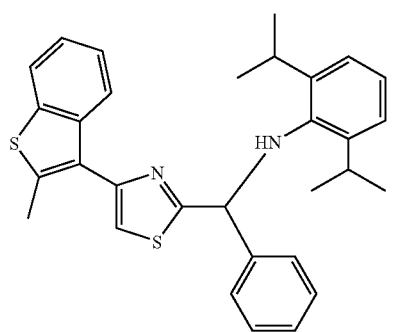 A42
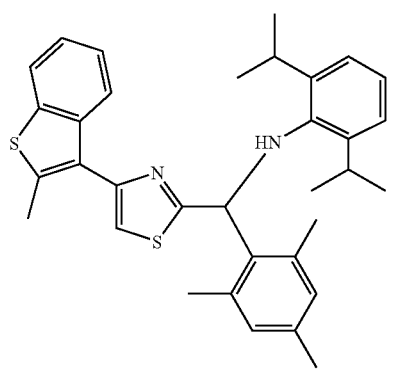 A43

TABLE 1-continued
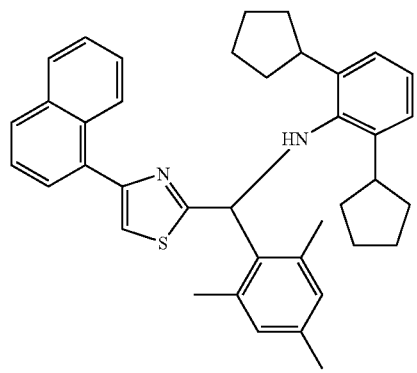
A44
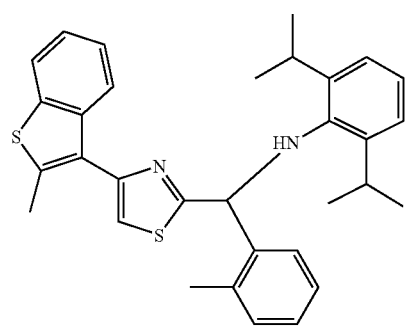
A45
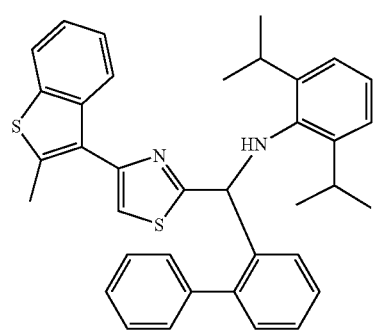
A46
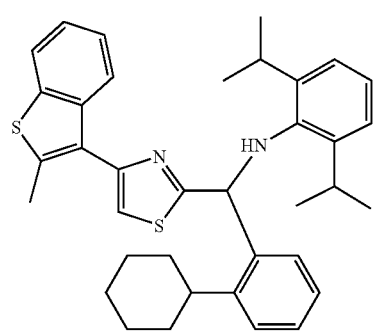
A47

TABLE 1-continued
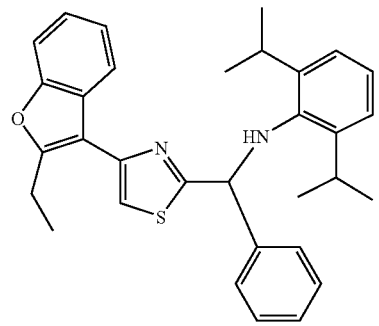 A48
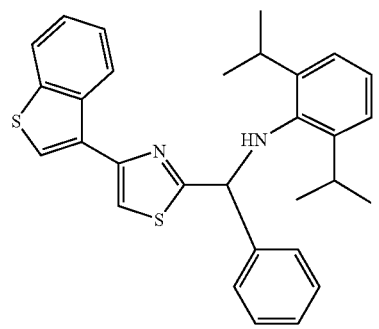 A49
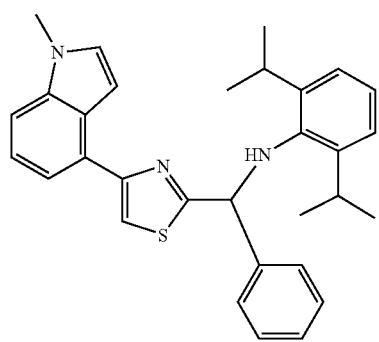 A50
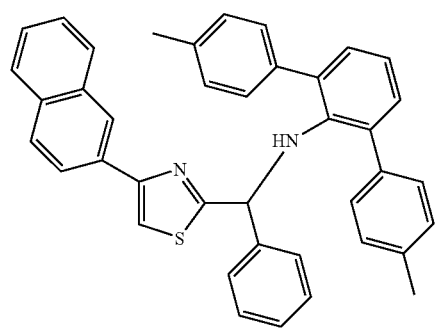 A51

TABLE 1-continued
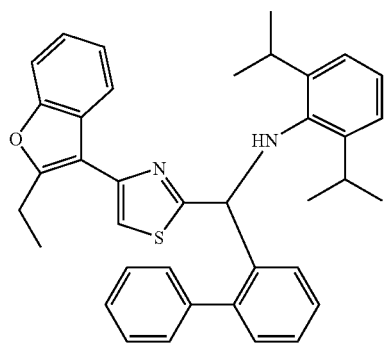
A52
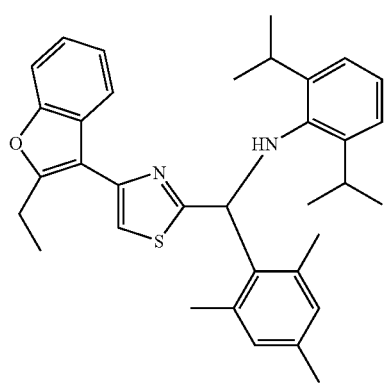
A53
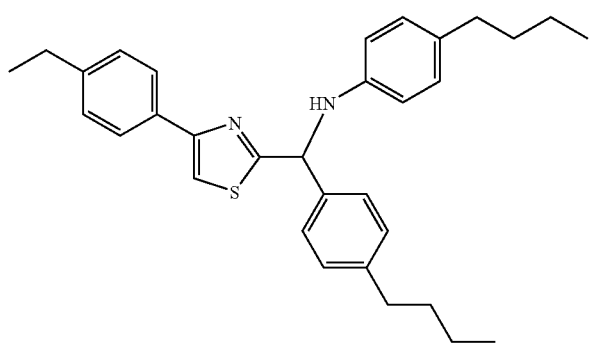
A54
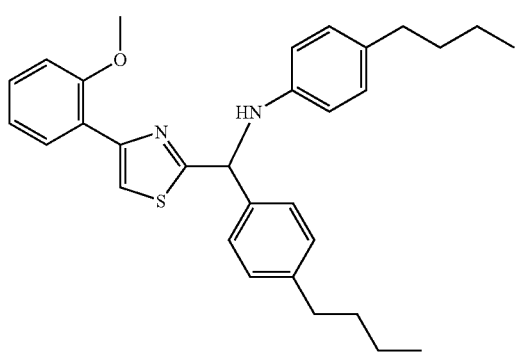
A55

TABLE 1-continued
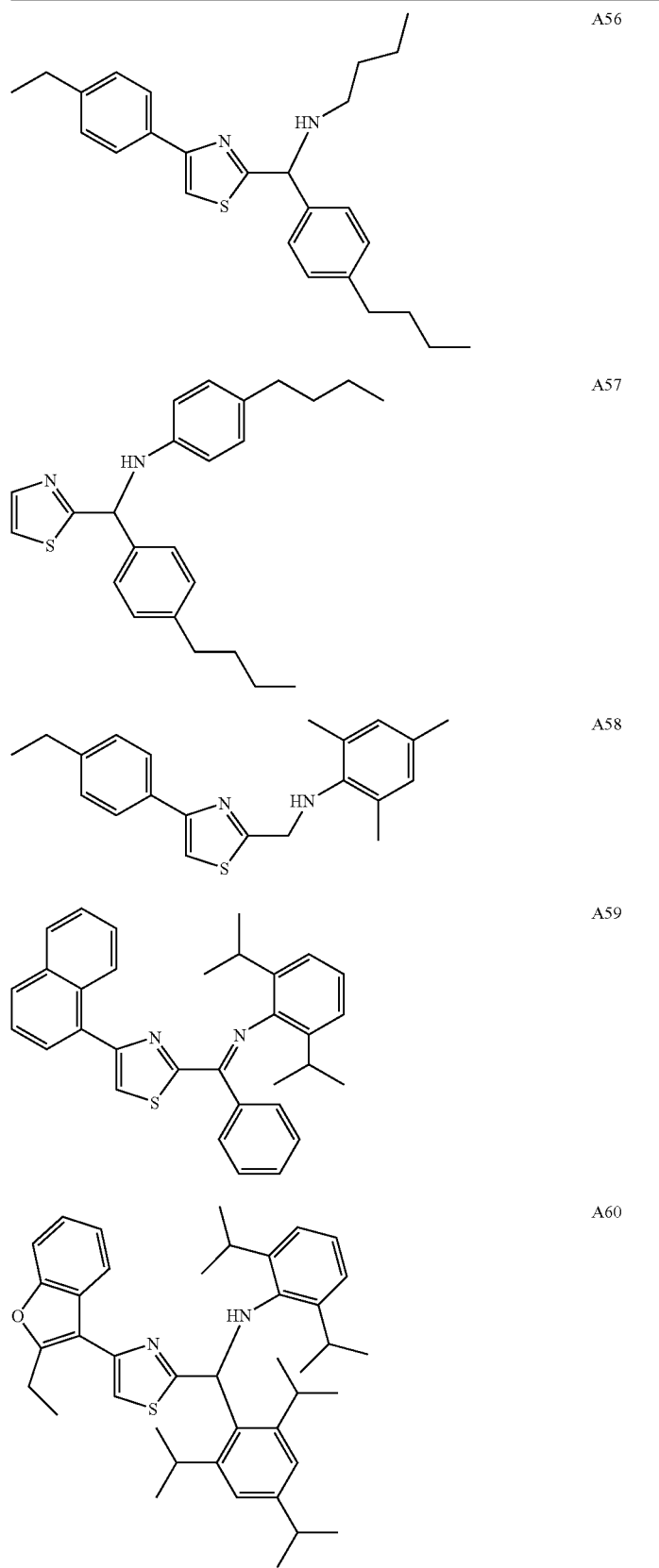

TABLE 1-continued
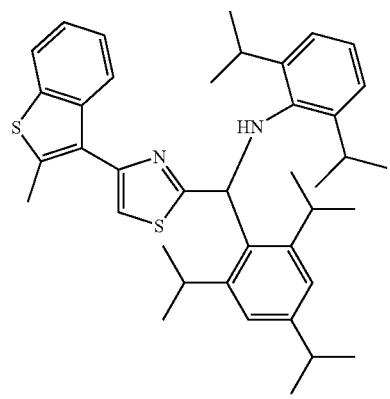
A61
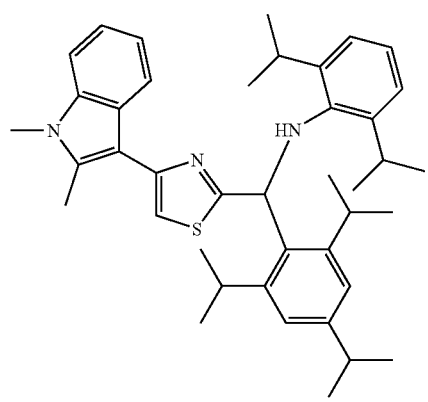
A62
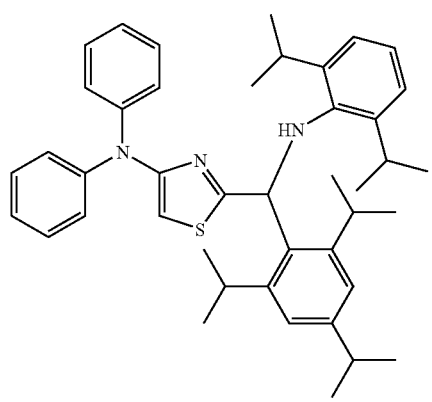
A63
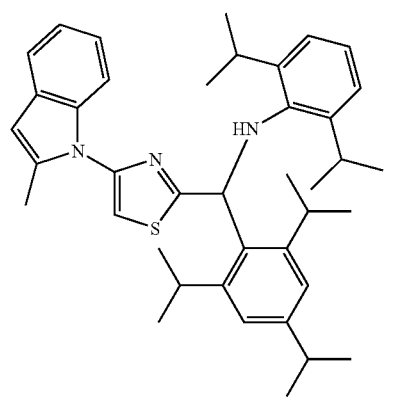
A64

TABLE 1-continued
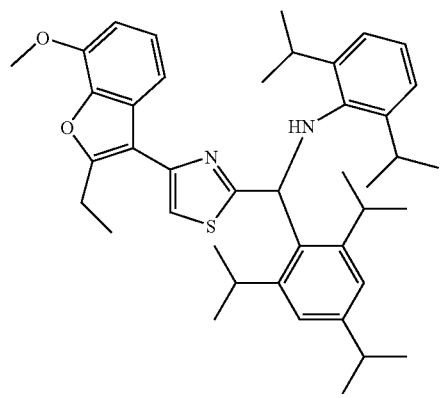
A65
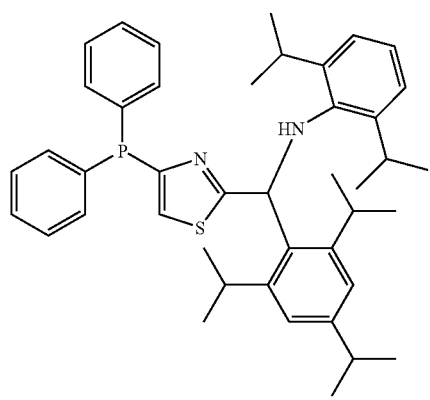
A66
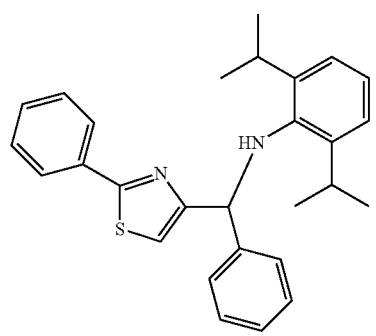
B1
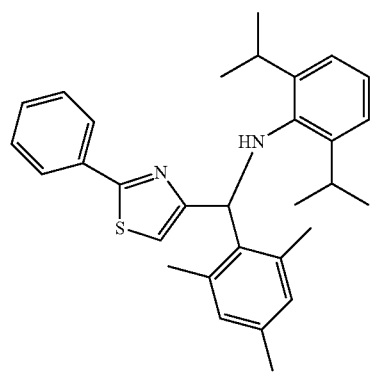
B2

TABLE 1-continued
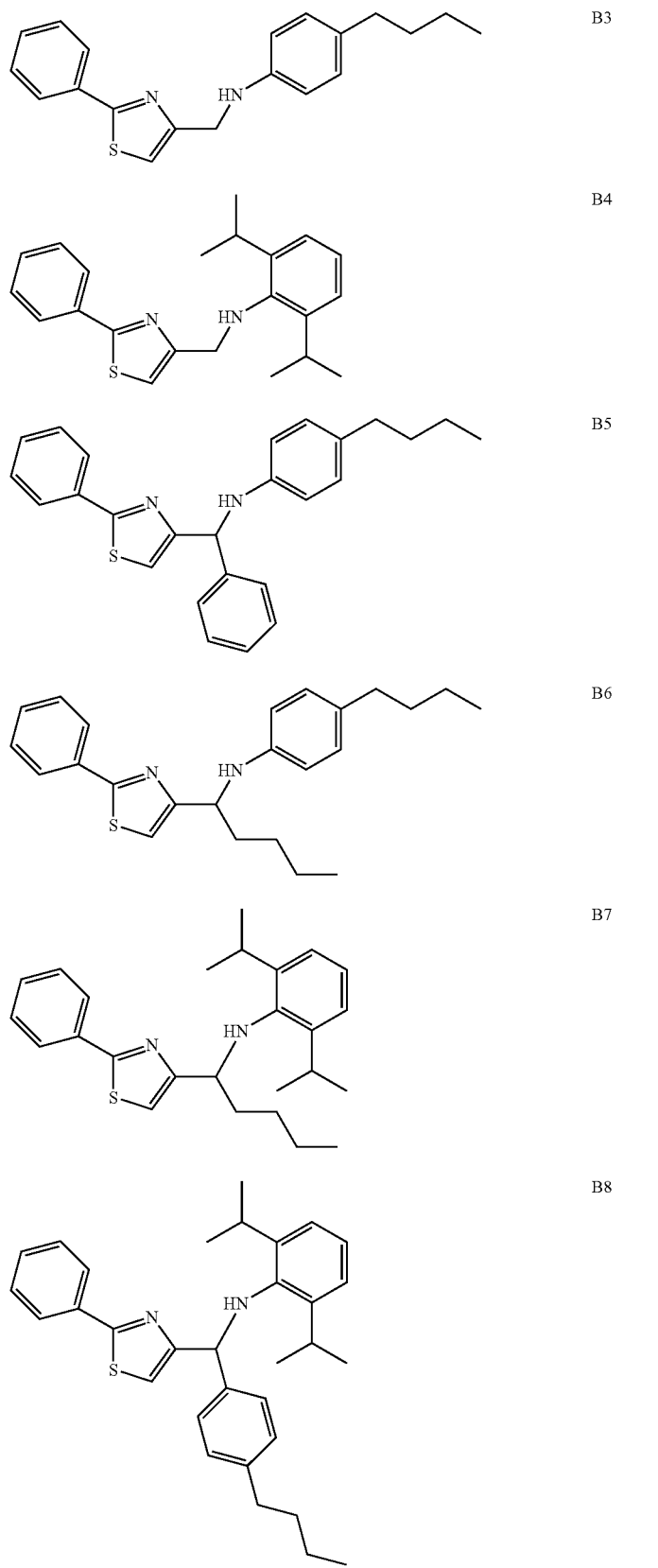

TABLE 1-continued
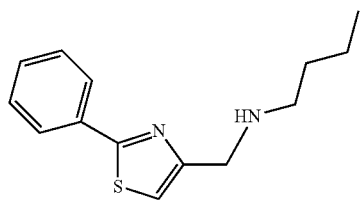 B9
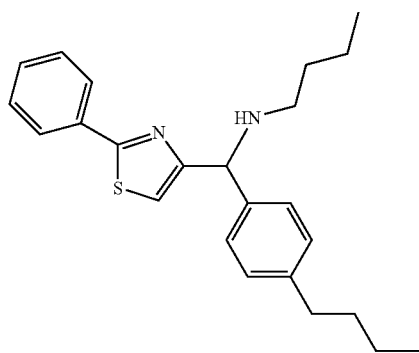 B10
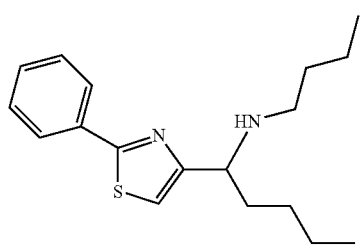 B11
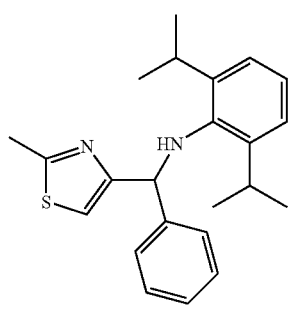 B12
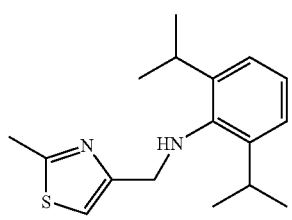 B13

TABLE 1-continued
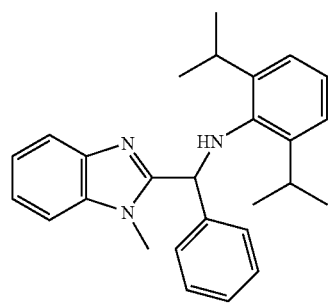 C1
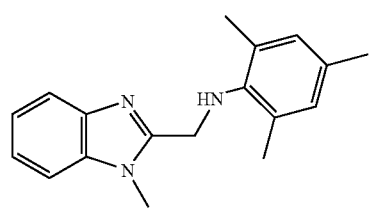 C2
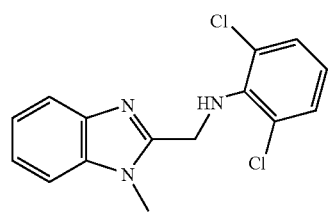 C3
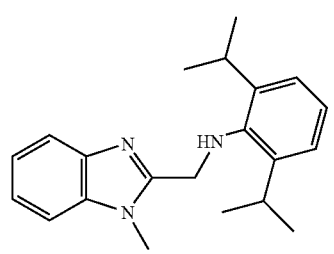 C4
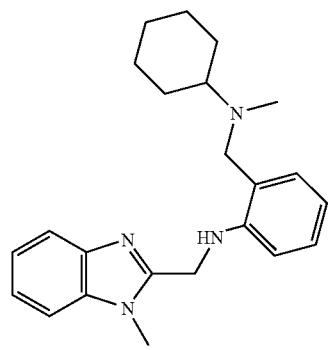 C5

TABLE 1-continued
| | |
|---|---|
| 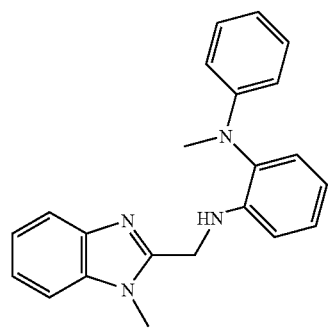 | C6 |
| 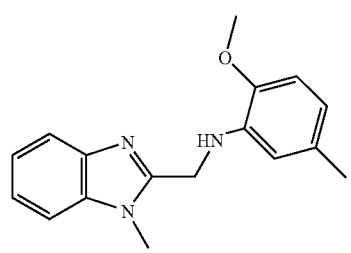 | C7 |
| 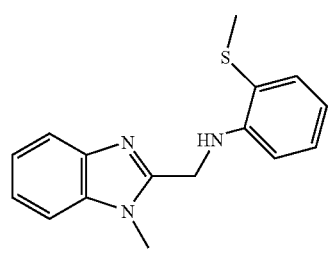 | C8 |
| 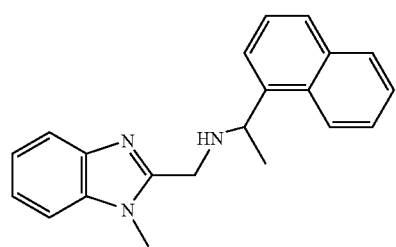 | C9 |
| 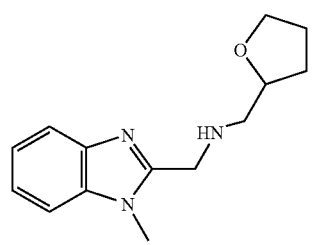 | C10 |

TABLE 1-continued
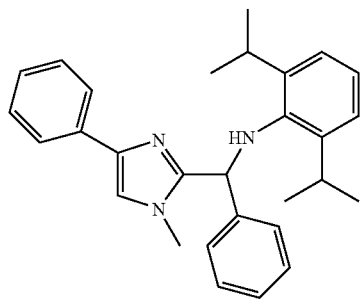
C11
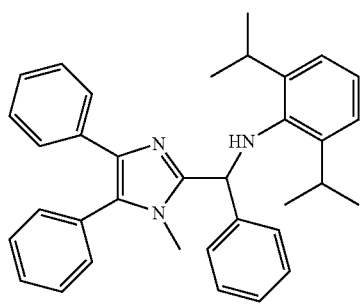
C12
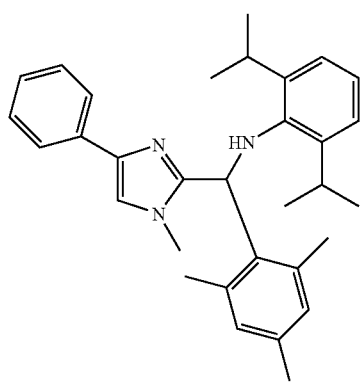
C13
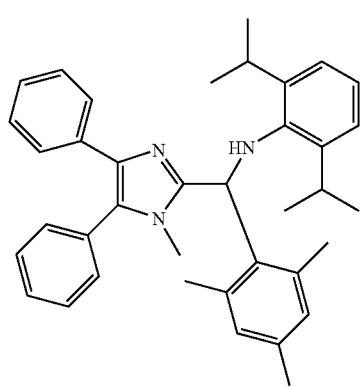
C14

TABLE 1-continued
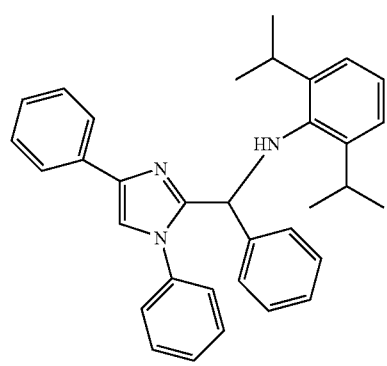
C15
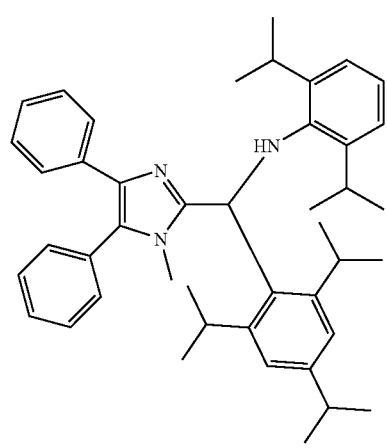
C16
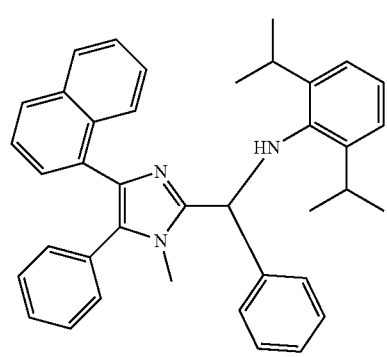
C17
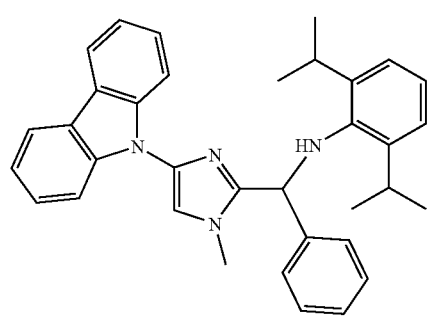
C18

TABLE 1-continued
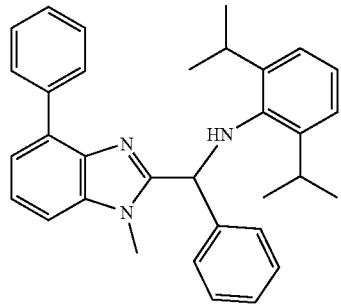 C19
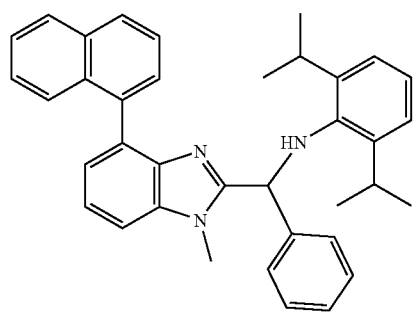 C20
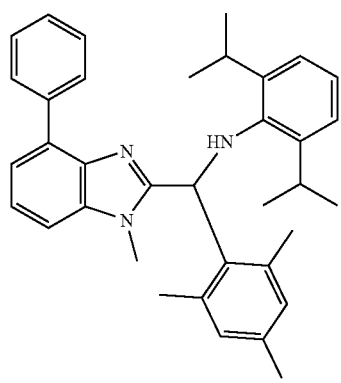 C21
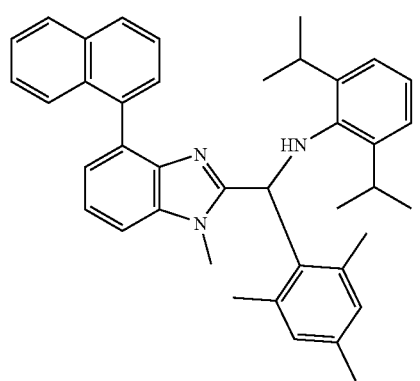 C22

TABLE 1-continued
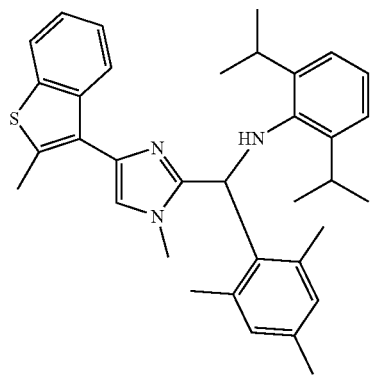
C23
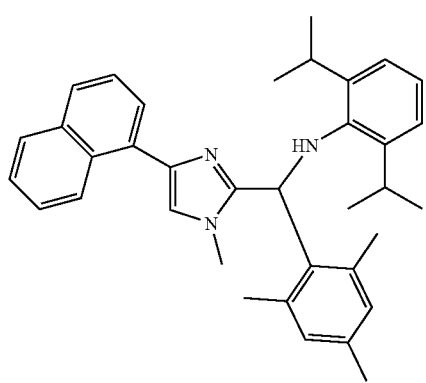
C24
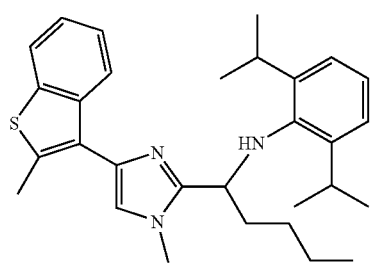
C25
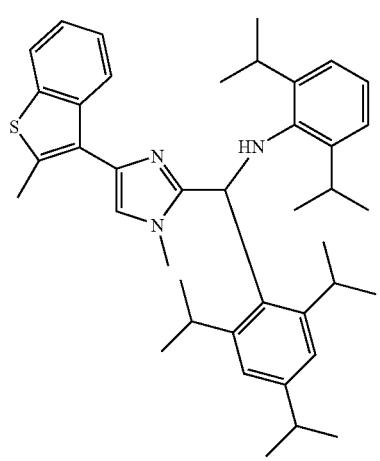
C26

TABLE 1-continued
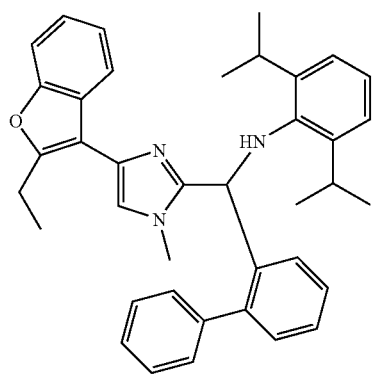
C27
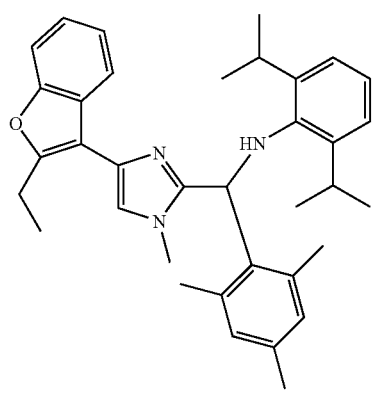
C28
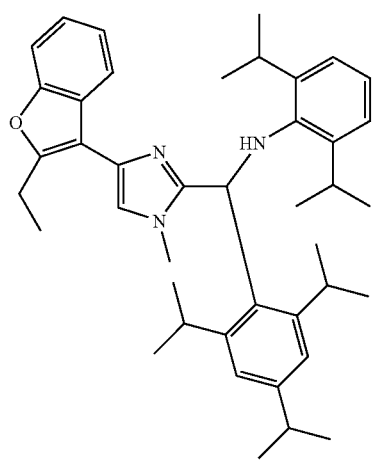
C29
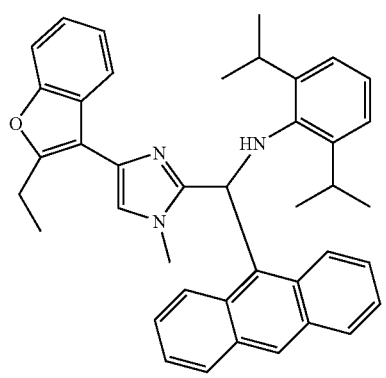
C30

TABLE 1-continued
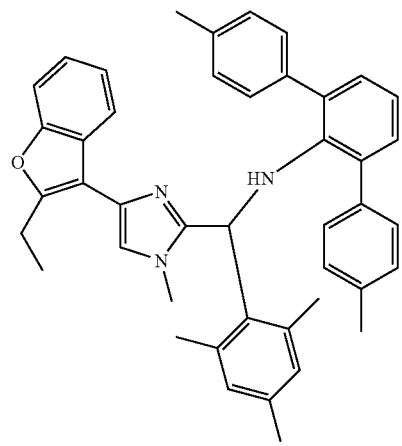
C31
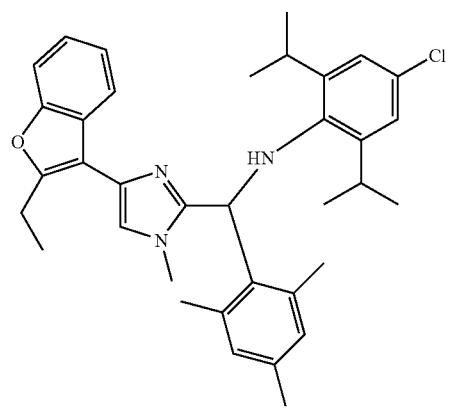
C32
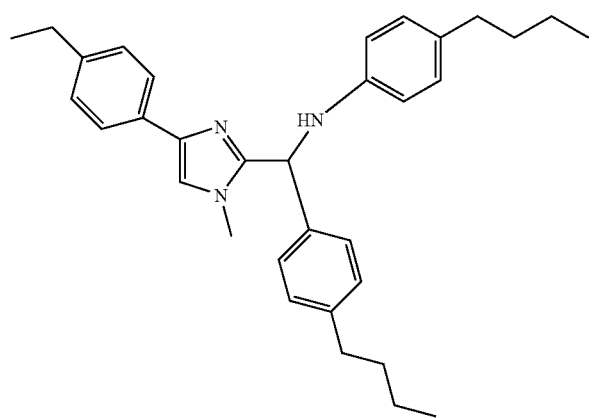
C33

TABLE 1-continued
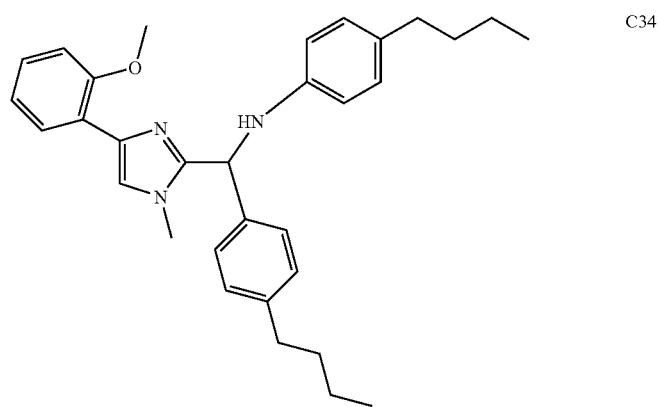
C34
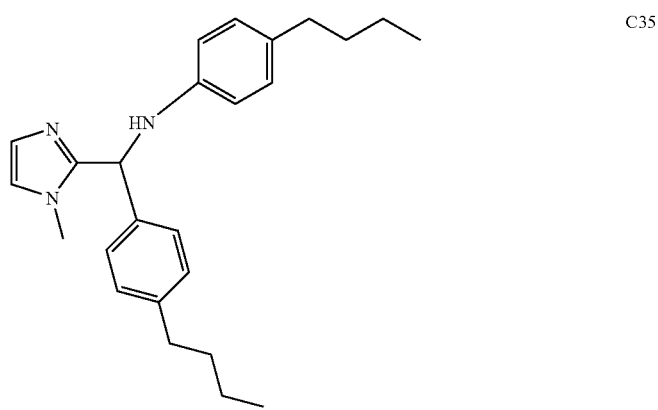
C35
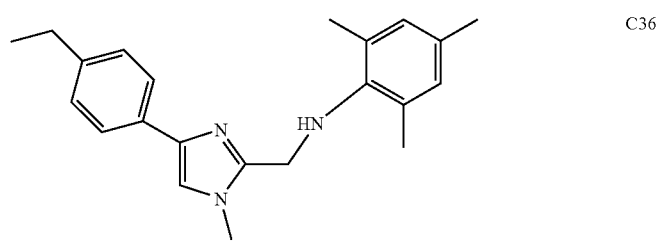
C36
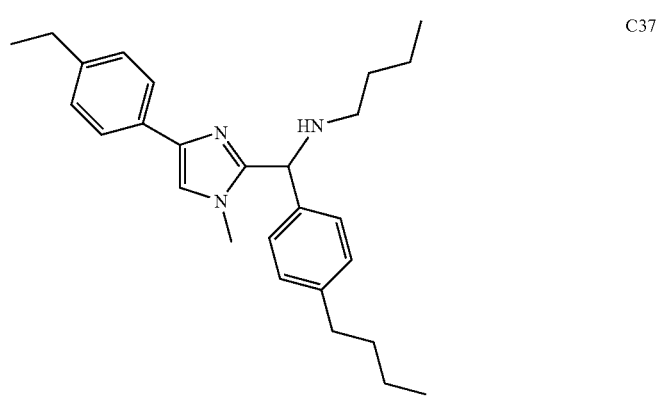
C37

TABLE 1-continued
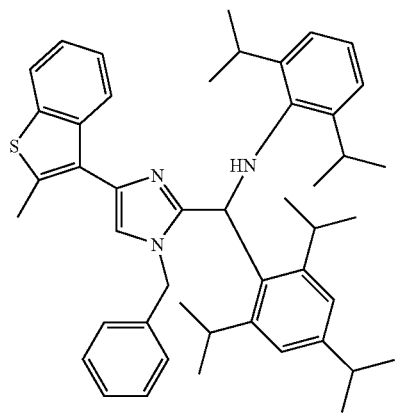
C39
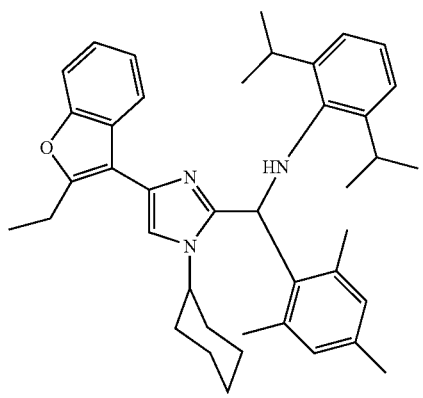
C40
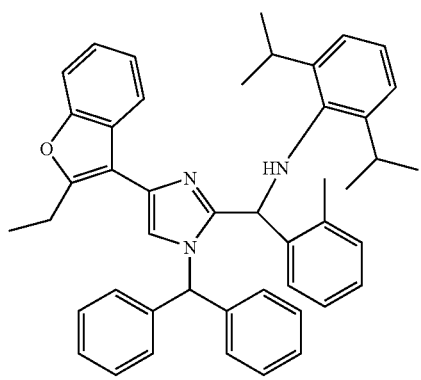
C41
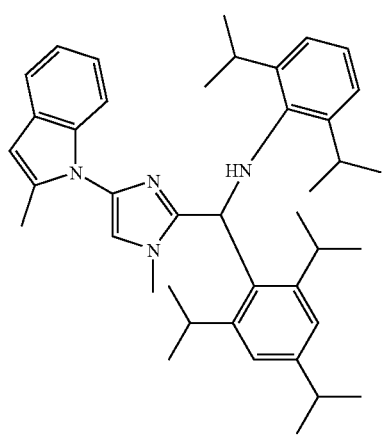
C42

TABLE 1-continued
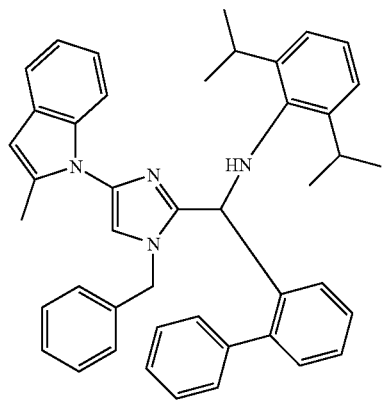
C43
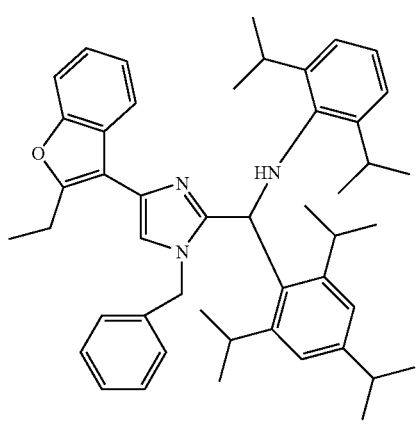
C45
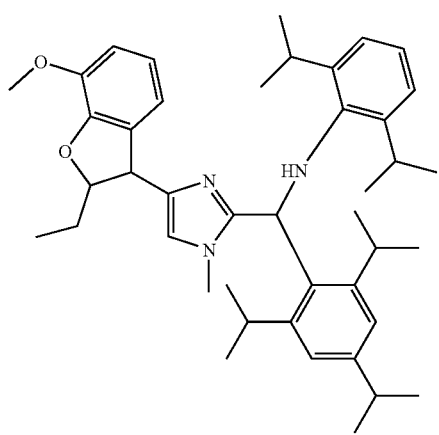
C46

TABLE 1-continued
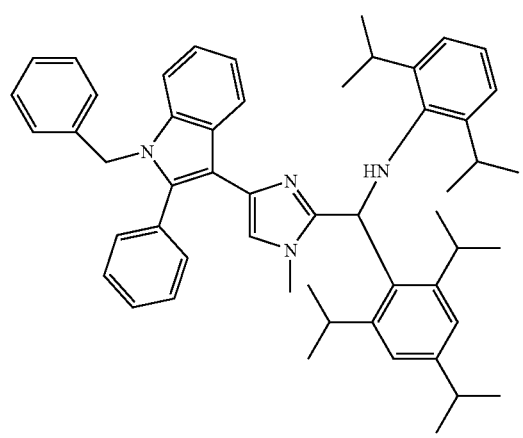
C47
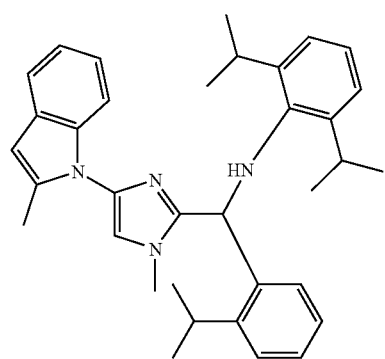
C48
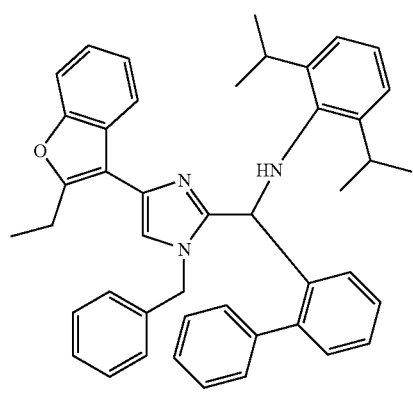
C49
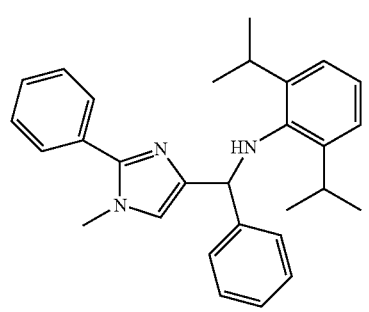
D1

TABLE 1-continued
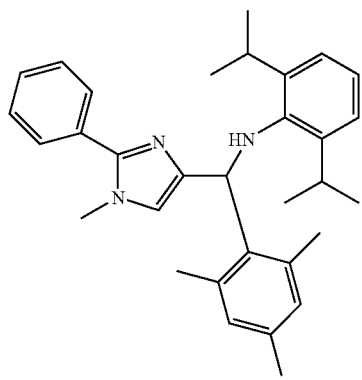
D2
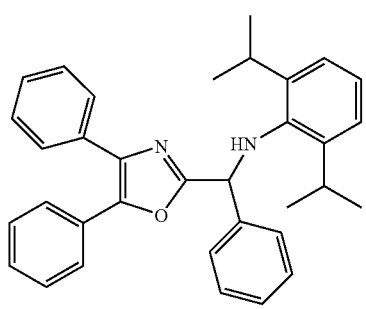
E1
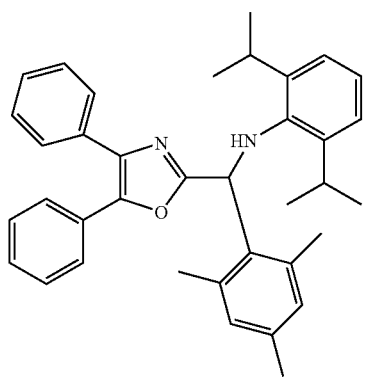
E2
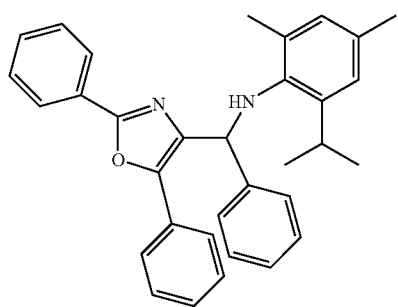
F1

TABLE 1-continued
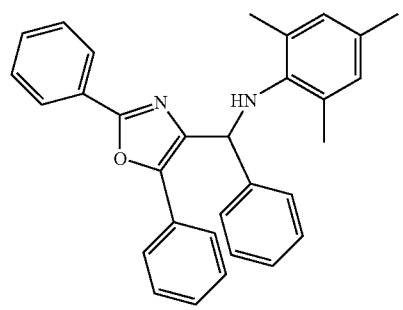 F2
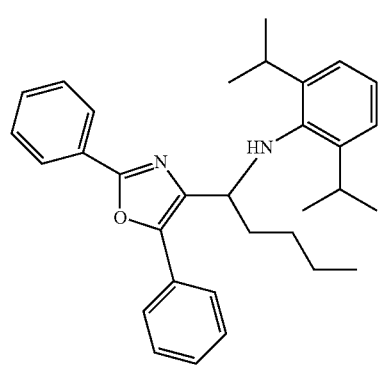 F3
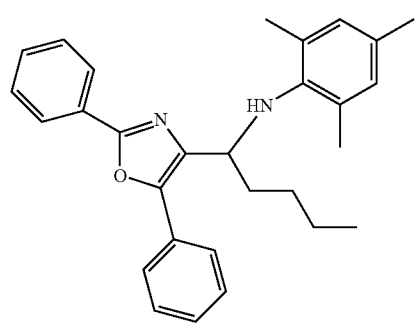 F4
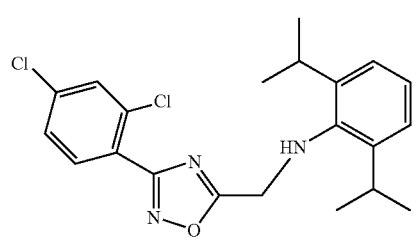 G1
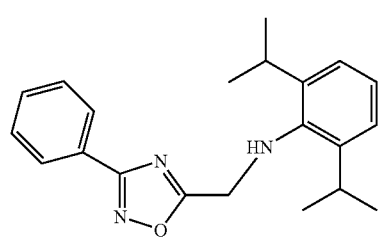 G2

TABLE 1-continued
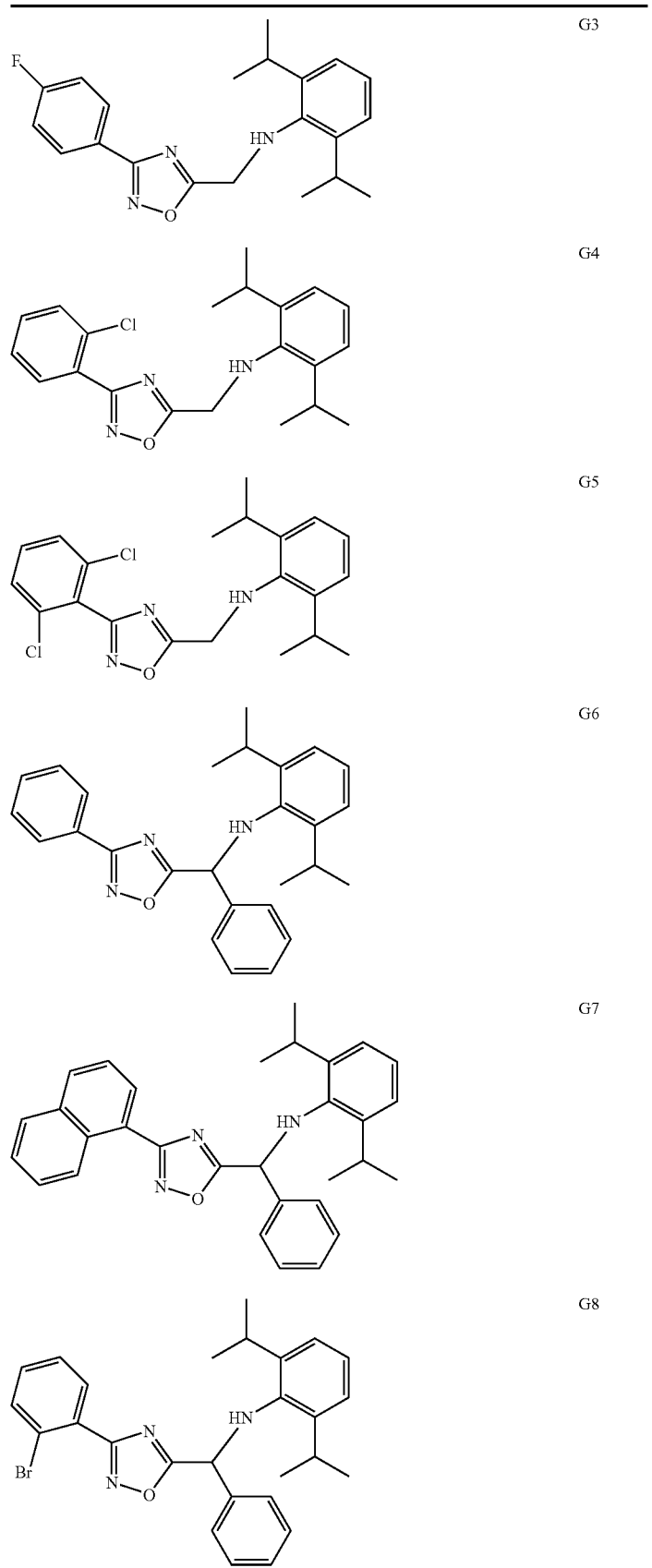

TABLE 1-continued
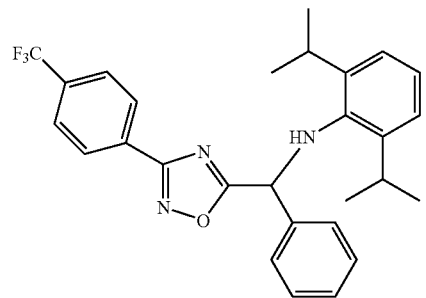
G9
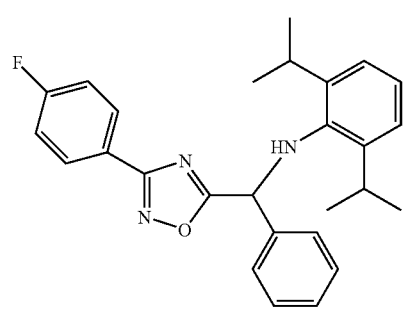
G10
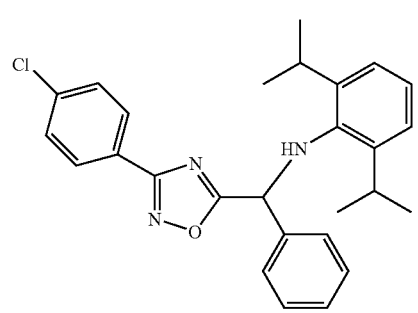
G11
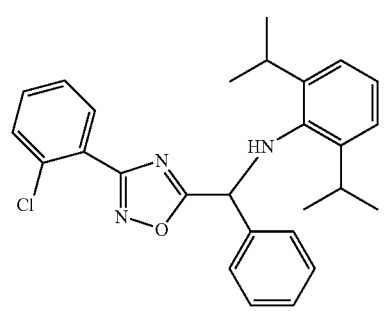
G12
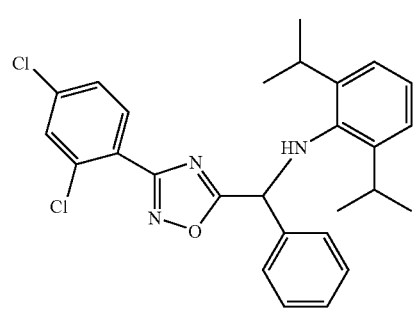
G13

TABLE 1-continued
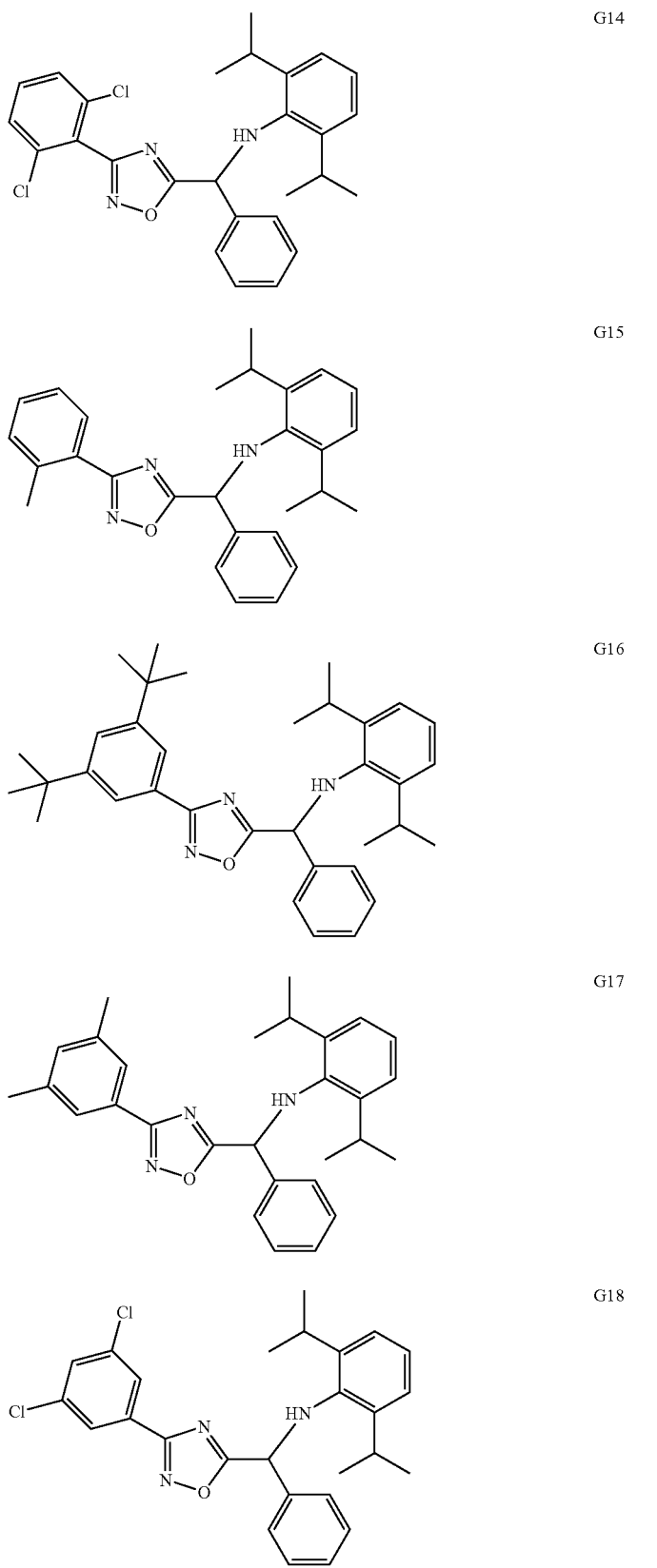
G14
G15
G16
G17
G18

TABLE 1-continued
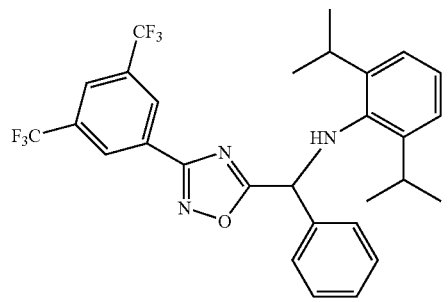
G19
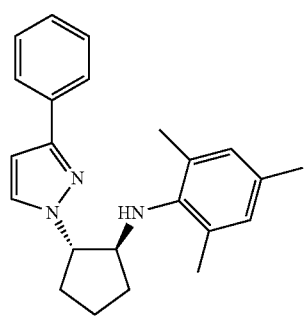
H1
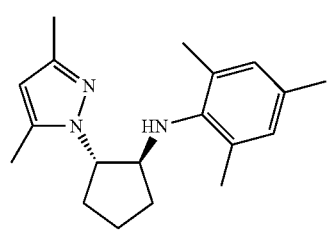
H2
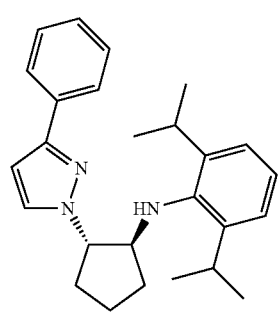
H3
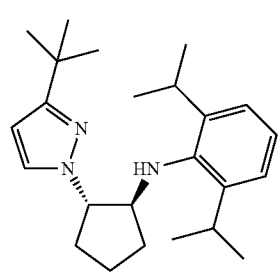
H4

TABLE 1-continued
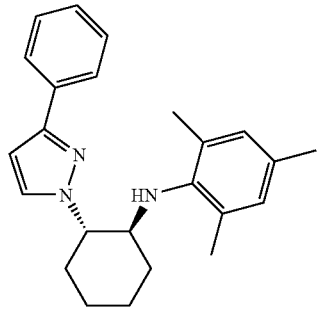  H5
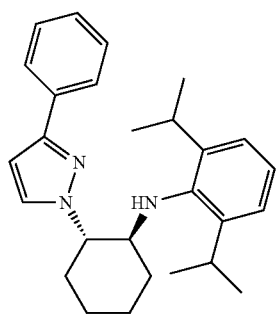  H6
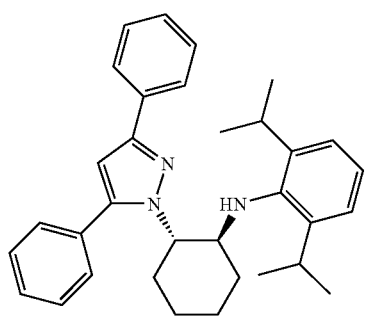  H7
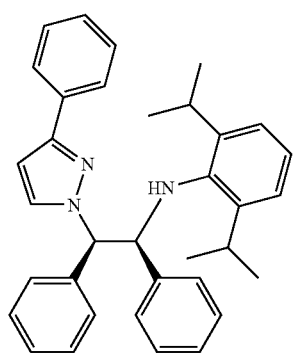  H8

TABLE 1-continued

H9
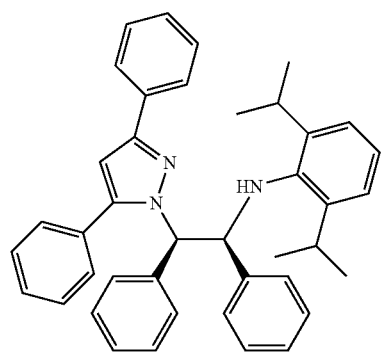

H10
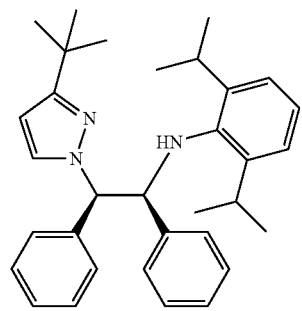

H11
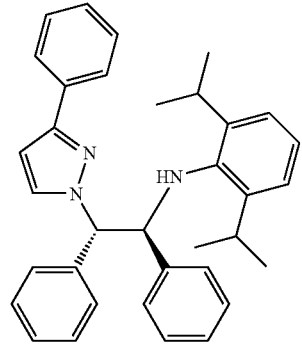

H12
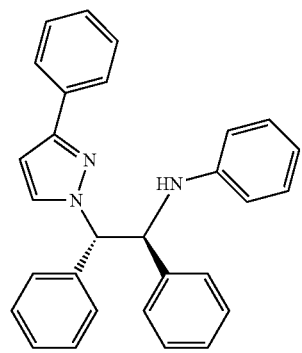

The choice of particular R, T and J groups can have a strong influence on the catalysis of particular transformations. Thus, the choice of substitutent in the ligands of the invention when incorporated in a polymerization catalyst can affect catalyst activity, thermal stability, molecular weight of the product polymer, or the degree and/or kind of stereo- or regioerrors, as well as other factors known to be significant in the production of various polymers.

Thus, for example, in some embodiments the choice of J and R substituents has an influence on the production of isotactic polypropylene in a solution process. More particularly, in some embodiments the identity of the five-membered ring J and the $R^1$, $R^2$, $R^3$, and $R^{4'}$ substituents has an influence on the production of isotactic polypropylene in a solution process, allowing for a range of isotactic polypropylene polymers to be prepared with desired properties. In some such embodiments, J is oxazole, thiazole, imidazole, pyrazole, or isomers of these, $R^1$, $R^3$ and $R^{4'}$ are independently selected from the group consisting of optionally substituted aryl and heteroaryl, and $R^2$ is different from $R^3$ (e.g., $R^2$ is hydrogen or alkyl). Specific $R^1$ groups in such embodiments include 2,6-($^i$Pr)$_2$—C$_6$H$_3$—, 2-$^i$Pr-6-Me-C$_6$H$_3$—, 2,6-Et$_2$-C$_6$H$_3$—, 2-sec-butyl-6-Et-C$_6$H$_3$—, and 2,4,6-($^i$Pr)$_3$—C$_6$H$_2$—. Specific $R^3$ groups include benzyl, phenyl, naphthyl, 2-biphenyl, 2-dimethylaminophenyl, 2-methoxyphenyl, anthracenyl, mesityl, 2-pyridyl, 3,5-dimethylphenyl, o-tolyl, phenanthrenyl, 2,6-($^i$Pr)$_2$—C$_6$H$_3$—, 2,4,6-($^i$Pr)$_3$—C$_6$H$_2$—, and 2,6-R'$_2$—C$_6$H$_3$—, where R' is optionally substituted alkyl, heteroalkyl, aryl, or heteroaryl. Specific $R^{4'}$ groups include phenyl, o-tolyl, o-hydroxyphenyl, napthyl, 2-methyl-3-benzothiophenyl, and 2-ethyl-3-benzofuranyl. Specific ligands that are preferred for the production of isotactic polypropylene are include ligands A13, A17, A34, A36, A42, A43, A46, A52, A61, A62, A64, A65, C14, C16, C23, C29, and C39-C49 shown in Table 1 above.

Similarly, in some embodiments the choice of J and R substituents has an influence on the production of ethylene-1-octene copolymers. Specific ligands that are preferred for ethylene-1-octene copolymer production include ligands A1, A17, B1, C1, C14, C16, C19, C27, C29, D1, E2, and F2, shown in Table 1 above.

Likewise, in some embodiments the choice of J and R substituents has an influence on the production of ethylene-styrene copolymers. Specific ligands that are preferred for ethylene-styrene copolymer production include A1, A13, A17, A34, A36, A42, A43, A46, A52, A61, A62, A64, A65, B1, C1, C14, C16, C19, C23, C27, C29, C39-C49, D1, E2, and F2 shown in Table 1 above.

In addition, in some embodiments, the choice of J and R can similarly have an influence on the production of copolymerization of ethylene and propylene, ethylene and cyclic olefins, and ethylene, propylene and diene monomers. Specific ligands that are preferred for such copolymerizations include A1, A13, A17, A34, A36, A42, A43, A46, A52, A61, A62, A64, A65, B1, C1, C14, C16, C19, C23, C27, C29, C39-C49, D1, E2, and F2 shown in Table 1 above.

The ligands of the invention can be prepared using known procedures, such as those described, for example, in March, *Advanced Organic Chemistry*, Wiley, New York 1992 (4$^{th}$ Ed.), in Katritzky et al., *Comprehensive Heterocyclic Chemistry*, Elsevier, New York 1984 (1$^{st}$ Ed.) & 1996 (2$^{nd}$ Ed.), and in Greene, *Protecting Groups in Organic Synthesis*, Wiley, New York 1999 (3$^{rd}$ Ed.). Specifically, in some embodiments the ligands of the invention can be prepared according to the general procedure outlined in Scheme 1, in which an aldehyde is reacted with a primary amine to form the intermediate imine, which is then alkylated, arylated or hydrogenated to provide the corresponding amine.

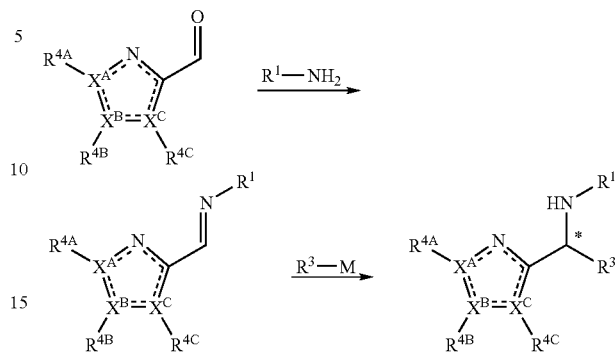

Scheme 1

In Scheme 1, the various X and R groups are defined consistent with the discussion elsewhere in this specification, depending on the desired ligand and/or complex. Generally, $R^3M$ is a nucleophile such as an alkylating, arylating or hydrogenating reagent and M is a metal such as a main group metal, or a metalloid such as boron. The alkylating, arylating or hydrogenating reagent may be a Grignard, alkyl or aryl-lithium or borohydride reagent. In the second step, a complexing agent such as magnesium bromide can be used to direct the nucleophile selectively to the imine carbon. Where the presence of functional groups impedes this approach, alternative strategies can be employed. For example, ligands having $R^3$=phosphino can be prepared as disclosed in U.S. Pat. No. 6,034,240 and No. 6,043,363. In addition, suitable M(L)$_m$ metal precursor complexes, where L is alkyl or aryl, may be employed in step 2, in accordance with the teachings of U.S. Pat. No. 6,103,657, which is incorporated herein by reference. In Scheme 1, the * represents a chiral center formed when $R^2$ and $R^3$ are different. Ancillary ligands that possess chirality may be important in certain transformations, as is discussed in more detail below.

Using this approach, it is possible in many embodiments to introduce a wide variety of diverse substituents in the ligands of the invention, which can be significant in the design of libraries or arrays for high throughput or combinatorial methods—for example, to assist in optimizing the selection of a particular ligand for a particular polymerization reaction.

In some embodiments, the starting aldehyde used in Scheme 1 is commercially available. Alternatively, appropriately-functionalized aldehydes can be prepared from the corresponding bromo-aldehyde in a cross-coupling reaction as shown in Scheme 2, below.

Scheme 2

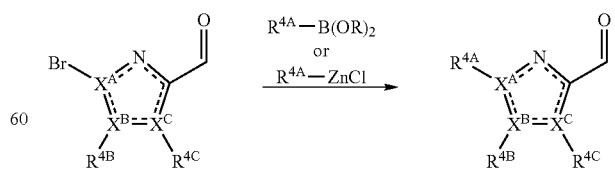

For ligands where the appropriate 4-bromo-heterocycle amine aldehyde is not commercially available, a variety of techniques can be used. In some such embodiments, the amine aldehyde is prepared from commercially available precursors, with the group in the $R^{4A}$ position being installed either before or after the introduction of the aldehyde functionality, depending on the particular chemistry.

Thus, for example, commercially available di-bromo thiazole AA(1) can be used as the starting point in the preparation of a variety of thiazole-amine (i.e., (thiazol-2-yl)-alkyl amine) ligands, such as ligands selected from A1-A59 in Table 1, yielding, bromo-aldehyde AA(2) upon regioselective lithium-halide exchange, followed by DMF addition as shown in Scheme A1. AA(2) can then be further functionalized according to Scheme 2, followed by Scheme 1, above.

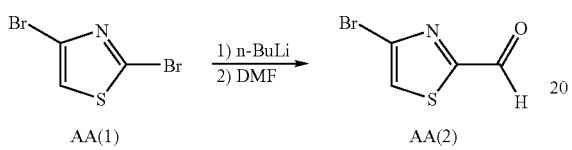

Similarly, AA(1) can also be used to prepare (thiazol-4-yl)-alkyl amine ligands (e.g., ligands selected from B1-B13 in Table 1) as shown in Scheme B1. The bromo group at the $R^{4A}$ position is known to be more reactive and undergoes lithium-halide exchange first. Subsequent $R^{4A}$ addition gives BB(1). Aldehyde BB(2) can then be generated by a second lithium-halide exchange followed by addition of DMF.

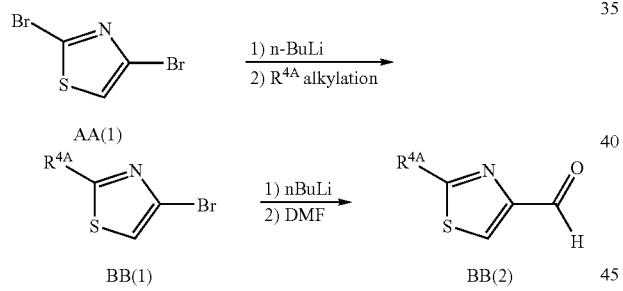

In the case of imidazole-containing ligands (e.g., imidazole-amines ((imidazol-2-yl)-alkyl amines) and (imidazol-4-yl)-alkyl amines), the imidazole ring can be prepared using known techniques, as described, for example, in *Hetereocycles* 1994, 39, 139-153. With the imidazole ring in hand, a number of approaches can be used for regioselective installation at the $R^{4A}$, $R^{4B}$, and $R^{4C}$ positions (see Schemes C1-C4). One approach begins with commercially available tribromoimidazole CC(2), as shown in Scheme C1. Two of the three bromine substituents in CC(2) can be removed in a regioselective manner because of the difference in reactivities, and the resulting bromo-imidazole CC(4) can then be further functionized by treatment with LDA, followed by DMF addition to give desired aldehyde CC(5). Where the appropriate tribromoimidazole CC(2) is not commercially available, it can be obtained through $R^{4C}$ substitution of tribromoimidazole CC(1). In many cases, bromo-imidazole CC(4) can also be accessed directly through substitution of 4-bromo-imdazole, which is commercially-available.

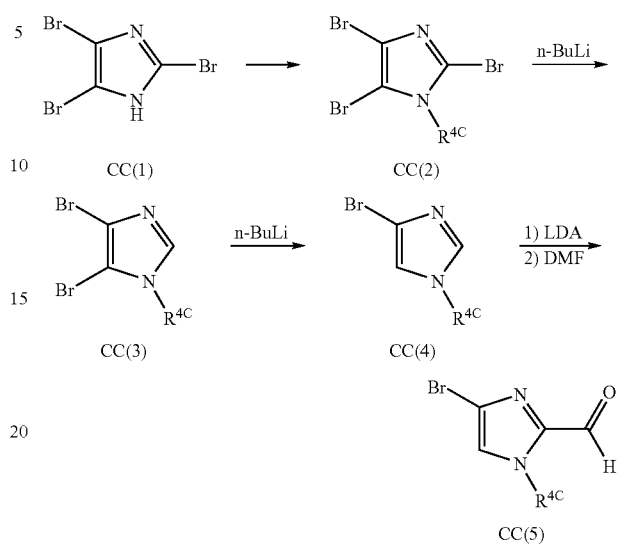

Aldehyde CC(5) can also be generated in a one-pot reaction from tribromo-imidazole CC(2), as shown in Scheme C2, where tribromo-imidazole is first treated with 2 equivalents of n-BuLi, followed by addition of acid and subsequent treatment DMF.

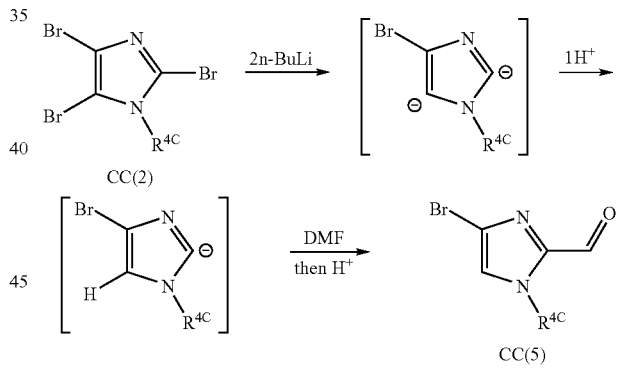

Dibromoimidazole CC(3) can be used as an access point for functionalization at the $R^{4B}$ position. The difference in reactivity of the two bromo substituents makes it possible to install different R groups at the $R^{4B}$ and $R^{4A}$ positions regioseletively, via sequential Suzuki couplings reactions to give aldehyde CC(8), as shown in Scheme C3.

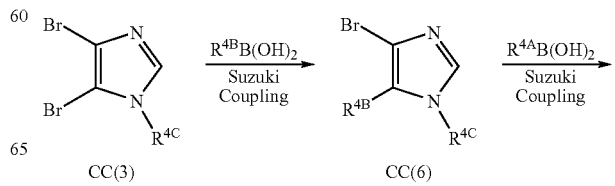

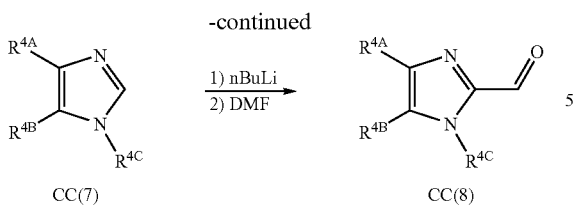

In some cases aldehyde CC(8) can also be prepared by first installing the aldehyde (to give CC(9)), followed by sequential Suzuki coupling reactions, as shown in Scheme C4.

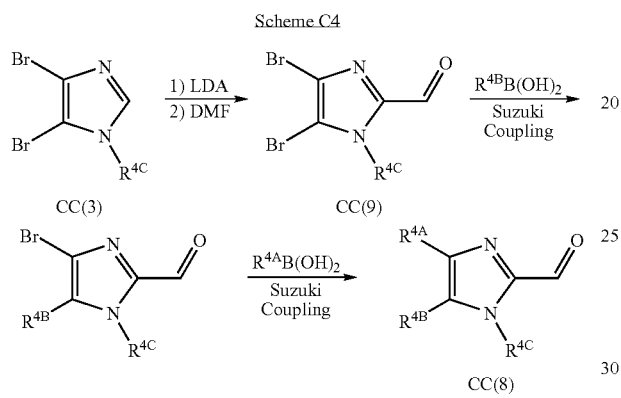

Similarly, in particular embodiments, oxazole-amines (e.g., (oxazol-2-yl)-alkyl amines E and (oxazol-4-yl)-alkyl amines F) can be prepared via imination of the corresponding 2- and 4-formyl-oxazoles ($R^3$=H) with amines and anilines in the presence of catalytic amounts of p-toluenesulfonic acid (see, e.g., U.S. Pat. No. 6,750,345), followed by the addition of organomagnesium and organolithium reagents, as illustrated in Schemes E1 and F1.

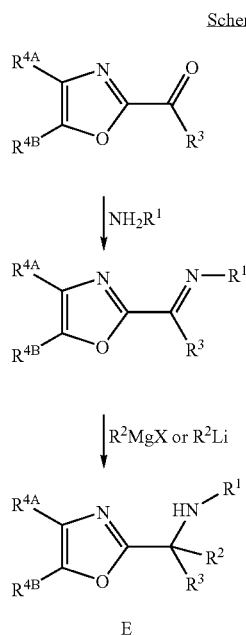

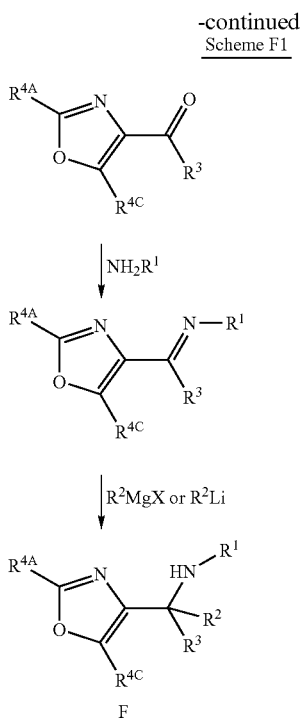

The carbonylic oxazoles (e.g., 2- and 4-formyl-oxazoles) can be prepared by the selective selenium oxide oxidation (Youssef, et al., *J. Heterocyclic. Chem.* 1984, 21, 1747-1752) of 4,5-diphenyl-2-methyl-oxazole ($R^{4A}$=$R^{4B}$=Ph), and by deprotonation of position 4 of the 2,5-diphenyl-oxazole ($R^{4A}$=$R^{4C}$=Ph) with n-butyllithium (Whitney, et al., *J. Org. Chem.* 1991, 56,3058-3063) and trapping of the anion with DMF to generate the corresponding 2- and 4-carbonyl-oxazoles ($R^3$=H), as shown in Schemes

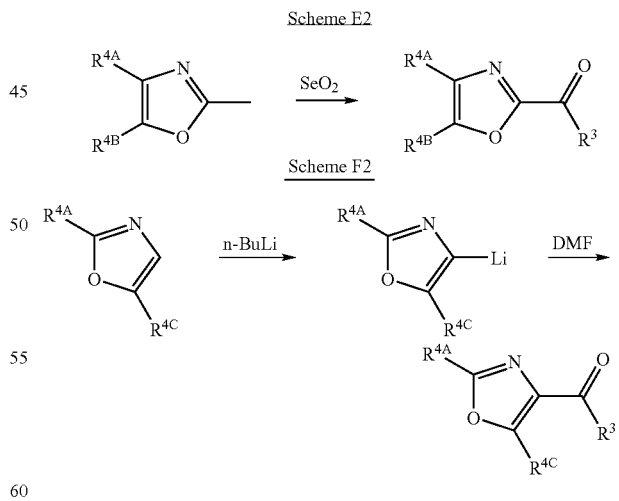

Alternatively, oxazole-amines can be prepared from oxazole-containing building blocks, as in the addition of oxazole-anions to imines, as described in Vedejs, et al., *J. Org. Chem.* 1999, 64, 1001-1014, and illustrated in Schemes E3 and F3, or the nucleophilic displacement reaction of amines with oxazole-electrophiles (LG=halogen, OSO$_2$R, etc.) (see March, *Advanced organic Chemistry*, Wiley, New York 2001 (5th Ed.), Chapter 10), as illustrated in Schemes E4 and F4.

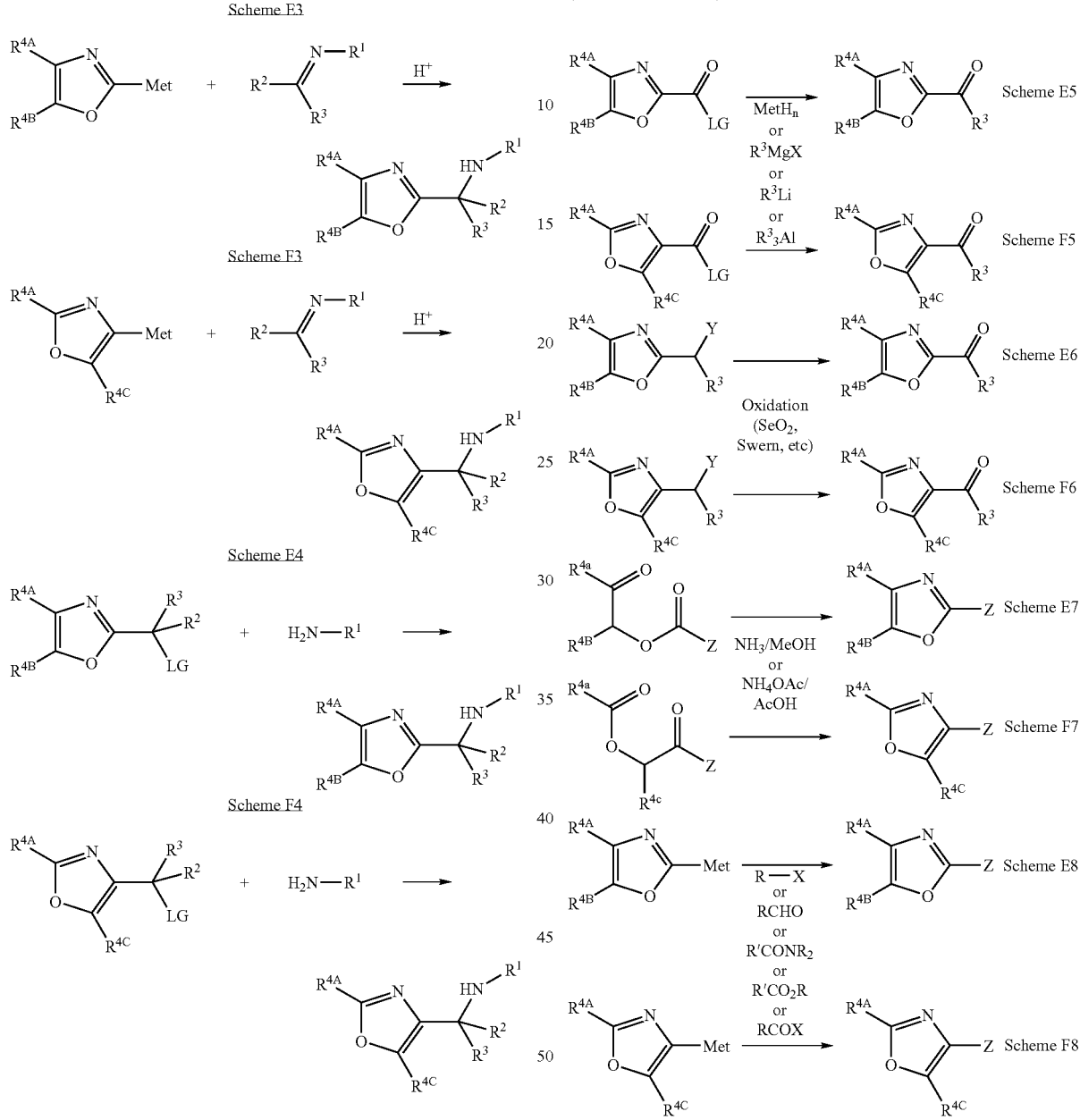

There are a variety of possible other synthetic routes to carbonyl-oxazoles, including selective reductive addition of hydrides (MetH$_n$) and organometallic reagents (RMgX, RLi, R$_3$Al, etc.) to oxazole-acyl-derivatives (LG=OH, OR, X, NR$_2$), as shown in Schemes E5 and F5, selective oxidation of alkyl-, haloalkyl, hydroxyalkyl-oxazole-derivatives (Y=H, halogen, OH) (Trost, *Comprehensive Organic Synthesis*, 1991, vol. 7, 653-670) (Schemes E6, F6), oxazole-ring formation from acyl-functionalized or acyl-protected derivatives (Z=H, CHO, CH(OR)2, CO$_2$H, CO$_2$R, CONR$_2$) with ammonia sources (NH$_3$/MeOH, NH$_4$OAc, etc.) (Whitney, et al., *J. Org. Chem.* 1990, 55, 929-935) (Schemes E7, F7), and oxazole-anion addition (Met=Li, Zn) to electrophiles (CH$_3$X, RCHO, R'CONR$_2$, R'CO$_2$R, R'COX) to generate carbonyl-oxazoles or carbonyl-oxazole-precursors (Z=CH$_3$, CRHOH, CO R'), which can be transformed to carbonyl-oxazoles by some of the mentioned transformations (Vedejs, et al., *J. Org. Chem.* 1999, 64, 1001-1014) (Schemes E8, F8).

Oxadiazole amine ligands (e.g., G1-G19) can be synthesized by the cycloaddition of hydroximinoyl chloride GG(1) with nitrile GG(2) as depicted in Scheme G1. GG(1) is converted, in situ, to the nitrile oxide dipole I(1) in the presence of base (Liu, et al., *J. Org. Chem.* 1980, 45, 3916-3918), which then undergoes a 3+2 cycloaddition with GG(2) (see Torssell, *Nitrile Oxides, Nitrones, and Nitronates in Organic Synthesis*; VCH: New York, 1988, pp. 55-74 and Jager, et al., "Nitrile Oxides," in *Synthetic Applications of 1,3-Dipolar Cycloaddition Chemistry Toward Heterocycles and Natural Products*; Padwa, et al., Eds; Wiley: Chichester, 2002. I(1) can also be formed by other methods, see Carriera, et al., *Org. Lett.* 2000, 2, 539-541 and Sibi, et al., *J. Am.*

Chem. Soc. 2004, 126, 5366-5367. Some examples of hydroximinoyl chlorides GG(1) are commercially available or can be prepared using known procedures (see, for example, the references cited above). Examples of GG(2), when $R^2$ and $R^3$=H or $R^2$=aryl and $R^3$=H, can be prepared according to known procedures (Jones, et al., *J. Med. Chem.* 1985, 28, 1468-1476 and McEwen, et al., *J. Org. Chem.* 1980, 45, 1301-1308). Alternatively GG(2) might be synthesized by cyanation of imines (see Naim, et al., *Indian J. Chem.* 1980, 19B, 622-624 and Kobayashi, et al., *J. Am. Chem. Soc.* 1997, 119, 10049-10053).

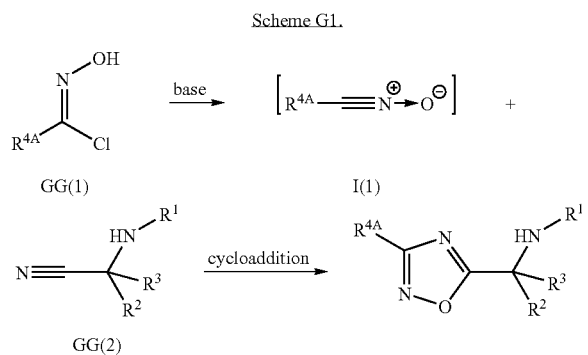

An alternative route to ligands of the type depicted in Scheme G1 is through the aldehyde GG(3) as shown in Scheme G2, utilizing chemistry described above and in U.S. Pat. No. 6,750,345.

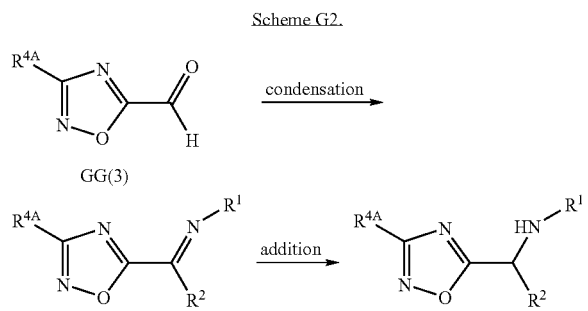

GG(3) can be prepared via the cycloaddition of GG(1) with diethoxyacetonitrile followed by acid catalyzed cleavage of the diethyl acetal as shown in Scheme G3.

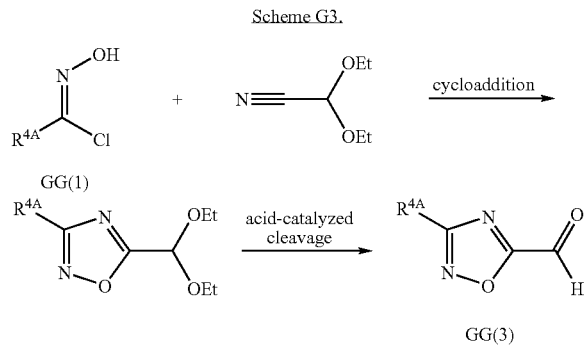

An alternative route to GG(3) is illustrated in Scheme G4, where cycloaddition of GG(1) with GG(4) (where Y=halogen) followed by oxidation of GG(5) (Trost, *Comprehensive Organic Synthesis,* 1991, vol. 7, 653-670) provides the desired aldehyde building block. GG(5) can also be prepared from the amidoxime GG(6) (see Scheme G5) using known procedures (e.g., Mylari, et al., *J. Med. Chem.* 1992, 35, 457-465).

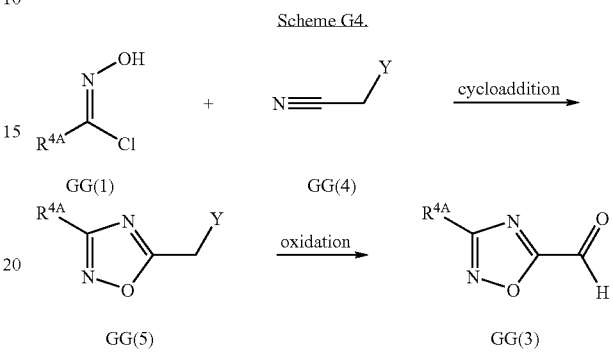

Oxadiazole amine ligands can also be prepared via coupling of amidoxime GG(6) with an amino acid GG(7) followed by cyclodehydration, shown in Scheme G5 (see Hamze, *J. Org. Chem.* 2003, 68, 7316-7321). Some amidoximes GG(6) are commercially available or can be synthesized following known procedures. One route to amino acids of type GG(7) is via the Strecker reaction (Groger, *Chem. Rev.* 2003, 103, 2795-2827).

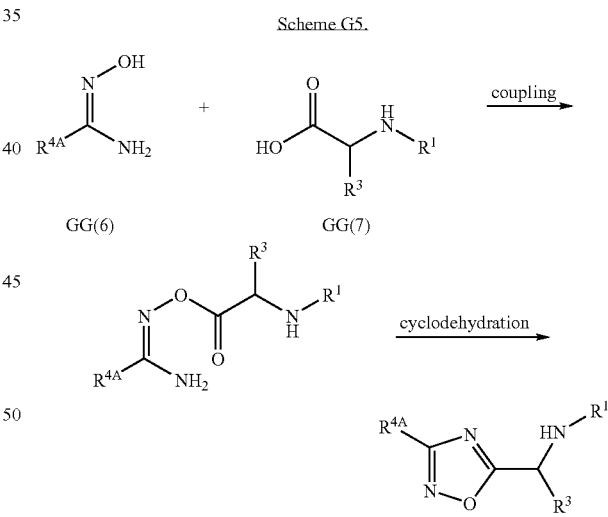

Once the desired ligand is formed, it can be combined with a metal atom, ion, compound or other metal precursor compound, and in some embodiments the present invention encompasses compositions that include any of the above-mentioned ligands in combination with an appropriate metal precursor and an optional activator. For example, in some embodiments, the metal precursor can be an activated metal precursor, which refers to a metal precursor (described below) that has been combined or reacted with an activator (described below) prior to combination or reaction with the ancillary ligand. As noted above, in one aspect the invention provides compositions that include such combinations of ligand and metal atom, ion, compound or precursor. In some applications, the ligands are combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

In general, the metal precursor compounds can be characterized by the general formula $M(L)_m$ where M is a metal selected from the group consisting of groups 3-6 and lanthanides of the periodic table of elements and m is 1, 2, 3, 4, 5, or 6. Thus, in particular embodiments M can be selected from scandium, yttrium, titanium, zirconium, hafnium, vanadium, niobium, tantalum, chromium, molybdenum, tungsten, lanthanum, cerium, praseodymium, neodymium, samarium, europium, gadolinium, terbium, dysprosium, holmium, erbium, thulium, ytterbium, and lutetium. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups are joined into a ring structure. One or more of the ligands L may be ionically bonded to the metal M and, for example, L may be a non-coordinated or loosely coordinated or weakly coordinated anion (e.g., L may be selected from the group consisting of those anions described below in the conjunction with the activators). See Marks et al., *Chem. Rev.* 2000, 100, 1391-1434, for a detailed discussion of these weak interactions. The metal precursors may be monomeric, dimeric or higher orders thereof. In particular embodiments, the metal precursor includes a metal selected from Ti, Zr, or Hf. In more specific embodiments, the metal precursor includes a metal selected from Zr and Hf.

Specific examples of suitable titanium, hafnium and zirconium precursors include, but are not limited to $TiCl_4$, $Ti(CH_2Ph)_4$, $Ti(CH_2CMe_3)_4$, $Ti(CH_2SiMe_3)_4$, $Ti(CH_2Ph)_3Cl$, $Ti(CH_2CMe_3)_3Cl$, $Ti(CH_2SiMe_3)_3Cl$, $Ti(CH_2Ph)_2Cl_2$, $Ti(CH_2CMe_3)_2Cl_2$, $Ti(CH_2SiMe_3)_2Cl_2$, $Ti(NMe_2)_4$, $Ti(NEt_2)_4$, $Ti(O\text{-}^iPr)_4$, and $Ti(N(SiMe_3)_2)_2Cl_2$; $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$, $Hf(N(SiMe_3)CH_2CH_2CH_2N(SiMe_3))Cl_2$, $Hf(N(Ph)CH_2CH_2CH_2N(Ph))Cl_2$, $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, $Zr(N(SiMe_3)_2)_2Cl_2$, $Zr(N(SiMe_3)CH_2\ CH_2CH_2N(SiMe_3))Cl_2$, and $Zr(N(Ph)CH_2CH_2CH_2N(Ph))Cl_2$. Lewis base adducts of these examples are also suitable as metal precursors, for example, ethers, amines, thioethers, phosphines and the like are suitable as Lewis bases. Specific examples include $HfCl_4(THF)_2$, $HfCl_4(SMe_2)_2$ and $Hf(CH_2Ph)_2Cl_2(OEt_2)$. Activated metal precursors may be ionic or zwitterionic compounds, such as $[M(CH_2Ph)_3^+][B(C_6F_5)_4^-]$ or $[M(CH_2Ph)_3^+][PhCH_2B(C_6F_5)_3^-]$ where M is Zr or Hf. Activated metal precursors or such ionic compounds can be prepared in the manner shown in Pellecchia et al., *Organometallics* 1994, 13, 298-302; Pellecchia et al., *J. Am. Chem. Soc.* 1993, 115, 1160-1162; Pellecchia et al., *Organometallics* 1993, 13, 3773-3775 and Bochmann et al., *Organometallics* 1993, 12, 633-640, each of which is incorporated herein by reference.

The ligand to metal precursor compound ratio is typically in the range of about 0.01:1 to about 100:1, more specifically in the range of about 0.1:1 to about 10:1 and even more specifically about 1:1.

As also noted above, in another aspect the invention relates to metal-ligand complexes. Generally, the ligand (or optionally a modified ligand as discussed above) is mixed with a suitable metal precursor (and optionally other components, such as activators) prior to or simultaneously with allowing the mixture to be contacted with the reactants (e.g., monomers). When the ligand is mixed with the metal precursor compound, a metal-ligand complex may be formed, which may itself be an active catalyst or may be transformed into a catalyst upon activation.

The (2,1) metal-ligand complexes according to the invention can be characterized by the following general formula:

(VII)

where M is a metal selected from the group consisting of groups 3-6 and lanthanides of the periodic table of elements. In particular embodiments, M is selected from the group consisting of Ti, Zr, or Hf. In still more particular embodiments, M is Zr or Hf. $R^1$ is optionally substituted hydrocarbyl or heteroatom containing hydrocarbyl. In some embodiments, $R^1$ is selected from optionally substituted alkyl, heteroalkyl, aryl, heteroaryl and combinations thereof. In more particular embodiments, $R^1$ is a ring having from 4-8 atoms in the ring generally selected from the group consisting of substituted cycloalkyl, heterocycloalkyl, aryl and heteroaryl.

In the complexes of formula VII, T is a bridging group of the general formula $—(T'R^2R^3)_n—$, where each T' is independently selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, and n is 1 or 2, provided that two or more $R^2$ and/or $R^3$ groups may be joined together to form one or more optionally substituted ring systems, such as saturated, unsaturated or aromatic ring systems having from 3-50 non-hydrogen atoms, and that one or more T' atoms may be involved in a double bond to a neighboring group (e.g., to an $R^2$, an $R^3$, or T') and correspondingly be bonded to only a single R substituent (i.e., just an $R^2$ or just an $R^3$)— for example, where $—(T'R^2R^3)_n—$ is a phenyl group bonded to N and J through adjacent ring carbon atoms. J is an optionally substituted heterocyclic group containing a five-membered heterocycle. The five-membered heterocycle includes at least one but no more than four heteroatoms, and includes a nitrogen, phosphorus, oxygen, sulfur or carbene in a ring position adjacent to the ring atom bonded to T, which nitrogen, oxygen, sulfur or carbene is bonded to M through a dative bond, and x is 1 or 2. In some embodiments, the heterocyclic group is bonded to M through a nitrogen, phosphorus, oxygen, or sulfur, and the five-membered heterocycle contains at least two heteroatoms. In certain more particular embodiments, the five-membered heterocycle includes a nitrogen in the ring position adjacent to the atom bonded to T. Each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups are joined into a ring structure. One or more of the ligands L may be ionically bonded to the metal M and, for example, L may be a non-coordinated or loosely coordinated or weakly coordinated anion. m' is 1, 2, 3, or 4, depending on x and M.

In some embodiments, the metal-ligand complexes can be characterized by the formula:

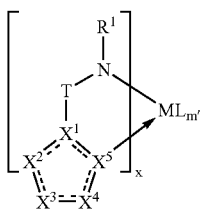

(VIII)

where M, $R^1$, T, x, L and m' are defined as set out above. In formula VIII, $X^1$ is nitrogen, phosphorus, or —$C(R^4)_{n''}$—, and $X^2$, $X^3$ and $X^4$ are independently selected from the group consisting of oxygen, sulfur, —$C(R^4)_{n'}$—, —$N(R^4)_{n''}$—, and —$P(R^4)_{n''}$—, $X^5$ is nitrogen, phosphorus, oxygen, sulfur or a carbene, each n' is 1 or 2, and each n" is 0 or 1. In some embodiments, at least one of $X^1$, or $X^2$, $X^3$, and $X^4$ is not carbon or —$C(R^4)_{n''}$—, respectively. In some embodiments, no more than three of $X^1$, $X^2$, $X^3$, and $X^4$ are carbon (in the case of $X^1$) or —$C(R^4)_{n'}$— (in the case of $X^2$, $X^3$, and/or $X^4$), respectively. Each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. In certain particular embodiments, at least one of $X^3$ and $X^4$ is —$N(R^{4'})$—, —$P(R^{4'})$—, or —$C(R^{4'})(R^4)_{n''}$—, where each $R^{4'}$ is selected from the group consisting of optionally substituted cyclic hydrocarbyl or heteroatom-containing hydrocarbyl. In some embodiments, $R^{4'}$ is optionally substituted bicyclic or polycyclic hydrocarbyl or heteroatom-containing hydrocarbyl, or optionally substituted aryl or heteroaryl, including optionally substituted bicyclic or polycyclic aryl or heteroaryl. Optionally any combination of two or more $R^1$, $R^2$, $R^3$, $R^4$ and/or $R^{4'}$ groups may be joined together to form one or more optionally substituted fused ring systems, such as ring systems having from 3-50 non-hydrogen atoms.

In more particular embodiments, $X^4$ is selected from the group consisting of —$C(R^4)_{n''}R^{4'}$—, —$NR^{4'}$—, and —$PR^{4'}$—, where n" is 0 or 1 as noted above. In some embodiments, discussed in more detail below, $R^{4'}$ and M can be joined to form a 5- or 6-membered metallocycle.

In some embodiments, the metal-ligand complexes can thus be further characterized by the formula:

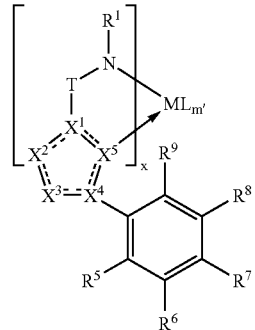

(IX)

where M, $R^1$, $R^2$, $R^3$, $X^1$, $X^2$, $X^3$, $X^5$, x, L and m' are defined as set out above. In formula IX, $X^4$ is nitrogen, phosphorus, or —$C(R^4)_{n''}$—, where n" is 0 or 1, and $R^5$, $R^6$, $R^7$, $R^8$ and $R^9$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more of $R^4$, $R^5$, $R^6$, $R^7$, $R^8$ and $R^9$ may be joined to form one or more optionally substituted fused ring systems, such as ring systems having from 3-50 non-hydrogen atoms.

In other such embodiments, the metal-ligand complexes can be characterized by the formula:

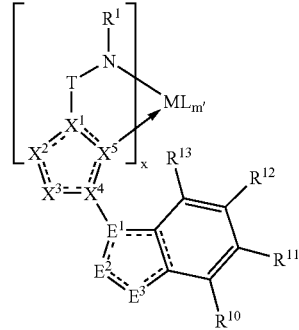

(X)

where M, $R^1$, $R^2$, $R^3$, $X^1$, $X^2$, $X^3$, $X^5$, x, L and m' are defined as set out above. In formula X, $X^4$ is nitrogen, phosphorus, or —$C(R^4)_{n''}$—, $E^1$ is selected from the group consisting of nitrogen, phosphorus, —$C(R^{14})_{n''}$—, and —$Si(R^{14})_{n''}$—, and $E^2$ and $E^3$ are selected from the group consisting of oxygen, sulfur, —$C(R^{14})_{n'}$—, —$N(R^{14})_{n''}$—, —$P(R^{14})_{n''}$— and —$Si(R^{14})_{n'}$—, where each n' is 1 or 2 and each n" is 0 or 1 (depending, e.g., on the degree of saturation of the bonds between $X^4$, $E^2$ and/or $E^3$ and their adjacent atoms). In particular embodiments, at least one of $E^1$, $E^2$ and $E^3$ is not —$C(R^{14})_{n''}$— (in the case of $E^1$) or —$C(R^{14})_{n'}$— (in the case of $E^2$ and/or $E^3$). Each $R^{10}$, $R^{11}$, $R^{12}$, $R^{13}$, and $R^{14}$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. In some embodiments, where $E^2$ and/or $E^3$ is —$N(R^{14})_{n''}$—, —$P(R^{14})_{n''}$— or —$Si(R^{14})_{n'}$—, the corresponding $R^{14}$ is selected from the group consisting of hydrogen, halogen, and optionally substituted alkyl, heteroalkyl, aryl, heteroaryl, alkoxy, aryloxy, silyl. Optionally, two or more of $R^4$, $R^{10}$, $R^{11}$, $R^{12}$, $R^{13}$, and $R^{14}$ may be joined to form one or more optionally substituted fused ring systems, such as ring systems having from 3-50 non-hydrogen atoms.

In certain other embodiments, the metal-ligand complexes can be characterized by the formula:

(XI)

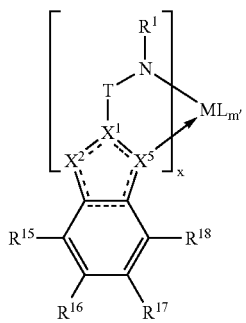

where M, $R^1$, $R^2$, $R^3$, $X^1$, $X^2$, $X^5$, x, L and m' are defined as set out above. Each $R^{15}$, $R^{16}$, $R^{17}$ and $R^{18}$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more of $R^4$, $R^{15}$, $R^{16}$, $R^{17}$ and $R^{18}$ may be joined to form one or more optionally substituted fused ring systems, such as ring systems having from 3-50 non-hydrogen atoms. In particular embodiments, $X^2$ is oxygen, sulfur, —N$(R^4)_{n''}$—, or —P$(R^4)_{n''}$—, where n∝ is 0 or 1, and $X^5$ is nitrogen.

Turning to the (3,2) metal-ligand complexes of the invention, the metal-ligand complexes in this aspect of this invention can be generally characterized by the formula:

(XII)

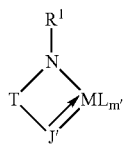

where M is a metal selected from the group consisting of groups 3-6 and lanthanides of the periodic table of elements. In particular embodiments, M is Ti, Zr, or Hf. In more particular embodiments, M is Zr or Hf, and m' is 2. $R^1$ is optionally substituted hydrocarbyl or heteroatom containing hydrocarbyl. In some embodiments, $R^1$ is selected from optionally substituted alkyl, heteroalkyl, aryl, heteroaryl and combinations thereof. In more particular embodiments, $R^1$ is a ring having from 4-8 atoms in the ring generally selected from the group consisting of substituted cycloalkyl, heterocycloalkyl, aryl and heteroaryl.

In the complexes of formula XII, T is a bridging group of the general formula —$(T'R^2R^3)_n$—, where each T' is independently selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, and n is 1 or 2, provided that two or more $R^2$ and/or $R^3$ groups may be joined together to form one or more optionally substituted ring systems, such as saturated, unsaturated or aromatic ring systems having from 3-50 non-hydrogen atoms, and that one or more T' atoms may be involved in a double bond to a neighboring group (e.g., to an $R^2$, an $R^3$, or T') and correspondingly be bonded to only a single R substituent (i.e., just an $R^2$ or just an $R^3$)— for example, where —$(T'R^2R^3)_n$— is a phenyl group bonded to N and J' through adjacent ring carbon atoms. J' is an optionally substituted heterocyclic group containing a five-membered heterocycle. The five-membered heterocycle includes at least one but no more than four heteroatoms, including a nitrogen, phosphorus, oxygen, sulfur, or carbene in a ring position adjacent to the atom bonded to T, provided that J' includes 2 atoms bonded to the metal M, one of which is the nitrogen, phosphorus, oxygen, sulfur, or carbene in the ring position adjacent to the atom bonded to T, which is bonded to M through a dative bond, and the other of which is bonded to the metal M through a covalent bond. Each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof, and m' is 1, 2 3, or 4, provided that optionally two or more L groups can be joined into a ring structure, and that one or more of the ligands L may be ionically bonded to the metal M and, for example, one or more L ligands may be a non-coordinated or loosely coordinated or weakly coordinated anion (A⁻), as in formula XIIA, below (where m"+m'''=m').

(XIIA)

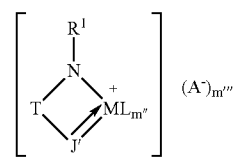

In some embodiments, the (3,2) ligand-metal complexes of the invention can be characterized by the formula:

(XIII)

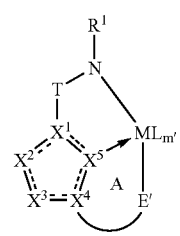

where M, $R^1$, T, L and m' are defined as set out above. In formula XIII, $X^1$ and $X^4$ are nitrogen, phosphorus, or —C$(R^4)_{n''}$—, and $X^2$ and $X^3$ are selected from the group consisting of oxygen, sulfur, —C$(R^4)_{n''}$—, —N$(R^4)_{n''}$—, and —P$(R^4)_{n''}$—, $X^5$ is nitrogen, phosphorus, oxygen, sulfur or a carbene, each n' is 1 or 2, and each n" is 0 or 1, and each $R^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. In particular embodiments, at least one of $X^1$, $X^4$, $X^2$, and $X^3$ is carbon (in the case of $X^1$ and/or $X^4$) or —C$(R^4)_{n'}$— (in the case of $X^2$ and/or $X^3$), respectively. Optionally any combination of two or more $R^1$, $R^2$, $R^3$, and/or $R^4$ groups may be joined together to form one or more optionally substituted fused ring systems, such as ring systems having from 3-50 non-hydrogen atoms. E' is selected from the group consisting of oxygen, sulfur, —C$(R^{21})_{n''}$—, —N$(R^{21})_{n''}$—, —P$(R^{21})_{n''}$— and —Si$(R^{21})_{n''}$—, where each n' is 1 or 2, each n" is 0 or 1, depending on the bond order of the adjacent bonds, and $R^{21}$ is independently selected from the group consisting of optionally substituted alkyl, heteroalkyl, aryl or heteroaryl, and E' is connected to $X^4$ through an optionally substituted divalent hydrocarbyl or heteroatom-containing hydrocarbyl group, such that the ring labeled "A" (hereinafter "Ring A") is a metallocycle containing five, six or seven members, including metal M, provided that $R^{21}$ can be joined to the divalent hydrocarbyl or heteroatom-containing hydrocarbyl group connecting E' to $X^4$ as part of a ring. Optionally two or more $R^4$ and/or $R^{21}$ groups are joined to form one or more optionally substituted ring structures having from 3 to 50 atoms each.

Thus, in particular embodiments, the (3,2) metal-ligand complexes can be characterized by the formula:

(XIV)

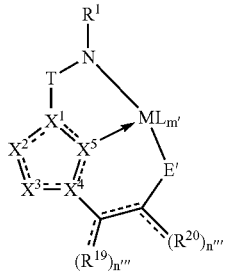

where M, $R^1$, T, $X^1$, $X^2$, $X^3$, $X^4$, $X^5$, E', L and m' are defined as set out for structure XIII above. Each $R^{19}$ and $R^{20}$ is independently selected from the group consisting of optionally substituted alkyl, heteroalkyl, aryl or heteroaryl, and optionally two or more $R^4$, $R^{19}$, $R^{20}$ and $R^{21}$ groups are joined to form one or more optionally substituted ring structures having from 3 to 50 atoms each. Each n''' is 1 or 2.

In some embodiments, the (3,2) ligand-metal complexes of the invention can be characterized by the formula:

(XV)

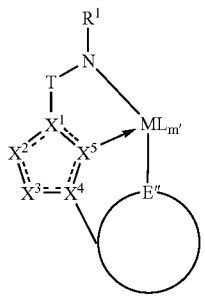

where $X^1$, $X^2$, $X^3$, $X^4$, $X^5$, M, $R^1$, T, L and m' are defined as set out for structure XIV above. In structure XV, E'' is nitrogen, phosphorus, —C($R^{14}$)$_{n''}$—, or —Si($R^{14}$)$_{n''}$—, and is part of an optionally substituted heterocyclic group.

In some particular embodiments, the metal-ligand complexes of the invention can be characterized by the formula:

(XVI)

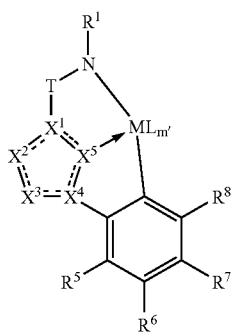

where M, $R^1$, T, $X^1$, $X^2$, $X^3$, $X^4$, $X^5$, L and m' are defined as in structure XV above. $R^5$, $R^6$, $R^7$, and $R^8$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more of $R^4$, $R^5$, $R^6$, $R^7$ and $R^8$ may be joined to form one or more optionally substituted fused ring systems, such as ring systems having from 3-50 non-hydrogen atoms.

In other embodiments, the metal-ligand complexes can be characterized by the formula:

(XVII)

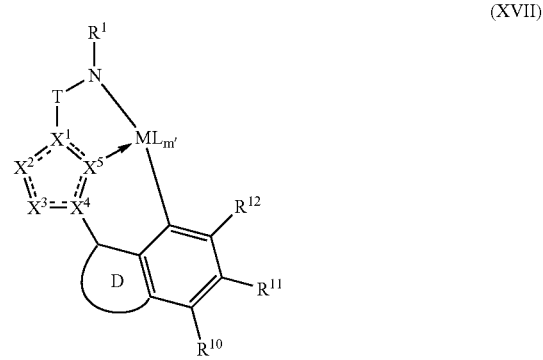

where M, $R^1$, $R^2$, $R^3$, $X^1$, $X^2$, $X^3$, $X^4$, $X^5$, L and m' are defined as in structure XVI above. $R^{10}$, $R^{11}$ and $R^{12}$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more of $R^4$, $R^{10}$, $R^{11}$ and $R^{12}$ may be joined to form one or more optionally substituted fused ring systems, such as ring systems having from 3-50 non-hydrogen atoms. Ring D is a ring selected from the group consisting of optionally substituted aryl and heteroaryl.

In some such embodiments, the metal-ligand complexes can be characterized by the formula:

(XVIII)

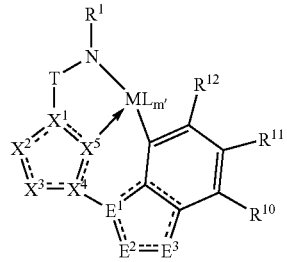

where M, $R^1$, $R^2$, $R^1$, $X^1$, $X^2$, $X^3$, $X^4$, $X^5$, L and m' are defined as for structure XVII above. $E^1$ is selected from the group consisting of nitrogen, phosphorus, —C($R^{14}$)$_{n''}$—, or —Si($R^{14}$)$_{n''}$—, and $E^2$ and $E^3$ are selected from the group consisting of oxygen, sulfur, —N($R^{14}$)$_{n''}$—, —C($R^{14}$)$_{n'}$—, —P($R^{14}$)$_{n''}$—, and —Si($R^{14}$)$_{n'}$—, where each n' is 1 or 2 and each n'' is 0 or 1 (depending, e.g., on the degree of saturation of the bonds between $E^1$ and $E^2$, and $E^2$ and $E^3$). Each $R^{10}$, $R^{11}$, $R^{12}$ and $R^{14}$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. In some embodiments, if $E^2$ and/or $E^3$ is $-N(R^{14})_{n''}-$ or $-P(R^{14})_{n''}-$ or $-Si(R^{14})_{n'}-$, the corresponding $R^{14}$ is selected from the group consisting of hydrogen, halogen, and optionally substituted alkyl, heteroalkyl, aryl, heteroaryl, alkoxy, aryloxy, silyl. Optionally, two or more of $R^4$, $R^{10}$, $R^{11}$, $R^{12}$ and $R^{14}$ may be joined to form one or more optionally substituted fused ring systems, such as ring systems having from 3-50 non-hydrogen atoms.

In other embodiments, the (3,2) metal-ligand complexes of the invention can be characterized by the formula:

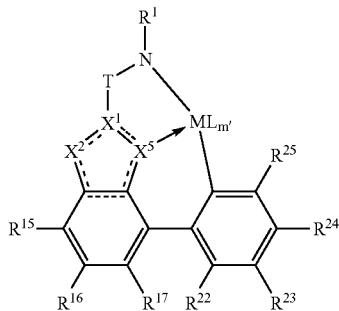

(XIX)

where M, $R^1$, $R^2$, $R^3$, $X^1$, $X^5$, L and m' are defined as set out above. $R^{15}$, $R^{16}$, $R^{17}$, $R^{22}$, $R^{23}$, $R^{24}$, and $R^{25}$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof. Optionally, two or more of $R^4$, $R^{15}$, $R^{16}$, $R^{17}$, $R^{22}$, $R^{23}$, $R^{24}$, and $R^{25}$ may be joined to form one or more optionally substituted fused ring systems, such as ring systems having from 3-50 non-hydrogen atoms. In particular embodiments, $X^2$ is oxygen, sulfur, $-NR^4-$, or $-PR^4-$.

In particular (3,2) complex embodiments, the five-membered heterocycle can include at least two heteroatoms, and can be, for example, optionally substituted imidazole, thiazole, oxazole, or oxadiazole, including isomeric forms of these. In more particular embodiments, $X^5$ is nitrogen, $X^1$ and $X^4$ are $-C(R^4)_{n''}-$, one of $X^2$ and $X^3$ is sulfur and the other of $X^2$ and $X^3$ is $-C(R^4)_{n'}-$. In other (3,2) complex embodiments, the five-membered heterocycle can include a single heteroatom, as in furan or thiophene.

Alternatively, the (3,2) metal-ligand complexes of some embodiments of the invention can be described as complexes containing three rings, including two metal-chelate rings (metallocycles A and B in structure XX below) and one 5-membered heterocycle (ring C), characterized by the formula:

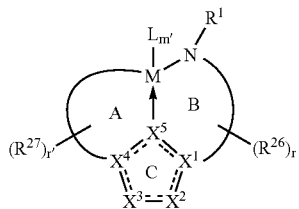

(XX)

In formula XX, M is a metal selected from the group consisting of groups 3-6 and lanthanides of the periodic table of elements. In particular embodiments, M is Ti, Zr, or Hf. In more particular embodiments, M is Zr or Hf, and m' is 2. Ring A is an optionally substituted metallocycle containing five, six or seven atoms in the ring, including M. Ring B is an optionally substituted metallocycle containing five or six atoms in the ring, including M. Ring C is an optionally substituted five-membered heterocycle, wherein $X^1$ and $X^4$ are selected from the group consisting of nitrogen, phosphorus, and $-C(R^4)_{n''}-$, and $X^2$ and $X^3$ are selected from the group consisting of oxygen, sulfur, $-C(R^4)_{n''}-$, $-N(R^4)_{n''}-$, and $-P(R^4)_{n''}-$, $X^5$ is nitrogen, carbon, oxygen, phosphorus, or sulfur, each n' is 1 or 2, and each n'' is 0 or 1. In particular embodiments, at least one of $X^1$ and $X^4$, or $X^2$ and $X^3$ is carbon (in the case of $X^1$ and/or $X^4$) or $-C(R^4)_{n'}-$ (in the case of $X^2$ and/or $X^3$), respectively.

In the complexes of formula XX, in general $R^1$ is optionally substituted hydrocarbyl or heteroatom containing hydrocarbyl. In some embodiments, $R^1$ is selected from optionally substituted alkyl, heteroalkyl, aryl, heteroaryl and combinations thereof. In more particular embodiments, $R^1$ is a ring having from 4-8 atoms in the ring generally selected from the group consisting of substituted cycloalkyl, heterocycloalkyl, aryl and heteroaryl. Each $R^4$, $R^{26}$ and $R^{27}$ is independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof. r is 1, 2, 3 or 4. r' is 1, 2, 3 or 4. Optionally any combination of two or more $R^4$, $R^{26}$ and/or $R^{27}$ groups may be joined together to form one or more optionally substituted fused ring systems, such as ring systems having from 3-50 non-hydrogen atoms. Each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups are joined into a ring structure. One or more of the ligands L may be ionically bonded to the metal M and, for example, L may be a non-coordinated or loosely coordinated or weakly coordinated anion. m' is 1, 2, 3 or 4. In some particular embodiments, one of Ring A or Ring B is a 5-membered optionally substituted heterocycle and the other of Ring A or Ring B is a 6-membered optionally substituted heterocycle, Ring A includes a carbon-metal bond, and ring C is a substituted pyrazole, imidazole, thiazole, oxazole, isothiazole, isoxazole, oxadiazole or a benzo-fused derivative of any of these. In some particular embodiments, metal M is bound in Ring A to carbon, nitrogen, oxygen, phosphorus or sulfur (in addition to the bond between M and $X^5$).

In particular embodiments, the metal-ligand complexes of the invention are formed using ligands having the particular substituents noted above. Specific examples of metal-ligand complexes within the scope of the invention include those set out in Table 2.

TABLE 2
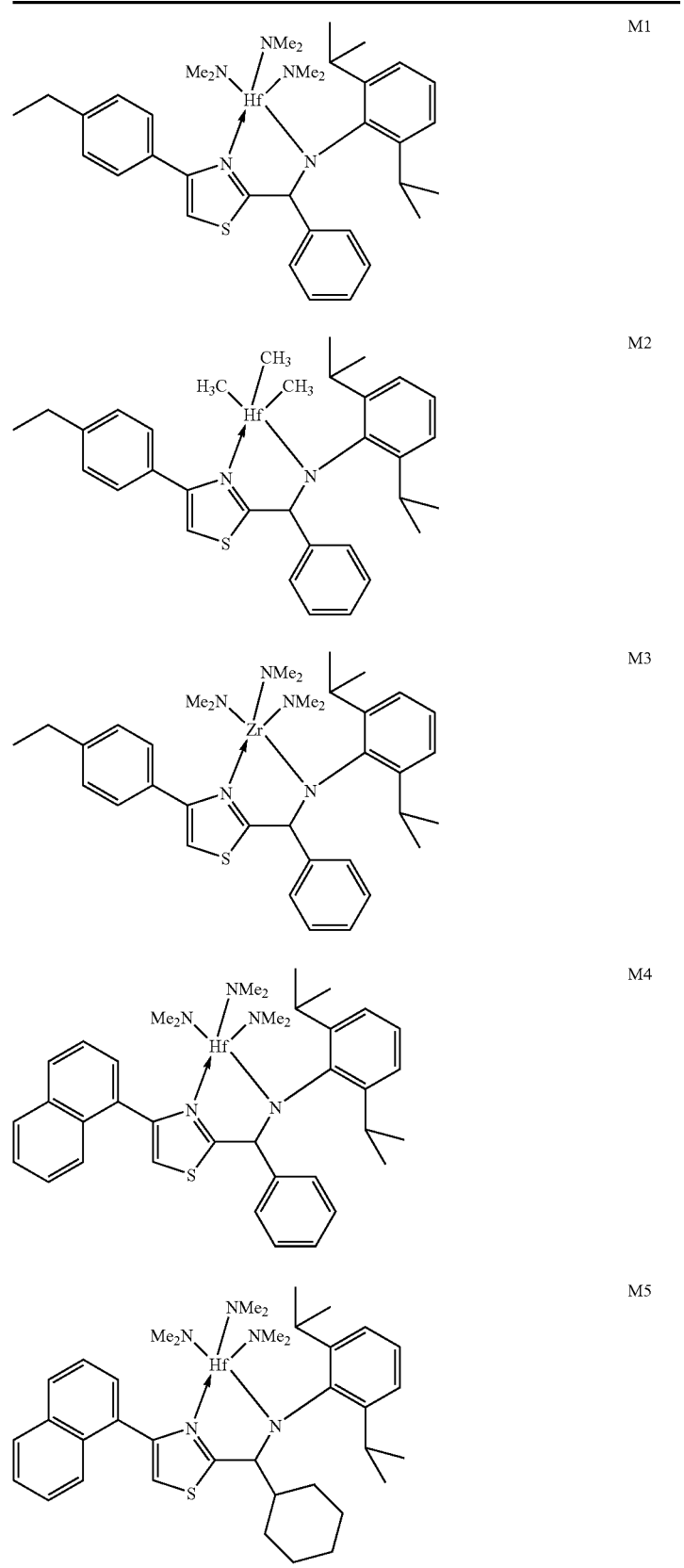

TABLE 2-continued
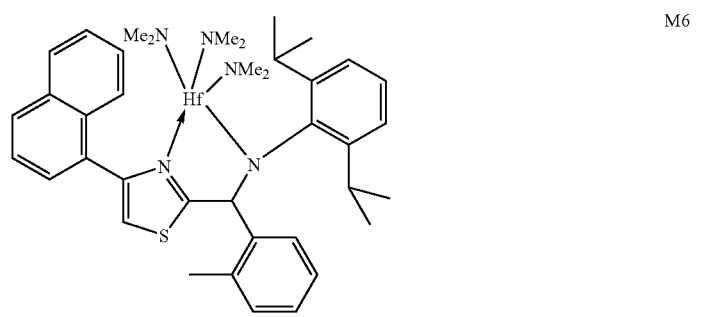 M6
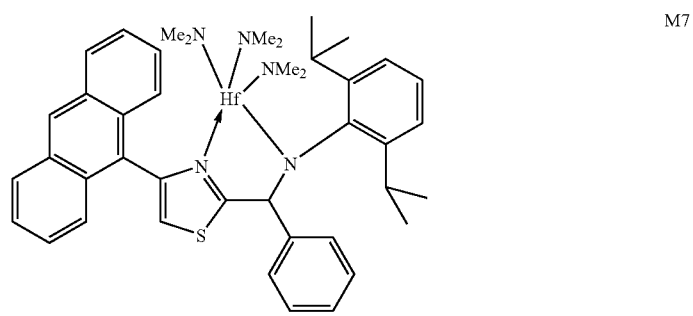 M7
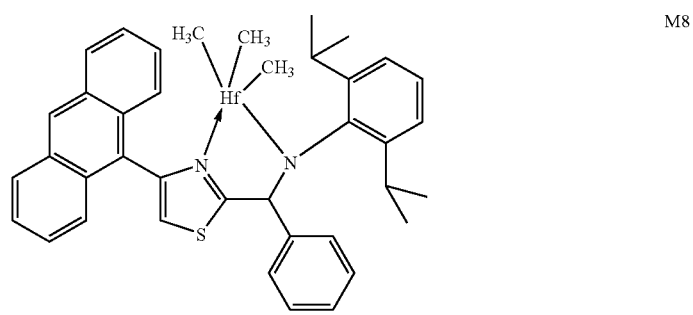 M8
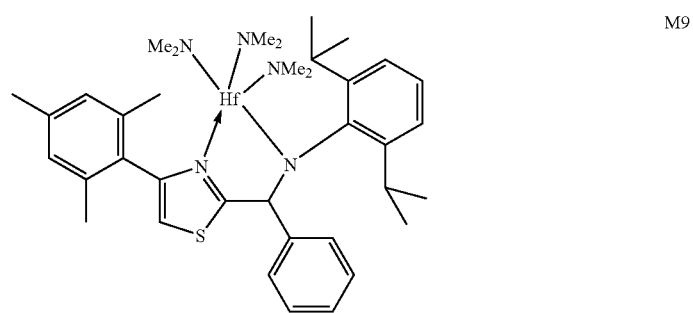 M9
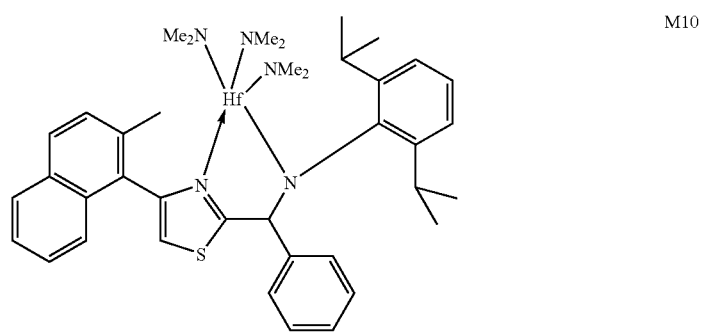 M10

TABLE 2-continued
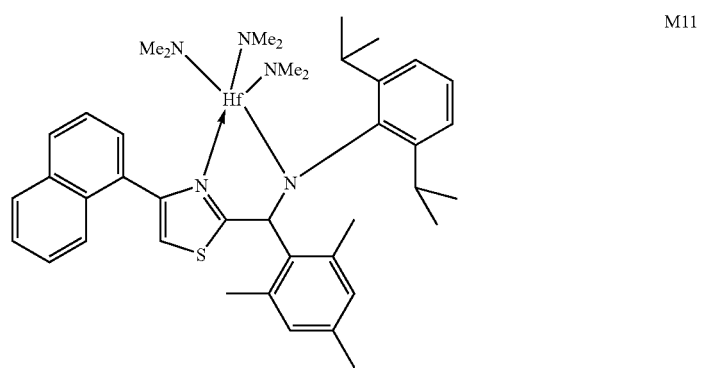
M11
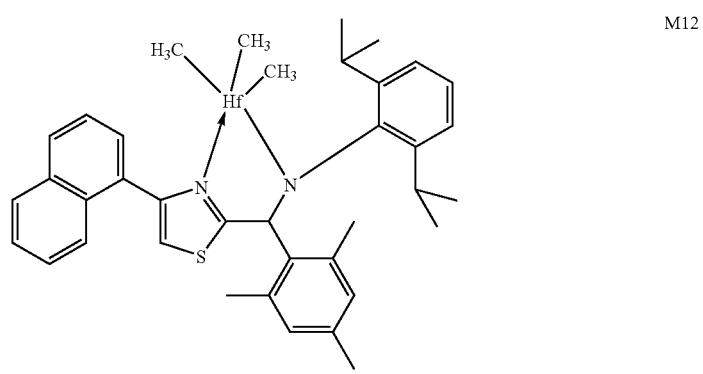
M12
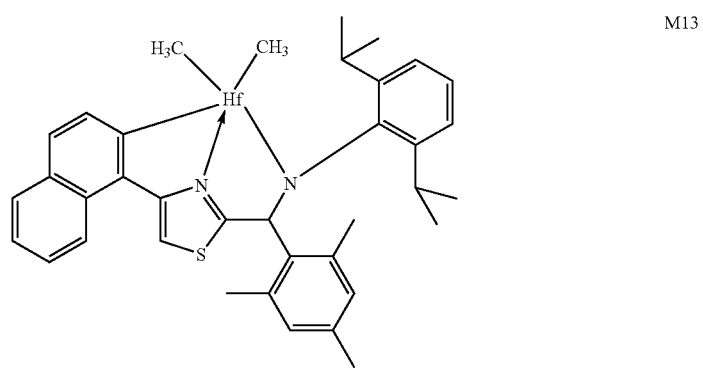
M13
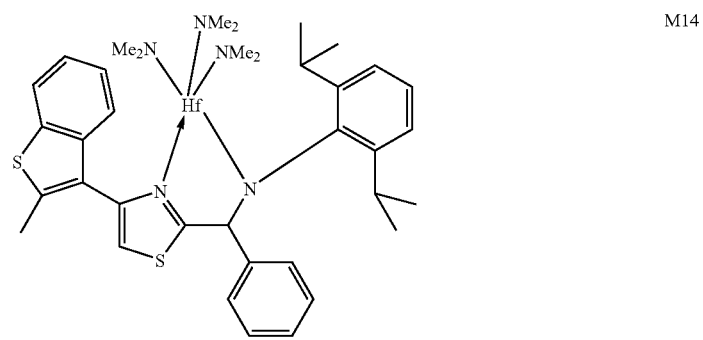
M14

TABLE 2-continued
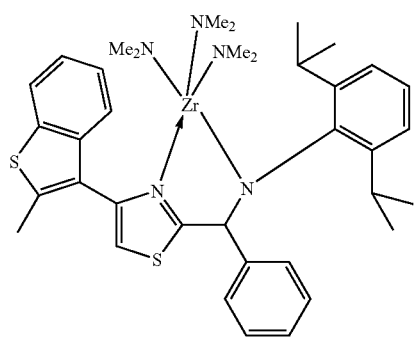
M15
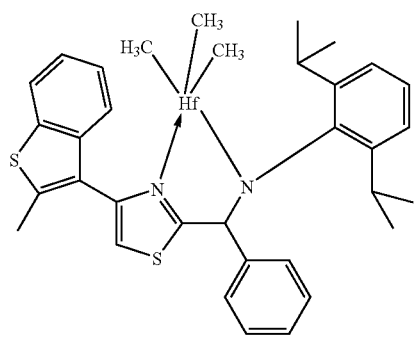
M16
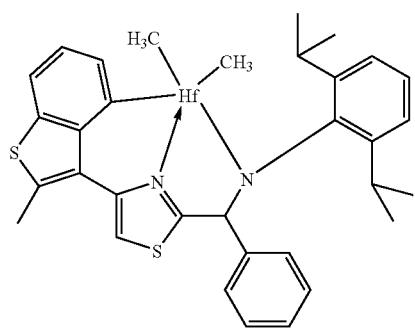
M17
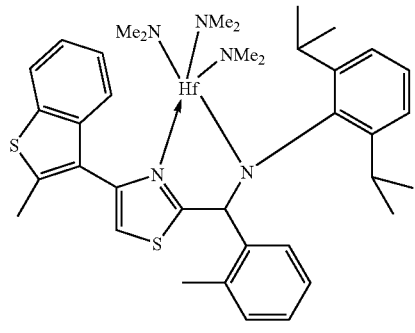
M18

TABLE 2-continued
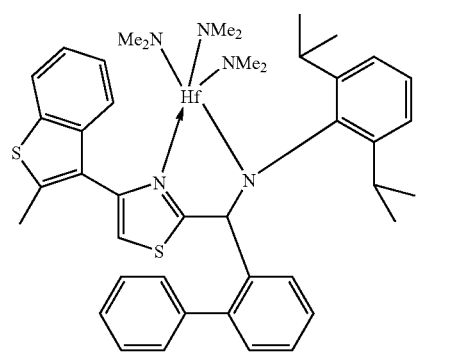
M19
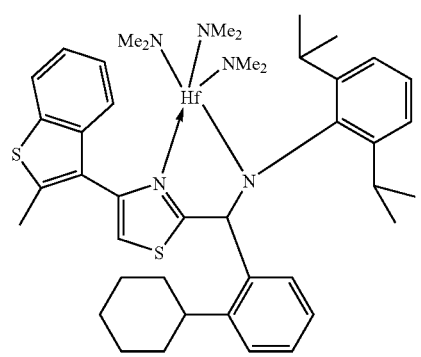
M20
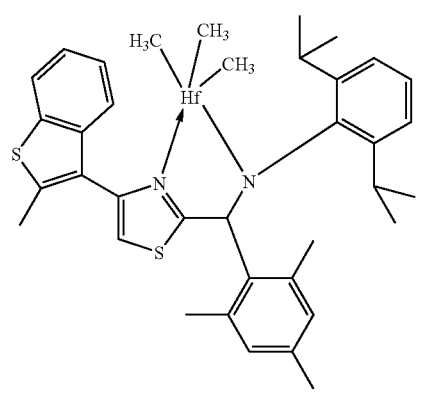
M21
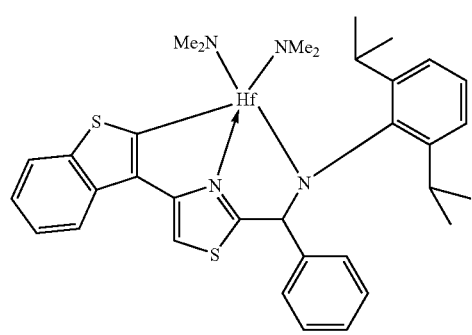
M22

TABLE 2-continued
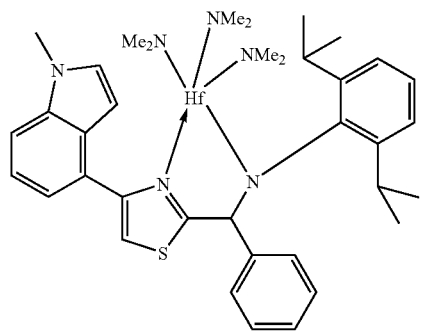
M23
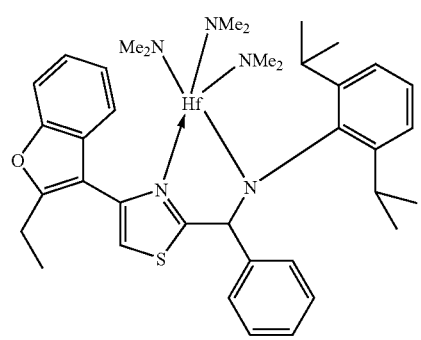
M24
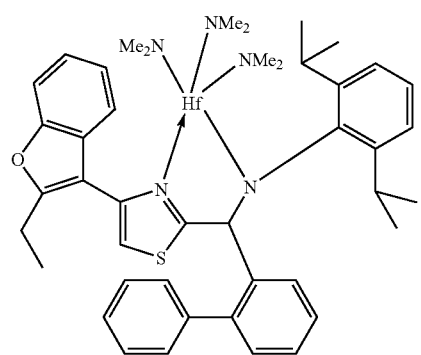
M25
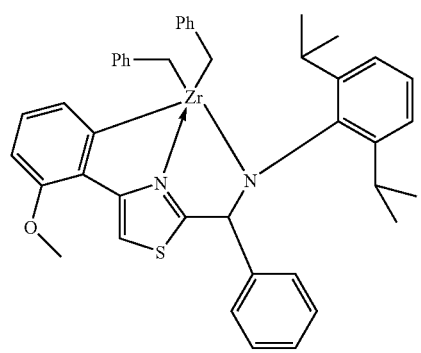
M26

TABLE 2-continued
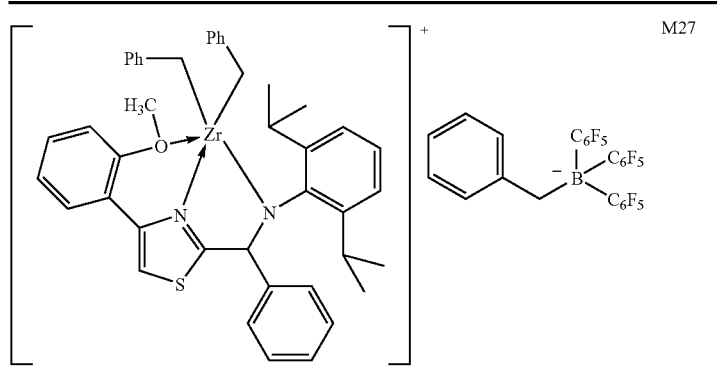 M27
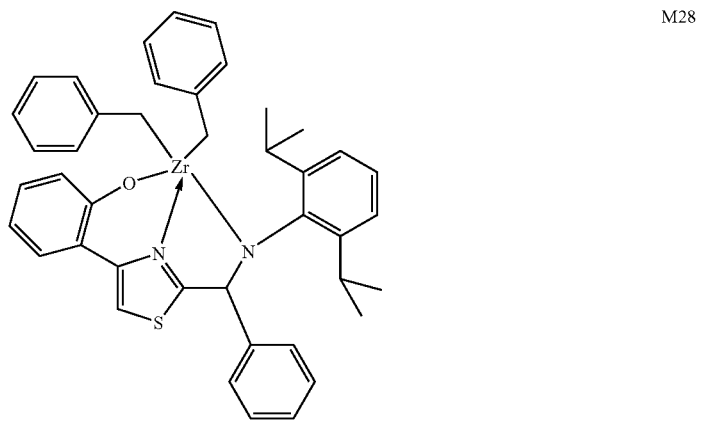 M28
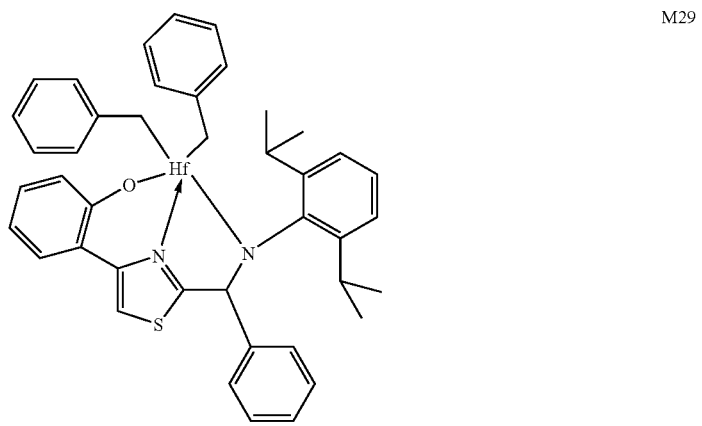 M29
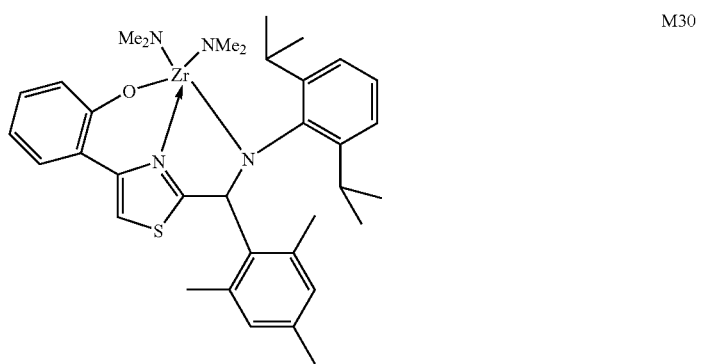 M30

TABLE 2-continued
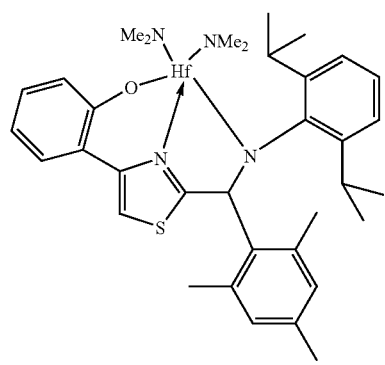
M31
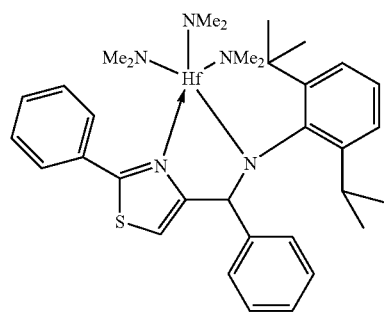
M32
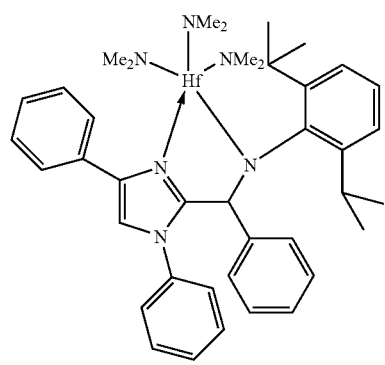
M33
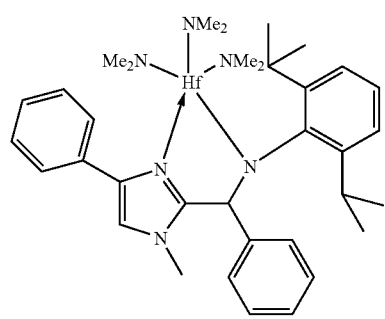
M34

TABLE 2-continued
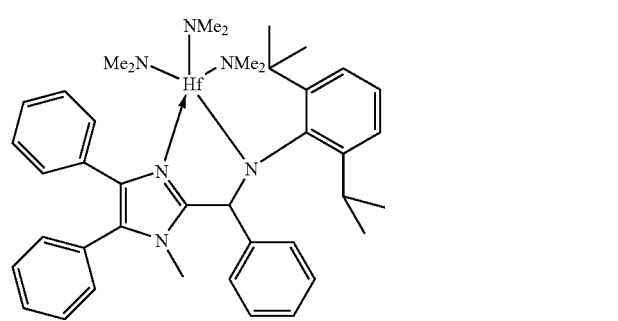
M35
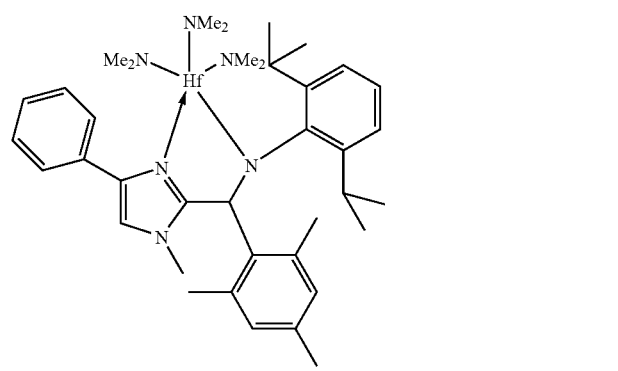
M36
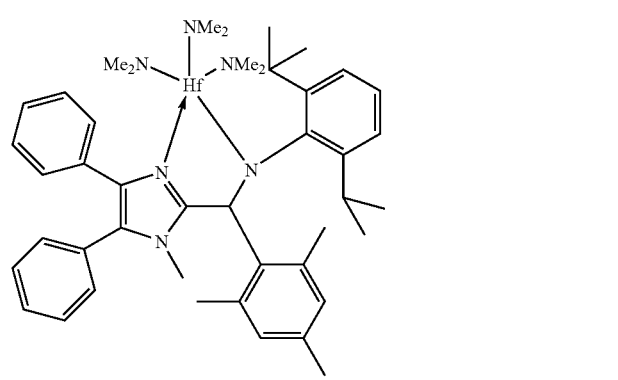
M37
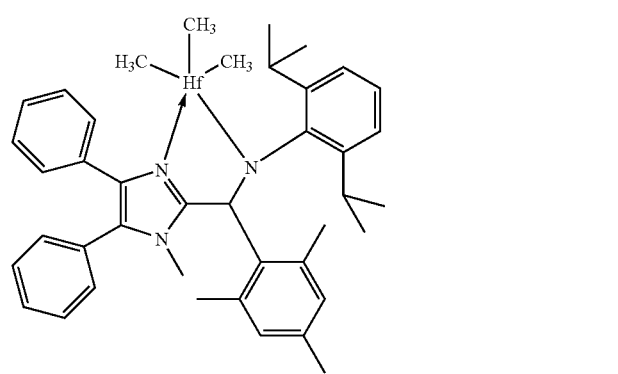
M38

TABLE 2-continued
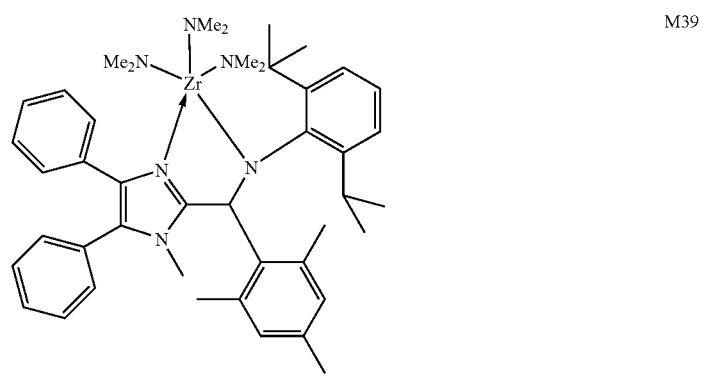
M39
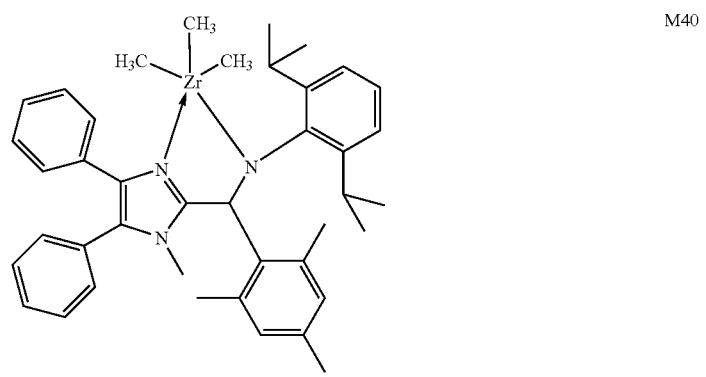
M40
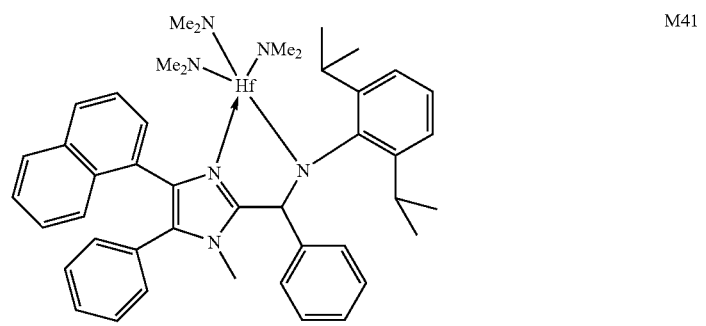
M41
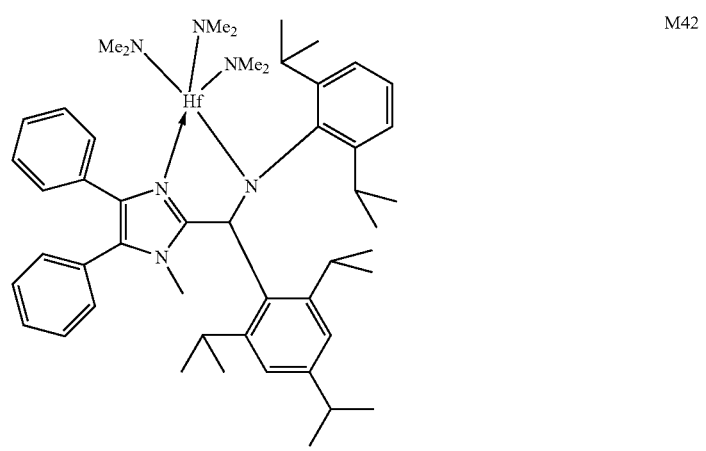
M42

TABLE 2-continued
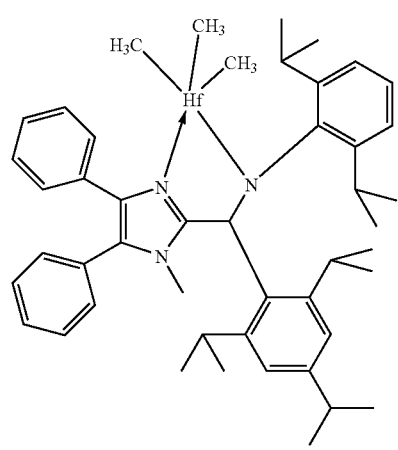
M43
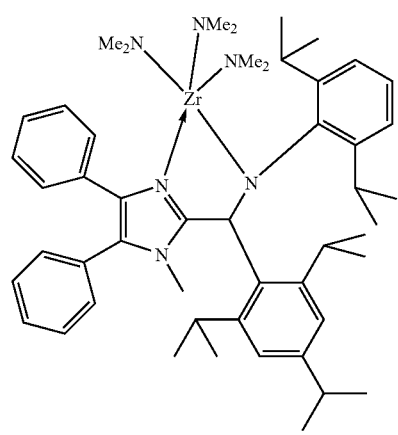
M44
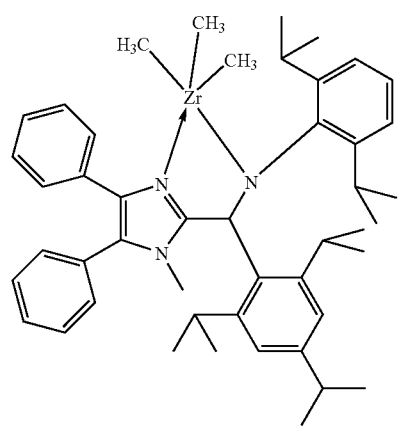
M45

TABLE 2-continued
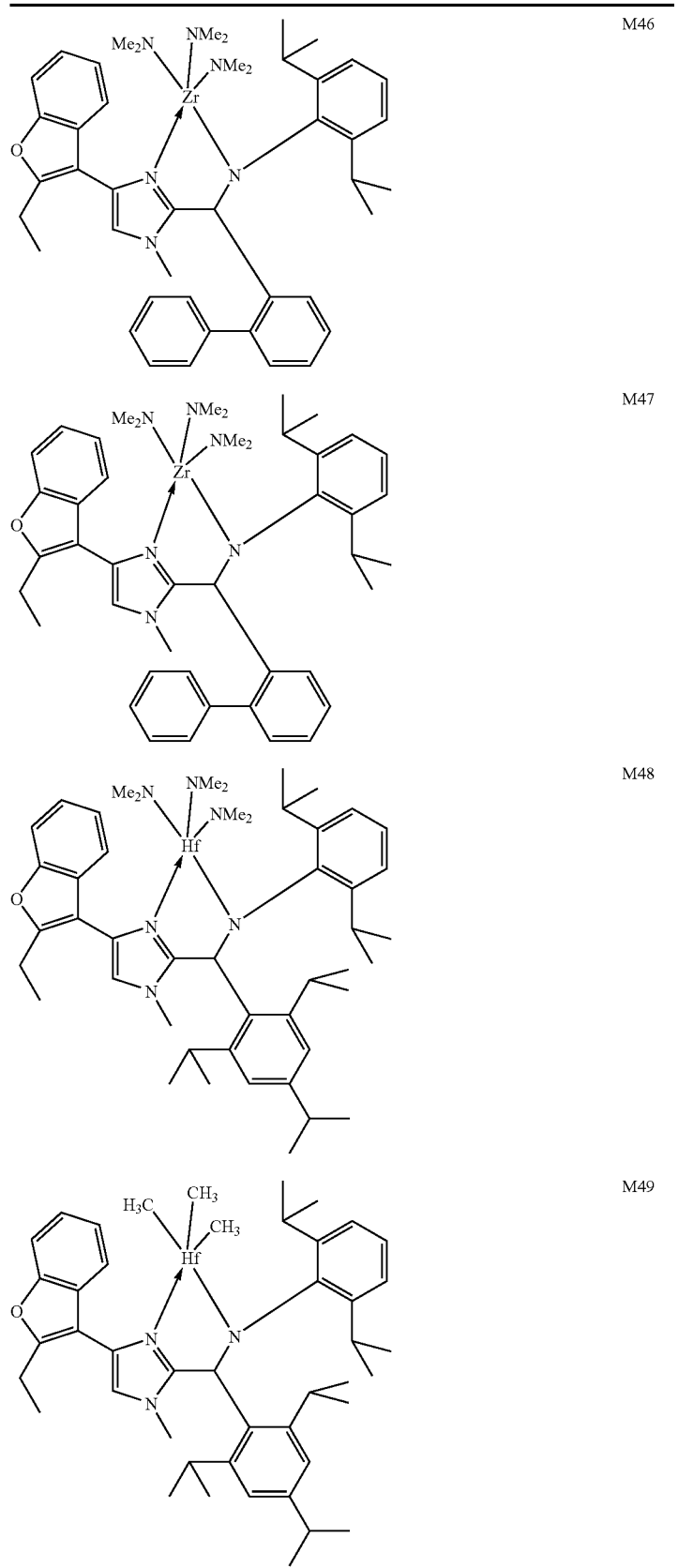

TABLE 2-continued
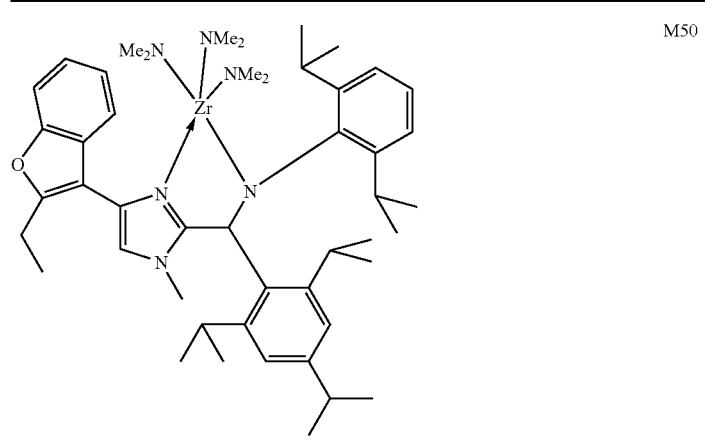 M50
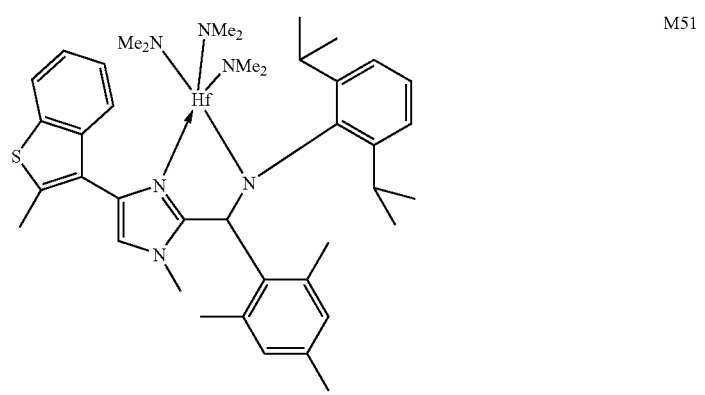 M51
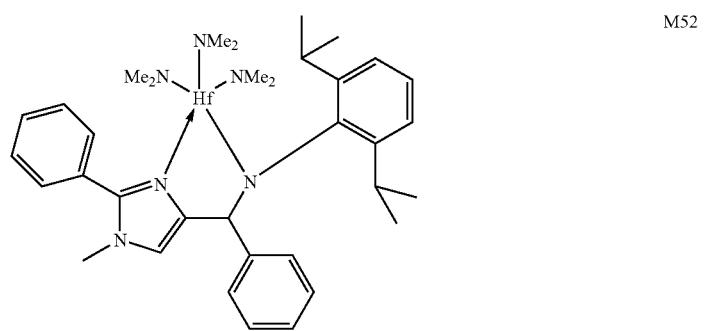 M52
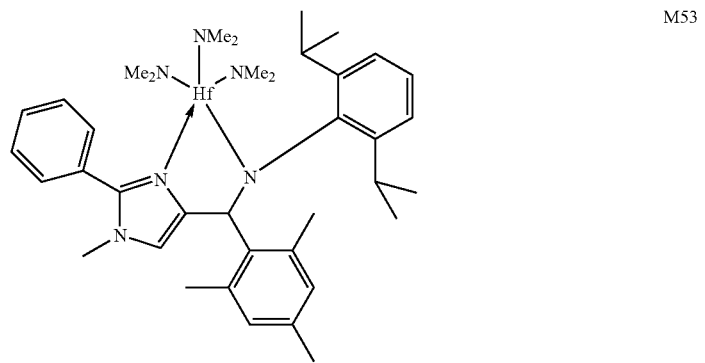 M53

TABLE 2-continued
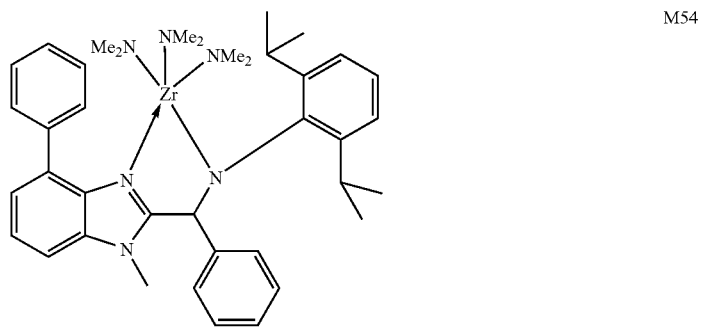
M54
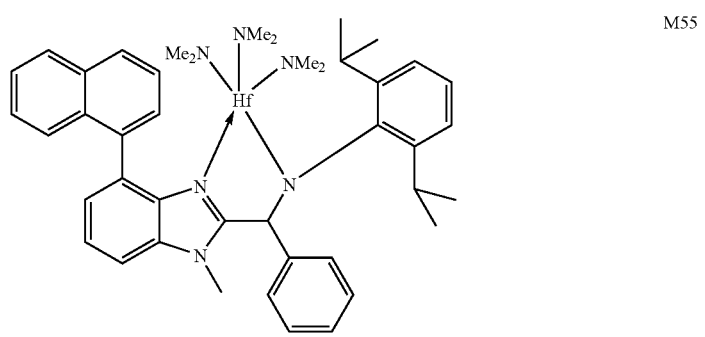
M55
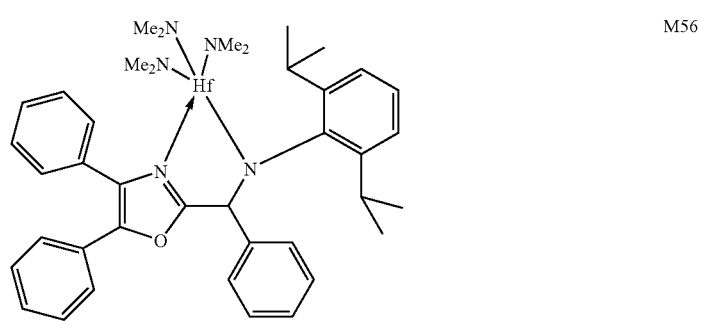
M56
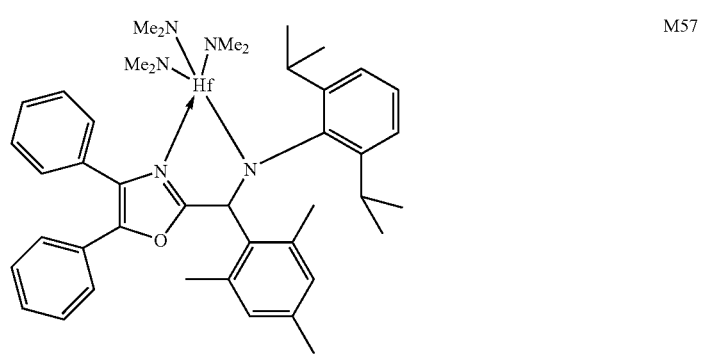
M57

TABLE 2-continued
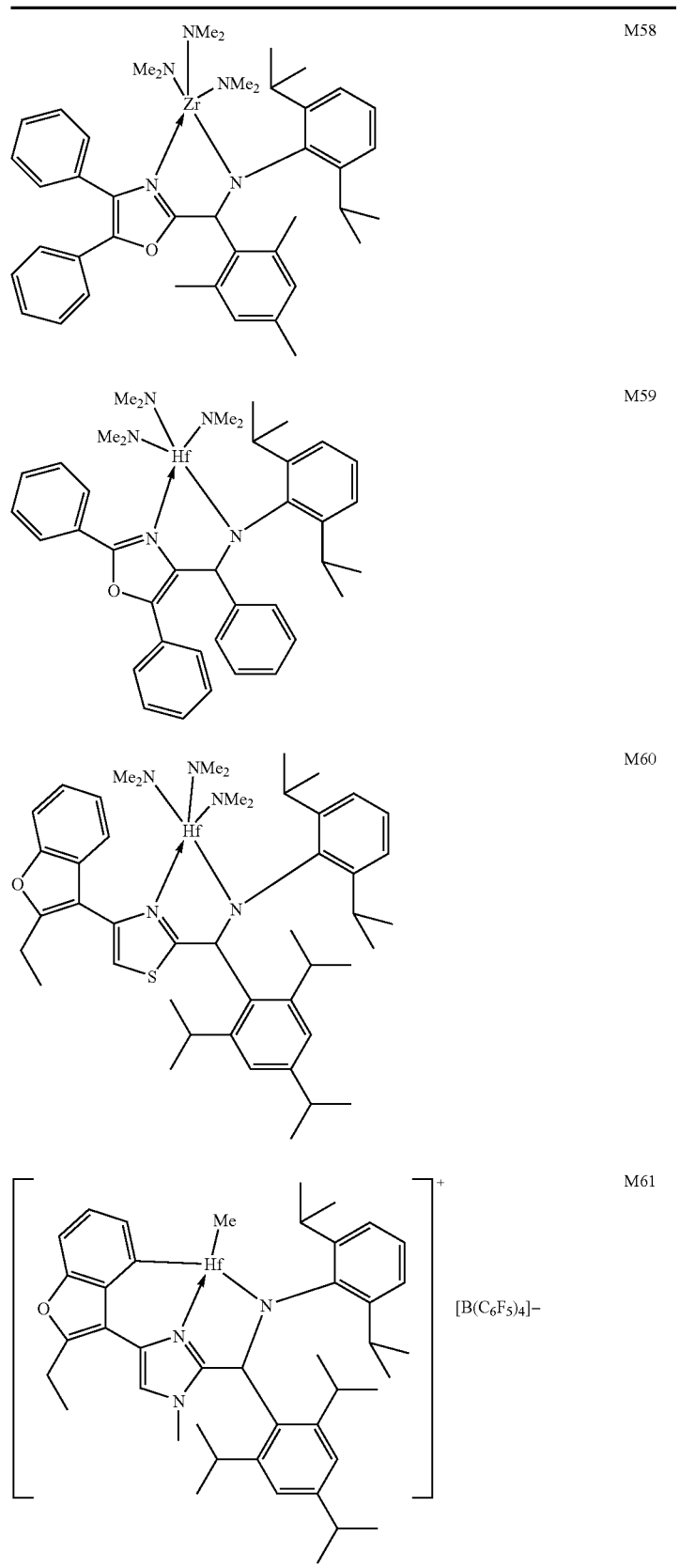

TABLE 2-continued
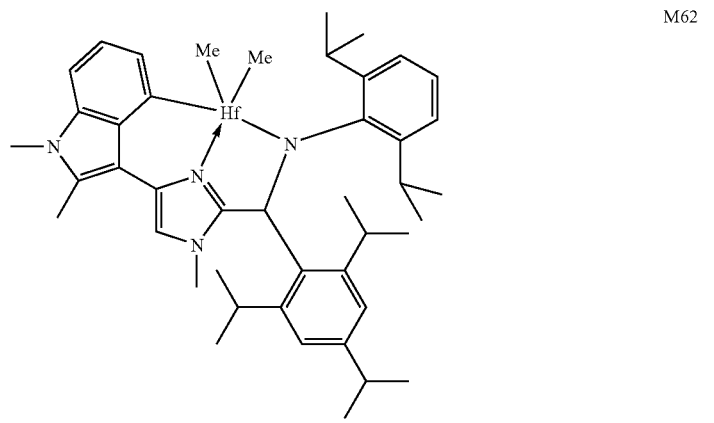
M62
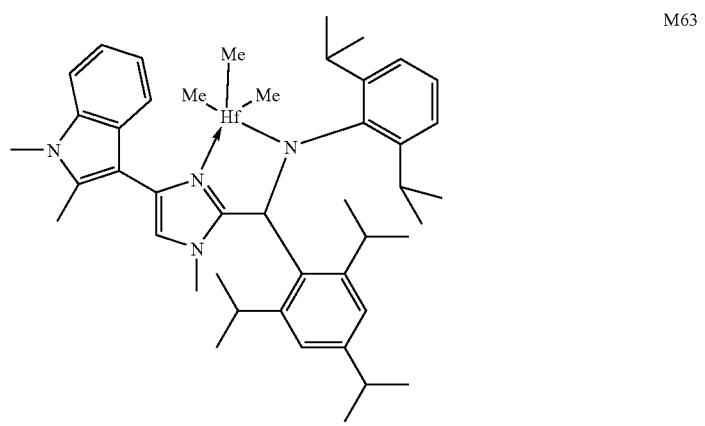
M63
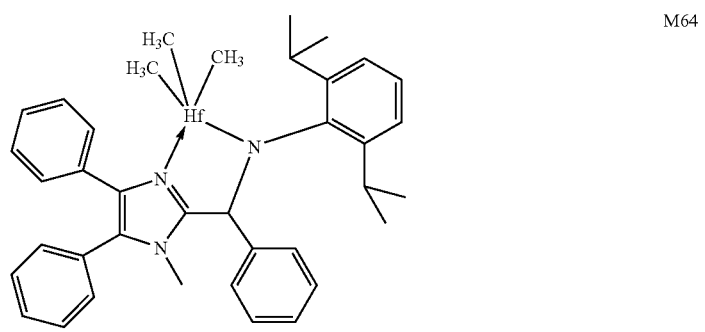
M64
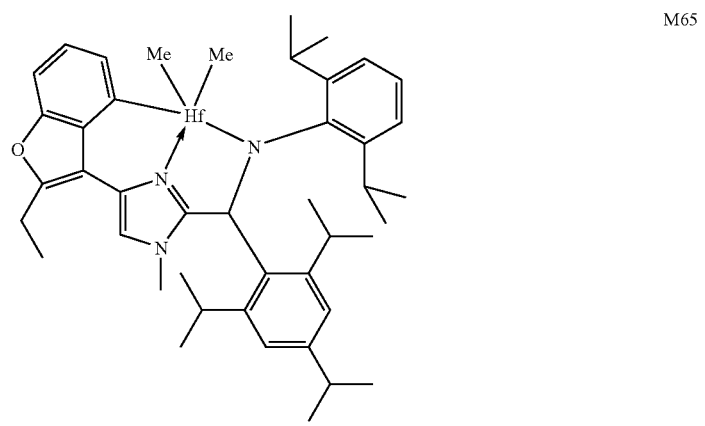
M65

TABLE 2-continued
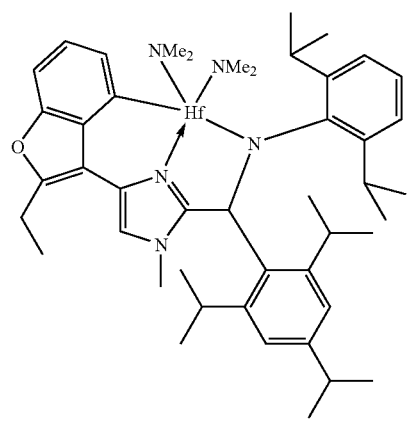
M66
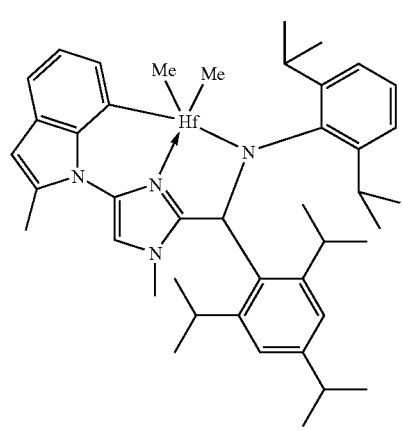
M67
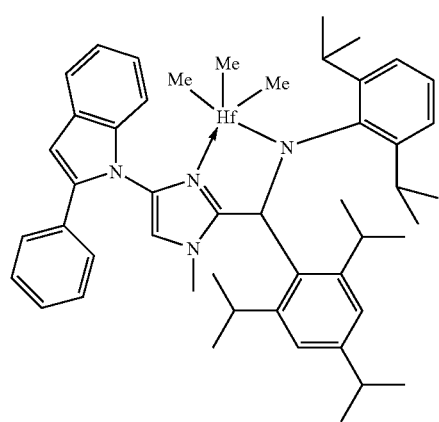
M68
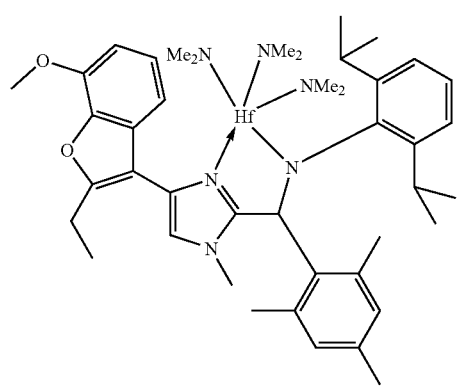
M70

TABLE 2-continued
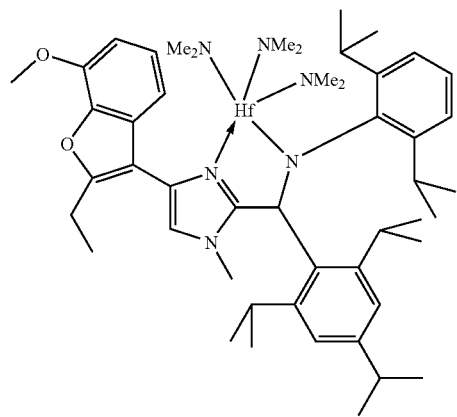
M71
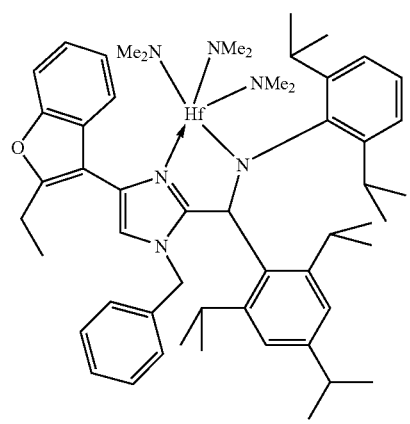
M72
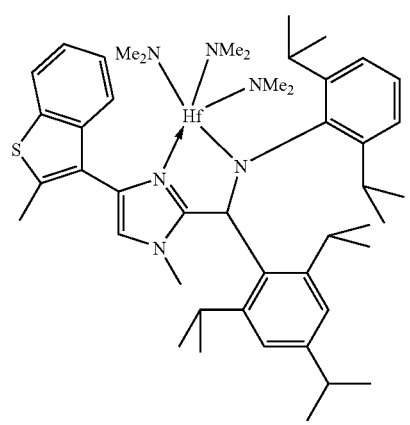
M73

TABLE 2-continued
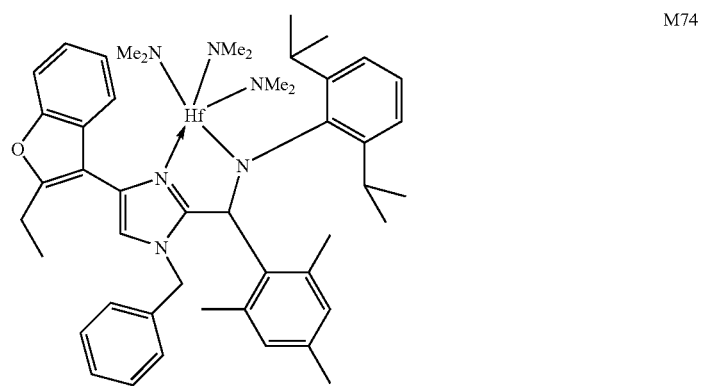
M74
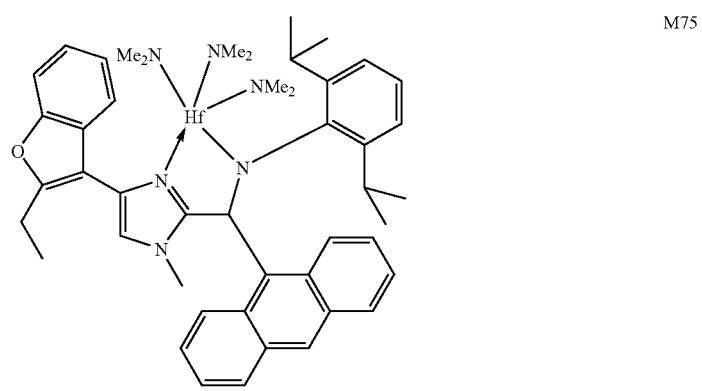
M75
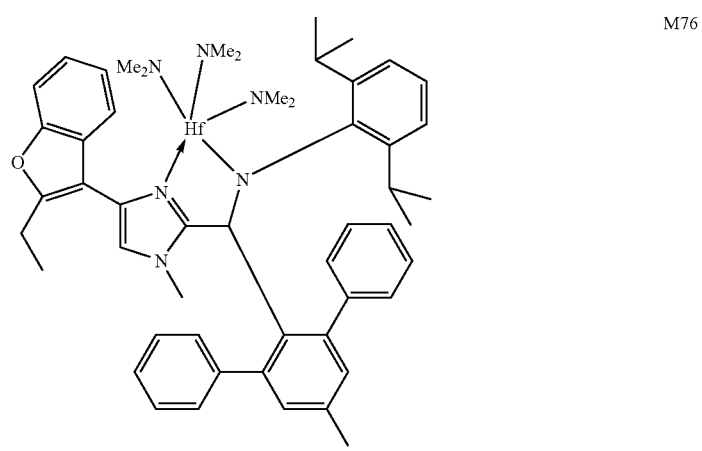
M76
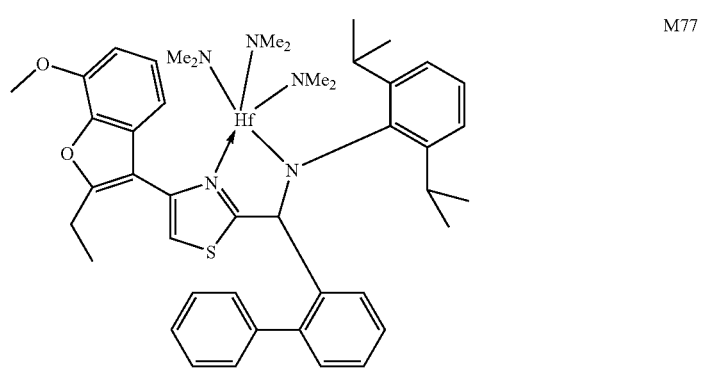
M77

TABLE 2-continued
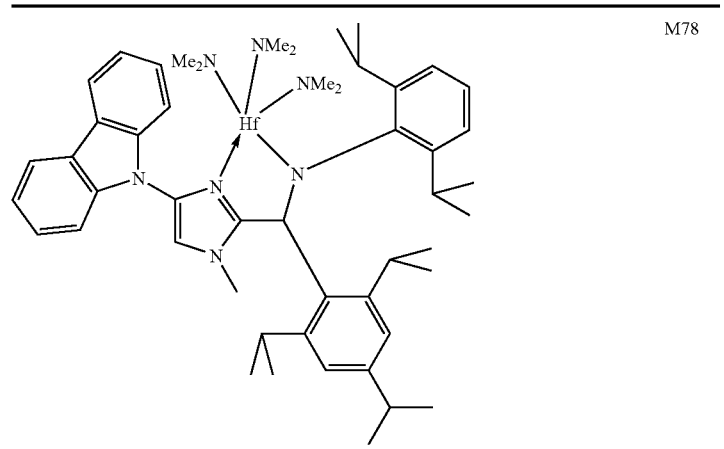
M78
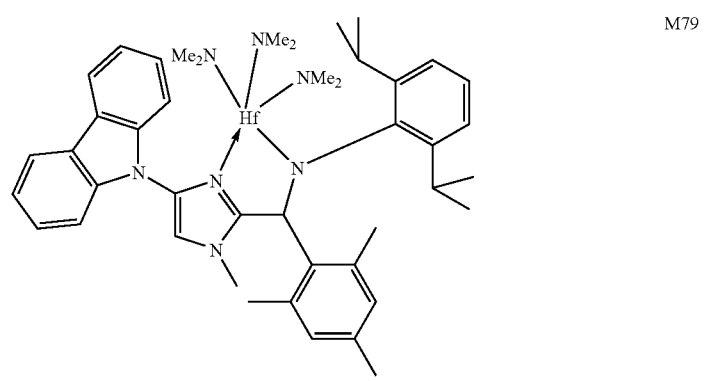
M79
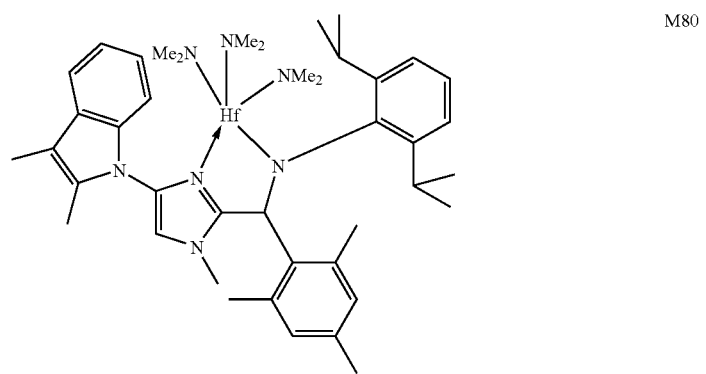
M80
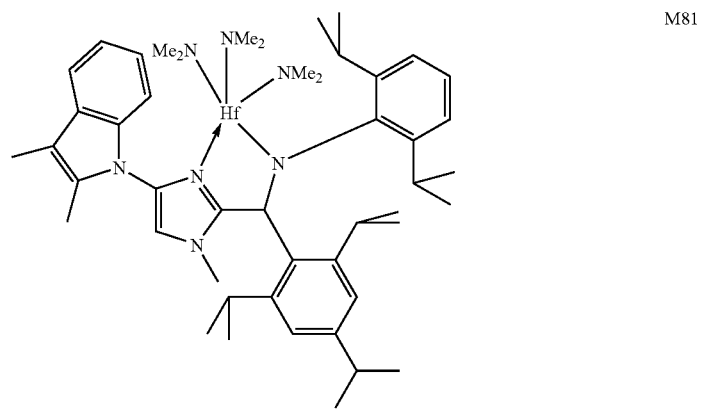
M81

TABLE 2-continued
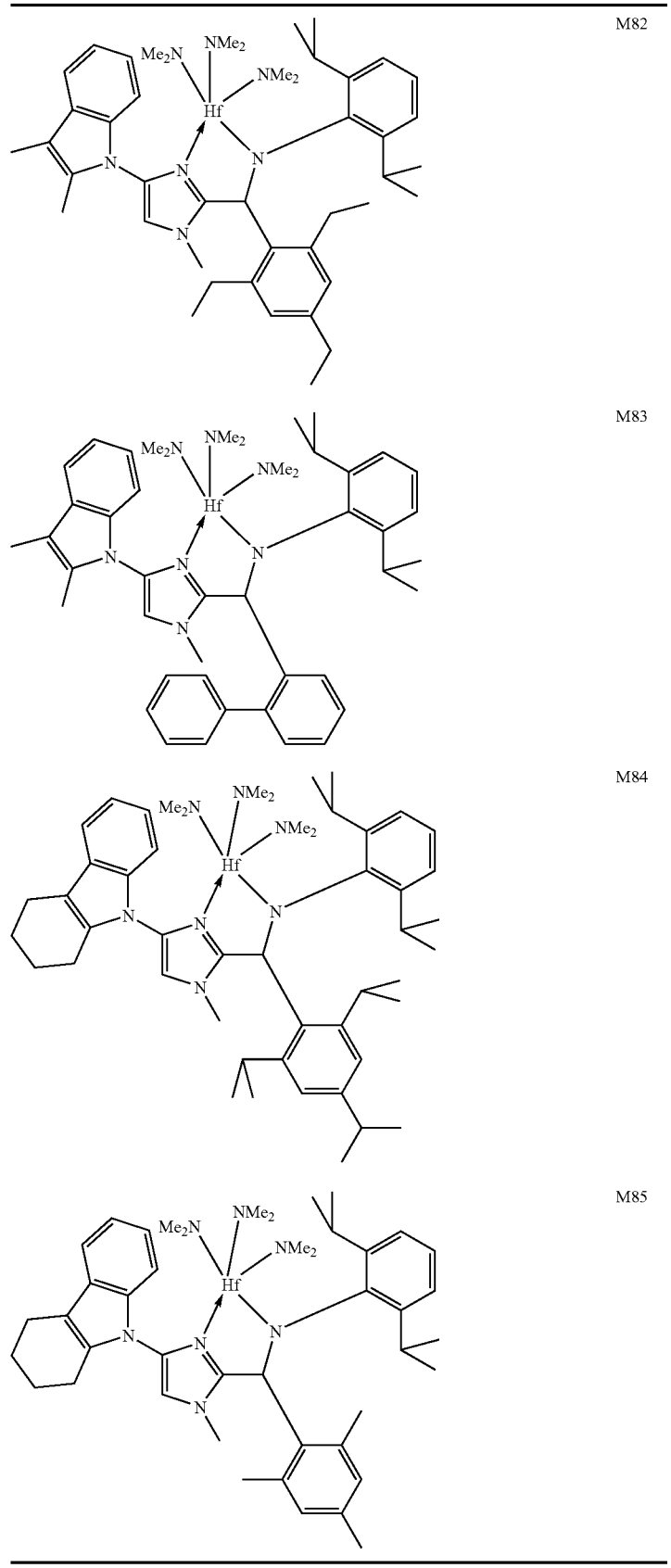

The choice of particular metals, R, T and J groups, and L ligands in the metal-ligand complexes of the invention can have a strong influence on the catalysis of particular transformations. Thus, for example, in particular polymerization reactions the choice of substitutent can affect catalyst activity, thermal stability, molecular weight of the product polymer, or the degree and/or kind of stereo- or regioerrors, as well as other factors known to be significant in the production of various polymers.

In particular, the choices of ligand R, T and J groups for production of isotactic polypropylene and ethylene-octene copolymers discussed above apply in particular embodiments of the metal-ligand complexes of the invention. In addition, in some embodiments involving catalysts for preparation of isotactic polypropylene, M is hafnium or zirconium and the ligands L are selected from the group consisting of alkyl and dialkyl amino, more specifically from the group consisting of methyl and dimethylamino. Specific (2,1) and (3,2) metal complexes that are useful for the production of isotactic polypropylene are shown in Table 3.

TABLE 3

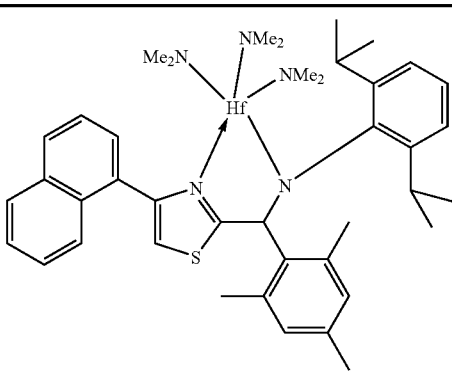

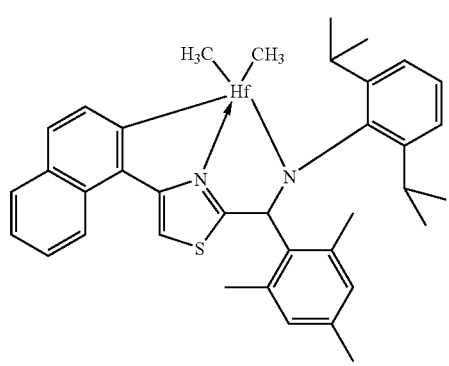

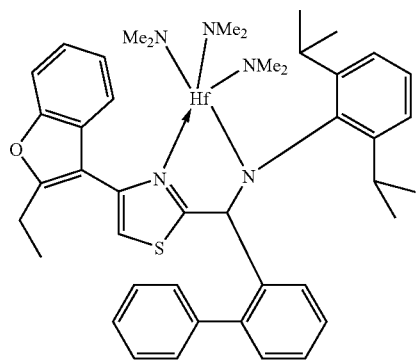

TABLE 3-continued

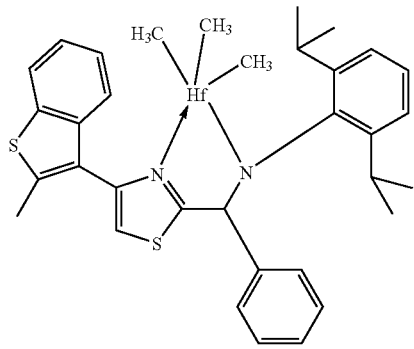

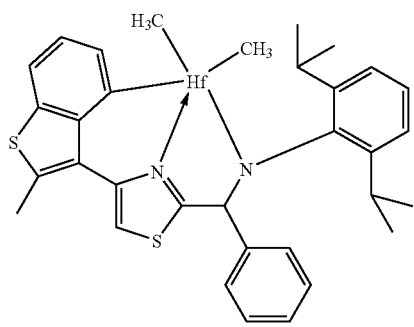

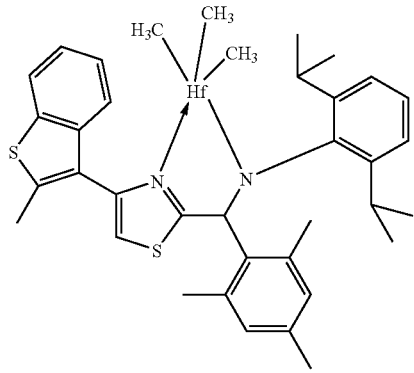

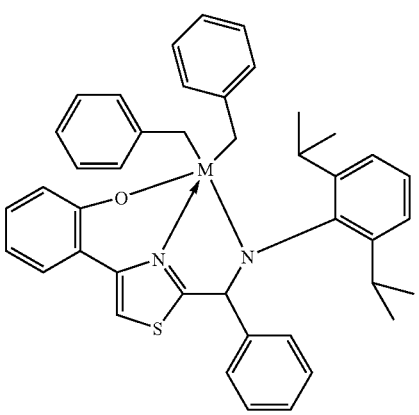

M = Zr, Hf

TABLE 3-continued
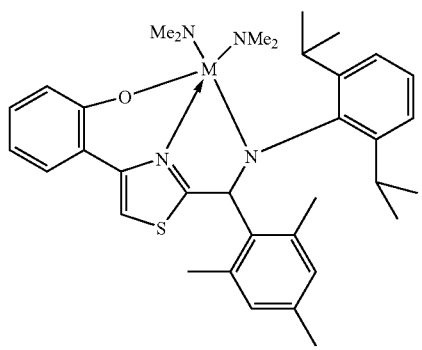
M = Zr, Hf
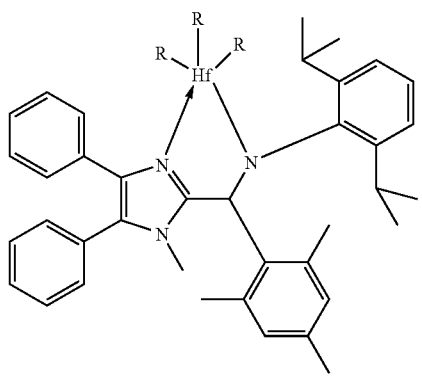
R = NMe₂, CH₃
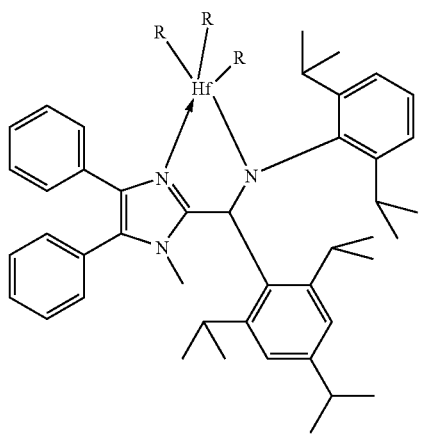
R = NMe₂, CH₃
TABLE 3-continued
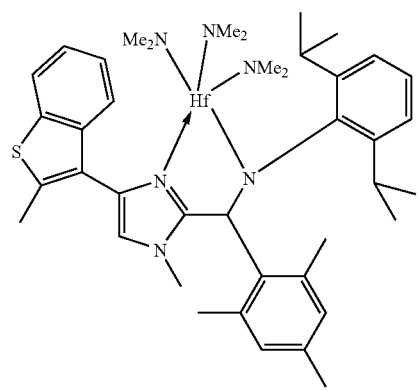
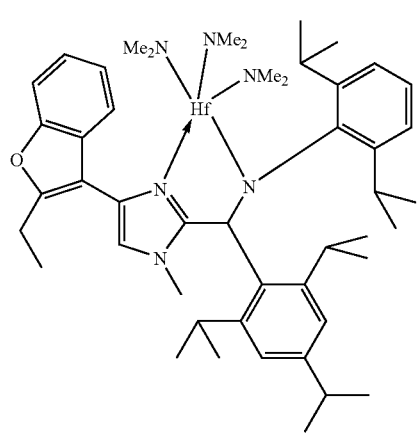
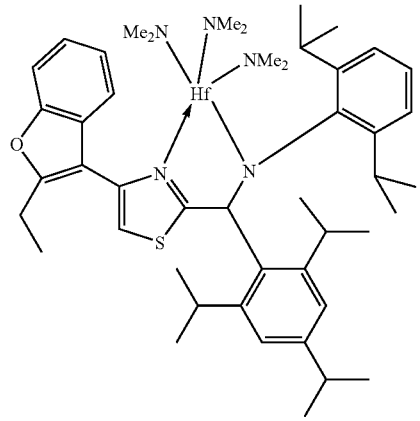

TABLE 3-continued
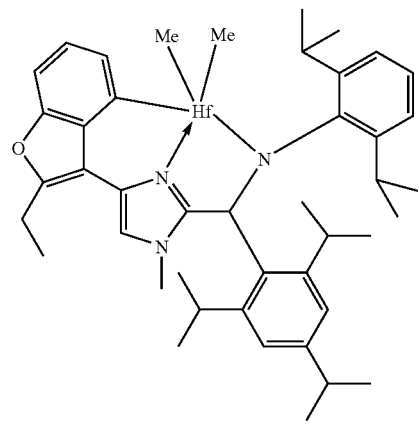
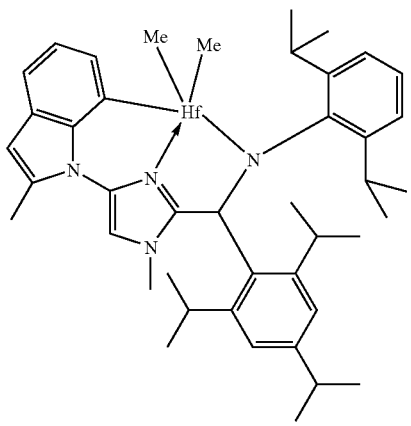
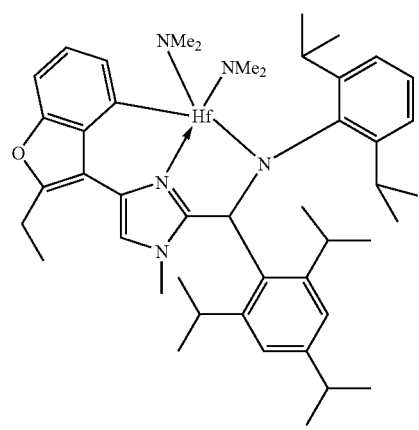
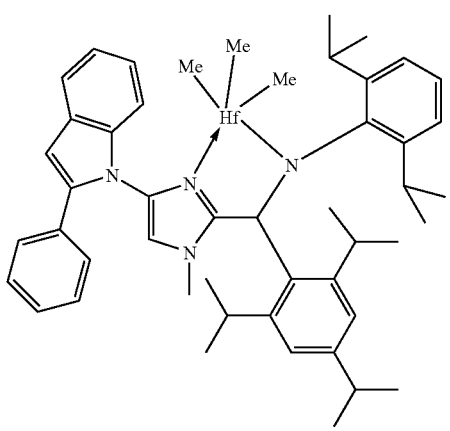
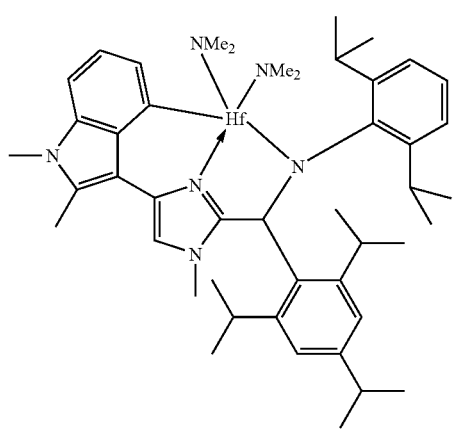
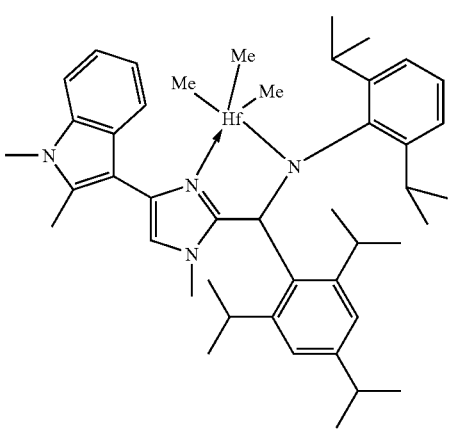

TABLE 3-continued

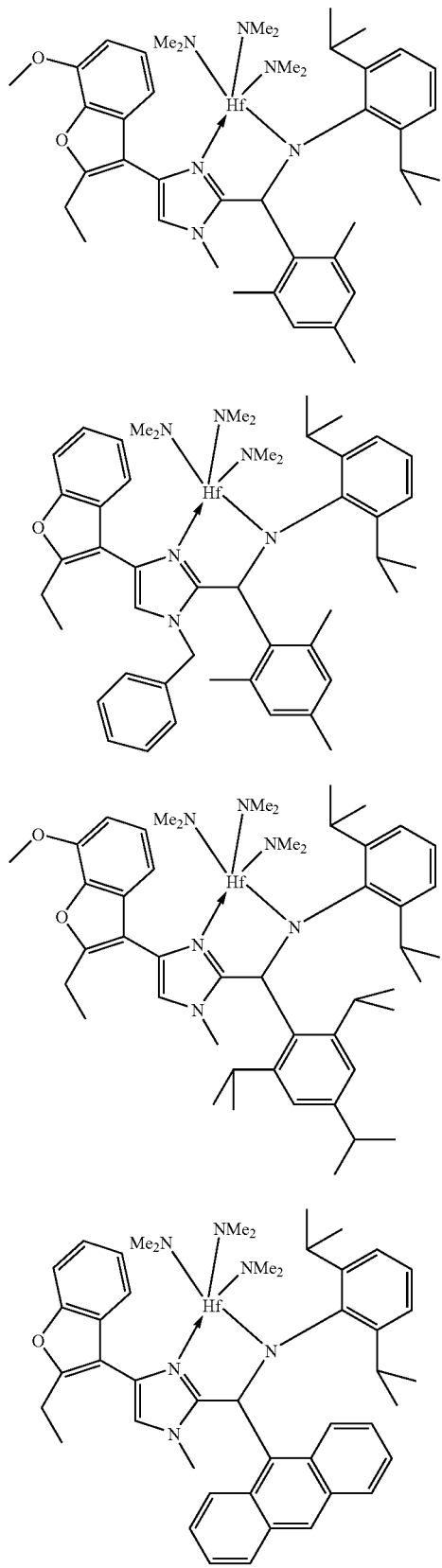

TABLE 3-continued

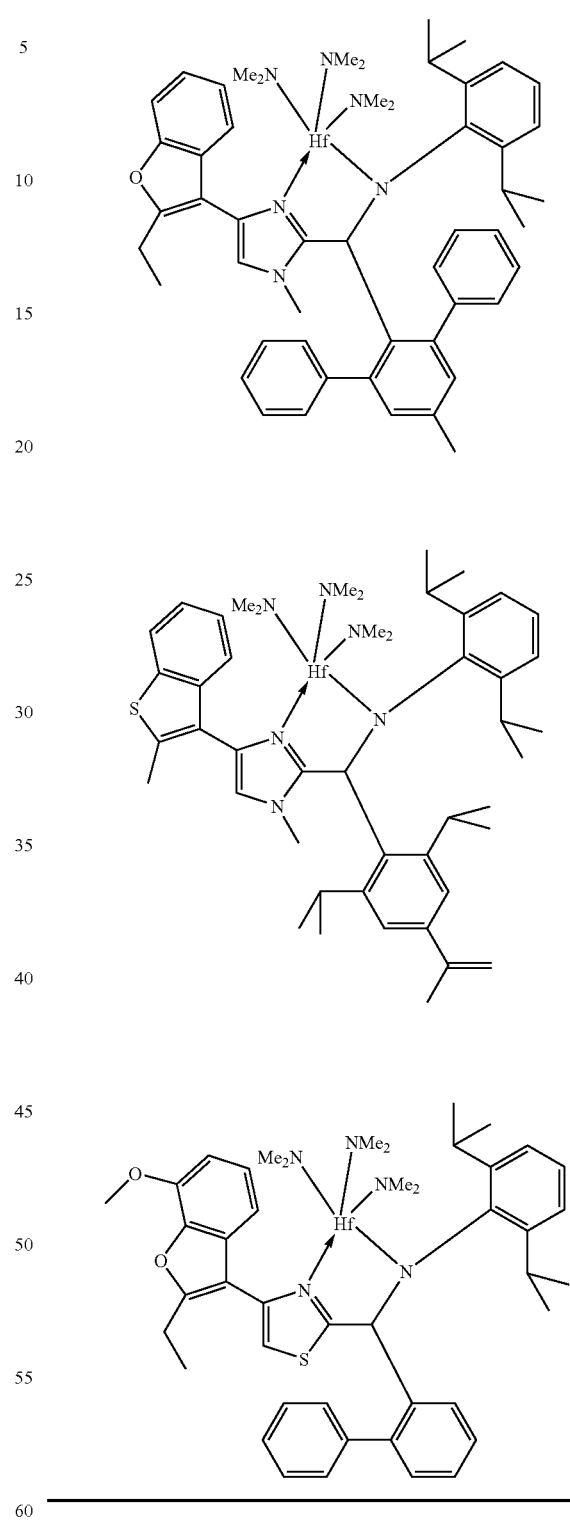

Likewise, in some embodiments involving catalysts for preparation of copolymers of ethylene and octene, M is hdafnium or zirconium and the ligands L are selected from the group consisting of methyl and dimethylamino. Specific ligand-metal complexes that are useful for production of ethylene-octene copolymers are shown in Table 4.

TABLE 4
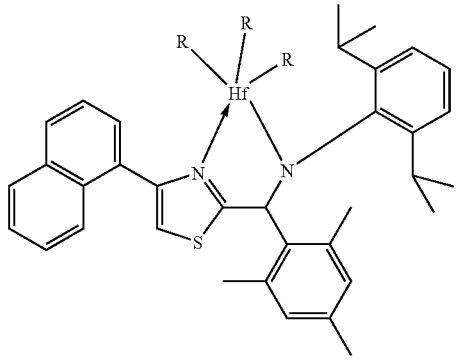
R = NMe₂, CH₃
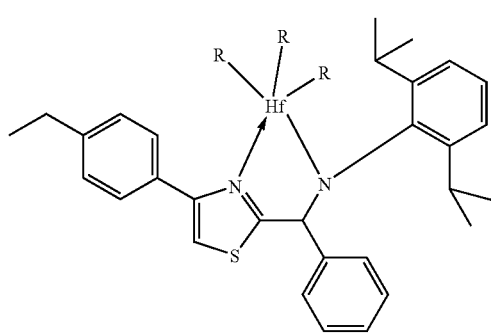
R = NMe₂, CH₃
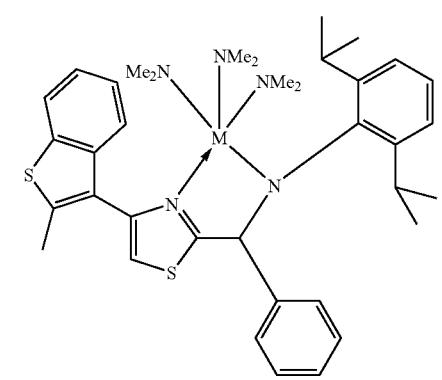
M = Zr, Hf
TABLE 4-continued
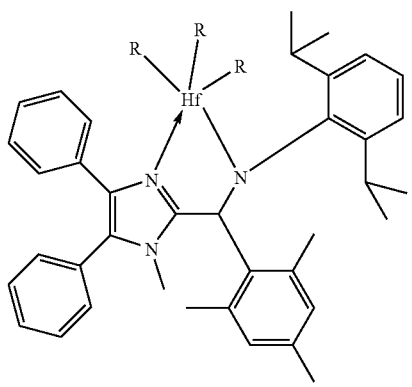
R = NMe₂, CH₃
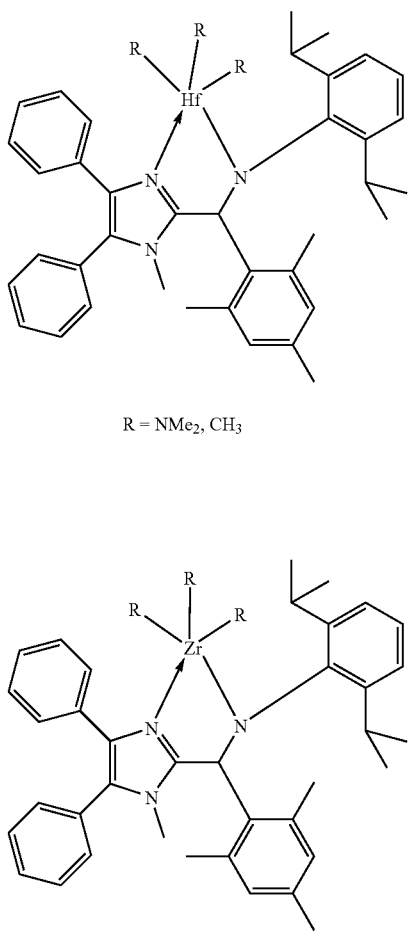
R = NMe₂, CH₃
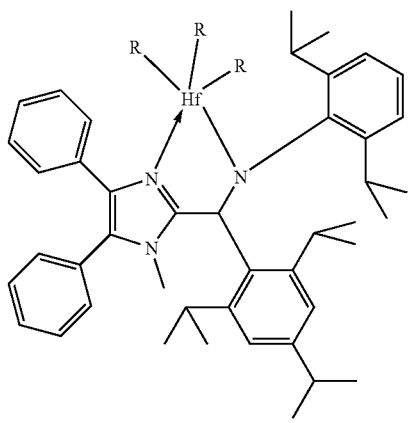
R = NMe₂, CH₃

TABLE 4-continued
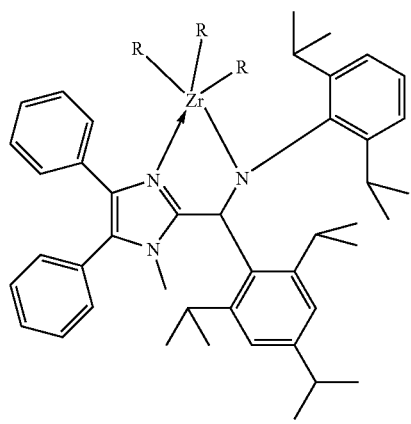
R = NMe₂, CH₃
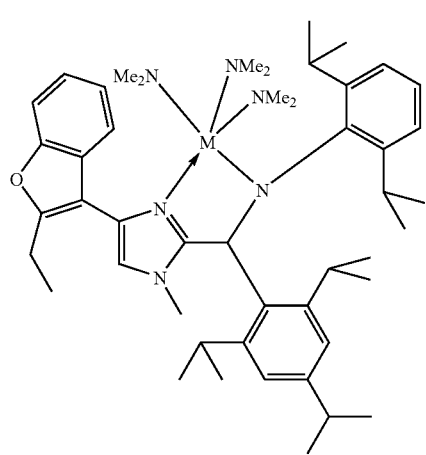
M = Zr, Hf
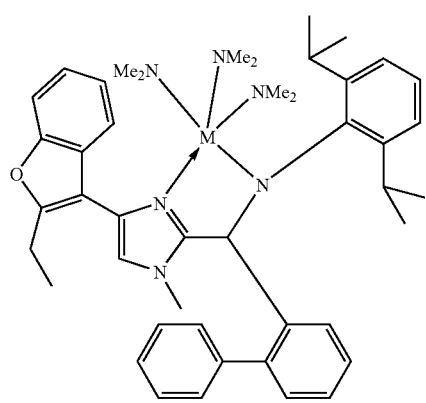
M = Zr, Hf
TABLE 4-continued
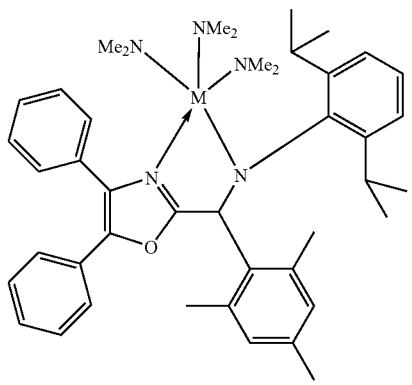
M = Zr, Hf
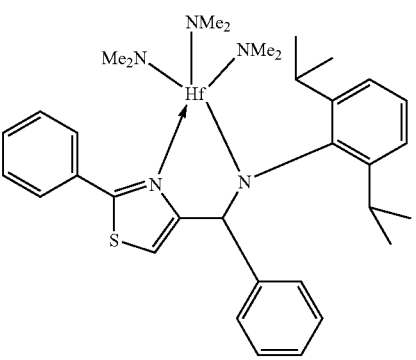
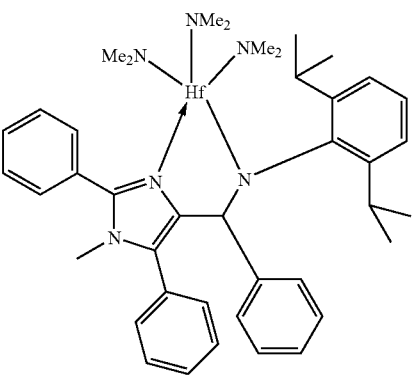
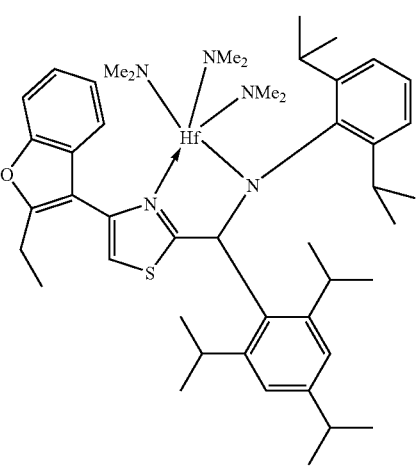

TABLE 4-continued
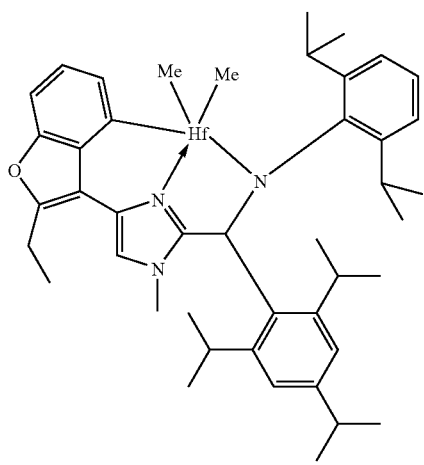
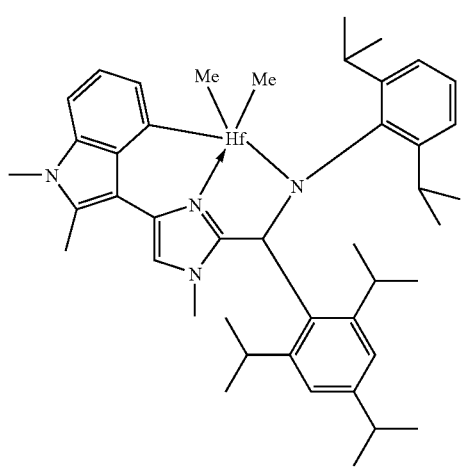
TABLE 4-continued
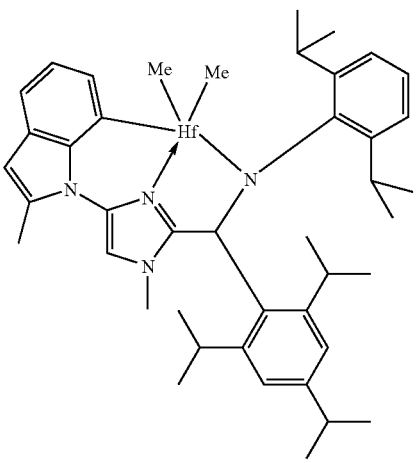
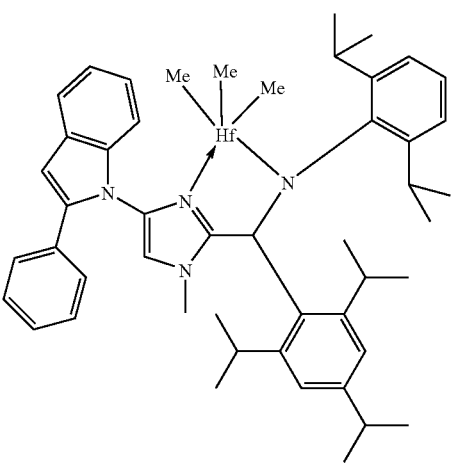

TABLE 4-continued
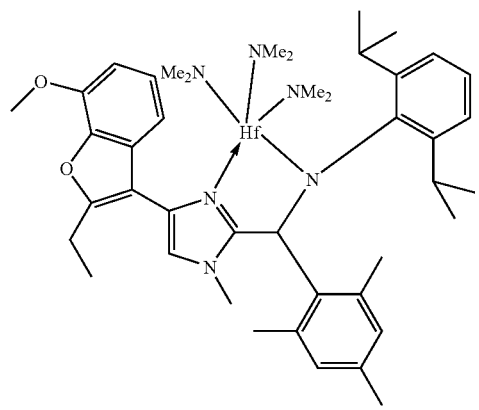
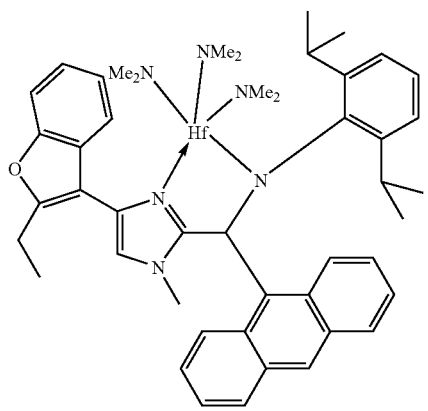
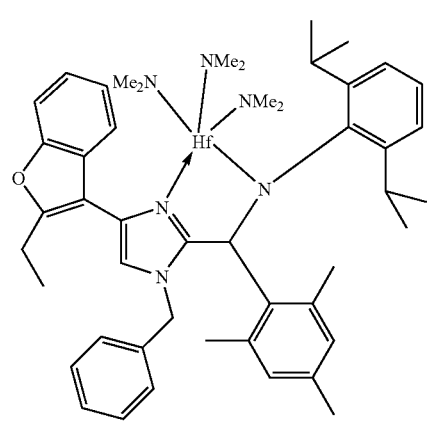
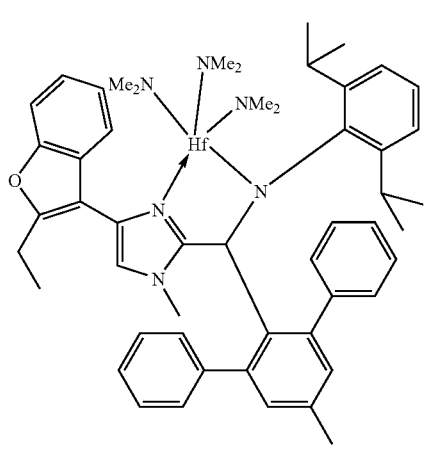
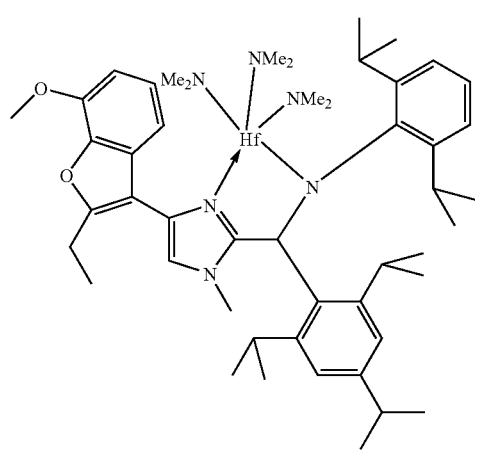
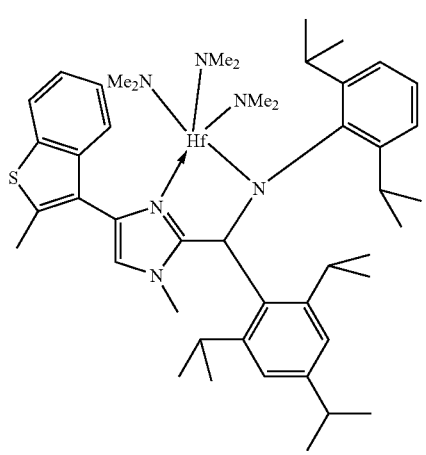

TABLE 4-continued

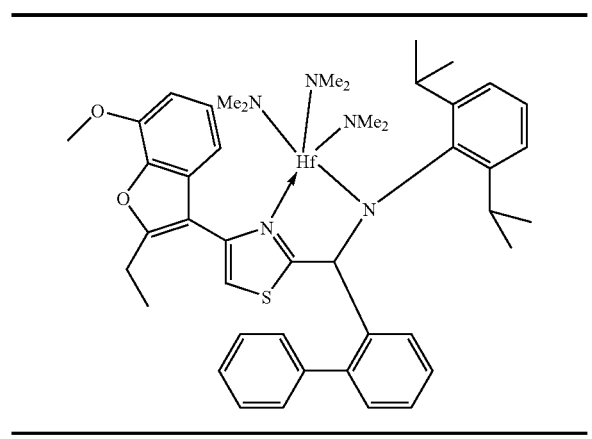

The complexation can be carried out using known methods, such as those described in U.S. Pat. No. 6,750,354 and references therein. It should be noted that in many cases the (3,2) complexes can be formed by thermolysis or activation of the (2,1) complexes. The synthetic routes used include the direct reaction of the ligand with a metal alkyl precursor (e.g. HfBz$_4$) to form the (2,1) (Scheme M1) or (3,2) (Scheme M2) complex with concurrent formation of alkane. See Boussie et al., *J. Am. Chem. Soc.* 2003, 125, 4306-4317; Kui et al., *Angew. Chem. Int. Ed.* 2003, 42, 1628-1632.

Scheme M1

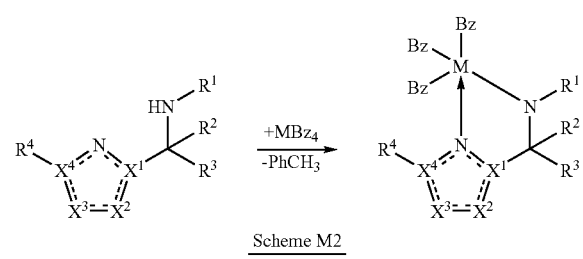

Scheme M2

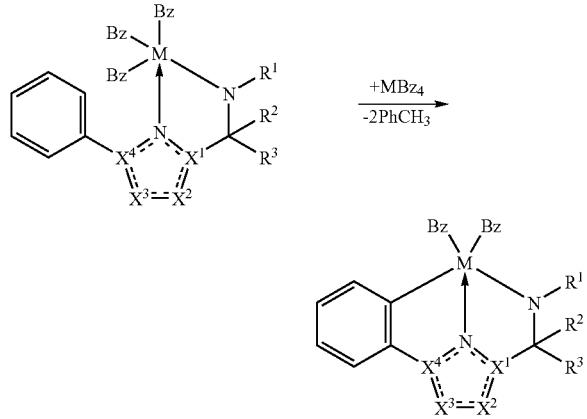

Alternatively, the ligand can be reacted with a metal amide precursor, such as Hf(NMe$_2$)$_4$, to form the (2,1) (Scheme M3) or (3,2) complex (Scheme M4) with concurrent formation of amine. Synthesis of amide precursors is described in U.S. Pat. No. 6,750,354 and references therein, as well as Diamond et al., *J. Am. Chem. Soc.* 1996, 118, 8024-8033, and Schrock et al., *Organometallics* 2000, 19, 5325-5341.

Scheme M3

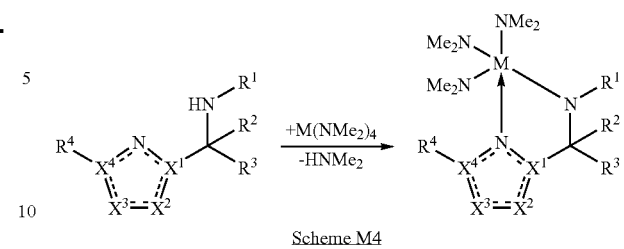

Scheme M4

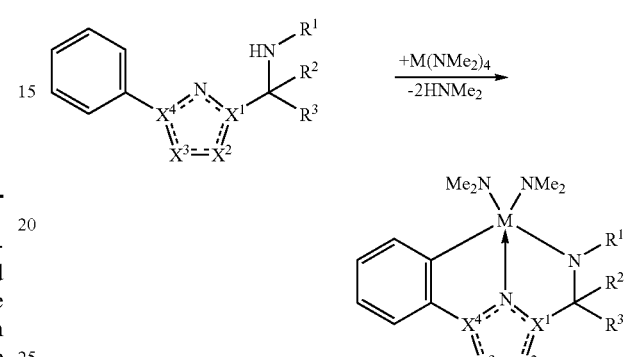

The amide complexes can be converted into alkyl complexes as shown in Scheme M5, via direct reaction with a Group 13 reagent such as AlMe$_3$, as described in U.S. Pat. No. 6,750,354 and references therein, and Diamond et al., *J. Am. Chem. Soc.* 1996, 118, 8024-8033.

Scheme M5

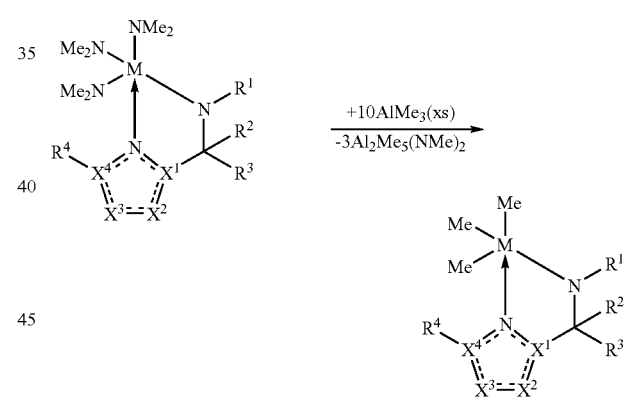

Alkyl complexes can also be prepared by exchange of amide ligands for halides followed by reaction with 3 equivalents of a Grignard reagent, as shown in Scheme M6 and described in Diamond et al., *J. Am. Chem. Soc.* 1996, 118, 8024-8033, and Schrock et al., *Organometallics* 2000, 19, 5325-5341.

Scheme M6

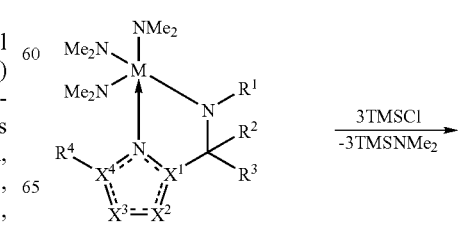

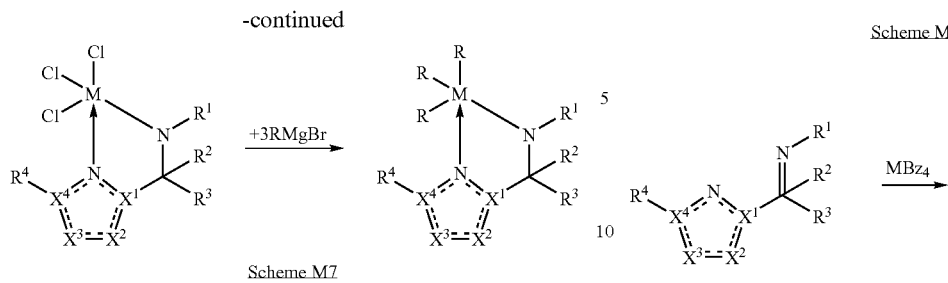

Scheme M7

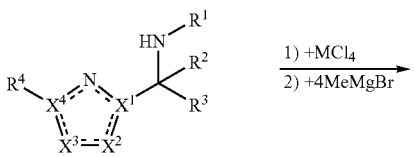

In a variation of the routes described in Schemes M6 and M7, it may be possible to prepare the metal-ligand complexes by formation of the lithium salt of the ligand followed by reaction with MCl₄ (or a Lewis base adduct thereof), as shown in Scheme M8, to generate the trichloride species, which is then alkylated to form the alkyl complex.

Scheme M8

In some instances, complexes can also be formed by reaction of a heteroaryl-imine ligand with 1 equivalent of a Group 4 metal alkyl complex such as M(CH₂Ph)₄(M=Zr, Hf). The complexation proceeds with net addition of the metal-alkyl across the imine C=N double bond to form a (2,1) complex, as shown in Scheme M9, below. (See, e.g., Jayaratne and Sita, *J. Am. Chem. Soc.* 2000, 122, 958-959). In other instances, a metal precursor and a heteroarylimine ligand may be combined with an activator and/or group 13 reagent (or a combination of an activator with a group 13 reagent) to convert the heteroarylimine ligand into a (2,1) complex.

Scheme M9

In some instances, the (2,1) metal complex resulting from the above reaction may undergo an orthometallation reaction to produce a (3,2) complex, as shown in Scheme M10.

Scheme M10

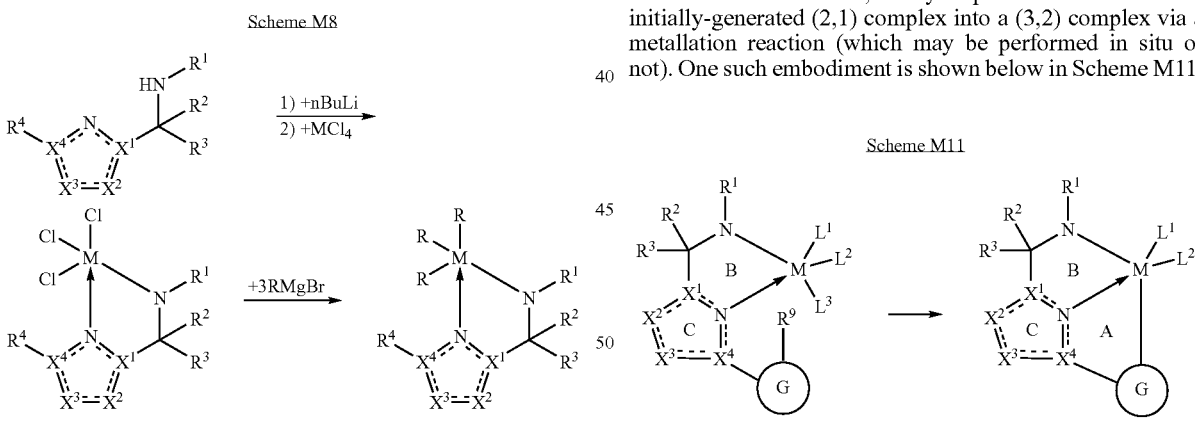

In some embodiments, it may be possible to transform an initially-generated (2,1) complex into a (3,2) complex via a metallation reaction (which may be performed in situ or not). One such embodiment is shown below in Scheme M11:

Scheme M11

Figure 1B:
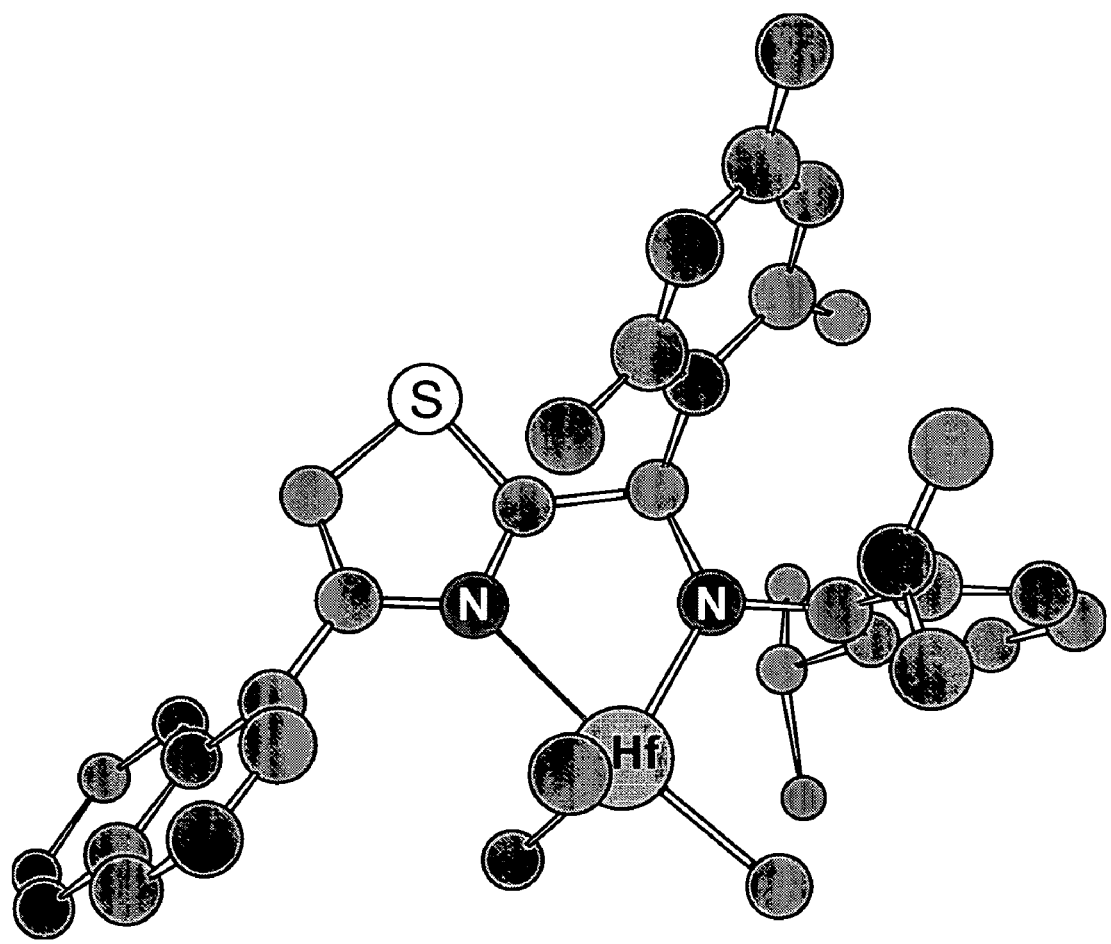
Figure 3:
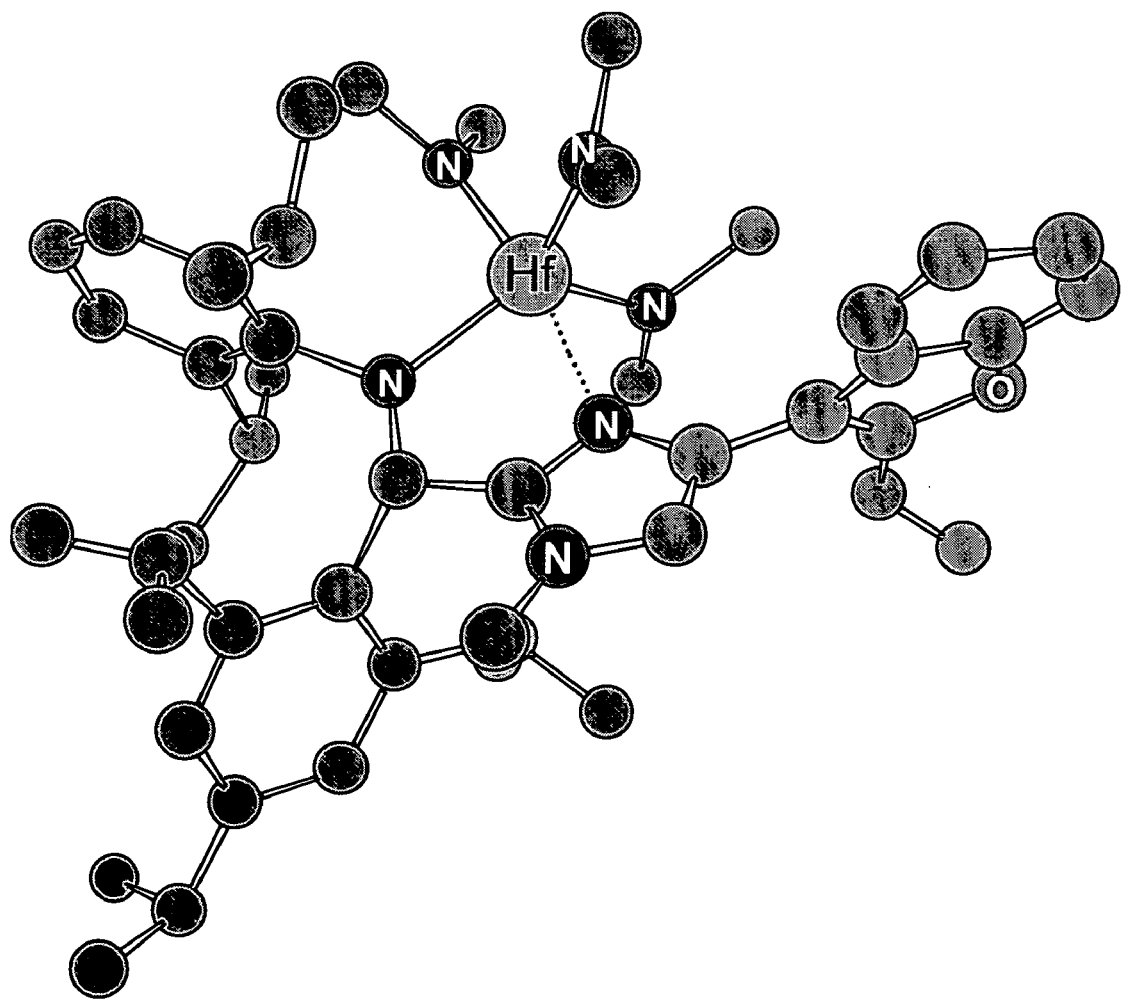
FIG. 3 is an X-ray structure determination of an imidazole-amine (2,1) complex according to one aspect of the invention.

In the embodiment illustrated in Scheme M11, R⁹ is hydrogen (but see above for the full definition of $R^9$ in other embodiments of the invention). The metallation reaction to convert the (2,1) complex on the left to the (3,2) complex on the right can occur via a number of mechanisms, likely depending on the substituents chosen for $L^1$, $L^2$ and $L^3$ and $R^1$-$R^3$, as well as the other substituents on Ring C and Ring G. In one embodiment, when $L^1$, $L^2$ and $L^3$ are each —N(CH₃)₂, the reaction can proceed by heating the (2,1) complex to a temperature above about 100° C. In this embodiment, it is believed that $L^1$ and $L^2$ remain —N(CH₃)₂ in the (3,2) complex. In another embodiment when $L^1$, $L^2$ and L³ are each —N(CH₃)₂, the reaction can proceed by adding a group 13 reagent (as described below) to the (2,1) complex at a suitable temperature (such as room temperature). Preferably the group 13 reagent for this purpose is di-isobutyl aluminum hydride, tri-isobutyl aluminum or trimethyl aluminum. In this embodiment, L¹ and L² are typically converted to the ligand (e.g., alkyl or hydride) stemming from the group 13 reagent (e.g., from trimethyl aluminum, L¹ and L² are each CH₃ in the (3,2) complex). In some cases, transformation from the (2,1) complex to the (3,2) complex occurs only at elevated temperatures, or not at all. For example, the hafnium thiazole-amine complex M12 (shown in Table 2, above), where R¹ is 2,6-di-isopropyl phenyl, R³ is mesityl and R⁴' is napthyl undergoes metallation to form the complex M13 (also shown in Table 2) at 100° C. The thiazole-amine ligand A1 (shown in Table 1), where R¹ is 2,6-di-isopropyl phenyl, R³ is phenyl and R⁴' is 4-ethyl phenyl under equivalent complexation conditions forms only the non-orthometallated (2,1) hafnium complex (e.g., M1) (shown in Table 2). Crystal structures of the thiazole-amine (2,1) complexes M11 and M12 are shown in FIGS. 1A and 1B, respectively. A crystal structure of imidazole-amine (2,1) complex M48 is shown in FIG. 3.

In some embodiments, it may be possible to form more than one (3,2) complex with a given ligand and metal precursor (for example, when R⁴' is napthyl, or phenyl substituted with O-Me, OBz or OH in the ortho position), and in some cases the particular (3,2) complex formed may depend upon the particular complexation method or conditions used. In some such embodiments, as illustrated in Scheme M12 below, a given ligand may react with a metal precursor under some conditions to form a (3,2) complex containing two 5-membered metallocycles, while under other conditions the same ligand and metal precursor may react to form a (3,2) complex containing one 5-membered metallocycle and one 6-membered metallocycle. The resulting complexes can exhibit markedly different catalytic performance.

Figure 2:
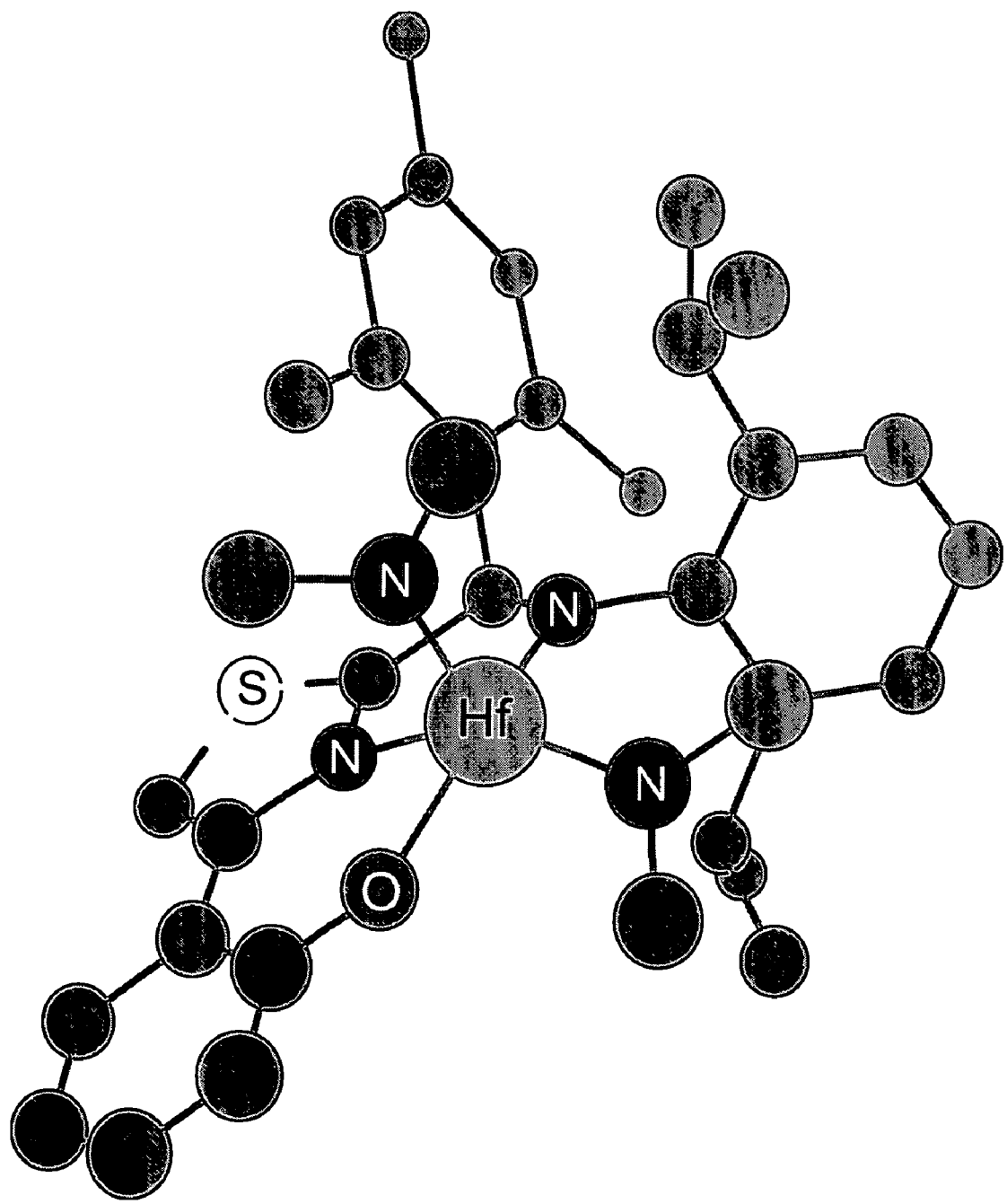
FIG. 2 is an X-ray structure determination of a thiazole-amine (3,2) complex according to one aspect of the invention.

Thus, in the example shown in Scheme M12, a carbon-metal-bound (3,2) complex M26, with two 5-membered metal-ligand chelate rings, is formed in the in absence of B(C₆F₅)₃, but in the presence of B(C₆F₅)₃, the heteroatom-metal-bound (3,1) complex M27 (with one 6-membered metal-chelate ring and one 5-membered metal-chelate ring) is formed. Upon activation, the (3,1) complex is demethylated to form a (3,2) complex. Polymerization of propylene with complex M26 was found to produce low tacticity polypropylene, while the latter (3,2) complex produces much higher tacticity polypropylene. The crystal structure of the thiazole-amine complex M31, which illustrates the two different chelate ring sizes, is shown in FIG. 2. Thus, by carefully selecting the complexation conditions, it may be possible in some embodiments to generate two or more active catalyst species from a single ligand-metal precursor combination, which can be used to provide particular mixtures of products—such as mixtures of polymers having different stereoconnectivity, or mixtures having bi- or multi-modal distributions of product composition or molecular weight.

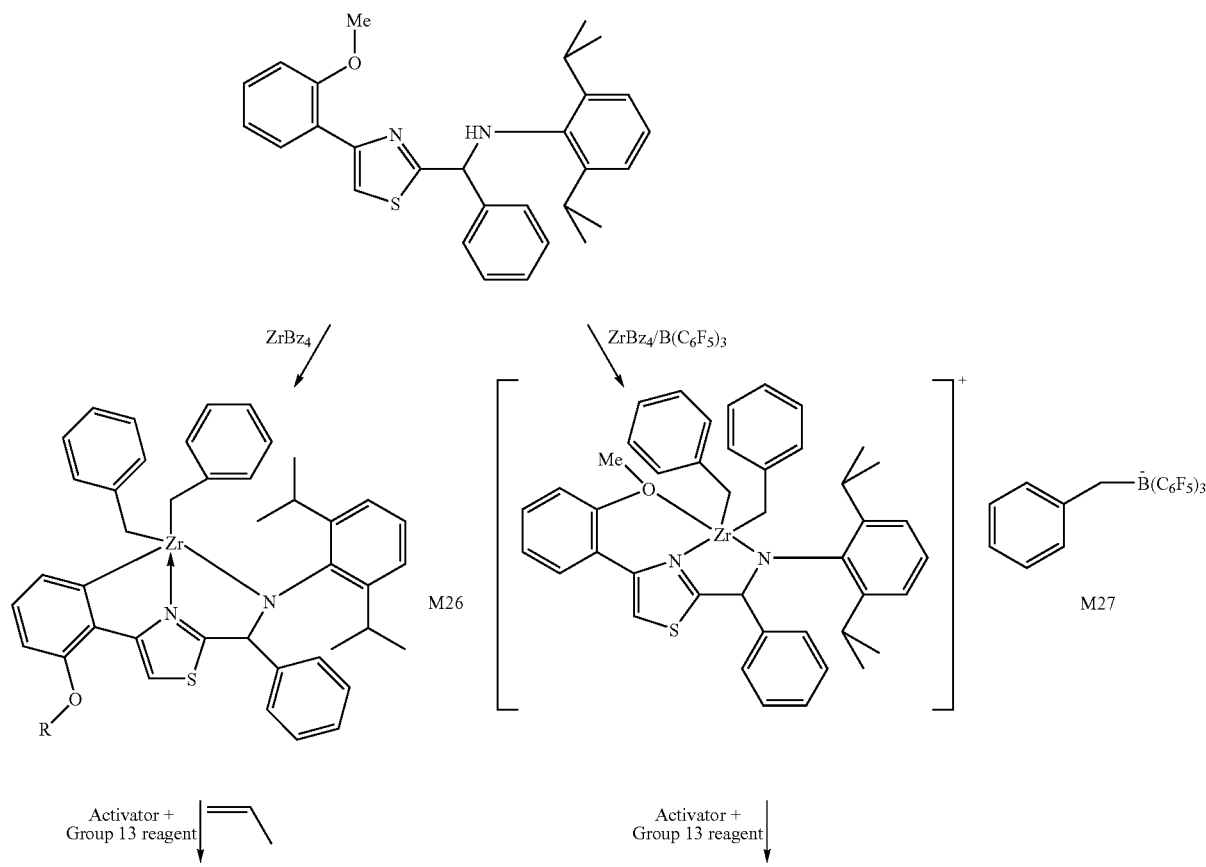

Scheme M12

Low tacticity Polypropylene

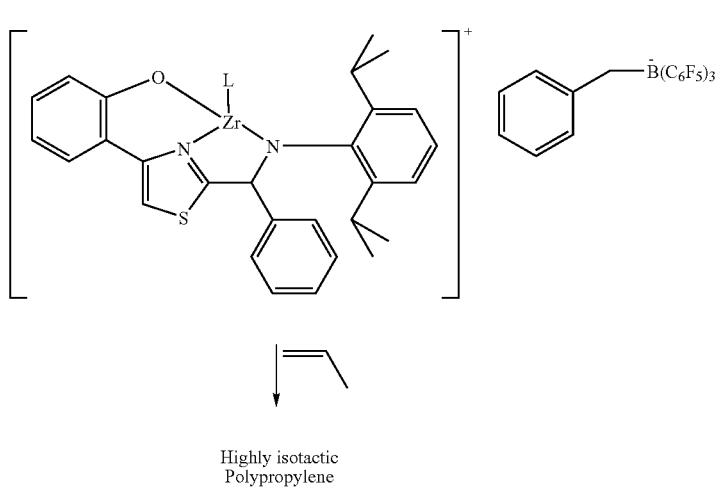

↓

Highly isotactic
Polypropylene

In some embodiments, the ligands, complexes and catalysts of the invention may be chiral (e.g., where $R^2$ and $R^3$ are different). Such chiral complexes may be useful as catalysts for a range of steroselective, enantioselective or asymmetric reactions, as will be discussed in more detail below.

In some embodiments, the ligands of this invention can exist as different stereoisomers, which may be enantiomeric or diastereomeric to each other. In some cases, it may be possible to separate mixtures of ligand enantiomers or diastereomers, for example by means of resolution of ligand enantiomers or diastereomers using a chiral reagent or chiral chromatography. See, for example, Jacques, et al., *Enantiomers, Racemates, and Resolution*", Krieger Publishing, Florida, 1991, and Beesley et al., *Chiral Chromatography*, John Wiley & Sons, New Jersey, 1999, and the references cited therein.

In some embodiments, the complexes according to the invention can exist as different stereoisomers, which may be enantiomeric or diastereomeric to each other. In some cases, it may also be possible to separate mixtures of enantiomers or diastereomers by means of resolution using a chiral reagent. See, for example, Ringwald et al., *J. Am. Chem. Soc.* 1999, 121, 1524-1527. Substantially enantiomerically pure complexes of this invention may also be obtained by employing substantially enantiomerically pure ligands of this invention in a suitable complexation reaction with a suitable metal precursor.

The ligands, complexes or catalysts may be supported on organic or inorganic supports. Suitable supports include silicas, aluminas, clays, zeolites, magnesium chloride, polystyrenes, substituted polystyrenes and the like. Polymeric supports may be cross-linked or not. Similarly, the ligands, complexes or catalysts may be supported on supports known to those of skill in the art. See for example, Hlatky, *Chem. Rev.* 2000, 100, 1347-1376 and Fink et al., *Chem. Rev.* 2000, 100, 1377-1390, both of which are incorporated herein by reference. The compositions, complexes and/or catalysts may be contacted with an activator (described below) before or after contact with the support; alternatively, the support may be contacted with the activator prior to contact with the composition, complex or catalyst. In addition, the catalysts of this invention may be combined with other catalysts in a single reactor and/or employed in a series of reactors (parallel or serial) in order to form blends of polymer products.

The metal-ligand complexes and compositions described herein are active catalysts typically in combination with a suitable activator, combination of activators, activating technique or activating package, although some of the ligand-metal complexes may be active without an activator or activating technique depending on the ligand-metal complex and on the process being catalyzed. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616, 664, 5,453,410, 5,153,157, 5,064,802, EP-A-277,004 and Marks et al., *Chem. Rev.* 2000, 100, 1391-1434. In some embodiments, ionic or ion forming activators are preferred. In other embodiments, alumoxane activators are preferred.

Suitable ion forming compounds useful as an activator in one embodiment comprise a cation that is a Bronsted acid capable of donating a proton, and an inert, compatible, non-interfering, anion, $A^-$. Suitable anions include, but are not limited to, those containing a single coordination complex comprising a charge-bearing metal or metalloid core. Mechanistically, the anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are well known and many, particularly such compounds containing a single boron atom in the anion portion, are available commercially.

Specifically, such activators may be represented by the following general formula:

$$(L^*-H)_d^+(A^{d-})$$

wherein $L^*$ is a neutral Lewis base; $(L^*-H)^+$ is a Bronsted acid; $A^{d-}$ is a non-interfering, compatible anion having a charge of d−, and d is an integer from 1 to 3. More specifically $A^{d-}$ corresponds to the formula: $(M'^{3+}Q_h)^{d-}$ wherein h is an integer from 4 to 6; h−3=d; M' is an element selected from group 13 of the periodic table; and Q is independently selected from the group consisting of hydrogen, dialkylamido, halogen, alkoxy, aryloxy, hydrocarbyl, and substituted-hydrocarbyl radicals (including halogen substituted hydrocarbyl, such as perhalogenated hydrocarbyl radicals), said Q having up to 20 carbons. In a more specific embodiment, d is one, i.e., the counter ion has a single negative charge and corresponds to the formula A$^-$.

Activators comprising boron or aluminum can be represented by the following general formula:

$$(L^*-H)^+(M''Q_4)^-$$

wherein: L* is as previously defined; M'' is boron or aluminum; and Q is a fluorinated $C_{1-20}$ hydrocarbyl group. Most specifically, Q is independently selected from the group consisting of fluorinated aryl group, such as a pentafluorophenyl group (i.e., a $C_6F_5$ group) or a 3,5-bis $(CF_3)_2C_6H_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium) tetraphenylborate, trimethylammonium tetrakis(pentafluorophenyl) borate, triethylammonium tetrakis (pentafluorophenyl) borate, tripropylammonium tetrakis (pentafluorophenyl) borate, tri(n-butyl)ammonium tetrakis (pentafluorophenyl) borate, tri(secbutyl)ammonium tetrakis (pentafluorophenyl) borate, N,N-dimethylanilinium tetrakis (pentafluorophenyl) borate, N,N-diethylanilinium tetrakis (pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate and N,N-dimethylanilinium tetrakis-(2,3,4,6-tetrafluorophenyl) borate; dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as: triphenylphospnonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate; N,N-dimethylanilinium tetrakis(3,5-bis (trifluoromethyl)phenyl)borate; $HNMe(C_{18}H_{37})_2{}^+B(C_6F_5)_4{}^-$; $HNPh(C_{18}H_{37})_2{}^+B(C_6F_5)_4{}^-$ and $((4-nBu-Ph)NH(n-hexyl)_2)^+B(C_6F_5)_4{}^-$ and $((4-nBu-Ph)NH(n-decyl)_2)^+B(C_6F_5)_4{}^-$. Specific $(L^*-H)^+$ cations are N,N-dialkylanilinium cations, such as $HNMe_2Ph^+$, substituted N,N-dialkylanilinium cations, such as $(4-nBu-C_6H_4)NH(n-C_6H_{13})_2{}^+$ and $(4-nBu-C_6H_4)NH(n-C_{10}H_{21})_2{}^+$ and $HNMe(C_{18}H_{37})_2{}^+$. Specific examples of anions are tetrakis(3,5-bis (trifluoromethyl)phenyl)borate and tetrakis (pentafluorophenyl)borate. In some embodiments, the specific activator is $PhNMe_2H^+B(C_6F_5)_4{}^-$.

Other suitable ion forming activators comprise a salt of a cationic oxidizing agent and a non-interfering, compatible anion represented by the formula:

$$(Ox^{e+})_d(A^{d-})_e$$

wherein: $Ox^{e+}$ is a cationic oxidizing agent having a charge of e+; e is an integer from 1 to 3; and $A^{d-}$, and d are as previously defined. Examples of cationic oxidizing agents include: ferrocenium, hydrocarbyl-substituted ferrocenium, $Ag^+$, or $Pb^{+2}$. Specific embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound that is a salt of a carbenium ion or silyl cation and a non-interfering, compatible anion represented by the formula:

$$©^+A^-$$

wherein: ©$^+$ is a $C_{1-100}$ carbenium ion or silyl cation; and A$^-$ is as previously defined. A preferred carbenium ion is the trityl cation, i.e. triphenylcarbenium. The silyl cation may be characterized by the formula $Z^4Z^5Z^6Si^+$ cation, where each of $Z^4$, $Z^5$, and $Z^6$ is independently selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, mercapto, alkylthio, arylthio, and combinations thereof. In some embodiments, a specified activator is $Ph_3C^+B(C_6F_5)_4{}^-$.

Other suitable activating cocatalysts comprise a compound that is a salt, which is represented by the formula $(A^*_{+a})_b(Z^*J^{*j})^{-c}{}_d$ wherein A* is a cation of charge +a; Z* is an anion group of from 1 to 50, specifically 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1 to 3, with the proviso that a×b is equal to c×d. See WO 99/42467, which is incorporated herein by reference. In other embodiments, the anion portion of these activating cocatalysts may be characterized by the formula $((C_6F_5)_3M''''-LN-M''''(C_6F_5)_3)^-$ where M'''' is boron or aluminum and LN is a linking group, which is specifically selected from the group consisting of cyanide, azide, dicyanamide and imidazolide. The cation portion is specifically a quaternary amine. See, e.g., LaPointe, et al., *J. Am. Chem. Soc.* 2000, 122, 9560-9561, which is incorporated herein by reference.

In addition, suitable activators include Lewis acids, such as those selected from the group consisting of tris(aryl) boranes, tris(substituted aryl)boranes, tris(aryl)alanes, tris (substituted aryl)alanes, including activators such as tris (pentafluorophenyl)borane. Other useful ion forming Lewis acids include those having two or more Lewis acidic sites, such as those described in WO 99/06413 or Piers, et al., *J. Am. Chem. Soc.*, 1999, 121, 3244-3245, both of which are incorporated herein by reference. Other useful Lewis acids will be evident to those of skill in the art. In general, the group of Lewis acid activators is within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion-forming activators. These compounds include a group 13 reagent that may be characterized by the formula $G^{13}R^{50}_{3-p}D_p$ where $G^{13}$ is selected from the group consisting of B, Al, Ga, In and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof. In other embodiments, the group 13 activator is an oligomeric or polymeric alumoxane compound, such as methylalumoxane and the known modifications thereof. See, for example, Barron, "*Alkylalumoxanes, Synthesis, Structure and Reactivity*", pp. 33-67 in *Metallocene-Based Polyolefins: Preparation, Properties and Technology*, J. Schiers and W. Kaminsky (eds.), Wiley Series in Polymer Science, John Wiley & Sons Ltd., Chichester, England, 2000, and references cited therein. In other embodiments, a divalent metal reagent may be used that is defined by the general formula $M'R^{50}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd and combinations thereof. In still other embodiments, an alkali metal reagent may be used that is defined by the general formula $M^{iv}R^{50}$ and in this embodiment $R^{50}$ is as defined above. $M^{iv}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1, 2, 3 or 4 and D is as defined above, with the proviso that there is at least one D that is a hydrogen.

The molar ratio of metal:activator (whether a composition or complex is employed as a catalyst) employed specifically ranges from 1: 10,000 to 100:1, more specifically from 1:5000 to 10:1, most specifically from 1:10 to 1:1. In one embodiment of the invention mixtures of the above compounds are used, particularly a combination of a group 13 reagent and an ion-forming activator. The molar ratio of group 13 reagent to ion-forming activator is specifically from 1:10,000 to 1000: 1, more specifically from 1:5000 to 100:1, most specifically from 1:100 to 100:1. In another embodiment, the ion forming activators are combined with a group 13 reagent. Another embodiment is a combination of the above compounds having about 1 equivalent of an optionally substituted N,N-dialkylanilinium tetrakis(pentafluorophenyl) borate, and 5-30 equivalents of a group 13 reagent. In some embodiments from about 30 to 2000 equivalents of an oligomeric or polymeric alumoxane activator, such as a modified alumoxane (e.g., alkylalumoxane), can be used.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

The ligands, compositions, complexes and/or catalysts of the invention can be used to catalyze a variety of transformations, including, for example, oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, Diels-Alder reactions, Baeyer-Villiger reactions, and other transformations. Some compositions, complexes and/or catalysts according to the invention are particularly effective at polymerizing ethylene or α-olefins (such as propylene, 1-butene, 1-pentene, 1-hexene, 1-heptene, 1-octene, and styrene), copolymerizing ethylene with α-olefins (such as propylene, 1-butene, 1-pentene, 1-hexene, 1-heptene, 1-octene, and styrene), copolymerizing ethylene with 1,1-disubstituted olefins (such as isobutylene), or copolymerizing ethylene, propylene and a diene monomer suitable for production of EPDM (Ethylene-Propylene-Diene Monomer) synthetic rubbers. Thus, for example, in some embodiments, metal-ligand compositions and complexes containing zirconium or hafnium may be useful in the polymerization of propylene to form isotactic polypropylene or in the copolymerization of ethylene and one or more α-olefins, as noted above. In other embodiments, vanadium and chromium compositions and/or complexes according to the invention may be useful in, for example, the polymerization of ethylene. The compositions, complexes and/or catalysts according to the invention may also polymerize monomers that have polar functionalities in homopolymerizations or copolymerizations and/or homopolymerize 1,1- and 1,2-disubstituted olefins. Also, diolefins in combination with ethylene and/or α-olefins or 1,1- and 1,2-disubstituted olefins may be copolymerized. In some embodiments, catalysts incorporating the ligands, compositions and/or complexes of the present invention exhibit high catalytic activity in the polymerization of such α-olefins, including at high temperatures.

In general monomers useful herein may be olefinically unsaturated monomers having from 2 to 20 carbon atoms either alone or in combination. Generally, monomers may include olefins (including cyclic olefins), diolefins and unsaturated monomers including ethylene and $C_3$ to $C_{20}$ α-olefins such as propylene, 1-butene, 1-hexene, 1-octene, 4-methyl-1-pentene, 1-norbornene, styrene and mixtures thereof; additionally, 1,1-disubstituted olefins, such as isobutylene, 2-methyl-1-butene, 2-methyl-1-pentene, 2-ethyl-1-pentene, 2-methyl-1-hexene, 3-trimethylsilyl-2-methyl-1-propene, α-methyl-styrene, either alone or with other monomers such as ethylene or $C_3$ to $C_{20}$ α-olefins and/or diolefins; additionally 1,2-substituted olefins, such as 2-butene. The α-olefins listed above may be polymerized in a stereospecific manner—for example, as in the generation of isotactic or syndiotactic or hemiisotactic polypropylene. Additionally the α-olefins may be polymerized to produce a polymer with differing tacticity sequences within the polymer chain, such as polypropylene containing atactic and isotactic sequences within the same polymer chain. Diolefins generally comprise 1,3-dienes such as (butadiene), substituted 1,3-dienes (such as isoprene) and other substituted 1,3-dienes, with the term substituted referring to the same types of substituents referred to above in the definition section. Diolefins also comprise 1,5-dienes and other nonconjugated dienes, such as ethylidene-norbornene, 1,4-hexadiene, dicyclopentadiene and other dienes used in the manufacture of EPDM synthetic rubbers. The styrene monomers may be unsubstituted or substituted at one or more positions on the aryl ring. The use of diolefins in this invention is typically in conjunction with another monomer that is not a diolefin. In some embodiments, acetylenically unsaturated monomers may be employed.

More specifically, it has been found that the catalysts of the present invention are particularly active for certain monomers, particularly α-olefins. Thus, the catalysts of the present invention may provide higher comonomer incorporation for copolymers of ethylene and co-monomers having three or more carbon atoms than is currently known from other catalysts. It has been found that particular catalysts of the present invention co-polymerize ethylene and styrene (or substituted styrenes), forming ethylene-styrene copolymers. Polymers that can be prepared according to the present invention include ethylene copolymers with at least one $C_3$-$C_{20}$ α-olefin, particularly propylene, 1-butene, 1-hexene, 4-methyl-1-pentene and 1-octene. The copolymers of ethylene with at least one $C_3$-$C_{20}$ α-olefin comprise from about 0.1 mol. % α-olefin to about 50 mol. % α-olefin, more specifically from about 0.2 mol. % α-olefin to about 50 mol. % α-olefin and still more specifically from about 2 mol. % α-olefin to about 30 mol. % higher olefin. For certain embodiments of this invention, product copolymers may include those of ethylene and a comonomer selected from the group consisting of propylene, 1-butene, 1-hexene, and 1-octene comprise from about 0.2 to about 30 mol. % comonomer, more specifically from about 1 to about 20 mol. % comonomer. In particular, in some embodiments ethylene copolymers with at least one $C_3$-$C_{20}$ α-olefin can be produced having a high molecular weight (e.g., greater than about 50,000, more specifically greater than about 150,000, and even more specifically greater than about 500,000) in a solution process at a temperature of greater than about 100° C., more specifically greater than about 130° C., and even more specifically greater than about 160° C. In certain embodiments, ethylene copolymers with at least one $C_3$-$C_{20}$ α-olefin can be produced with a low molecular weight (e.g., less than about 30,000, more specifically, less than about 15,000, and even more specifically less than about 5,000).

The ligands, compositions, complexes, and/or catalysts of the invention may also be used to catalyze other (i.e., non-polymerization) transformations. For example, in some instances, substantially diastereomerically pure or substantially enantiomerically pure complexes may be useful for stereoselective, asymmetric, enantioselective, or diastereoselective reactions or transformations. Thus, in some embodiments substantially enantiomerically- or diastereomerically-pure complexes, ligand-metal compositions, and catalysts according to the invention may be used as asymmetric catalysts for a range of reactions, including polymerization reactions and other (non-polymerization) reactions, including many reactions useful in organic synthesis. In some embodiments, catalysts incorporating the compositions and complexes of the invention may be used to catalyze the asymmetric production of reaction products with enantiomeric excess (ee) or diastereomeric excess (de) of greater than 90% or greater than 99%. The asymmetric synthesis of chiral organic molecules is an important field, and is critical in the synthesis of many pharmaceuticals and other products. Single enantiomers of a chiral product can be prepared by a variety of techniques, including the resolution of racemates, or the use of substantially enantiomerically pure starting materials from the chiral pool of natural products, but for large scale synthesis the use of enantioselective catalysis is often the most attractive, and most economical, choice. See, e.g., Blaser et al., "Enantioselective Synthesis", pp. 1131-1149, in *Applied Homogeneous Catalysis with Organometallic Compounds*, Vol. 3, Cornils, B., & Herrmann, W. (eds.), 2nd Edition, Wiley-VCH, Weinheim, Germany, 2002, and *Catalytic Asymmetric Synthesis*, Ojima (ed.), VCH Publishers, Inc., New York, 1993, and the references cited therein.

In recent years there have been many reports in the literature of the use of chiral Group 4 (titanium, zirconium or hafnium) ligand-metal compositions and complexes as stereoselective catalysts for a range of non-polymerization reactions, including many enantioselective (or asymmetric) reactions useful in organic synthesis. See, e.g., Maruoka, "Asymmetric Reactions with Chiral Lewis Acid Catalysts", pp. 413-440, in *Catalytic Asymmetric Synthesis*, Ojima (ed.), VCH Publishers, Inc., New York, 1993; see also *Titanium and Zirconium in Organic Synthesis*, Marek (ed.), Wiley-VCH Verlag GmbH & Co. KGaA, Weinheim, Germany, 2002, and in particular Hoveyda, "Chiral zirconium catalysts for enantioselective synthesis", included therein at pp. 180-229; see also Negishi, *Pure Appl. Chem.* 2001, 73, 239-242, and Scott et al., *Chemical Comm.* 2004, 894-895, and the references cited therein. Examples of asymmetric or enantioselective reactions catalyzed by chiral Group 4 catalysts include olefin hydrogenation, olefin epoxidation, olefin isomerization, olefin-pyridine coupling, imine hydrogenation, aldol reactions, imino aldol reactions, epoxidation of allylic alcohols, alkylation of aldehydes, alkylation of imines, Diels-Alder reactions, Baeyer-Villiger reactions, hydroamination/cyclization of amino-alkenes, pinacol coupling of aldehydes, and hydrosilation of imines, ketones, and olefins. In some embodiments catalysts incorporating the ligands, compositions and complexes of the invention may be useful in catalyzing such reactions.

In some embodiments, the complexes and catalysts of the invention may be chiral (e.g., where $R^2$ and $R^3$ are different). Chiral group 4 metallocene complexes, especially chiral ansa-bridged metallocene complexes, have been used as asymmetric or enantioselective catalysts. See, e.g., Kuber, "Metallocenes as a Source of Fine Chemicals", pp. 893-902, in *Applied Homogeneous Catalysis with Organometallic Compounds*, Vol 2, Cornils, B., & Herrmann, W. (eds.), VCH, Weinheim, Germany, 1996, and Diamond et al., *J. Am. Chem. Soc.* 1996, 118, 8024-8033, and the references cited therein. Some of the disadvantages of group 4 metallocene based catalysts are described in WO 02/085820, including difficulty of synthesis and lack of thermal robustness. In common with the chiral group 4 metallocene systems described above, ligand-metal complexes, compositions, and catalysts of some embodiments of the invention possess Lewis-acidic metal centers in a chiral environment. However, in some embodiments the ligand-metal complexes, compositions, and catalysts of this invention show high thermal robustness and maintain high activity and high stereoselectivity at high temperatures, and may thus offer advantages over chiral Group 4 metallocenes for asymmetric or enantioselective catalysis.

In some embodiments, novel products, such as polymers, copolymers or interpolymers, may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, bottles, containers, foams, coatings, insulating devices and household items. Also, such functionalized polymers are useful as solid supports for organometallic or chemical synthesis processes.

The α-olefins listed above may be polymerized in a stereoselective manner to produce a substantially stereoregular polymer product (that is, a polymer product that is detectably enriched in m or r dyads (as determined, e.g., by $^{13}$C NMR) as compared to a corresponding atactic material), as in the generation of isotactic, syndiotactic or hemiisotactic poly-x-olefins. For example, in some embodiments 1-butene may be polymerized into isotactic poly-1-butene. Additionally, the α-olefins may be polymerized to produce a polymer with differing tacticity sequences within the polymer chain, such as polypropylene containing atactic and isotactic sequences within the same polymer chain. The stereoregularity may be interrupted by stereoerrors, in particular isolated stereoerrors, which is an indication of enantiomorphic side control. Also, in some embodiments the isotactic polypropylene may include regioerrors as described in the literature (see, e.g., Resconi et al., *Chem. Rev.* 2000, 100, 1253-1345).

More specifically, it has been found that particular catalysts of the present invention polymerize propylene to isotactic or crystalline polypropylene, forming polymers with novel properties. In particular, in some embodiments isotactic polypropylene can be produced having a narrow polydispersity (e.g., less than about 3.0 and more specifically less than 2.5) combined with a high molecular weight (e.g., greater than about 50,000, more specifically greater than about 100,000, even more specifically greater than about 150,000, and even more specifically greater than about 500,000) in a solution polymerization process at a temperature of greater than about 100° C., more specifically greater than 110° C. and even more specifically greater than 130° C. In certain embodiments, isotactic polypropylene can be produced with a low molecular weight (e.g., less than about 30,000, more specifically less than about 15,000, and even more specifically less than about 5,000). In some embodiments, broader polydispersities can be obtained for the isotactic polypropylene or other polymers (e.g., copolymers of ethylene and α-olefins as discussed in more detail below) produced according to the invention. In addition the isotactic polypropylene produced by certain embodiments of this invention can be prepared with few or no detectible using $^{13}$C NMR regio-errors (also known as regio-irregularities).

The isotactic polypropylene polymers formed from these catalysts in a solution polymerization process can be produced at a higher temperature than has been previously described, such as at a temperature of greater than about 100° C., more specifically greater than 110° C. and even more specifically greather than 130° C. The polymerization conditions are described herein, producing isotactic polypropylene with a crystallinity index of between about 0.35 and about 0.95, more specifically between about 0.65 and 0.95 and in some embodiments specifically above about 0.8, under the polymerization conditions employed. The crystallinity index is determined using FTIR as is known to those of skill in the art and calibrated based on a relative scale. In one embodiment, the crystallinity index value can be determined using commercially available FTIR equipment (such as a Bruker Equinox 55 with an IR Scope II in reflection mode using Pike MappIR software). The crystallinity index is obtained from the ratio of band heights at 995 cm$^{-1}$ and 972 cm$^{-1}$. Atactic polypropylene has a ratio of band heights or crystallinity index of 0.2. Greater than 98% isotactic polypropylene has a crystallinity index ratio of greater than 0.95. Generally, the amount of error in crystallinity index measurements is ±0.05. Polymer blends of various compositions show a linear relationship between % isotacticity and crystallinity index. See, for example, J. P. Luongo, *J. Appl. Polym. Sci.* 1960, 3, 302-309 and T. Sundell, et al., *Polymer* 1996, 37, 3227-3231, each of which is incorporated herein by reference.

As those of skill in the art will recognize, isotacticity can also be represented by percent pentads (% mmmm) as determined by $^{13}$C NMR spectroscopy. Proton decoupled $^{13}$C NMR spectroscopy can be performed using commercially available equipment (such as a Bruker 300 MHz at 100° C. probe temperature) to determine the degree of tacticity as % mmmm pentads (for assignment of $^{13}$C signals see the review H. H. Brintzinger et al., *Angew. Chem. Int. Ed. Eng.* 1995, 34, 1143, which is incorporated herein by reference; and Resconi, *Chem. Rev.* 2000, 100, 1253-1345 and Gibson et al., *Chem Rev.* 2003, 103, 283-315). For example, a 15-30 mg polymer sample is dissolved in a 1:1 mixture of $C_2D_2Cl_4$ and $C_2Cl_4$ by heating the sample to ca. 100° C. The % mmmm is determined by the ratio of peak integral from 23.5 to 21.5 ppm and peak integral 23.5 to 19 ppm (in the absence of significant chain end regio-irregularity signals in this region). Proton decoupled $^{13}$C NMR spectroscopy can be also performed to determine the frequency of and nature of stereoerrors and regioerrors.

In addition, the melting point of the crystalline polypropylene is generally in the range of from about 115° C. to about 165° C., more specifically between about 120° C. and 155° C., and in some embodiments specifically above about 150° C. Melting points are determined by differential scanning calorimetry, as is known in the art (see also the example section, herein).

Novel polymers, copolymers or interpolymers may be formed having unique physical and/or melt flow properties. Polymers that can be prepared according to the present invention include copolymers of ethylene and one or more α-olefins, such as copolymers of ethylene with at least one $C_4$-$C_{20}$ α-olefin, such as 1-butene, 1-hexene, 4-methyl-1-pentene, 1-octene or styrene. Similarly, the techniques described herein can be used to prepare propylene copolymers with at least one $C_4$-$C_{20}$ α-olefin. In some embodiments, the copolymers of ethylene or propylene with at least one $C_4$-$C_{20}$ α-olefin comprise from about 0.01 mol. % higher olefin to about 50 mol. % higher olefin, more specifically from about 0.1 mol. % higher olefin to about 50 mol. % higher olefin and still more specifically from about 1 mol. % higher olefin to about 30 mol. % higher olefin. For certain embodiments of this invention, crystalline copolymers include those of ethylene or propylene and a comonomer selected from the group consisting of ethylene, 1-butene, 1-hexene, 1-octene and styrene comprise from about 0.1 to about 50 mol. % comonomer, more specifically from about 1 to about 20 mol. % comonomer, even more specifically from about 2 to about 15 mol. % comonomer and most specifically from about 5 to about 12 mol. % comonomer.

The novel polymers disclosed herein can be employed alone or with other natural or synthetic polymers in a blend. Such other natural or synthetic polymers can be polyethylene (including linear low density polyethylene, low density polyethylene, high density polyethylene, etc.), atactic polypropylene, nylon, EPDM, ethylene-propylene elastomer copolymers, polystyrene (including syndiotactic polystyrene), ethylene-styrene copolymers and terpolymers of ethylene-styrene and other $C_3$-$C_{20}$ olefins (such as propylene).

Melt flow rate (MRF) for polypropylene and copolymers of propylene and one or more $C_4$-$C_{20}$ α-olefins is measured according to ASTM D-1238, condition L (2.16 kg, 230° C.). In some embodiments of this invention, the MFR is in the range of 0.005-1,000, more specifically 0.01-500 and even more specifically 0.1-100. Flex modulus for polypropylene and copolymer of propylene and one or more $C_4$-$C_{20}$ α-olefins is measured according to ASTM D-790. In some embodiments of this invention, the flex modulus ranges from 20,000-400,000 psi, more specifically from 20,000-300,000 psi and even more specifically from 100,000-200,000 psi. Notch izod impact for polypropylene and copolymer of propylene and one or more $C_4$-$C_{20}$ α-olefins is measured according to ASTM D-256A. In some embodiments of this invention, the notch izod impact ranges from 0.1 to no break in ft-lbs/in.

The novel polypropylene and copolymers of propylene and one or more $C_4$-$C_{20}$ α-olefins disclosed in the present invention are useful for a wide variety of applications, including films (such as blown and cast film, clarity film and multi-layer films), thermoforming (such as cups, plates, trays and containers), injection moulding, blow-moulding, foams (such as structural foams), pipe (such as potable water pipe and high pressure pipe), automotive parts, and other applications that will be evident to those of skill in the art.

Melt strength (measured in cN) and melt drawability (measured in mm/s) tests are conducted by pulling ("taking-up") strands of the molten polymers or blends at constant acceleration until breakage occurs. An experimental set-up comprises a capillary rheometer and a Rheotens apparatus as a take-up device. The molten strands are drawn uniaxially to a set of accelerating nips located 100 mm below the die. The force required to uniaxially extend the strands is recorded as a function of the take-up velocity or the nip rolls. In the case of polymer melts exhibiting draw resonance (indicated by the onset of a periodic oscillation of increasing amplitude in the measured force profile), the maximum force and wheel velocity before the onset of draw resonance are taken as the melt strength and melt drawability, respectively. In the absence of draw resonance, the maximum force attained during testing is defined as the melt strength and the velocity at which breakage occurs is defined as the melt drawability. These tests are typically run under the following conditions:

| | |
|---|---|
| Mass flow rate | 1.35 grams/min |
| Temperature | 190° C. |
| Equilibration time at 190° C. | 10 minutes |
| Die | 20:1 (with entrance angle of approximately 45 degrees) |
| Capillary length | 41.9 mm |
| Capillary diameter | 2.1 mm |
| Piston diameter | 9.54 mm |
| Piston velocity | 0.423 mm/s |
| Shear rate | 33.0 s$^{-1}$ |
| Draw-down distance (die exit to take-up sheels) | 100 mm |
| Cooling conditions | Ambient air |
| Acceleration | 2.4 mm/s$^2$ |

For some aspects of the present invention the novel polymers are useful to produce foams having improved properties. For foams and other applications requiring melt strength, the MFR is typically in the range of 0.1-10, more specifically in the range of 0.3-3 and most specifically in the range of 0.5-2. The melt strength is typically greater than 5 cN, more specifically greater than 9 cN and most specifically greater than 12 cN. The drawability is typically greater than 15 mm/sec, more specifically greater than 25 mm/sec and most specifically greater than 35 mm/sec.

In some aspects of the present invention, the novel polymers disclosed herein are useful for a wide variety of applications where certain optical properties are beneficial. Gloss is measured according to ASTM D-1746. Haze is measured according to ASTM D-1003 and clarity is measured according to ASTM D-2457. The novel polymers disclosed herein in some aspects are films having haze of less than 10%. In addition films having clarity of greater than 91% may be beneficially obtained.

Polymerization is carried out under polymerization conditions, including temperatures of from −100° C. to 300° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Slurry, suspension, gas phase and high-pressure processes as known to those skilled in the art may also be used with supported catalysts of the invention.

Other additives that are useful in a polymerization reaction may be employed, such as scavengers, promoters, modifiers and/or chain transfer agents, such as hydrogen, aluminum alkyls and/or silanes.

As discussed herein, catalytic performance can be determined a number of different ways, as those of skill in the art will appreciate. Catalytic performance can be determined by the yield of polymer obtained per mole of metal complex, which in some contexts may be considered to be activity. The examples provide data for these comparisons.

Another measure of catalyst polymerization performance is co-monomer incorporation. As is well known in the art, many ethylene copolymers are prepared using ethylene and at least one other monomer. These copolymers or higher order polymers in some applications require higher amounts of additional co-monomer(s) than have been practical with known catalysts. Since ethylene tends to be the most reactive monomer, obtaining higher co-monomer incorporations is a benefit that is examined for polymerization catalysts. Two useful co-monomers are 1-octene and styrene. This invention offers the possibility of higher incorporation of co-monomers such as 1-octene and styrene.

As stated herein, a solution process is specified for certain benefits, with the solution process being run at a temperature above 90° C., more specifically at a temperature above 100° C., further more specifically at a temperature above 110° C. and even further more specifically at a temperature above 130° C. Suitable solvents for polymerization are non-coordinating, inert liquids. Examples include straight and branched-chain hydrocarbons such as isobutane, butane, pentane, isopentane, hexane, isohexane, heptane, octane, Isopar-E® and mixtures thereof; cyclic and alicyclic hydrocarbons such as cyclohexane, cycloheptane, methylcyclohexane, methylcycloheptane, and mixtures thereof; perhalogenated hydrocarbons such as perfluorinated $C_{4-10}$ alkanes, chlorobenzene, and aromatic and alkyl substituted aromatic compounds such as benzene, toluene, mesitylene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, and vinyltoluene (including all isomers alone or in admixture). Mixtures of the foregoing are also suitable.

In some embodiments, a solution process is specified for crystalline polypropylene production. The solution process to prepare isotactic polypropylene comprises adding a catalyst and propylene monomer to a reactor and subjecting the contents to polymerization conditions.

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. Nos. 5,985,356, 6,030,917 and WO 98/03521, all of which are incorporated herein by reference, generally disclose combinatorial methods. In this regard, the ligands, metal-ligand complexes or compositions may be prepared and/or tested in rapid serial and/or parallel fashion, e.g., in an array format. When prepared in an array format, ligands, metal-ligand complexes or compositions may be take the form of an array comprising a plurality of compounds wherein each compound can be characterized by any of the above general formulas (i.e., I, II, III, etc.). An array of ligands may be synthesized using the procedures outlined previously. The array may also be of metal precursor compounds, the metal-ligand complexes or compositions characterized by the previously described formulae and/or description. Typically, each member of the array will have differences so that, for example, a ligand or activator or metal precursor or R group in a first region of the array may be different than the ligand or activator or metal precursor or R group in a second region of the array. Other variables may also differ from region to region in the array.

In such a combinatorial array, typically each of the plurality of compositions or complexes has a different composition or stoichiometry, and typically each composition or complex is at a selected region on a substrate such that each compound is isolated from the other compositions or complexes. This isolation can take many forms, typically depending on the substrate used. If a flat substrate is used, there may simply be sufficient space between regions so that there cannot be interdiffusion between compositions or complexes. As another example, the substrate can be a microtiter or similar plate having wells so that each composition or complex is in a region separated from other compounds in other regions by a physical barrier. The array may also comprise a parallel reactor or testing chamber.

The array typically comprises at least 8 compounds, complexes or compositions each having a different chemical formula, meaning that there must be at least one different atom or bond differentiating the members in the array or different ratios of the components referred to herein (with components referring to ligands, metal precursors, activators, group 13 reagents, solvents, monomers, supports, etc.). In other embodiments, there are at least 20 compounds, complexes or compositions on or in the substrate each having a different chemical formula. In still other embodiments, there are at least 40 or 90 or 124 compounds, complexes or compositions on or in the substrate each having a different chemical formula. Because of the manner of forming combinatorial arrays, it may be that each compound, complex or composition may not be worked-up, purified or isolated, and for example, may contain reaction by-products or impurities or unreacted starting materials.

The catalytic performance of the compounds, complexes or compositions of this invention can be tested in a combinatorial or high throughput fashion. Polymerizations can also be performed in a combinatorial fashion, see, e.g., U.S. Pat. Nos. 6,306,658, 6,508,984 and WO 01/98371, each of which is herein incorporated by reference.

EXAMPLES

General: All air sensitive reactions were performed under a purified argon or nitrogen atmosphere in a Vacuum Atmospheres or MBraun glove box. All solvents used were anhydrous, de-oxygenated and purified according to known techniques. All ligands and metal precursors were prepared according to procedures known to those of skill in the art, e.g., under inert atmosphere conditions, etc. Ethylene/1-octene copolymerizations and propylene polymerizations were carried out in a parallel pressure reactor, which is described in U.S. Pat. Nos. 6,306,658, 6,455,316, 6,489,168, and 6,548,026, and WO 00/09255, each of which is incorporated herein by reference.

High temperature Size Exclusion Chromatography was performed using an automated "Rapid GPC" system as described in U.S. Pat. Nos. 6,491,816, 6,491,823, 6,475,391, 6,461,515, 6,436,292, 6,406,632, 6,175,409, 6,454,947, 6,260,407, and 6,294,388 each of which is incorporated herein by reference. In the current apparatus, a series of two 30 cm×7.5 mm linear columns in used, with both columns containing PLgel 10 um, MixB (available from Polymer Labs). The GPC system was calibrated using narrow polystyrene standards. The system was operated at an eluent flow rate of 1.5 mL/min and an oven temperature of 160° C. o-dichlorobenzene was used as the eluent. The polymer samples were dissolved 1,2,4-trichlorobenzene at a concentration of about 5 mg/mL. 200 µL of a polymer solution were injected into the system. The concentration of the polymer in the eluent was monitored using an evaporative light scattering detector. All of the molecular weight results obtained are relative to linear polystyrene standards.

The ratio of 1-octene to ethylene incorporated in the ethylene-octene copolymer products was determined by Raman spectroscopy. All spectra were obtained using a Jobin Yvon Spectrometer LABRAM 3/203IM, 1×50 objective, YAG Laser with an acquisition from 100 cm-1 to 3450 cm-1, 1 second exposure, 5 repeat scans. Analysis was performed using LabSpec Spectral Software package by taking the absorbance of the peaks at 2955, 2956, and 2957 cm-1 (for the asymmetric CH3 stretch) and the peak maximum between 2844 and 2854 cm-1 (for the symmetric CH2 stretch). The absorbance of the baseline at 3200 cm-1 was then subtracted from these values and the peaks were ratioed. Mol % 1-octene values determined from x=A2956/A2848 ratio where Mol %=1068.7×2−35.711x+1.6825. This method was calibrated using a set of ethylene/1-octene copolymers with a range of known mol % 1-octene content.

Crystallinity in polypropylene was determined by FTIR spectroscopy. FTIR spectra of thin films deposited from solution onto gold coated Si wafers are acquired at 4 cm$^{-1}$ resolution and with 16 scans in reflection-absorption mode on a Bruker Equinox 55 FTIR spectrometer equipped with a Pike MappIR accessory. The height ratio of two bands at 997 cm$^{-1}$ (C—H bending and $CH_3$ rocking mode from regular crystalline isotactic helices) and 973 cm$^{-1}$ (coupled C—C stretching and $CH_3$ rocking mode, independent of crystallinity) is determined as a measure of isotacticity (as known in the art, see, e.g., J. P. Luongo, *J. Appl. Polym. Sci* 1960, 3, 302-309, and T. Sundell et al., *Polymer* 1996, 37, 3227-3231, each of which is incorporated herein by reference). For blends of atactic and isotactic polypropylene (PP) with 0-70% isotactic PP, the IR ratio is proportional to the percentage of isotactic PP. For greater than 98% isotactic PP the ratio is greater than 0.95, for amorphous PP the ratio is 0.2.

Differential Scanning Calorimetry (DSC) measurements were performed on a TA instrument DSC 2920 to determine the melting point of polymers. 3-5 mg of polymer were despoited as a 40 mg/mL solution in dichlorobenzene into an Aluminium substrate and dried. The sample was equilibrated at 200° C. and held for 10 minutes. The sample was then cooled with a rate of 10° C. per minute to −50° C. and data were collected during the cooling period. The sample was held at −50° C. for 4 minutes. Then, the sample was heated to 200° C. at a rate of 10° C./min and data were collected during that heating period. Reported are the peak maxima of the melting transition. In case of multiple peaks in the transition, multiple melting temperatures are reported, ("#/#").

I. Synthesis
  A. Synthesis of Ligands
    1. (Thiazol-2-yl)-alkyl Amine) Ligands
    a. General Synthetic Methods Method A1: Formation of 4-Bromo-2-Thiazolecarbaldehyde AA(2) from Dibromothiazole AA(1).

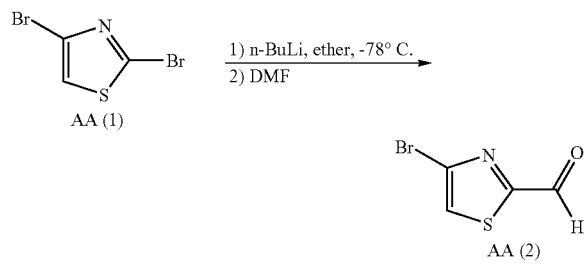

To a solution of n-BuLi (4.53 mmol, 1.6 M, 2.83 mL) in 10 mL of dry ether was added dropwise dibromothiazole AA(1) (1000 mg, 4.12 mmol) in 5 mL of dry ether at −78° C. The reaction mixture was then stirred at this temperature for 20 additional minutes. DMF (452 mg, 479 µL, 6.18 mmol) was then added and the resulting reaction mixture was then warmed up to room temperature and stirred for 1 hour. The reaction was quenched with saline (20 mL) and extracted with ether (2×30 mL). The organic layers were combined, dried over Na$_2$SO$_4$, and concentrated under reduced pressure. The crude product was purified by flash chromatography (Biotage FLASH 40M KP-Sil silica, 4:1; Hex: Ether) to give 505 mg of aldehyde AA(2) (64%). $^1$H NMR (CDCl$_3$, 300 MHz): 9.96 (d, J=1.2 Hz, 1H), 7.69 (d, J=1.2 Hz, 1H).

General Method A2: Boronic Acid Formation from Benzo-Heterocycle

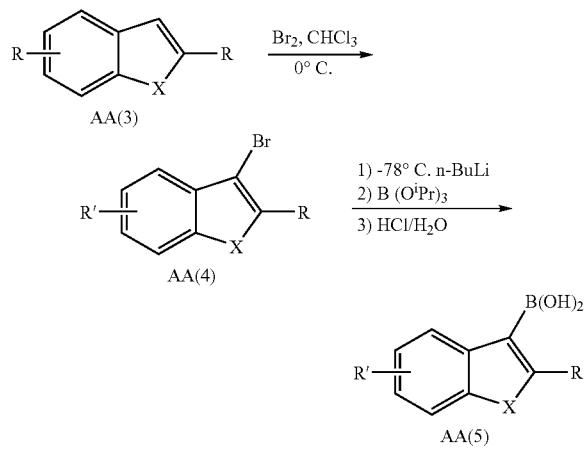

To a solution of benzo-heterocycle AA(3) (40.1 mmol) in 50 mL of CHCl$_3$ was added Br$_2$ (2.16 mL, 42.1 mmol) in 10 mL of CHCl$_3$ at 0° C. dropwise (within 15 minutes). After 10 minutes, the reaction was completed (by GC/MS). The reaction mixture was quenched with saturated Na$_2$S$_2$O$_3$ (sodium thiasulfate) aqueous solution and extracted with CH$_2$Cl$_2$ (2×50 mL). The organic layers were then combined and dried over Na$_2$SO$_4$ and concentrated under reduced pressure. Bromide AA(4) was then purified by column chromatography.

The purified bromide AA(4) (1.92 mmol) was dissolved in 20 mL of dry ether, and n-BuLi (1.32 mL, 2.11 mmol, 1.6 M) was added dropwise at −78° C. Dry B(O$^i$Pr)$_3$ (2.88 mmol, 662 µL) was added to the reaction mixture at −78° C. after the Li—Br exchange had taken place (GC/MS monitoring). The reaction was kept at this temperature for 10 additional minutes, and then gradually warmed up to room temperature. White precipitate was gradually formed. After 1 hour at room temperature, the reaction mixture was quenched with 1N HCl/H$_2$O (2×20 mL) and extracted with EtOAc (20 mL). The combined organic layers were then washed with 1N HCl/H$_2$O (40 mL), dried over Na$_2$SO$_4$ and concentrated under reduced pressure. Boronic acid AA(5) obtained was directly used for the Suzuki coupling reaction (General Method A3).

General Method A3: Suzuki Coupling

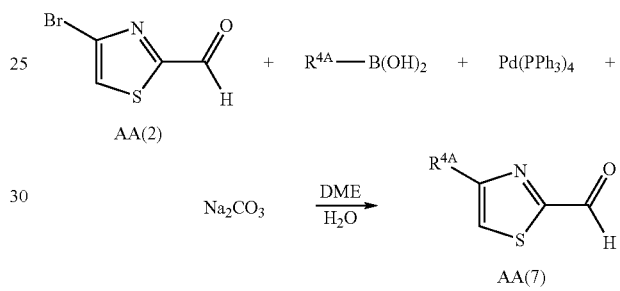

To a solution of 4-bromo-2-thiazolecarbaldehyde AA(2) (1 mmol) in a mixture of DME (10 mL) and H$_2$O (3 mL) was added R$^{4A}$—B(OH)$_2$ (1.5 mmol, 1.5 eq.) and Na$_2$CO$_3$ (318 mg, 3 eq.) at room temperature. The mixture was degassed by bubbling argon through the reaction mixture for 3 min. Pd(PPh$_3$)$_4$ (115 mg, 0.1 mmol, 0.1 eq.) was then added in the glove box and the resulting mixture was stirred at 85° C. under sealed-tube conditions overnight. The reaction mixture was then quenched with 20 mL of saline. The organic layer was stripped off and the residue was purified by column chromatography to give aldehyde AA(7).

General Method A4: Imination of Aldehyde AA(7)

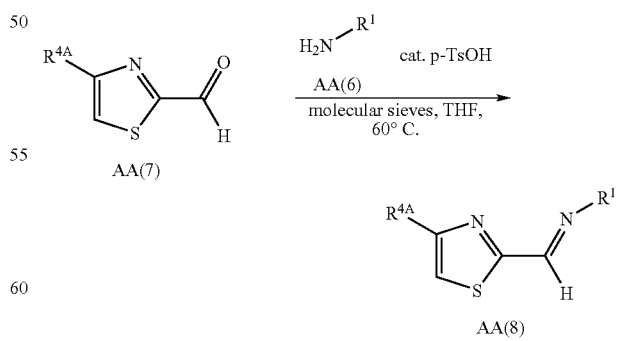

To a solution of aldehyde AA(7) (5.29 mmol) in 30 mL of dry THF was added amine AA(6) (5.53 mmol) and catalytic amounts of TsOH—H$_2$O (about 15 rig) sequentially at room temperature. To this reaction mixture was then added oven-dried hot molecular sieves (about 5 g), followed by vigorous stirring for 15 min at 60° C. The reaction mixture was then filtered and concentrated under reduced pressure. Crude imine AA(8) was then used in the next reaction (General Method A5).

General Method A5: Grignard Addition to Imine AA(8)

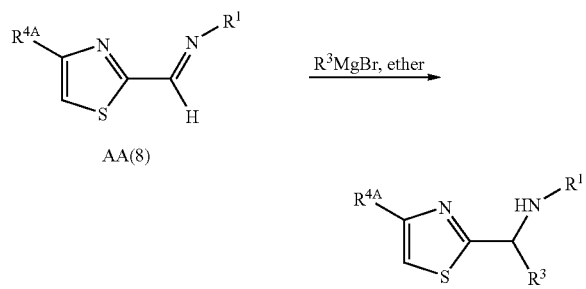

Crude imine AA(8) was redissolved in 60 mL of dry ether. To this solution was added $R^3MgBr$ (2 eq. vs. the starting aldehyde AA(7) in General Method A4) at −30° C. The reaction mixture was gradually warmed up to room temperature and stirred overnight. The reaction was quenched with saturated NaCl aqueous solution (50 mL) and extracted with EtOAc (2×30 mL). The organic layers were then combined and dried with $Na_2SO_4$. After concentration under reduced pressure, the crude product was then purified by column chromatography to give the final ligand.

General Method A6: Lithium Addition to Imine AA(8)

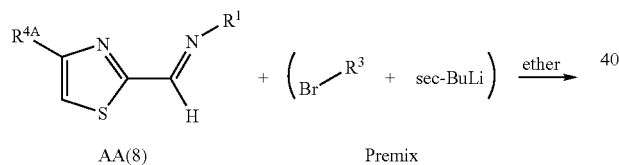

To a solution of $R^3Br$ (2.37 mmol, 3 eq. vs. starting aldehyde AA(7) in General Method A4) in 15 mL of dry ether was added sec-BuLi (1.69 mL, 2.37 mmol, 1.4 M) at −30° C. The reaction was gradually warmed up to room temperature and stirred for 40 minutes. Crude imine AA(8) from the condensation reaction was redissolved in 10 mL of dry ether. The $R^3$—Li solution was added at −30° C., and the reaction mixture was gradually warmed up to room temperature and stirred overnight. The reaction was quenched with saturated. NaCl aqueous solution (50 mL) and extracted with EtOAc (2×30 mL). The organic layers were then combined and dried with $Na_2SO_4$. After concentration under reduced pressure, the crude product was purified by column chromatography to give the final ligand.

General Method A7: Reduction of Imine AA(8)

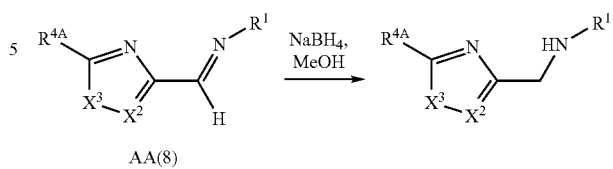

To a solution of crude imine AA(8) in 10 mL of MeOH was added $NaBH_4$ (4 eq. vs. starting AA(7) in General Method A4) at room temperature for 15 minutes. The reaction mixture was directly onto a pad of silica gel. After evaporating the methanol from the silica gel, the crude product was purified by column chromatography to give the final ligand.

b. Specific Ligand Syntheses

Ligands A1-A36, A38, A44, A51, A54-A56 and A58 were prepared from the corresponding 4-$R^{4A}$-2-thiazolecarbaldehyde (ACB Blocks, Ltd., Moscow, Russia). Ligand A57 was prepared from 2-thiazolecarbaldehyde (Sigma-Aldrich, St. Louis, Mo.). These ligands were prepared using General Method A4 to form the corresponding imine AA(8), followed by General Method A5, A6, or A7 depending on the desired final ligand structure. The syntheses of ligands A34 and A36 involve additional steps for phenol protection and deprotection, and described below, and in accord with Greene, *Protecting Groups in Organic Synthesis*, Wiley, New York 1999 ($3^{rd}$ Ed.).

The $R^{4A}$ group of ligands A37, A39-A50, A52-A53 were installed using Suzuki coupling (General Method A3). All boronic acids used are either commercially available or were prepared using conventional methods or General Method A2.

Example 1

Synthesis of Ligands A34 and A36

Step 1

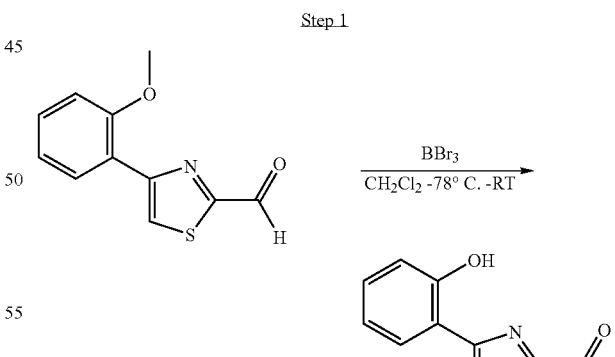

Under a nitrogen atmosphere, 1.5 ml of a 1.0 M solution of $BBr_3$ in hexane (1.5 mmol) was added dropwise, at −78° C., to a $CH_2Cl_2$ solution (5 mL) containing 220 mg (1.0 mmol) of the thiazole-aldehyde. The resultant orange suspension was allowed to warm to room temperature and stirred overnight. The reaction was then quenched by the slow addition of saturated aqueous solution of $NaHCO_3$ and diluted with additional CH₂Cl₂. The phases were separated and the organic phase was washed with H₂O and NaCl solution, and then dried over Na₂SO₄. The solvent was then removed to produce an orange solid. The product was purified by column chromatography (1:1 hexanes:CH₂Cl₂) yielding 159 mg of a yellow solid.

Step 2

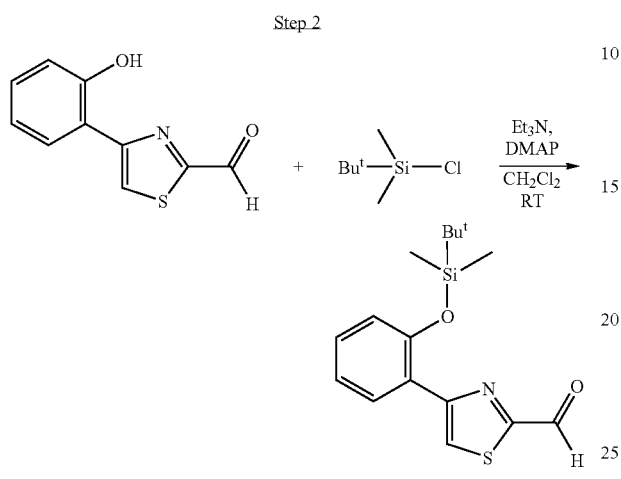

Under a nitrogen atmosphere, a solution containing 156 µL Et₃N in 3 ml CH₂Cl₂ (1.12 mmol) was added to a mixture of 153 mg of the phenol-thiazole-aldehyde (0.75 mmol) and 18 mg DMAP (4-dimethylaminopyridine 0.15 mmol). The tert-butyldimethylsilylchloride (169 mg, 1.12 mmol) was added to the mixture which was subsequently stirred overnight. The product was purified by column chromatography (20:1 hexanes:EtOAc) yielding 204 mg of a pale yellow viscous oil.

General methods A4 and A5 were then followed to produce silylether protected derivatives of A34 and A36. A silylether deprotection step is shown below:

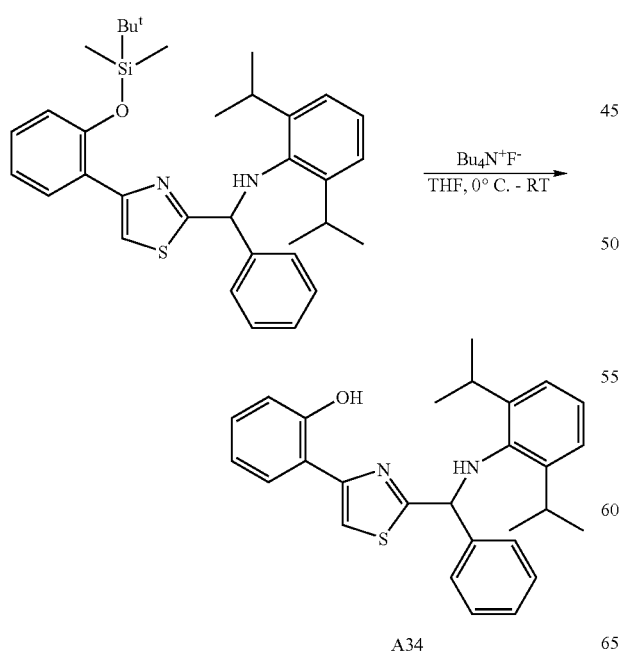

Under nitrogen, 582 µL of Bu₄N⁺F⁻ (1.0 M in THF; 0.58 mmol) was added dropwise at 0° C. to a solution of the silylether protected derivative of A34 in 5 mL THF (216 mg, 0.39 mmol). The reaction was allowed to warm slowly to room temperature and stirred for 6 hours. The product was purified by column chromatography (2:1 hexanes:CH₂Cl₂) to produce 143 mg of A34.

Example 2

Synthesis of Ligand A43

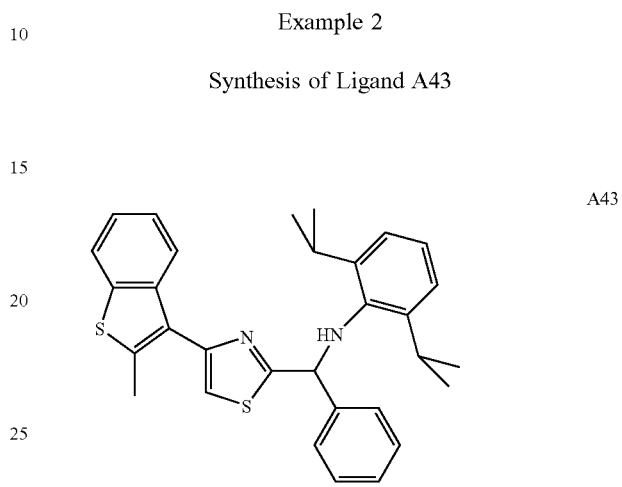

Step 1: Synthesis of Boronic Acid AA(9)

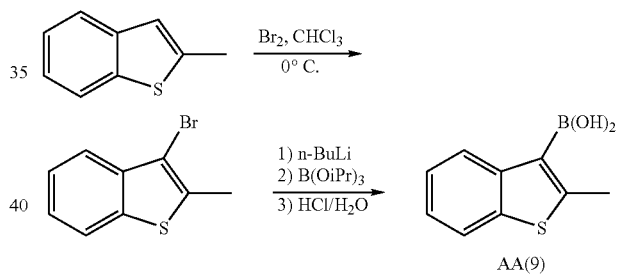

Step 2: Suzuki Coupling

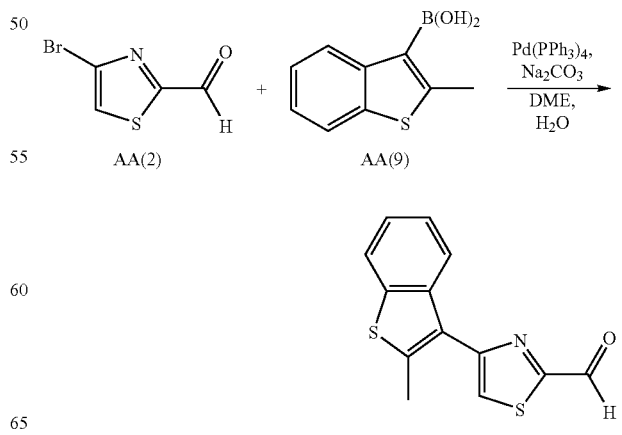

Step 3: Imine Formation and Lithium Addition

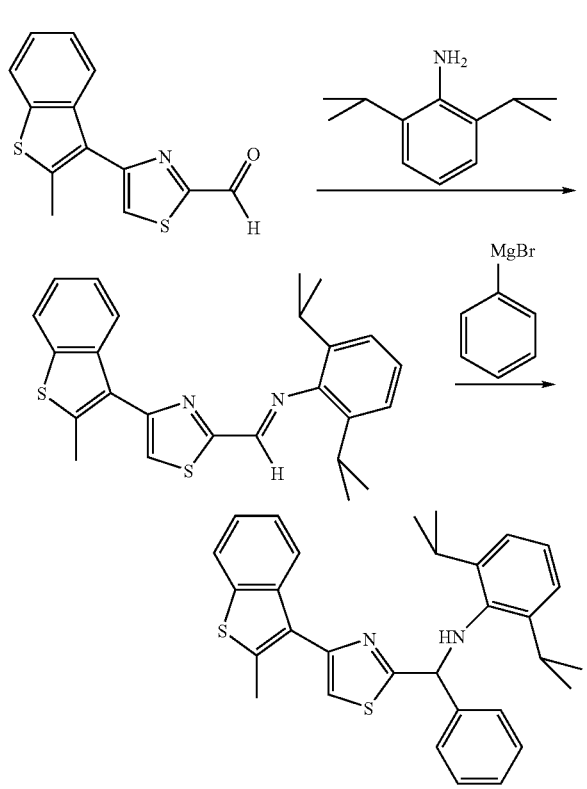

Experimental Details

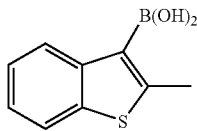

Synthesized by General Method A2. Crude 2-methyl-3-bromo-benzothiophene (AA(4); X=S, R=Me) was used without purification in the second step (lithiation/boronic acid formation). 2-methyl-benzothiophene-3-boronic acid was obtained and used without further purification.

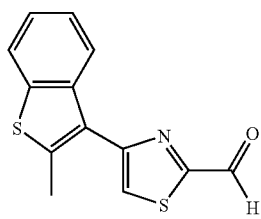

Synthesized by General Method A3 from the boronic acid and AA(2) prepared using method A1. The final aldehyde was purified by flash chromatography (Biotage FLASH 40M KP-Sil silica, 9:1; Hex: Ether) to give 457 mg of the product (66%). $^1H$ NMR (CDCl$_3$, 300 MHz): 10.14 (d, J=1.5 Hz, 1H), 7.86-7.82 (m, 2H), 7.80 (d, J=1.2 Hz, 1H), 7.40-7.35 (m, 2H), 2.69 (s, 3H).

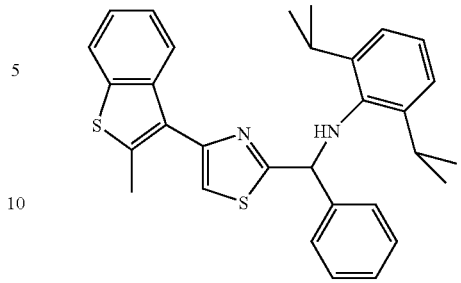

Synthesized by General Methods A4 and A5. Purified by flash chromatography (Biotage FLASH 40M KP-Sil silica, 9:1; Hex:Ether) to give 196 mg of the product (60%). $^1H$ NMR (CDCl$_3$, 300 MHz): 7.77-7.73 (m, 2H), 7.36-7.26 (m, 8H), 7.09 (s, 3H), 5.40 (s, 1H), 4.22 (br s, 1H), 3.03 (dddd, J=6.9, 6.9, 6.9, 6.9 Hz, 2H), 2.61 (s, 3H), 1.13 (d, J=6.6 Hz, 6H), 1.03 (d, J=6.9 Hz, 6H).

2. (Thiazol-4-yl)-alkyl Amine) Ligands
    a. General Synthetic Methods

General Method B1: Synthesis of 2-$R^{4A}$-4-Thiazolecarbaldehyde (BB(2))

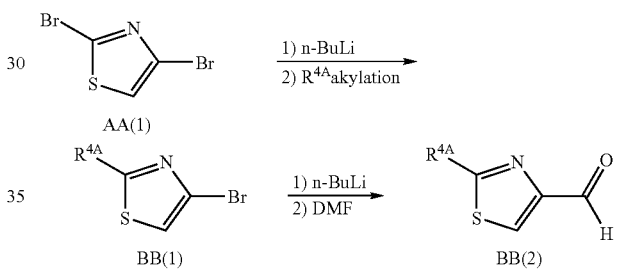

To a solution of dibromothiazole AA(1) (0.92 mmol) in 10 mL of ether was added n-BuLi (1.00 mmol) at −78° C. After 20 min at this temperature, the appropriate $R^{4A}$ precursor (1.00 mmol) was added, and the reaction was warmed to room temperature. After 20 minutes, the reaction was quenched with saturated NaCl aqueous solution (30 mL) and extracted with EtOAc (2×20 mL). The organic layers were then combined and dried with Na$_2$SO$_4$. After concentration under reduced pressure, the crude product BB(1) was purified by column chromatography.

A solution of the purified bromothiazole BB(1) (1.38 mmol) in 5 mL of dry ether was added dropwise to a solution of n-BuLi (1.52 mmol, 1.6 M, 950 µL) in 10 mL of dry ether at −78° C. The reaction mixture was stirred at this temperature for 20 additional minutes. DMF (151 mg, 160 µL, 2.27 mmol) was then added and the resulting reaction mixture was warmed to room temperature and stirred for 1 hour. The reaction was then quenched with saline (20 mL) and extracted with ether (2×30 mL). The organic layers were combined, dried over Na$_2$SO$_4$, and concentrated under reduced pressure. The crude product was purified by flash chromatography.

b. Specific Ligand Syntheses

Ligands B1-B11 were prepared from 2-phenyl-4-thiazolecarbaldehyde (ABCR Specialty Chemicals, Karlsruhe, Germany), using General Method A4 to form the imine (corresponding to imine AA(8)) followed by General Method A5, A6, or A7 depending on the desired final ligand structure. Ligands B12 and B13 were prepared using General Method B(1), followed by either General Method A5 or A7.

Example 3

Synthesis of Ligand B13

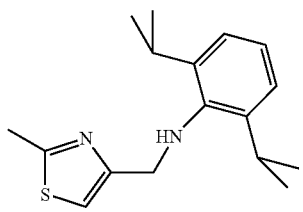
B13

Step 1: Synthesis of Aldehyde BB(3)

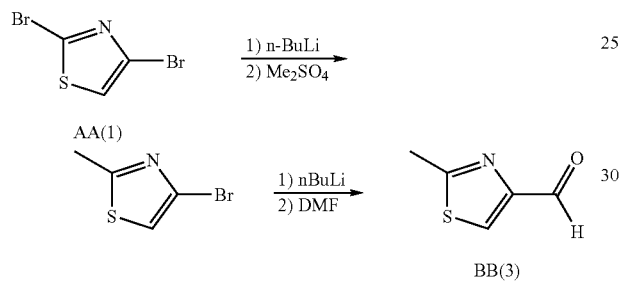

Step 2: Synthesis of Final Ligand B13

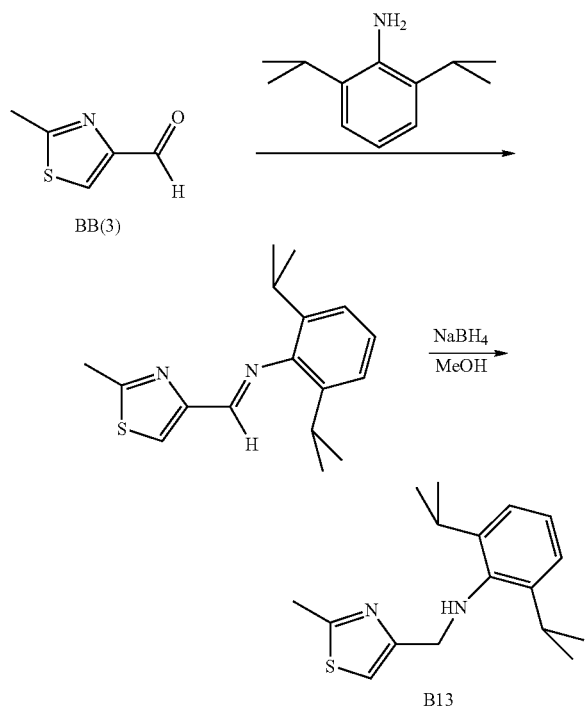

Experimental Details

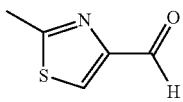

Synthesized by General Method B1. In this case, crude aldehyde BB(3) was used directly in the next reaction.

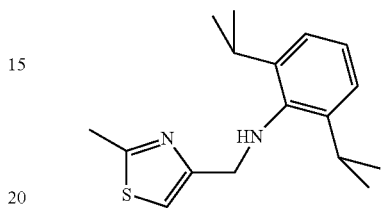

Synthesized from BB(3) using General Methods A4 and A7. Purified by flash chromatography (Biotage FLASH 40M KP-Sil silica, 9:1; Hex: EtOAc) to give the final ligand. $^1$H NMR (CDCl$_3$, 300 MHz): 7.11-7.06 (m, 3H), 6.92 (s, 1H), 4.11 (s, 2H), 3.57 (br. s, 1H) 3.29 (dddd, J=6.9, 6.9, 6.9, 6.9 Hz, 2H), 2.71 (s, 3H), 1.20 (d, J=6.9 Hz, 12H).

3. Imidazole Amine Ligands a. General Synthetic Methods

General Method C1: Formation of 4-Bromo Imidazole CC(4) from Tribromo-Imidazole CC(2)

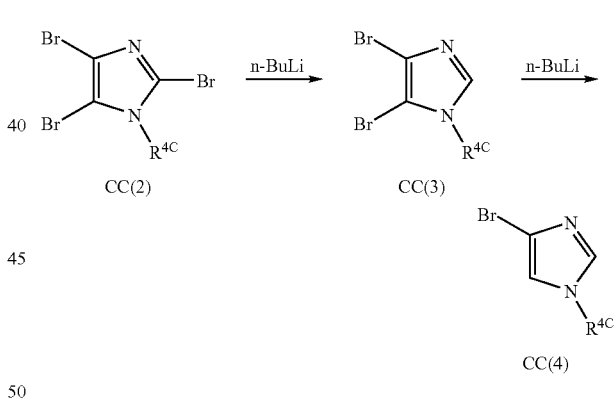

To a solution of starting tribromoimidazole CC(2) (1.4 mmol) in 10 mL of THF was added n-BuLi (1.68 mmol, 1.05 mL, 1.6 M) at −78° C. The reaction mixture was stirred for 5 minutes at this temperature, by which time GC/MS showed full conversion. The reaction was quenched with saturated NaCl aqueous solution, followed by ether extraction. The organic layer was then concentrated to give crude CC(3). n-BuLi (1.49 mmol, 0.93 mL, 1.6 M) was added to a solution of crude CC(3) in 10 mL of THF at −78° C. The reaction mixture was stirred for 15 minutes at this temperature, and the reaction was quenched with saturated NaCl aqueous solution, followed by ether extraction. The organic layers were combined and dried with Na$_2$SO$_4$. After concentration under reduced pressure, the crude product was purified by column chromatography.

General Method C2: Formation of Aldehyde CC(5)

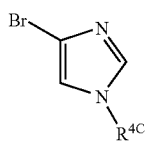 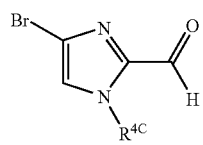

CC(1)      CC(5)

To a solution of bromo-imidazole CC(4) (5.48 mmol) in 20 mL of dry ether was added LDA (2.0 M, 3.0 mL) at −78° C. After 20 minutes at this temperature, dry DMF (637 μL, 8.22 mmol) was added, and the reaction was gradually warmed to room temperature. After 1 hour, the reaction was quenched with saturated NH$_4$Cl aqueous solution and extracted with EtOAc. The organic layers were then combined and dried with Na$_2$SO$_4$. After concentration under reduced pressure, the crude product was purified by column chromatography to give aldehyde CC(5).

b. Specific Ligand Syntheses

Example 4

Synthesis of Ligand C29

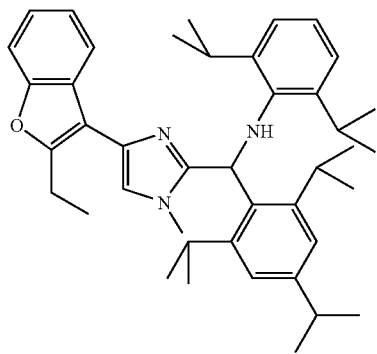

C29

Step 1: Synthesis of 1-Methyl-Tribromo-Imidazole

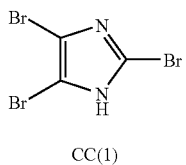 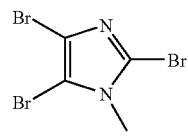

CC(1)

Step 2: Synthesis of 1-Methyl-4-Bromo-Imidazole

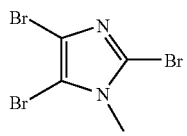

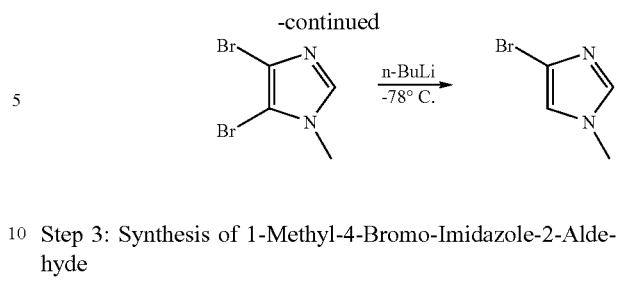

Step 3: Synthesis of 1-Methyl-4-Bromo-Imidazole-2-Aldehyde

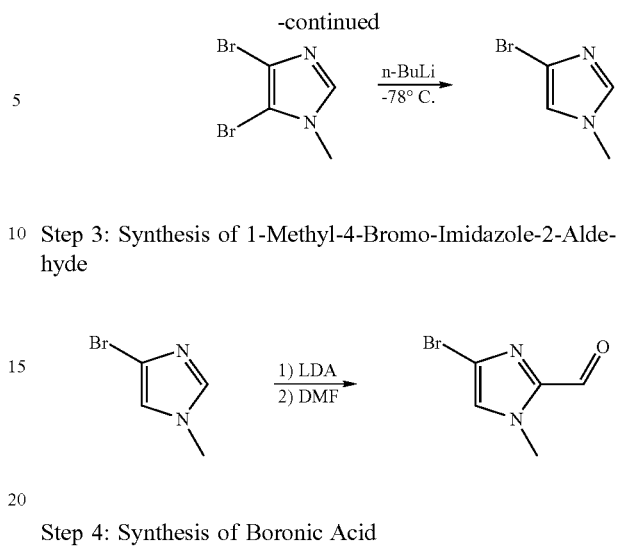

Step 4: Synthesis of Boronic Acid

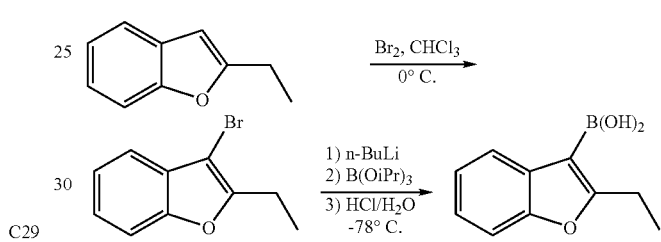

Step 5: Suzuki Coupling

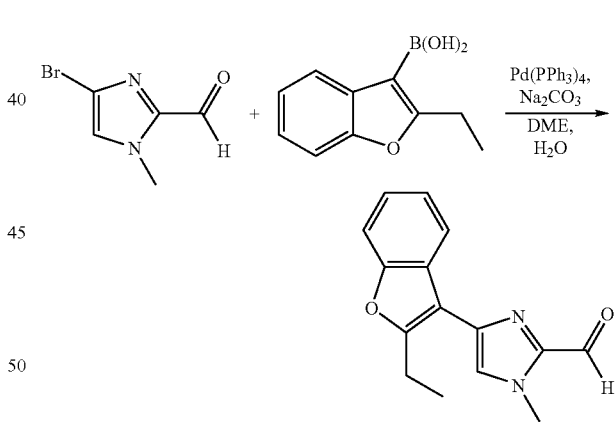

Step 6: Imine Formation and Lithium Addition

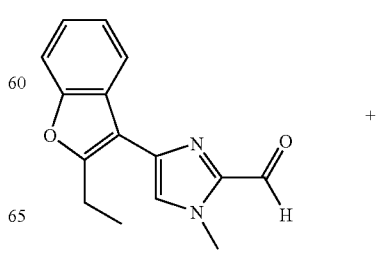

-continued

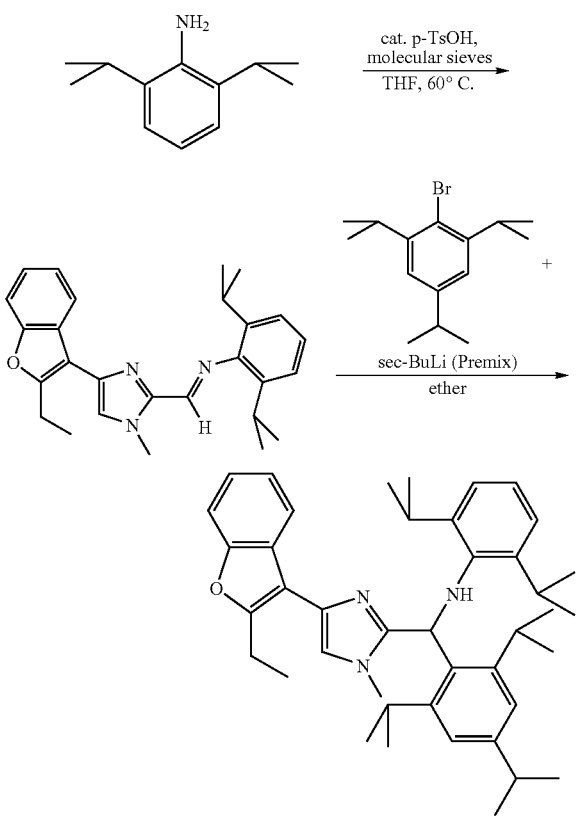

Experimental Details

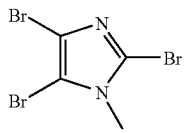

To a suspension of commercially-available 2,4,5-tribromoimidazole (500 mg, 1.64 mmol) and K$_2$CO$_3$ (453 mg, 3.28 mmol) in 10 mL of acetone was added Me$_2$SO$_4$ (248 mg, 1.97 mmol) at room temperature. The reaction suspension was stirred at room temperature for 0.5 hours. After filtration and acetone wash, the solvent was stripped off to give 445 mg light yellow solid product. This crude product was then used directly in the next reaction.

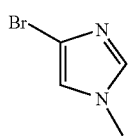

Synthesized by General Method C1. Compound was obtained as a light yellow liquid (76%, 2 steps). $^1$H NMR (CDCl$_3$, 300 MHz): 7.26 (s, 1H), 6.82 (d, J=1.2 Hz, 1H), 3.63 (s, 3H).

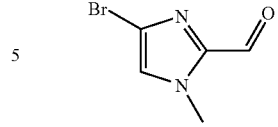

Synthesized by General Method C2. Purified by flash chromatography (Biotage FLASH 40M KP-Sil silica, 1:4; EtOAc:Hex) to give 642 mg of the product (62%). $^1$H NMR (CDCl$_3$, 300 MHz): 9.67 (d, J=0.9 Hz, 1H), 7.06 (s, 1H), 3.97 (s, 3H).

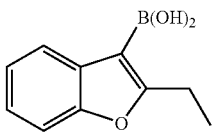

Synthesized by General Method A2. 2-Ethyl-3-bromobenzofuran was purified by flash chromatography (Biotage FLASH 40M KP-Sil silica, 99:1; Hex: Ether) to give 7.0 g of the product (78%). 2-Ethyl-benzofuran-3-boronic acid was obtained and used without further purification.

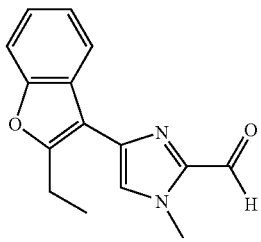

Synthesized by General Method A3. Purified by flash chromatography (Biotage FLASH 40M KP-Sil silica, 1:4; EtOAc:Hex) to give 1.79 g of the product (80%). $^1$H NMR (CDCl$_3$, 300 MHz): 9.92 (s, 1H), 7.87-7.84 (m, 1 H), 7.50-7.47 (m, 1H), 7.33-7.28 (m, 3H), 4.12 (d, J=3.6 Hz, 3H), 3.15 (q, J=7.5 Hz, 2H), 1.40 (t, J=7.5 Hz, 3H).

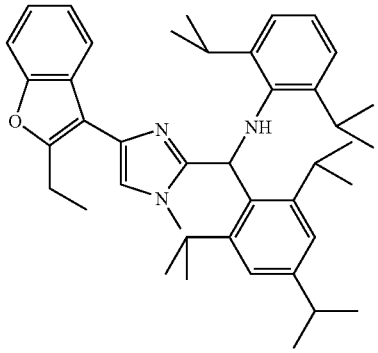

Synthesized by General Methods A4 and A6. Purified by flash chromatography (Biotage FLASH 40M KP-Sil silica, 2:98; EtOAc:Hex) to give 547 mg of the product (59%, 2 steps). $^1$H NMR (CDCl$_3$, 300 MHz): 7.79-7.76 (m, 1H), 7.46-7.42 (m, 1H), 7.26-7.21 (m, 2H), 7.12-7.01 (m, 4H), 6.91 (s, 1H), 6.86 (br s, 1H), 5.46 (s, 1H), 5.10 (br s, 1H), 3.77 (br s, 1H), 3.32 (dddd, J=6.9, 6.9, 6.9, 6.9 Hz, 2H), 3.25-3.03 (m, 2H), 3.00 (s, 3H), 2.83 (dddd, J=6.9, 6.9, 6.9, 6.9 Hz, 1H), 2.71 (br s, 1H), 1.36 (t, J=7.5 Hz, 3H), 1.27-1.04 (m, 6H), 1.20 (d, J=6.9 Hz, 6H), 1.10 (d, J=6.9 Hz, 6H), 0.78 (d, J=6.9 Hz, 6H), 0.54-0.48 (br m, 6H).

4. (Oxazol-2-yl)-alkyl Amine and (Oxazol-4-yl)-alkyl Amine Ligands a. General Synthetic Methods

General Method E1: Imination of Oxazole-2-carbaldehydes with Anilines.

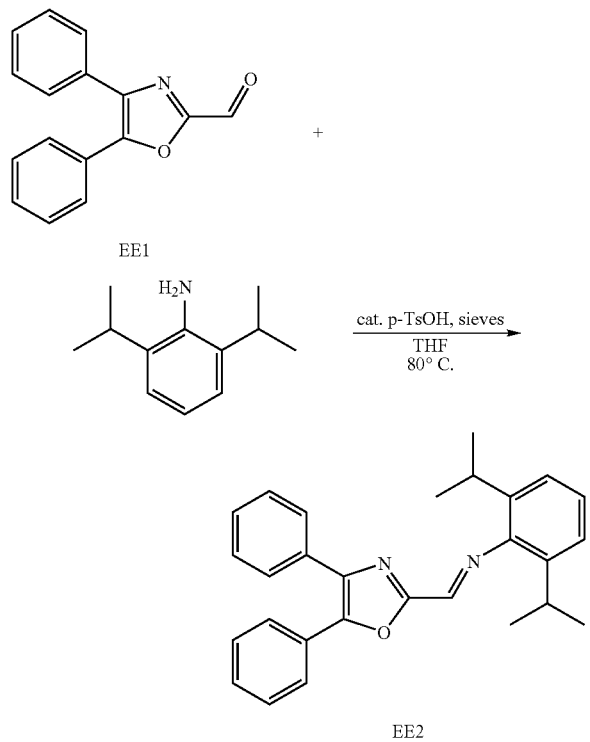

In a typical procedure, a solution of 4,5-diphenyloxazole-2-carbaldehyde EE1 (400 mg, 1.60 mmol), 2,6-diisopropylaniline (312 mg, 1.77 mmol) and p-toluenesulfonic acid (20.0 mg, 0.11 mmol) in 20 mL THF and 100 mg of molecular sieves (4 Å) was heated at 80° C. for 4 hours. The reaction was diluted with 15 mL ether, washed with 20 mL of a saturated aqueous solution of sodium bicarbonate, 20 mL water, dried over MgSO4, filtered and concentrated to give 667 mg of EE2, which was used without further purification in the next reaction.

General Method E2: Addition of Phenylmagnesium Bromide to Oxazol-Imines.

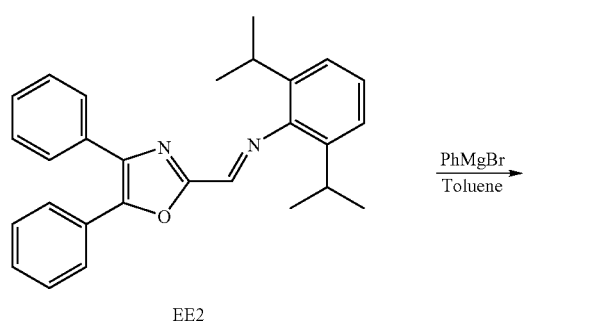

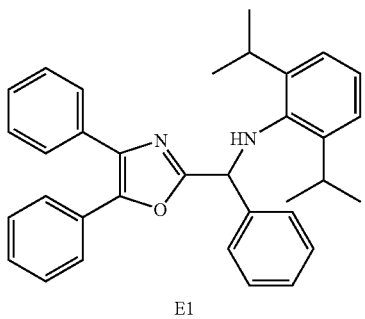

In a typical procedure, a 3.0 M solution of phenylmagnesium bromide in ether (0.326 mL, 0.98 mmol) was added to a solution of imine EE2 (200 mg, 0.47 mmol) in 5 mL toluene at room temperature (ca. 20° C.) over a period of 5 minutes under nitrogen-atmosphere, and then the reaction was stirred for 12 hrs. After quenching with a saturated aqueous solution of ammonium chloride (30 mL), the reaction was extracted with ether (3×10 mL). The combined organic layers were dried over MgSO$_4$, filtered and concentrated under vacuum. Residue was purified by silica-gel column chromatography.

General Method E3: Addition of Organolithium Reagents to Oxazol-Imines.

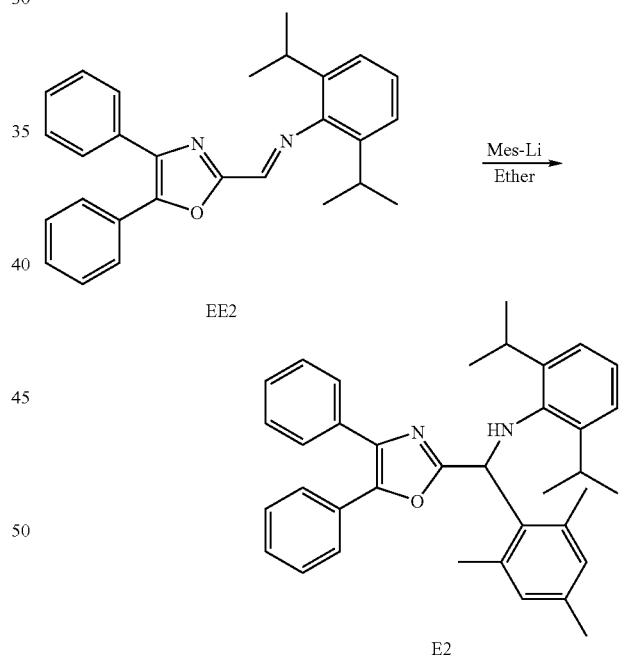

In a typical procedure a 0.1 M solution of Mesityllithium in ether (5.18 mL, 0.518 mmol) was added to a solution of imine EE2 (200 mg, 0.47 mmol) in 10 mL ether at −30° C. under nitrogen-atmosphere over a period of 5 minutes. The reaction was allowed to warm to room temperature (ca. 20° C.) and stirred for a period of 12 hours. After quenching with a saturated aqueous solution of ammonium chloride (30 mL), the reaction was extracted with ether (3×10 mL). The combined organic layers were dried over MgSO$_4$, filtered and concentrated under vacuum. Crude product was purified by flash chromatography.

b. Specific Ligand Syntheses

Example 5

Synthesis of Ligand E1

Step 1: Imination of EE1 with 2,6-Di-isopropyl aniline

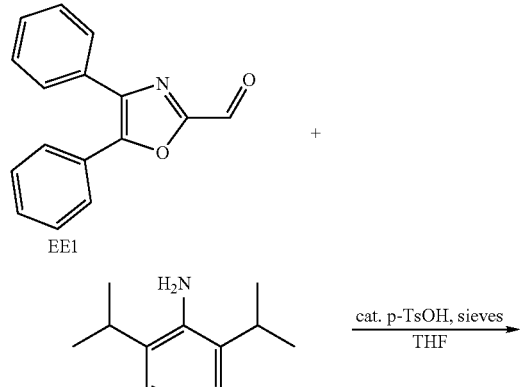

Step 2: Alkylation of EE2

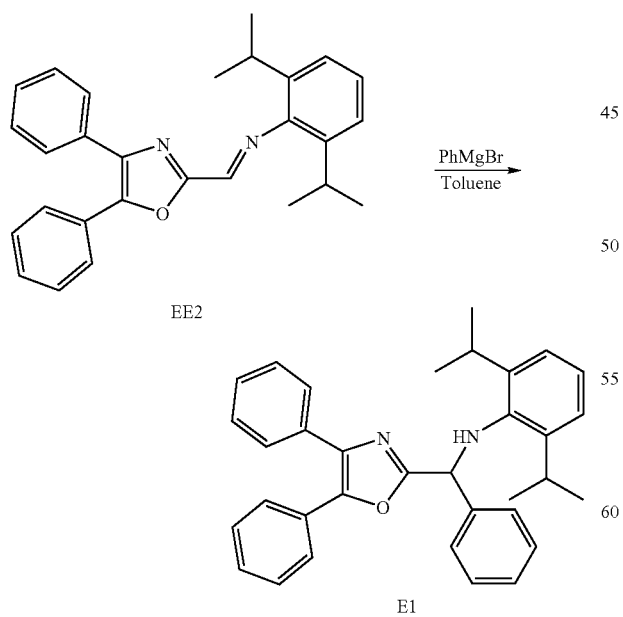

Experimental Details

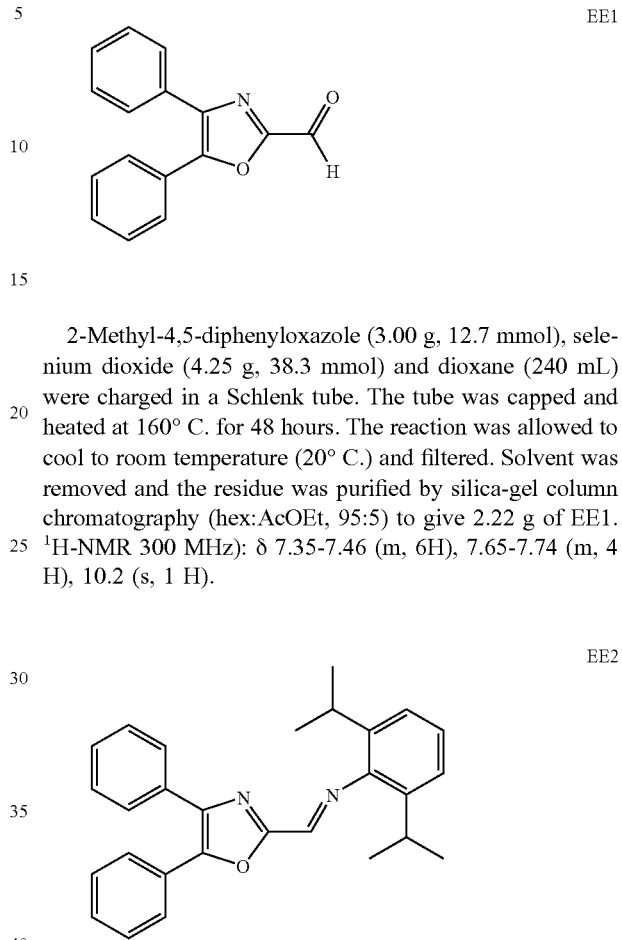

2-Methyl-4,5-diphenyloxazole (3.00 g, 12.7 mmol), selenium dioxide (4.25 g, 38.3 mmol) and dioxane (240 mL) were charged in a Schlenk tube. The tube was capped and heated at 160° C. for 48 hours. The reaction was allowed to cool to room temperature (20° C.) and filtered. Solvent was removed and the residue was purified by silica-gel column chromatography (hex:AcOEt, 95:5) to give 2.22 g of EE1. $^1$H-NMR 300 MHz): δ 7.35-7.46 (m, 6H), 7.65-7.74 (m, 4 H), 10.2 (s, 1 H).

Synthesized by General Method E1. $^1$H-NMR (300 MHz): δ 1.20 (d, J=6.82 Hz, 12H), 3.03 (sept, J=6.84 Hz, 2H), 7.12-7.22 (m, 3H), 7.38-7.48 (m, 6H), 7.70-7.80 (m, 4H), 8.16 (s, 1H).

Synthesized by General Method E2. Purified by flash chromatography (hex:AcOEt, 97:3) to give 229 g of E1. $^1$H-NMR (300 MHz): δ 1.12 (d, J=6.79 Hz, 6H), 1.14 (d, J=6.74 Hz, 6H), 2.93 (br s, exchangeable with D$_2$O, 1H), 3.25 (sept, J=6.82 Hz, 2H), 5.36 (s, 1H), 7.02 (s, 3H), 7.28-7.41 (m, 9H), 7.50-7.57 (m, 4H), 7.62-7.68 (m, 2H).

Example 6

Synthesis of Ligand E2

Step 1: Imination of EE1 with 2,6-Di-isopropyl aniline

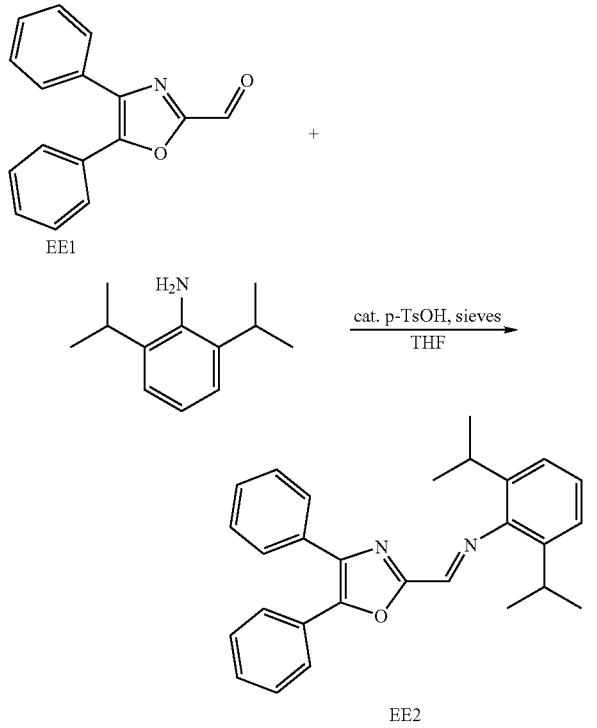

Step 2: Alkylation of EE2

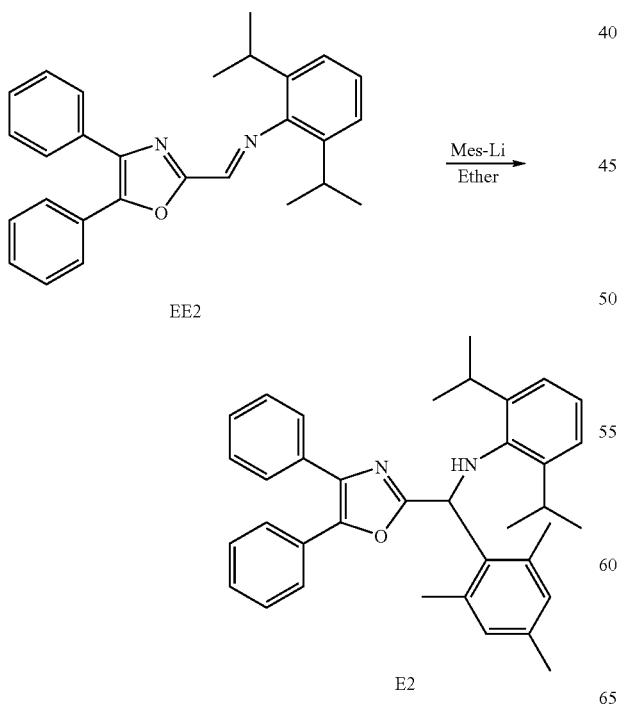

Experimental Details

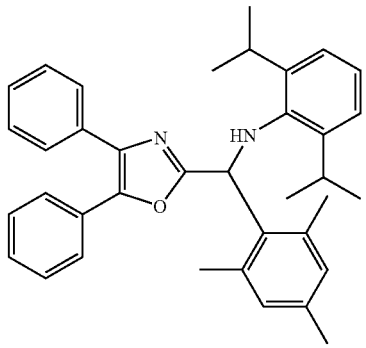

Synthesized by General Method E3, from EE2 prepared according to General Method E2. Purified by silica gel column chromatography (hex:AcOEt, 97:3) to yield 195 g of E2. $^1$H-NMR (300 MHz): δ 0.98(d, J=6.80 Hz, 6H), 1.14 (d, J=6.84 Hz, 6H), 2.21 (s, 6H), 2.27 (S, 3H), 2.90 (br s, exchangeable with D$_2$O, 1H), 3.23 (sept, J=6.82 Hz, 2H), 5.55 (s, 1H), 6.82 (s, 2H), 7.04-7.10 (m, 3H), 7.27-7.44 (m, 6H), 7.46-7.53 (m, 2H), 7.68-7.74 (m, 2H).

Example 7

Synthesis of Ligand F1

Step 1: Imination of 4-Formyl-2,5-diphenyloxazole FF1

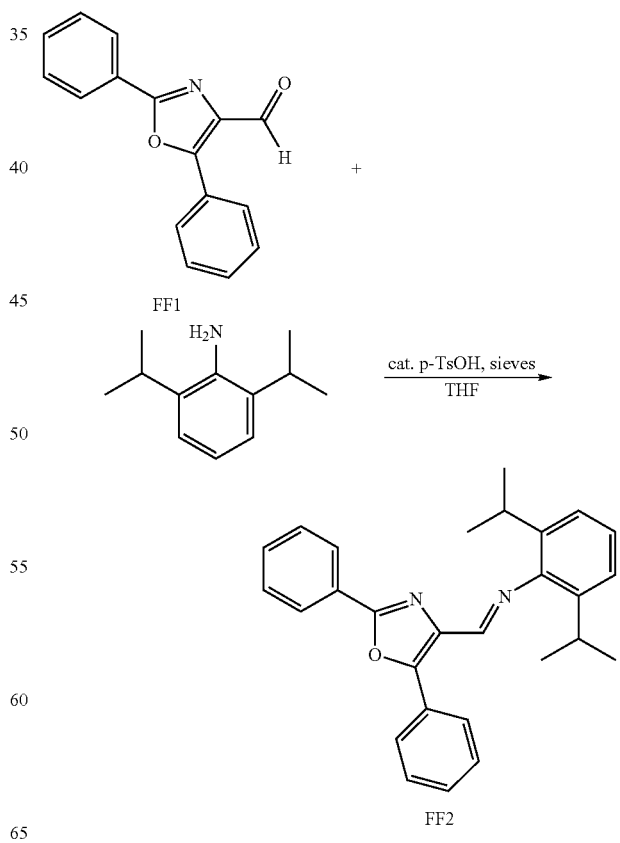

Step 2: Alkylation of FF2

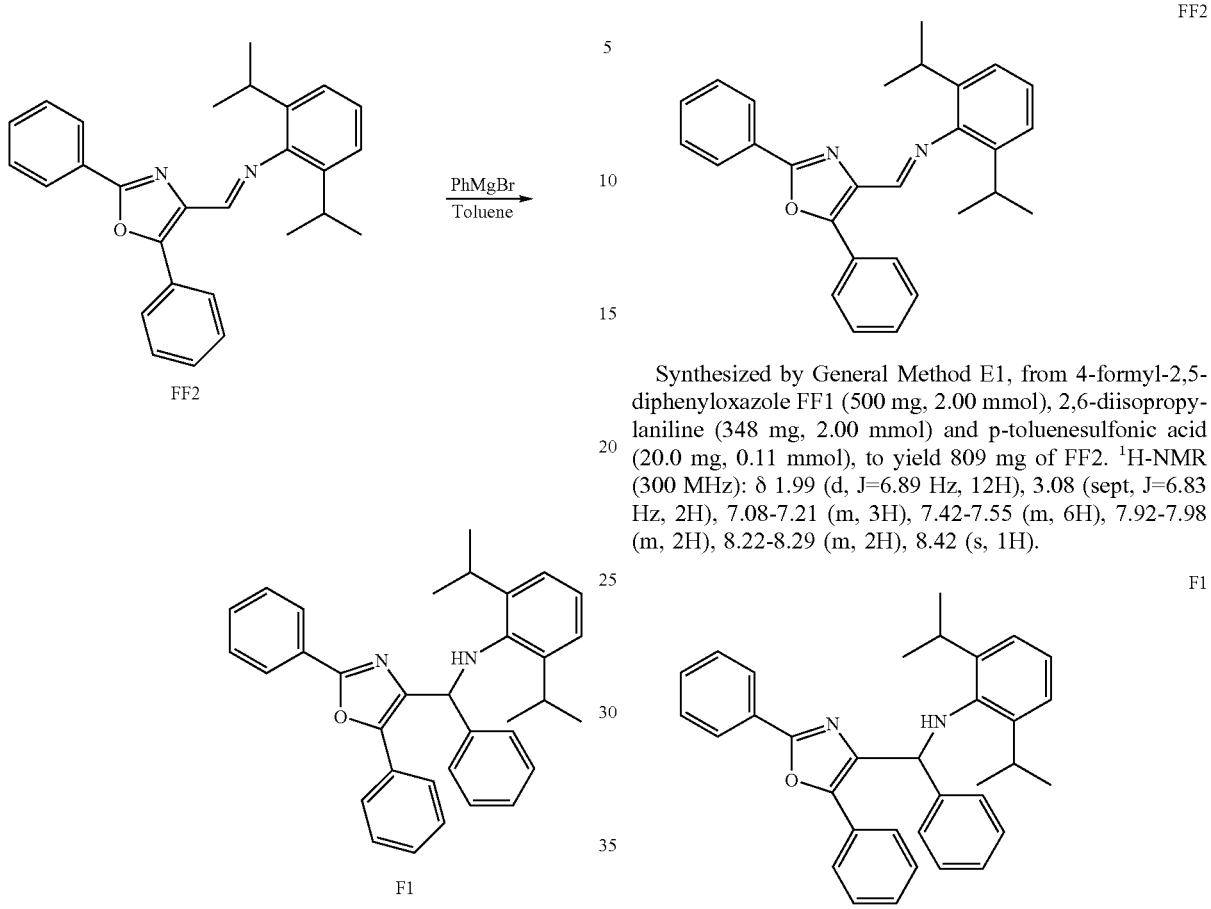

Experimental Details

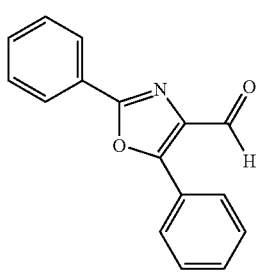

To a solution of 2,5-diphenyloxazole (2.21 g, 10 mmol) in 30 mL THF at −78° C. under nitrogen-atmosphere, a solution of butyllithium 1.6 M in hexane (6.87 mL, 11.0 mmol) was added over a period of 5 min. The reaction was stirred for 1 hr at −78° C., treated with DMF (2.92 g, 40 mmol) and allowed to warm-up slowly over a period of 12 hrs. After quenching with a saturated aqueous solution of ammonium chloride (30 mL), reaction was extracted with ether (3×50 mL). The combined organic layers were dried over MgSO$_4$, filtered and concentrated under vacuum. Crude product was purified by silica-gel column chromatography (hex:AcOEt, 95:5) to give 1.20 g of FF1. $^1$H-NMR (300 MHz): δ 7.50-7.60 (m, 6H), 8.13-8.20 (m, 4 H), 10.2 (s, 1 H).

Synthesized by General Method E1, from 4-formyl-2,5-diphenyloxazole FF1 (500 mg, 2.00 mmol), 2,6-diisopropylaniline (348 mg, 2.00 mmol) and p-toluenesulfonic acid (20.0 mg, 0.11 mmol), to yield 809 mg of FF2. $^1$H-NMR (300 MHz): δ 1.99 (d, J=6.89 Hz, 12H), 3.08 (sept, J=6.83 Hz, 2H), 7.08-7.21 (m, 3H), 7.42-7.55 (m, 6H), 7.92-7.98 (m, 2H), 8.22-8.29 (m, 2H), 8.42 (s, 1H).

Synthesized by General Method E2, from imine FF2 (200 mg, 0.47 mmol) and phenylmagnesium bromide 3.0 M in ether (0.326 mL, 0.98 mmol), to yield 229 mg of F1. $^1$H-NMR (300 MHz): δ 1.01 (d, J=6.72 Hz, 12H), 3.24 (sept, J=6.78 Hz, 2H), 4.30 (br s, exchangeable with D$_2$O, 1H), 5.32 (s, 1H), 7.01 (s, 3H), 7.19-7.36 (m, 9H), 7.42-7.58 (m, 4H), 8.11-8.17 (m, 2H).

Example 8

Synthesis of Ligand F2

Step 1: Imination of 4-Formyl-2,5-diphenyloxazole FF1

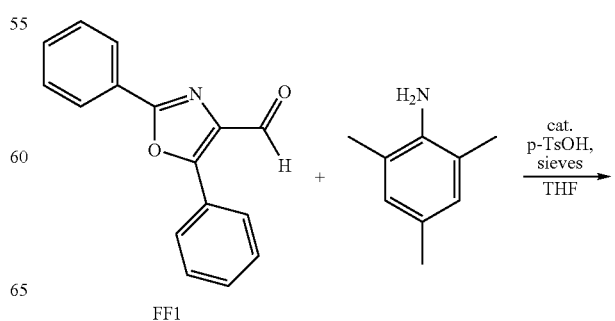

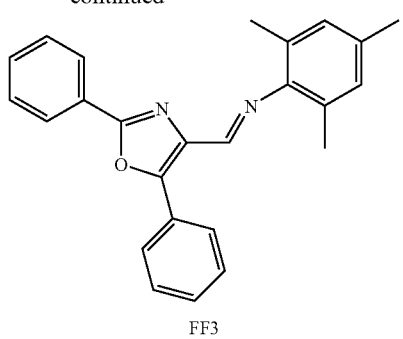

FF3

Step 2: Alkylation of FF3

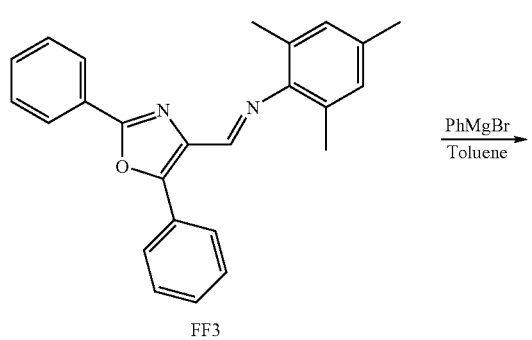

Experimental Details

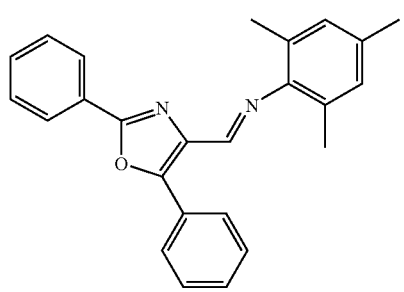

FF3

Synthesized using General Method E1, from 4-formyl-2,5-diphenyloxazole FF1 (500 mg, 2.00 mmol), 2,4,6-trimethylaniline (270 mg, 2.00 mmol) and p-toluenesulfonic acid (20.0 mg, 0.11 mmol), to yield 660 mg of FF3. ¹H-NMR (300 MHz): δ 2.18 (s, 6H), 2.29 (s, 3H), 6.91 (s, 2H), 7.43-7.54 (m, 6H), 7.95-8.00 (m, 2H), 8.22-8.29 (m, 2H), 8.44 (s, 1H).

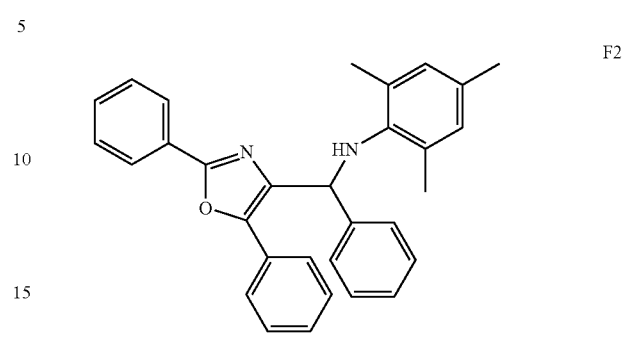

Synthesized according to General Method E2, from imine FF3 (183 mg, 0.50 mmol) and phenylmegnesium bromide 3.0 M in ether (0.333 mL, 1.00 mmol), to yield 211 mg of F2. ¹H-NMR (300 MHz): δ 2.23 (s, 3H), 2.24 (s, 6H), 4.48 (br s, exchangeable with D₂O, 1H), 5.70 (s, 1H), 6.77 (s, 2H), 7.27-7.56 (m, 11H), 7.63-7.70 (m, 2H), 8.16-8.23 (m, 2H).

Example 9

Synthesis of Ligand F3

Step 1: Imination of 4-Formyl-2,5-diphenyloxazole FF1

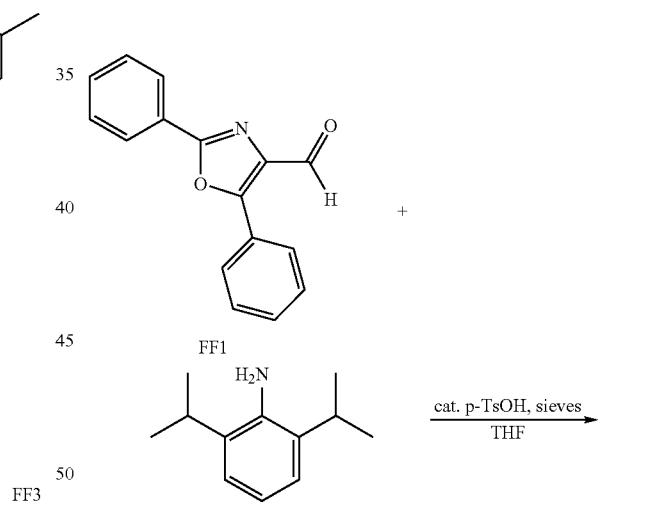

FF2

Step 2: Alkylation of FF2

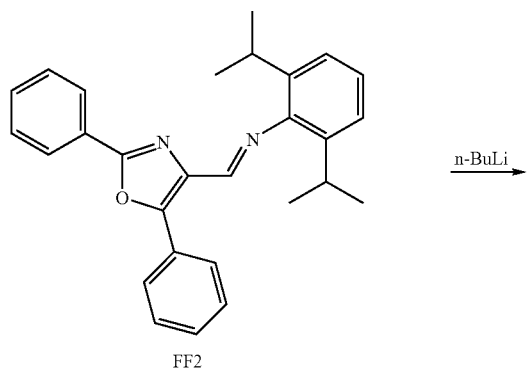

FF2 n-BuLi →

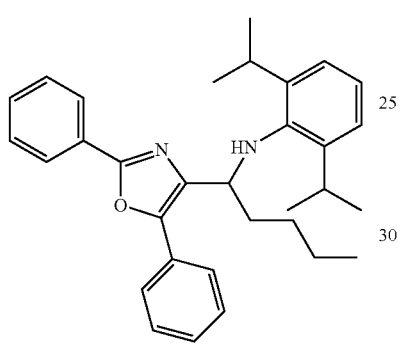

F3

Experimental Details

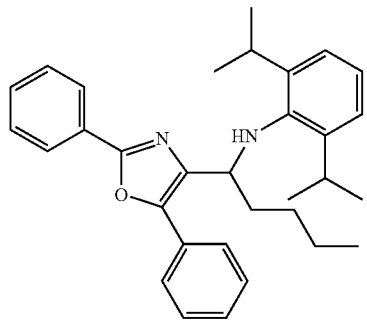

F3

Synthesized according to General Method E3, from imine FF2 (200 mg, 0.47 mmol) (prepared according to General Method E1 from oxazolecarbaldehyde FF1) and n-butyl-lithium 1.6 M in hexene (0.370 mL, 0.59 mmol), to yield 157 mg of F3. $^1$H-NMR (300 MHz): δ 0.80-1.50 (m, 21H), 2.92 (sept, J=6.94 Hz, 2H), 3.25 (br s, exchangeable with D$_2$O, 1H), 5.61 (s, 1H), 6.90-7.35 (m, 7H), 7.44-7.51 (m, 4H), 8.10-8.17 (m, 2H).

Example 10

Synthesis of Ligand F4

Step 1: Imination of 4-Formyl-2,5-diphenyloxazole FF1

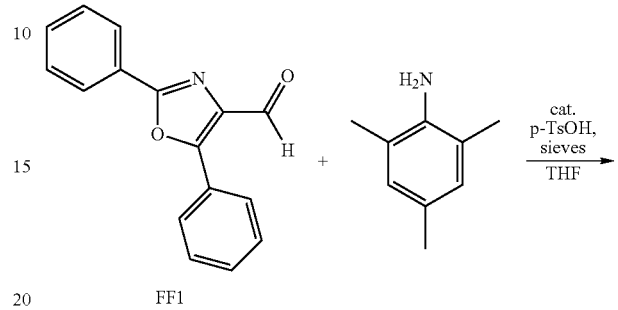

FF1

$\xrightarrow{\text{cat. p-TsOH, sieves}}{\text{THF}}$

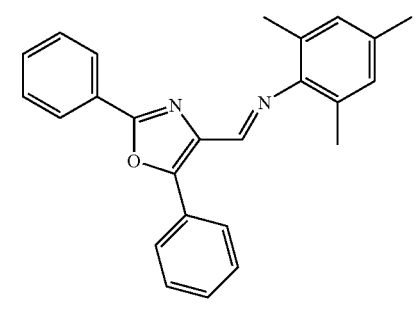

FF3

Step 2: Alkylation of FF3

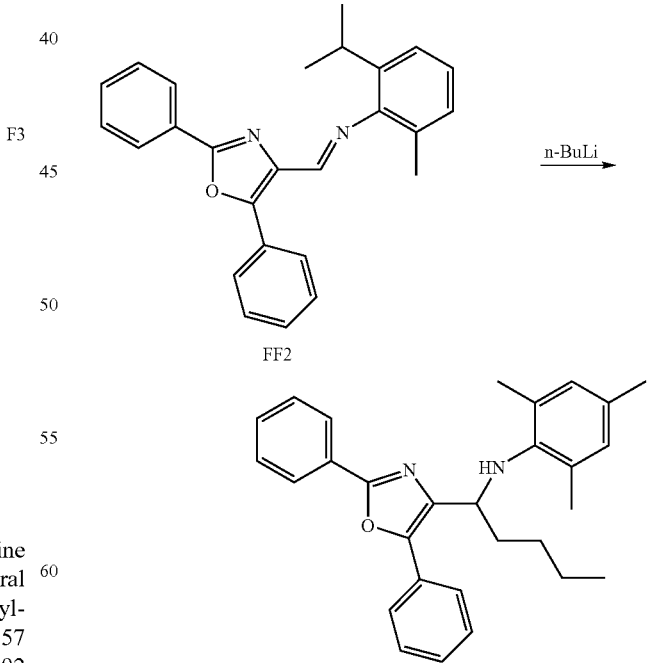

FF2 n-BuLi →

F4

Experimental Details

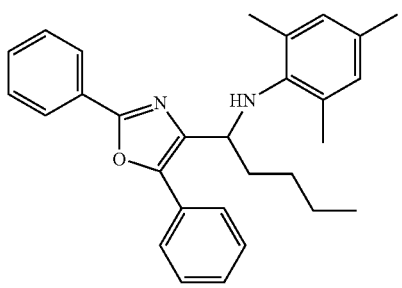

F4

Synthesized according to General Method E3, from imine FF3 (200 mg, 0.55 mmol) (prepared according to General Method E1 from oxazolecarbaldehyde FF1) and n-butyllithium 1.6 M in hexene (0.370 mL, 0.59 mmol), to yield 180 mg of F4. $^1$H-NMR (300 MHz): δ 0.85-1.40 (m, 9H), 2.12 (s, 6H), 2.23 (s, 3H), 3.50 (br s, exchangeable with D$_2$O, 1H), 5.78 (s, 1H), 6.80-7.30 (m, 6H), 7.38-7.51 (m, 4H), 8.06-8.13 (m, 2H).

5. Oxadiazoleamine Ligands

Hydroximinoyl chlorides of the type GG(1) were synthesized according to known procedures (Liu., et al., *J. Org. Chem.* 1980, 45, 3916-3918), with the exception of $R^{4A}$=2,4-dichlorophenyl and 2,6-dichlorophenyl, which were purchased from Maybridge.

Example 11

Synthesis of GG(8)

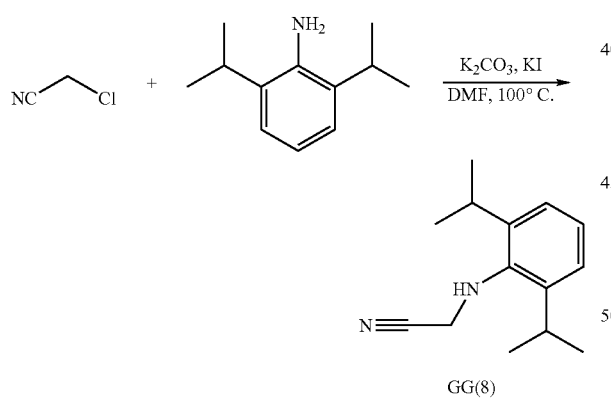

A reaction flask was charged with chloroacetonitrile (0.17 mL, 2.65 mmol), 2,6-diisopropylaniline (0.10 mL, 0.53 mmol), K$_2$CO$_3$ (147 mg, 1.06 mmol), KI (176 mg, 1.06 mmol), and DMF (2 mL), then flushed with N$_2$. The reaction was heated at 100° C. for 18 hours. The reaction was diluted with Et$_2$O then washed twice with H$_2$O, once with brine, and dried over Na$_2$SO$_4$. Purified by flash chromatography on silica gel eluting with hexanes/ethyl acetate=10/1. Isolated 76 mg, 66% yield, of product as a viscous yellow oil. $^1$H NMR (300 MHz, C$_6$D$_6$) δ 1.10 (d, J=6.6 Hz, 12H, CH$_3$), 2.70 (br m, 1H, NH), 2.95-3.05 (m, 3H, CH$_2$ and CH), 7.02 (m, 3H, aromatic CH).

Example 12

Synthesis of GG(9)

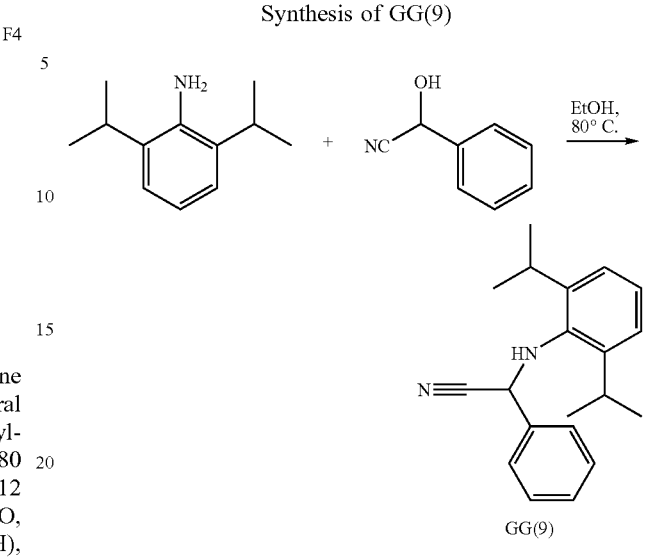

Mandelonitrile (0.80 mL, 6.72 mmol), 2,6-diisopropylaniline (0.63 mL, 3.35 mmol), and EtOH (8.0 mL) were heated at 80° C. in a sealed scintillation vial for 18 hours. Purified by flash chromatography on silica gel eluting with hexanes/ethyl acetate=20/1. Isolated 506 mg, 52% yield, of product as a light yellow oil. $^1$H NMR (300 MHz, C$_6$D$_6$) δ 0.99 (d, J=6.9 Hz, 6H, CH3), 1.28 (d, J=6.9 Hz, 6H, CH3), 3.26 (m, J=6.9 Hz, 2H, CH), 3.47 (d, J=11.4 Hz, 1H, NH), 4.86 (d, J=11.4 Hz, 1H, CH), 7.05-7.10 (m, 6H), 7.49 (m, 2H).

Example 13

Synthesis of Ligands G2-G4

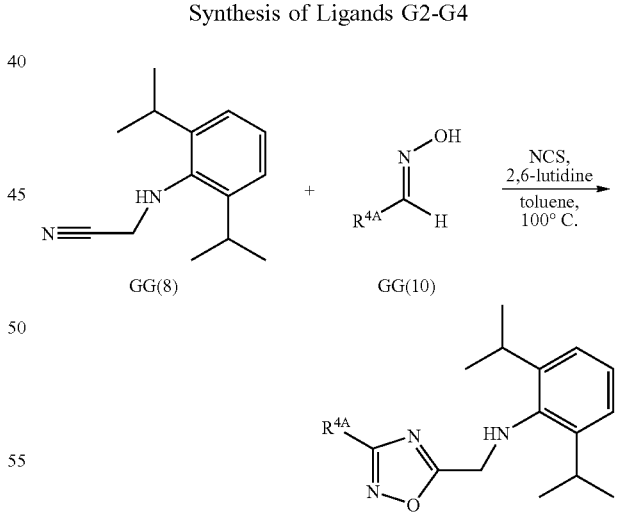

A reaction flask was charged under N$_2$ with GG(10) (0.60 mmol), GG(8) (0.20 mmol), and toluene (4 mL), 2,6-lutidine (0.60 mmol), or N-chlorosuccinimide (0.60 mmol). The reaction was heated at 100° C. for 18 hours. After cooling to room temperature, the reaction was diluted with Et$_2$O, washed twice with H$_2$O, once with brine, and then dried over Na$_2$SO$_4$. The crude material was purified by flash chromatography on silica gel. Ligand G2=63%, Ligand G3=43%, and Ligand G4=39%.

Example 14

Synthesis of Ligands G1 and G5

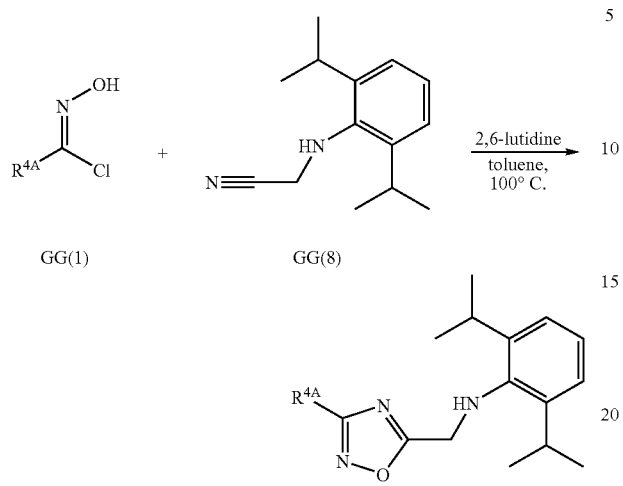

A reaction flask was charged under $N_2$ with GG(1) (0.87 mmol), GG(8) (0.29 mmol), and toluene (6 mL) or 2,6-lutidine (0.87 mmol). The reaction was heated at 100° C. for 18 hours. After cooling to room temperature, the reaction was diluted with $Et_2O$, washed twice with $H_2O$, once with brine, and then dried over $Na_2SO_4$. The crude material was purified by flash chromatography on silica gel. Ligand G1=64% and Ligand G5=42%.

Example 15

Synthesis of Ligands G6-G19

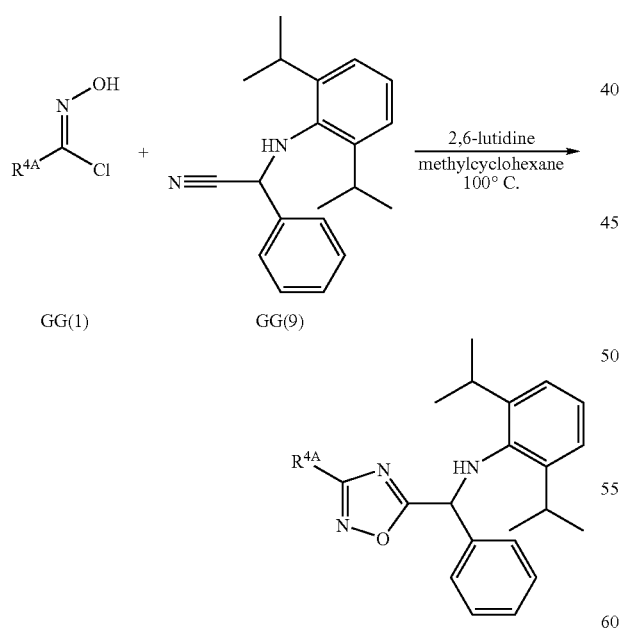

A reaction flask was charged under $N_2$ with GG(9) (0.30 mmol), GG(1) (0.90 mmol), methylcyclohexane (6 mL), and 2,6-lutidine (0.90 mmol). The reaction was stirred at room temperature for 30 minutes then heated at 100° C. for 18 hours. After cooling to room temperature, the reaction was filtered to remove insoluble material. The filtrate was concentrated and purified by flash chromatography on silica gel. Yields of Ligands G6-G19 were in the range of 44-80% with the exception of G14 which was 28%.

6. Pyrazoleamine Ligands

In the following examples, 3(5)-phenylpyrazole and 3(5)-tert-butylpyrazole were synthesized according to known procedures (Trofimenko, et. al., *Inorg. Chem.*, 1987, 26, 1507-1514). All other pyrazoles used were available commercially. All epoxides used below are commercially available. Amino alcohols were prepared using a reported procedure (Begue, et al., *J. Org. Chem.* 2000, 65, 6749-6751). Aziridines were synthesized as described below, except for cis-1,2,3-triphenylaziridine which was commercially available from Aldrich.

a. General Synthetic Methods

General Method H1: Synthesis of Amino Alcohols from Cyclopentene Oxide and Substituted Anilines

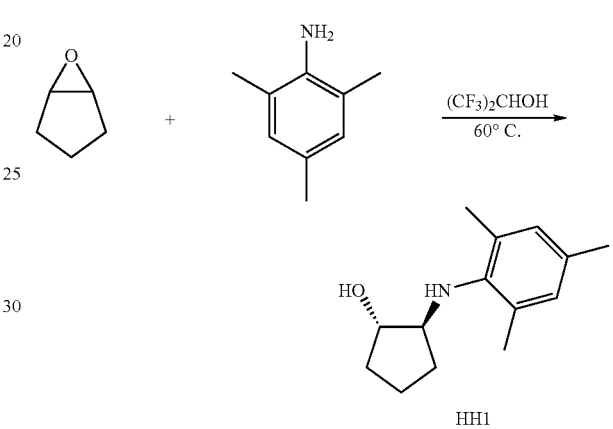

In a typical procedure, a 40 mL scintillation vial was charged with 1,1,1,3,3,3-hexafluoro-2-propanol (10 mL), cyclopentene oxide (1.74 mL, 19.90 mmol) and 2,4,6-trimethylaniline (3.40 mL, 24.20 mmol). The vial was flushed with argon, equipped with a septum-lined cap, and heated at 60° C. for 24 hours. The crude product mixture was purified by flash chromatography on silica gel.

General Method H2: Synthesis of Aziridines from Amino Alcohols

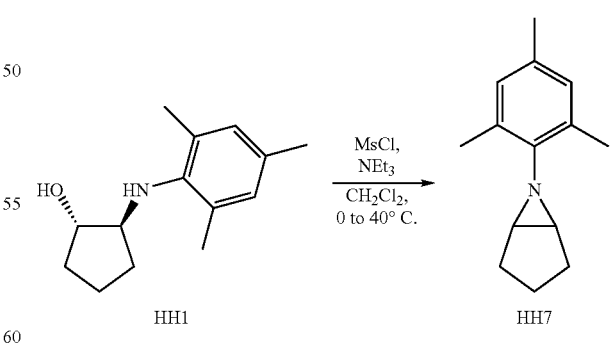

In a typical procedure, to a $CH_2Cl_2$ (30 mL) solution of amino alcohol HH1 (3.21 g, 14.6 mmol) and $NEt_3$ (6.10 mL, 44.0 mmol) at 0° C. under Argon was added methanesulfonyl chloride (1.25 mL, 16.2 mmol) dropwise via syringe. The reaction was kept at 0° C. for 1 hour then heated at 40° C. for 18 hours. The reaction mixture was washed with $H_2O$ and the aqueous phase was extracted twice with CH₂Cl₂. The combined organic layers were washed with brine and dried over Na₂SO₄. The product was isolated by flash chromatography on silica gel.

General Method H3: Synthesis of Pyrazole Amine Ligands

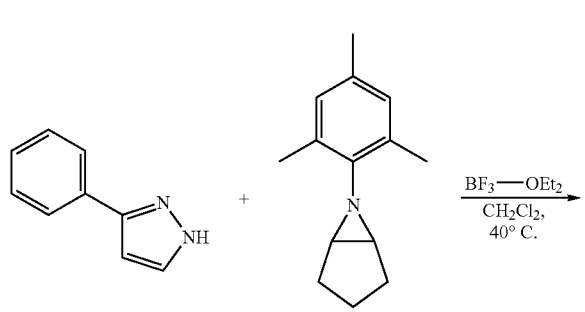

Step 2: Synthesis of Aziridine HH7

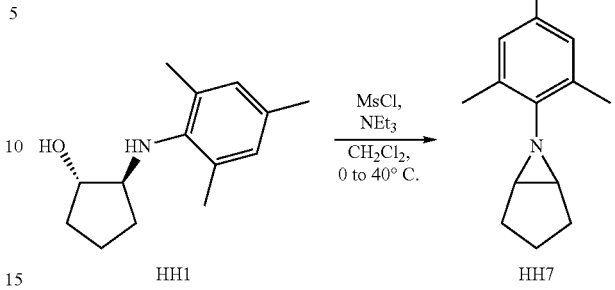

Step 3: Reaction of HH7 with Phenylpyrazole

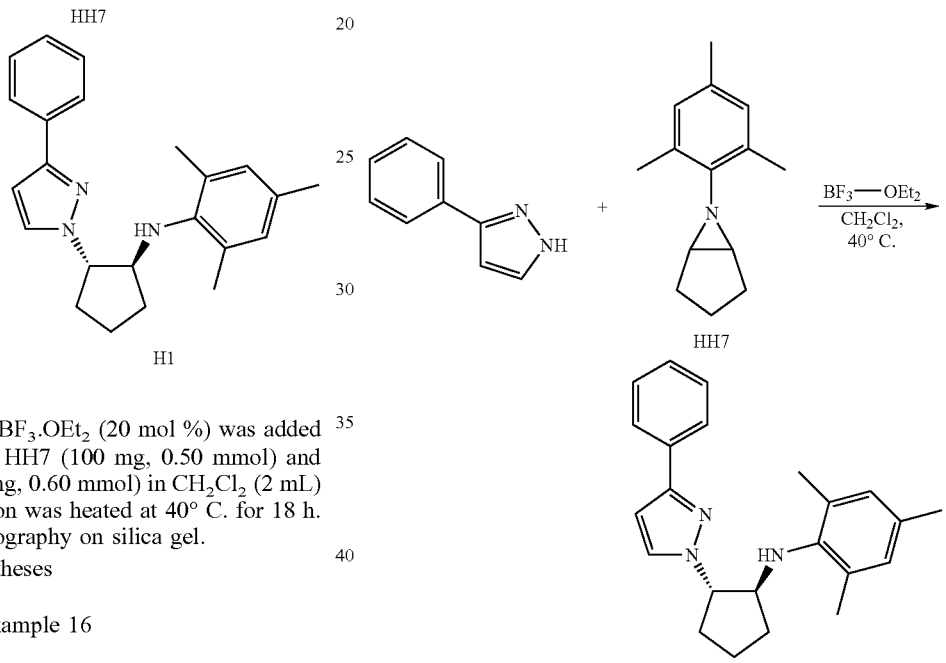

In a typical procedure, BF₃·OEt₂ (20 mol %) was added to a solution of aziridine HH7 (100 mg, 0.50 mmol) and 3(5)-phenylpyrazole (86 mg, 0.60 mmol) in CH₂Cl₂ (2 mL) at rt under N₂. The reaction was heated at 40° C. for 18 h. Purified by flash chromatography on silica gel.

b. Specific Ligand Syntheses

Example 16

Synthesis of Ligand H1

Step 1: Synthesis of Amino Alcohol HH1

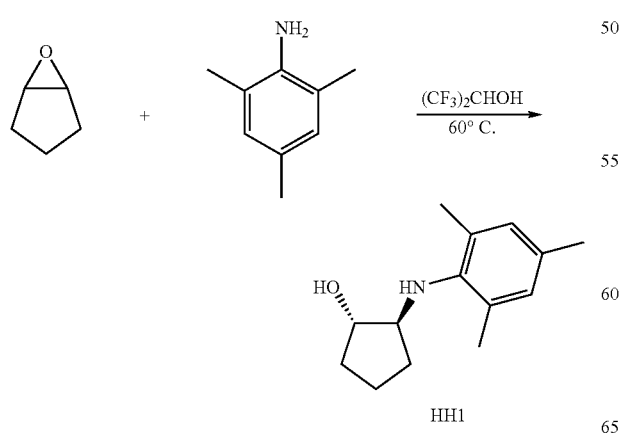

Experimental Details

Prepared according to General Method H1. Eluted with hexanes/EtOAc=5/1 and 2/1. Isolated 3.22 g, 74% yield, of amino alcohol HH1 as a faint yellow solid. $^1$H NMR (300 MHz, CDCl₃) δ 1.3-1.8 (m, 4H), 1.95-2.05 (m, 2H), 2.21 (s, 3H, CH₃), 2.25 (s, 6H, CH₃), 2.35-2.7 (br, 2H, NH and OH), 3.85 (m, 1H, CH), 3.92 (m, 1H, CH), 6.80 (s, 2H, aromatic CH).

HH7

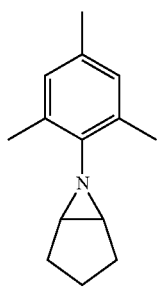

Prepared according to General Method H2. Eluted with hexanes/EtOAc=20/1 and 10/1. Isolated 2.4 g, 81% yield of HH7 as a white powder. $^1$H NMR (300 MHz, CDCl$_3$) δ 1.50-1.75 (m, 4H), 2.05-2.16 (m, 2H), 2.19 (s, 3H, CH$_3$), 2.27 (s, 6H, CH$_3$), 2.66 (s, 2H, CH), 6.74 (s, 2H, aromatic CH).

H1

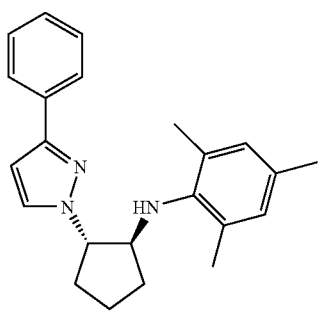

Prepared according to General Method H3. Eluted first with CH$_2$Cl$_2$ then with CH$_2$Cl$_2$/EtOAc=20/1. Isolated 124 mg, 72% yield of H1 as a light yellow, viscous oil. $^1$H NMR (300 MHz, C$_6$D$_6$) δ 1.15-1.29 (m, 1H), 1.38-1.53 (m, 1H), 1.59-1.75 (m, 1H), 1.78-2.00 (m, 2H), 2.03 (s, 6H, CH$_3$), 2.13 (s, 3H, CH$_3$), 2.16-2.28 (m, 1H), 2.69 (br s, 1H, NH), 3.80-4.00 (m, 2H, CH), 6.40 (d, J=2.3 Hz, 1H, pyrazole CH), 6.72 (s, 2H), 6.92 (d, J=2.3 Hz, 1H, pyrazole CH), 7.09-7.13 (m, 1H), 7.23-7.29 (m, 2H), 8.01-8.06 (m, 2H).

Example 17

Synthesis of Ligand H2

Step 1: Synthesis of Amino Alcohol HH1

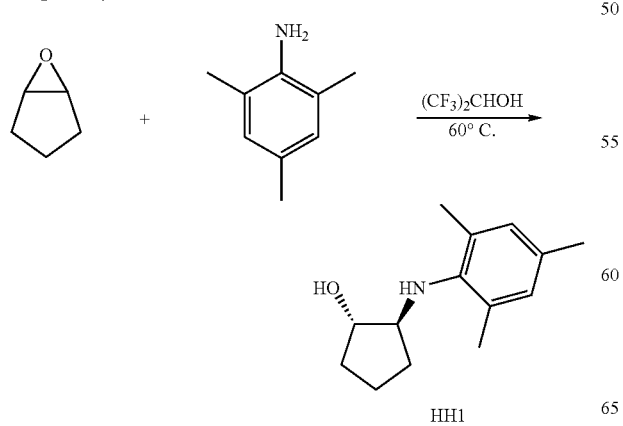

Step 2: Synthesis of Aziridine HH7

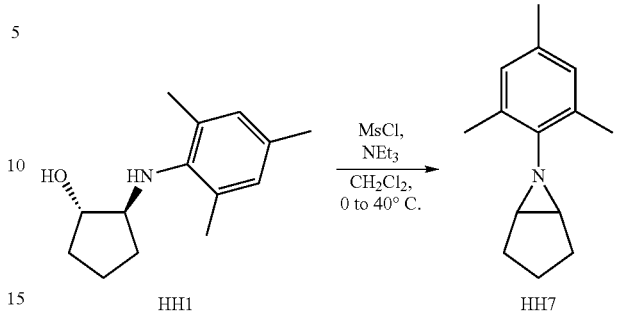

Step 3: Reaction of HH7 with Dimethylpyrazole

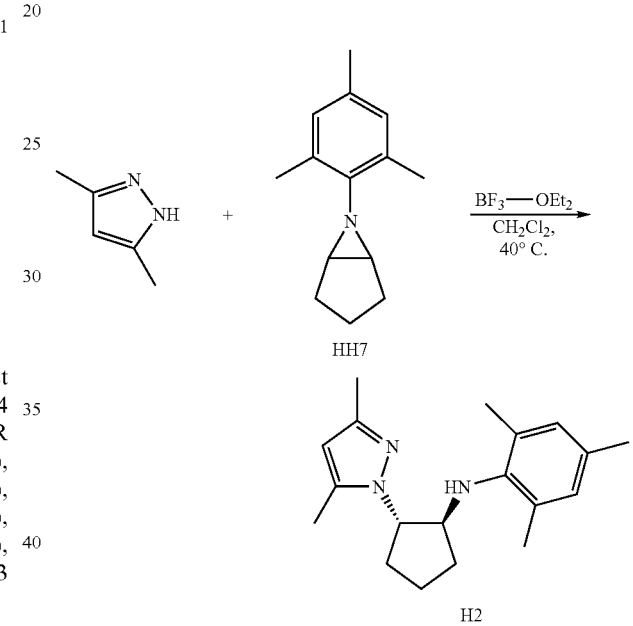

Experimental Details

H2

Prepared according to General Method H3 by reaction of HH7 (Example 16, above) with 3,5-dimethylpyrazole. The reaction was run for 48 hours. Eluted with hexanes/EtOAc=5/1 to isolate H2 in 85% yield as a faint yellow, viscous oil.

Example 18

Synthesis of Ligand H3

Step 1: Synthesis of Amino Alcohol HH2

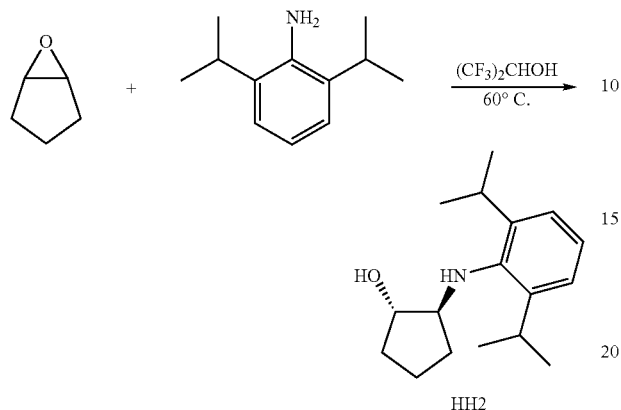

Step 2: Synthesis of Aziridine HH8

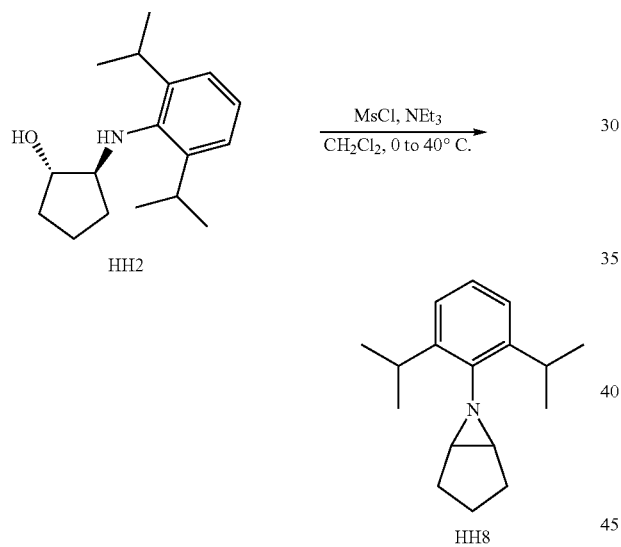

Step 3: Reaction of HH8 with Phenylpyrazole

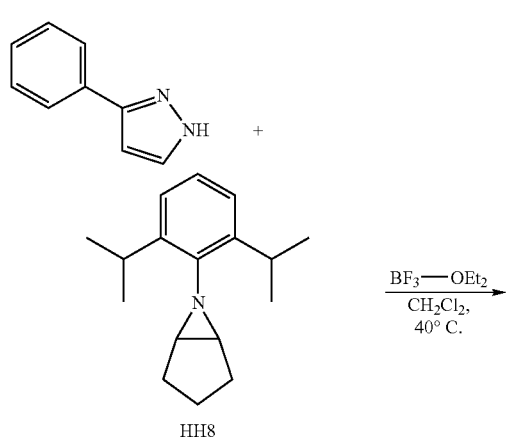

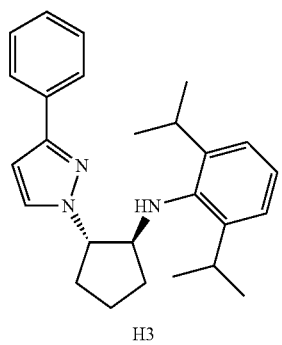

Experimental Details

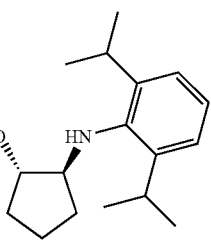

HH2

Prepared according to General Method H1, by reaction of cyclopentene oxide with 2,6-diisopropylaniline. Eluted with hexanes/EtOAc=10/1 and 5/1 to isolate HH2 in 72% yield as a white solid.

HH8

Prepared according to General Method H2. Eluted with hexanes/EtOAc=20/1 to isolate 84% yield of HH8 as a white solid.

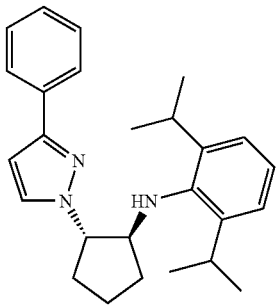

H3

Prepared according to General Method 3, by reaction of HH8 with 3(5)-phenylpyrazole. Eluted with hexanes/$CH_2Cl_2$=1/5 to isolate 71% yield of H3 as a white solid.

Example 19

Synthesis of Ligand H4

Step 1: Synthesis of Amino Alcohol HH2

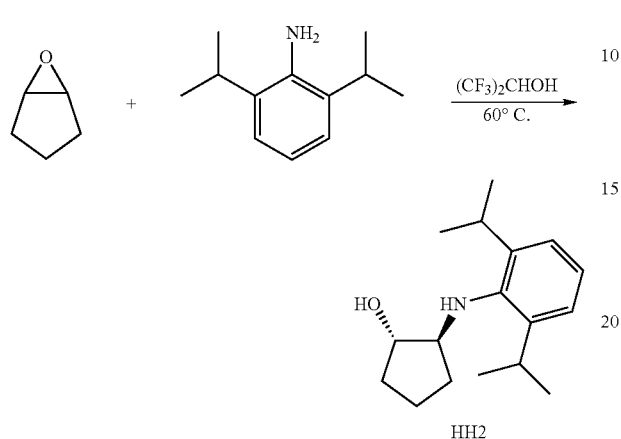

Step 2: Synthesis of Aziridine HH8

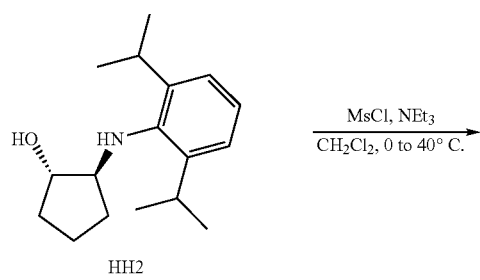

Step 3: Reaction of HH8 with t-Butylpyrazole

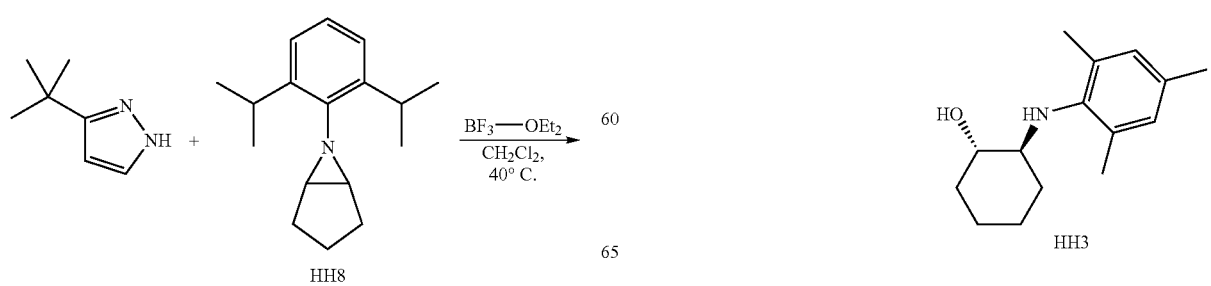

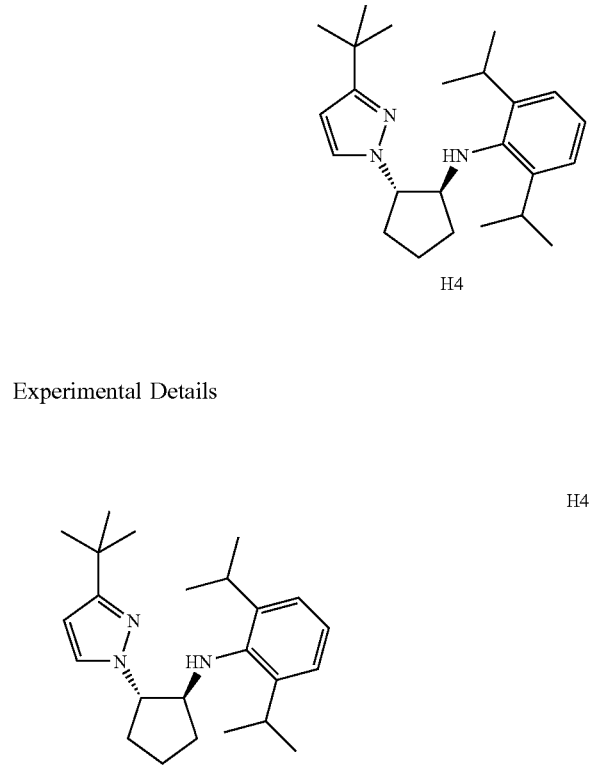

Experimental Details

Prepared according to General Method H3, by reaction of Reaction of HH8 (Example 28) with 3(5)-tert-butylpyrazole. Eluted with hexanes/EtOAc=10/1 to isolate H4 in 92% yield as a colorless oil.

Example 20

Synthesis of Ligand H5

Step 1: Synthesis of Amino Alcohol HH3

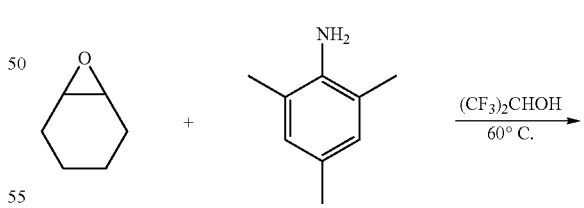

Step 2: Synthesis of Aziridine HH9

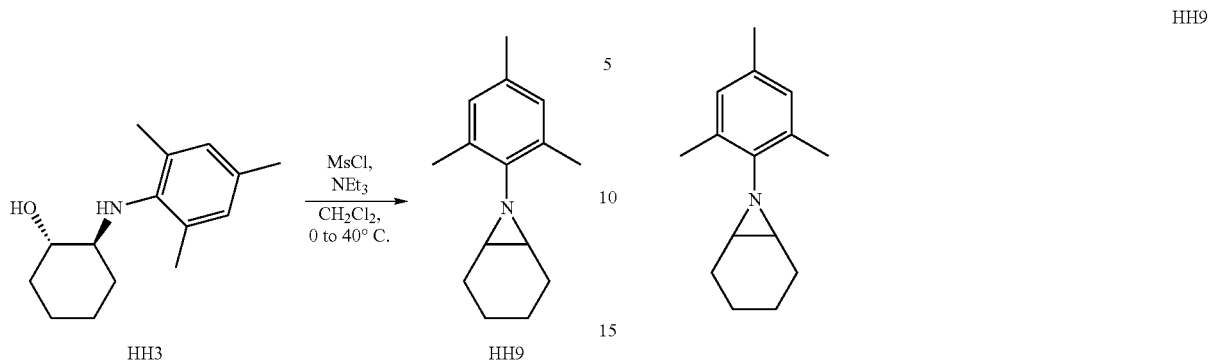

Prepared according to General Method 2. Eluted with hexanes/EtOAc=20/1 and 10/1 to isolate 70% yield of HH9 as a low melting point solid.

Step 3: Reaction of HH9 with Phenylpyrazole

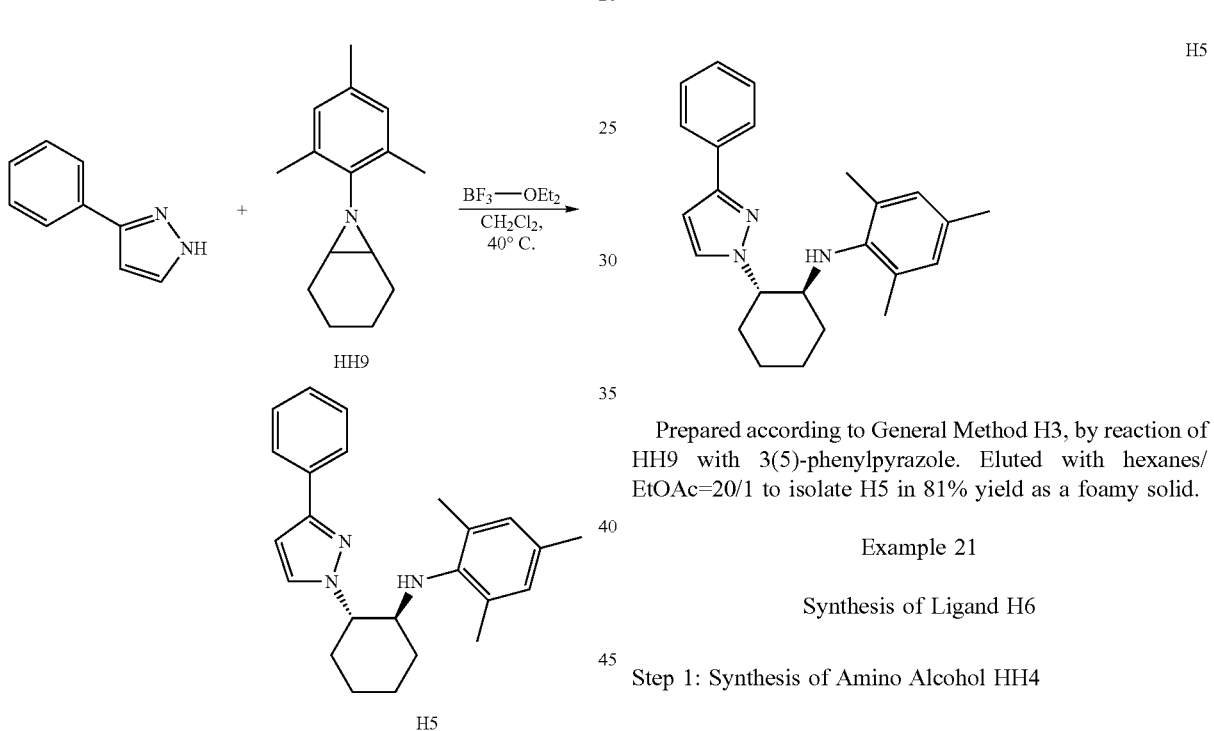

Prepared according to General Method H3, by reaction of HH9 with 3(5)-phenylpyrazole. Eluted with hexanes/EtOAc=20/1 to isolate H5 in 81% yield as a foamy solid.

Example 21

Synthesis of Ligand H6

Step 1: Synthesis of Amino Alcohol HH4

Experimental Details

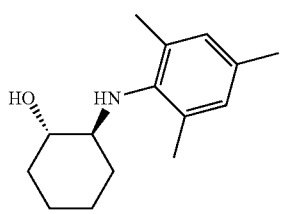

Prepared according to General Method H1, by reaction of cyclohexene oxide with 2,4,6-trimethylaniline. Eluted with hexanes/EtOAc=10/1 and 5/1 to isolate HH3 in 78% yield as a viscous light yellow oil.

Step 2: Synthesis of Aziridine HH10

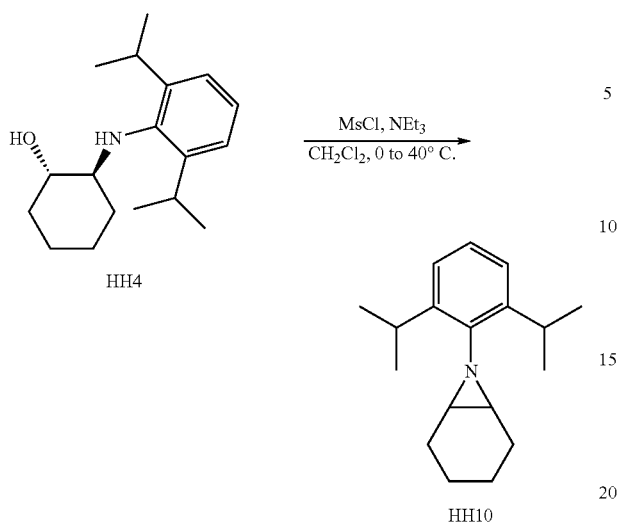

Step 3: Reaction of HH10 with Phenylpyrazole

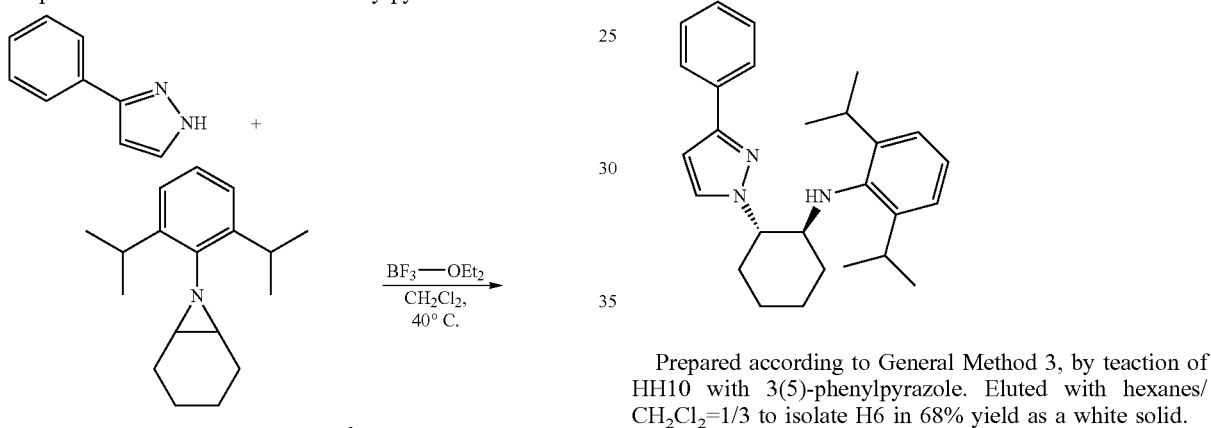

Experimental Details

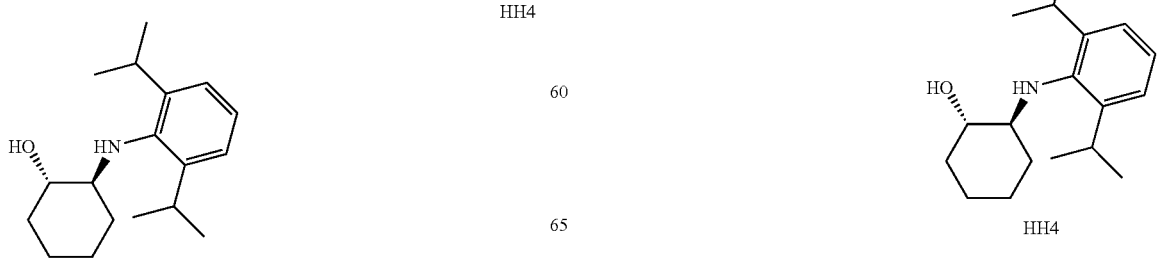

Prepared according to General Method H1, by reaction of cyclohexene oxide with 2,6-diisopropylaniline. Eluted with hexanes/EtOAc=20/1 to isolate HH4 in 79% yield as a viscous light yellow oil.

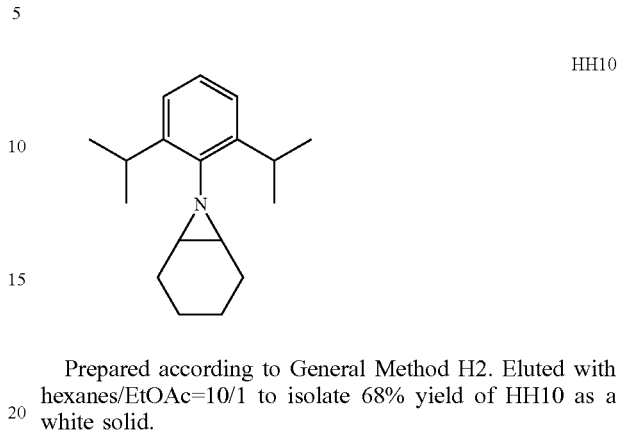

Prepared according to General Method H2. Eluted with hexanes/EtOAc=10/1 to isolate 68% yield of HH10 as a white solid.

Prepared according to General Method 3, by reaction of HH10 with 3(5)-phenylpyrazole. Eluted with hexanes/CH$_2$Cl$_2$=1/3 to isolate H6 in 68% yield as a white solid.

Example 22

Synthesis of Ligand H7

Step 1: Synthesis of Amino Alcohol HH4

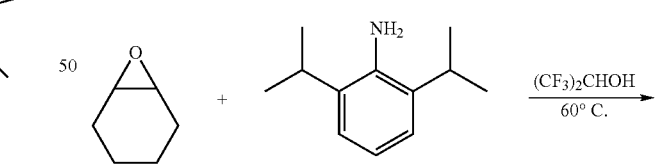

Step 2: Synthesis of Aziridine HH10
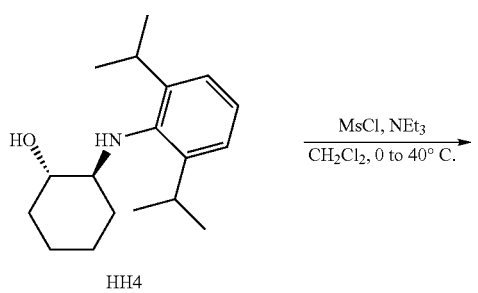
Step 3: Reaction of HH10 with Diphenylpyrazole
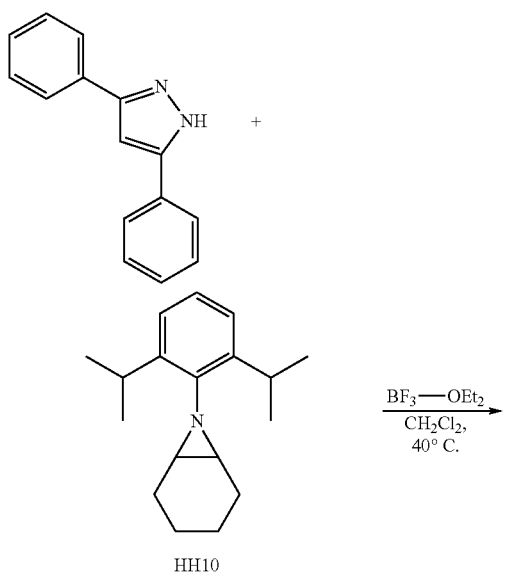
Experimental Details
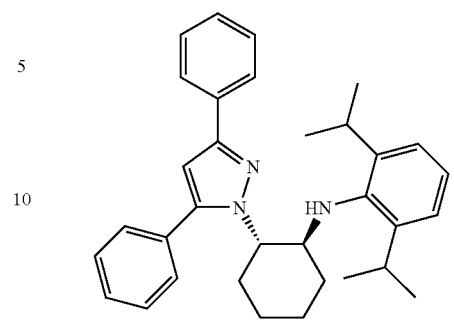
Prepared according to General Method H3, by reaction of HH10 (Example 21) with 3,5-diphenylpyrazole. Eluted with hexanes/CH$_2$Cl$_2$=2/1 to isolate H7 in 89% yield as a white solid.
Example 23
Synthesis of Ligand H8
Step 1: Synthesis of Amino Alcohol HH5
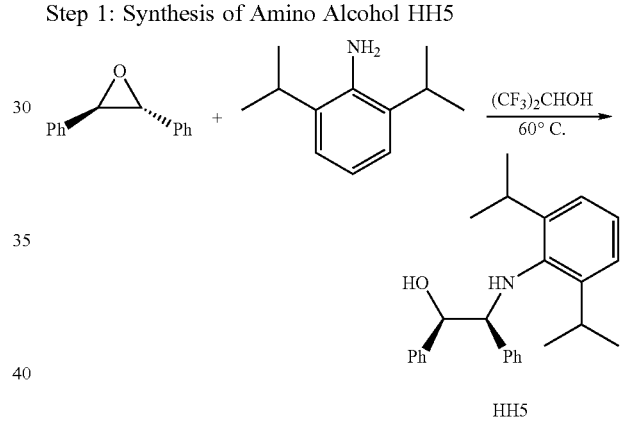
Step 2: Synthesis of Aziridine HH11
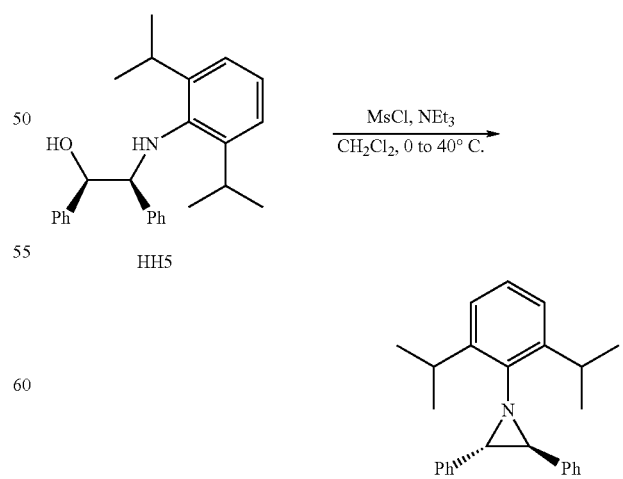

Step 3: Reaction of HH11 with Phenylpyrazole

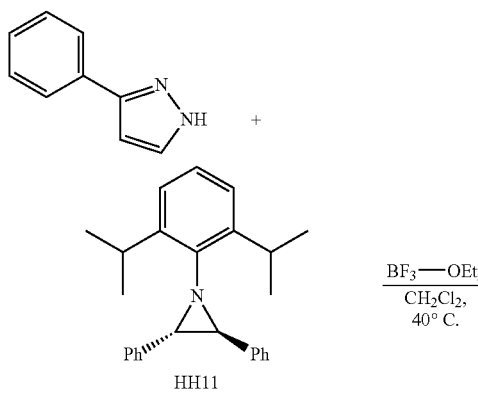

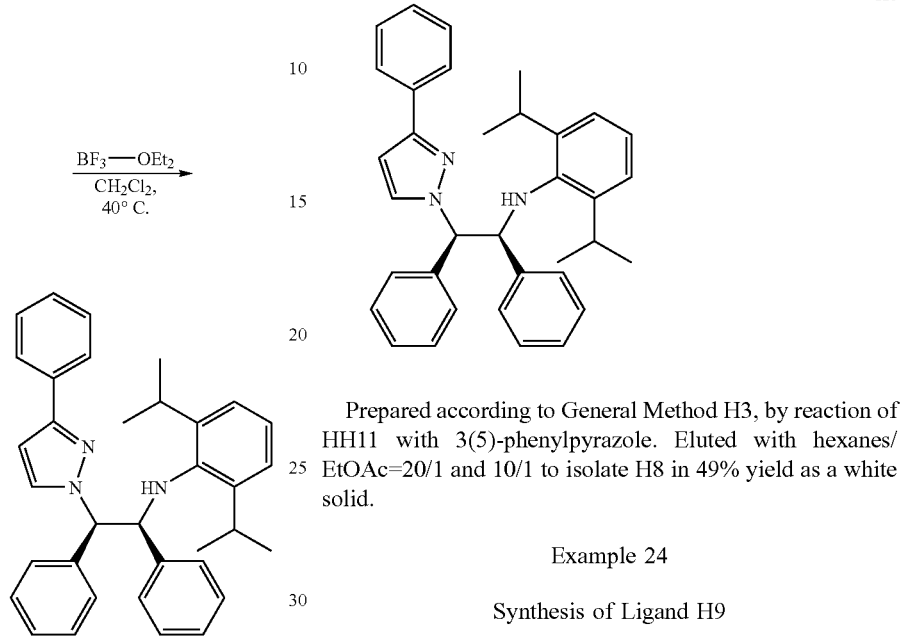

Experimental Details

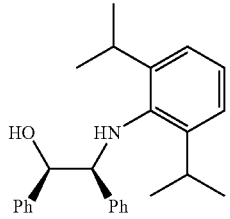
HH5

Prepared according to General Method H1, by teaction of trans-stilbene oxide with 2,6-diisoproplyaniline. The reaction was run at 60° C. in 2,2,2-trifluoroethanol instead of 1,1,1,3,3,3-hexafluoro-2-propanol. Eluted with hexanes/CH$_2$Cl$_2$=3/1 and 1/1 to isolate HH5 in 78% yield as a white solid.

HH11

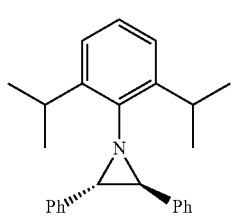

Prepared according to General Method H2, except that the reaction was run at room temperature for 18 hours instead of 40° C. Eluted with hexanes/EtOAc=40/1 to isolate 83% yield of HH11 white solid.

Prepared according to General Method H3, by reaction of HH11 with 3(5)-phenylpyrazole. Eluted with hexanes/EtOAc=20/1 and 10/1 to isolate H8 in 49% yield as a white solid.

Example 24

Synthesis of Ligand H9

Step 1: Synthesis of Amino Alcohol HH5

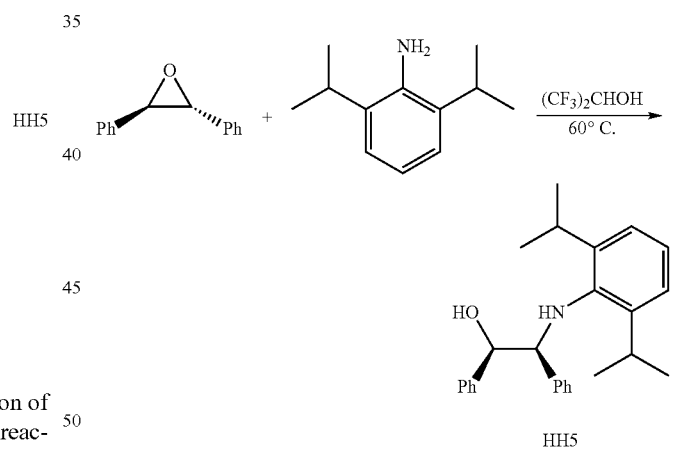

Step 2: Synthesis of Aziridine HH11

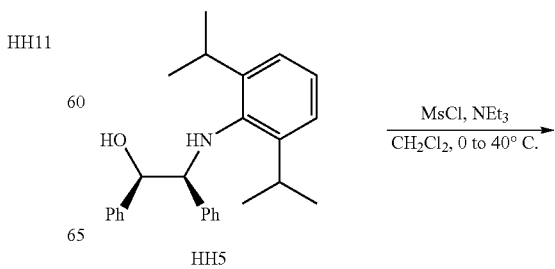

-continued

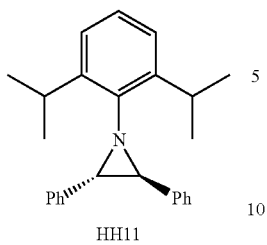
HH11

Step 3: Reaction of HH11 with Dihenylpyrazole

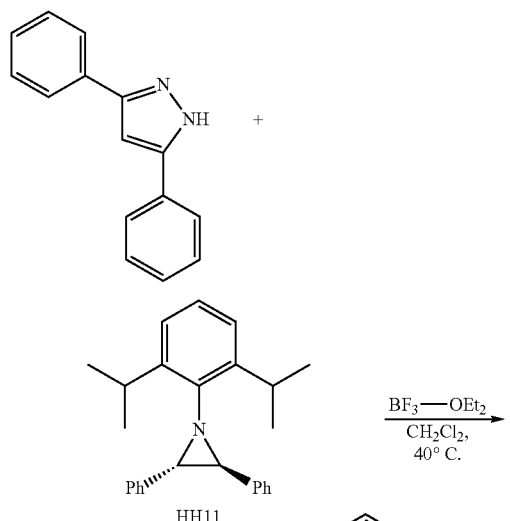

Experimental Details

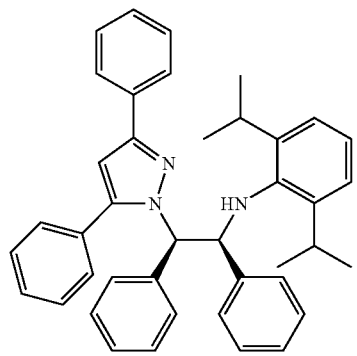
H9

Prepared according to General Method H3, by reaction of HH11 (Example 23) with 3,5-diphenylpyrazole. Eluted with hexanes/EtOAc=20/1 to isolate H9 in 90% yield as a white solid.

Example 25

Synthesis of Ligand H10

Step 1: Synthesis of Amino Alcohol HH5

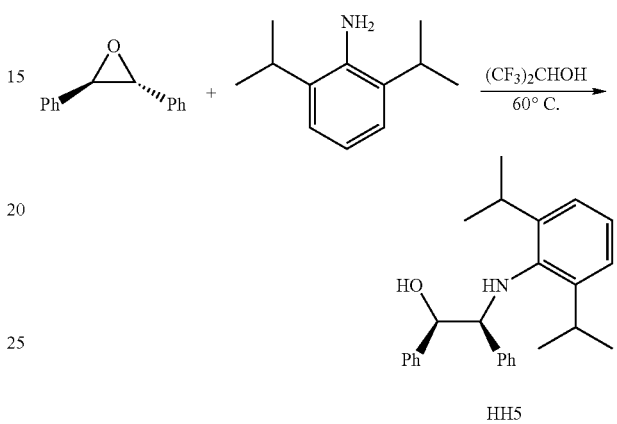

Step 2: Synthesis of Aziridine HH11

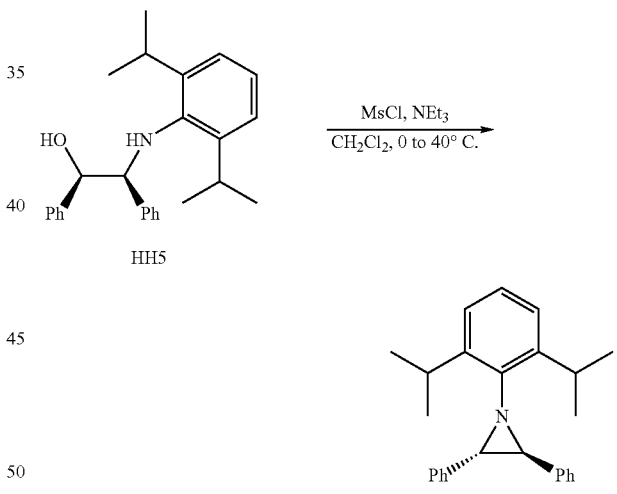

Step 3: Reaction of HH11 with t-Butylpyrazole

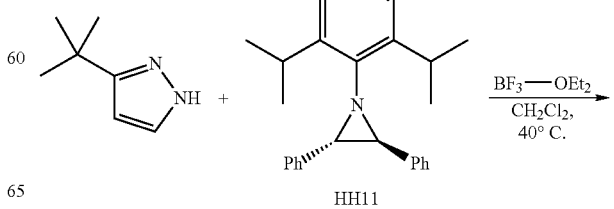

Step 2: Synthesis of Aziridine HH12
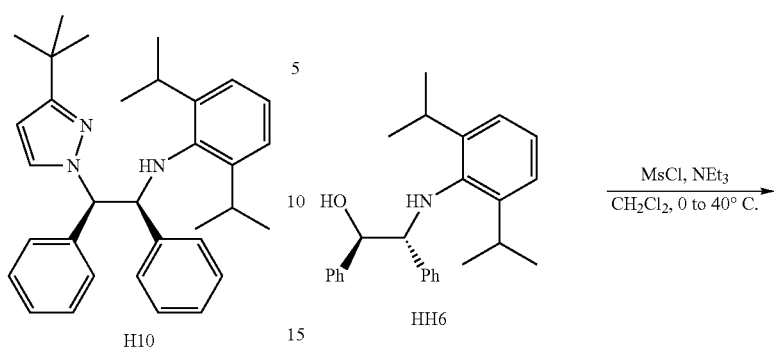
Experimental Details
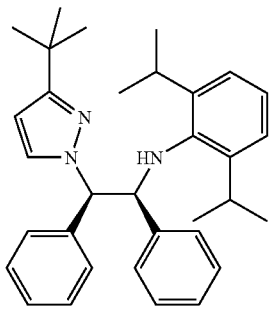
H10
Prepared according to General Method H3, by reaction of HH11 (Example 23) with 3(5)-tert-butylpyrazole. Eluted with hexanes/EtOAc=10/1 to isolate H10 in 90% yield as a colorless solid.
Example 26
Synthesis of Ligand H11
Step 1: Synthesis of Amino Alcohol HH6
Step 3: Reaction of HH12 with Phenylpyrazole
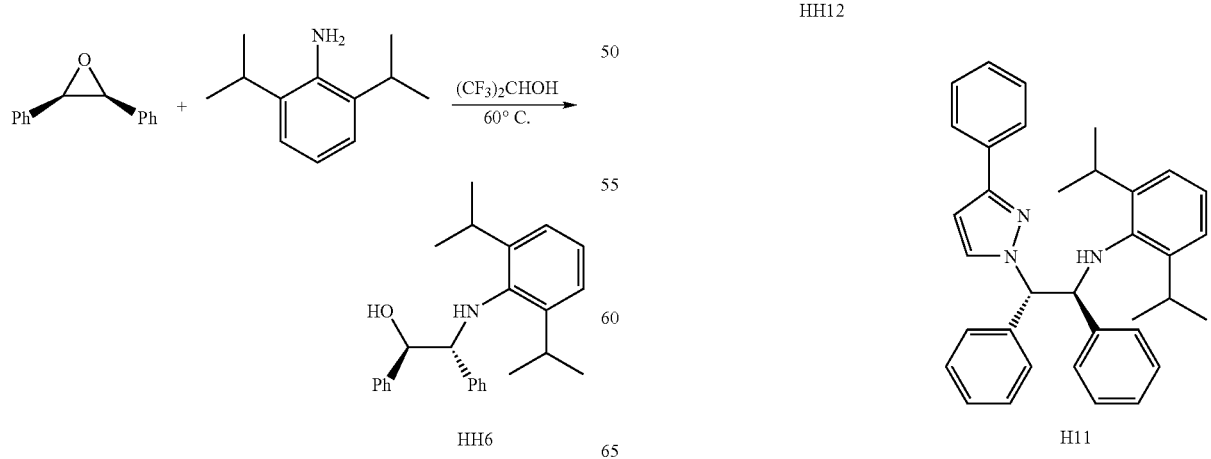

Experimental Details

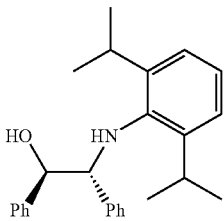
HH6

Prepared according to General Method H1, by reaction of cis-stilbene oxide with 2,6-diisoproplyaniline. The reaction was run at 80° C. for 48 hours in 2,2,2-trifluoroethanol instead of 1,1,1,3,3,3-hexafluoro-2-propanol. Eluted with hexanes/EtOAc=20/1 and 10/1 to isolate HH6 in 45% yield as a white solid.

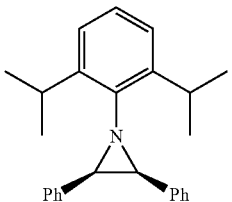
HH12

Prepared according to General Method H2, except that the reaction was run at room temperature for 18 hours instead of 40° C. Eluted with hexanes/EtOAc=20/1 to isolate 77% yield of HH12 white solid.

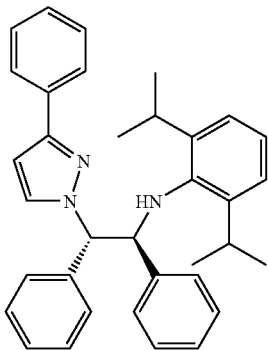
H11

Prepared according to General Method H3, by reaction of HH12 with 3(5)-phenylpyrazole. The reaction was run for 5 days at 40° C. Eluted with hexanes/EtOAc=40/1 and 20/1 to isolate H11 in 41% yield as a white solid.

Example 27

Synthesis of Ligand H12

Step 1: Reaction of Triphenylaziridene with Phenylpyrazole

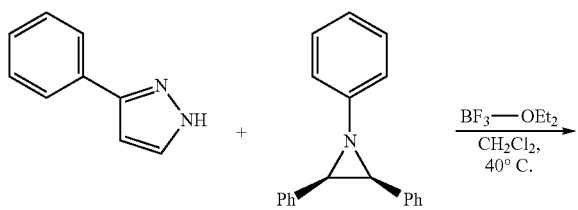

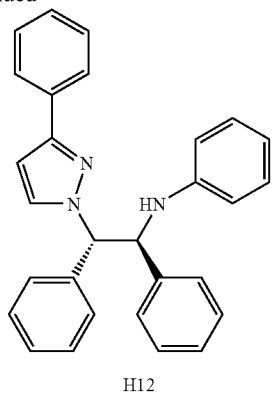
H12

Experimental Details

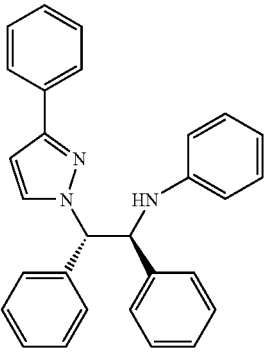
H12

Prepared according to General Method H3, by reaction of cis-1,2,3-triphenylaziridine with 3(5)-phenylpyrazole. The reaction was run at 60° C. in 1,2-dichloroethane for 18 h. Eluted with hexanes/EtOAc=10/1 to isolate H12 in 59% yield as a white solid.

B. Synthesis of Heteroaryl-Amine Complexes M1-M60

In the following sections, "Me" refers to methyl, "Ar" refers to aromatic, "Et" refers to ethyl, and "Bz" refers to benzyl. Unless otherwise noted, all manipulations were conducted under an atmosphere of dry, deoxygenated argon in a Vacuum Atmospheres or MBraun glovebox. HfCl4, MBz$_4$ (M=Hf, Zr) and M(NMe$_2$)$_4$ (M=Zr, Hf) were purchased from Strem Chemicals, Inc. in Newburyport, Mass., U.S.A. [MBz$_3$][BzB(C$_6$F$_5$)$_3$] (M=Hf, Zr) were synthesized as described in Pellecchia et al., *Organometallics* 1994, 13, 298-302; Pellecchia et al., *J. Am. Chem. Soc.* 1993, 115, 1160-1162; Pellecchia et al., *Organometallics* 1993, 13, 3773-3775 and Bochmann et al., *Organometallics* 1993, 12, 633-640, each of which is incorporated herein by reference. Hexane, pentane, diethyl ether, THF, and toluene were sparged with nitrogen and passed though columns of activated Al$_2$O$_3$ and CU-0226S (Engelhart; a commerically available oxygen scavenger). Anhydrous benzene-d$_6$ and toluene-d$_8$ were purchased from Cambridge Isotopes, degassed and stored over 4 Å molecular sieves. All other reagents were purchased from Aldrich in the highest available purity and used without further purification.

NMR spectra were recorded on a Bruker 300 MHz spectrometer. $^1$H chemical shifts were referenced relative to residual protio solvent peaks. Due to the large number of aromatic substituents and the complexity of the spectra in the 6.8-7.5 ppm region, the peaks corresponding to the hydrogens on the aromatic rings are generally not assigned and are denoted as "Ar" in the lists of NMR data.

Example 28

Synthesis of M1. Solid A1 (560 mg, 1.23 mmol) and $Hf(NMe_2)_4$ (603 mg, 1.7 mmol) were combined and 5 mL toluene was added. The mixture was heated to 75° C. for 2 h. Solvent was removed and the resulting yellow solid was recrystallized from pentane at −35° C. (800 mg, 85%) $^1H$ NMR (δ, $C_6D_6$ 7.68 (d, 2, Ar), 6.8-7.3 (m, 10, Ar+thiazole), 6.50 (s, 1, thiazole) 6.17 (s, 1, CHPh), 3.75 (sept., 1, $CH(CH_3)_2$), 3.30 (sept+s, 1, $CH(CH_3)_2$), 2.96 (br s, 6, $NMe_2$), 2.88 (br s, 6, $NMe_2$), 2.81 (br s, 6, $NMe_2$), 2.51 (q, 2, $CH_2CH_3$), 1.55 (d, 3, $CH(CH_3)_2$), 1.51 (d, 3, $CH(CH_3)_2$), 1.33 (d, 3, $CH(CH_3)_2$), 1.15 (t, 3, $CH_2CH_3$) 0.24 (d, 3, $CH(CH_3)_2$).

Example 29

Synthesis of M2. M1 (542 mg, 0.71 mmol) was dissolved in 15 mL of pentane. The mixture was cooled to −35° C. Neat $AlMe_3$ (680 µL, 6.6 mmol) was added. A pale yellow oil precipitated which solidified as the mixture was allowed to warm to room temperature. The solid was crushed with a spatula to ensure proper mixing. The slurry was stirred for 1 h and then the volume was decreased to 5 mL. The mixture was chilled at −35 C overnight, and then the precipitate was collected, washed with 2 mL pentane and dried, yielding an off-white solid. (402 mg, 85%). $^1H$ NMR (δ, $C_6D_6$) 7.60 (d, 2, Ar), 6.9-7.2 (m, 10, Ar), 6.34 (s, 1, thiazole SC—H), 5.90 (s, 1, CHPh), 3.60 (overlapping sept., 2, $CH(CH_3)_2$), 2.45 (q., 4, $CH_2CH_3$), 1.40 (d, 6, $CH(CH_3)_2$), 1.32 (d, 3, $CH(CH_3)_2$), 1.07 (t, 3, $CH_2CH_3$) 0.55 (s, 9, $Hf(CH_3)_3$), 0.27 (d, 3, $CH(CH_3)_2$).

Example 30

Synthesis of M3. A1 (149 mg, 0.34 mmol) and $Zr(NMe_2)_4$ (100 mg, 0.37 mmol) were combined and 2 mL benzene was added. The mixture was heated to 75° C. for 2 h. Solvent was removed and the resulting solid was recrystallized from pentane at −35° C. (175 mg, 78%) $^1H$ NMR was consistent with the proposed structure.

Example 31

Synthesis of M4. Solid A3 (107 mg, 0.22 mmol) and $Hf(NMe_2)_4$ (104 mg, 0.29 mmol) were combined and 2 mL benzene was added. The mixture was heated to 75° C. for 2 h. Solvent was removed and the resulting beige solid was recrystallized from pentane at −35° C. (145 mg, 84%) $^1H$ NMR (δ, $C_6D_6$) 6.9-7.9 (m, 15, Ar), 6.51 (s, 1, thiazole SC—H), 6.19 (s, 1, CHPh), 3.68 (sept., 1, $CH(CH_3)_2$), 3.32 (sept., 1, $CH(CH_3)_2$), 2.85 (br s, 6, $NMe_2$), 2.69 (br s, 6, $NMe_2$), 2.59 (br s, 6, $NMe_2$), 1.59 (d, 3, $CH(CH_3)_2$), 1.51 (d, 3, $CH(CH_3)_2$), 1.26 (d, 3, $CH(CH_3)_2$), 0.24 (d, 3, $CH(CH_3)_2$).

Example 32

Synthesis of M5. A12 (50 mg, 0.11 mmol) was dissolved in 2 mL toluene and $Hf(NMe_2)_4$ (40 mg, 0.11 mmol) was dissolved in 1 mL toluene. The solutions were combined and the mixture was heated to 80° C. for 3.5 h. Solvent was removed, yielding a sticky light green solid which was triturated with hexane and dried in vacuo. (65 mg, 75%) $^1H$ NMR was consistent with the proposed structure.

Example 33

Synthesis of M6. A6 (25 mg, 0.05 mmol) was dissolved in 2 mL toluene and $Hf(NMe_2)_4$ (18 mg, 0.05 mmol) was dissolved in 1 mL toluene. The solutions were combined and the mixture was heated to 80° C. for 3.5 h. Solvent was removed, yielding a sticky light green solid which was triturated with hexane and dried in vacuo. $^1H$ NMR was consistent with the proposed structure.

Example 34

Synthesis of M7. Solid A37 (199 mg, 0.38 mmol) and $Hf(NMe_2)_4$ (160 mg, 0.45 mmol) were combined and 4 mL benzene was added. The mixture was heated to 70° C. for 1 h. Solvent was removed and the resulting yellow oil was recrystallized from pentane at −35° C. (164 mg, 52%) $^1H$ NMR (δ, $C_6D_6$) 8.35 (d, 2, Ar), 7.40 (d, 2, Ar), 6.8-7.3 (m, 14, Ar+thiazole), 6.05 (s, 1, CHPh), 3.67 (sept., 1, $CH(CH_3)_2$), 3.24 (overlapping sept+s, 7, $CH(CH_3)_2+N(CH_3)_2$), 2.88 (s, 6, $NMe_2$), 2.84 (s, 6, $NMe_2$), 1.54 (d, 3, $CH(CH_3)_2$), 1.48 (d, 3, $CH(CH_3)_2$), 1.37 (d, 3, $CH(CH_3)_2$), 0.32 (d, 3, $CH(CH_3)_2$).

Example 35

Synthesis of M8. M7 (41 mg, 0.049 mmol) was dissolved in 4 mL of a pentane/toluene mixture (1:1 v/v). The mixture was cooled to −35° C. Neat $AlMe_3$ (49 µL, 0.48 mmol) was added. A pale yellow oil precipitated which dissolved as the mixture was allowed to warm to room temperature. The mixture was stirred for 1 h and then solvent was removed. The resulting colorless solid was washed with pentane. (24 mg, 60%). $^1H$ NMR (δ, $C_6D_6$) 8.30 (m, 2, Ar), 6.9-7.8 (m, 6, Ar), 6.47 (s, 1, thiazole SC—H), 6.13 (s, 1, CHPh), 3.73 (sept., 1, $CH(CH_3)_2$), 3.59 (sept., 1, $CH(CH_3)_2$), 1.48 (d, 3, $CH(CH_3)_2$), 1.34 (d, 3, $CH(CH_3)_2$), 1.26 (d, 3, $CH(CH_3)_2$), 0.27 (d, 3, $CH(CH_3)_2$), 0.00 (s, 9, $Hf(CH_3)_3$).

Example 36

Synthesis of M9. Solid A40 (55 mg, 0.12 mmol) and $Hf(NMe_2)_4$ (48 mg, 0.14 mmol) were combined and 2 mL benzene was added. The mixture was heated to 50° C. for 1 h. Solvent was removed and the resulting solid was recrystallized from pentane at −35° C. (61 mg, 66%) $^1H$ NMR (δ, $C_6D_6$) 6.9-7.4 (m, 10, Ar), 6.30 (thiazole) 6.26 (s, 1, CHPh), 3.89 (sept., 1, $CH(CH_3)_2$), 3.51 (sept, 6, $CH(CH_3)_2$), 2.91 (br s, 18, $NMe_2$), 2.38 (s, 3, Mes $CH_3$), 2.31 (s, 3, Mes $CH_3$), 2.16 (s, 3, Mes $CH_3$), 1.74 (d, 3, $CH(CH_3)_2$), 1.62 (d, 3, $CH(CH_3)_2$), 1.45 (d, 3, $CH(CH_3)_2$), 0.37 (d, 3, $CH(CH_3)_2$).

Example 37

Synthesis of M10. Solid A41 (41 mg, 0.09 mmol) and $Hf(NMe_2)_4$ (37 mg, 0.10 mmol) were combined and 2 mL benzene was added. The mixture was heated to 50° C. for 1 h. Solvent was removed and the resulting solid was dried in vacuo. $^1H$ NMR was consistent with the proposed structure.

Example 38

Synthesis of M11. Solid A17 (52 mg, 0.1 mmol) and Hf(NMe$_2$)$_4$ (46 mg, 0.13 mmol) were combined and 2 mL toluene was added. The mixture was heated to 110° C. for 2 days with occasional venting. Solvent was removed and the resulting solid was recrystallized from peritane at −35° C. The identity of the complex was confirmed by $^1$H NMR and X-ray structure determination. (64 mg, 77%) $^1$H NMR (δ, C$_6$D$_6$) 7.0-7.4 (m, 10, Ar), 6.74 (s, 1, Mes Ar), 6.58 (s, 1, thiazole SC—H), 6.50 (s, 1, Mes Ar), 6.47 (s, 1, CHMes), 3.76 (sept., 1, CH(CH$_3$)$_2$), 3.43 (sept., 1, CH(CH$_3$)$_2$), 2.90 (br s, 6, NMe$_2$), 2.64 (br s, 6, NMe$_2$), 2.48 (br s, 6, NMe$_2$), 2.31 (s, 3, MesCH$_{3(a)}$), 2.07 (s, 3, MesCH$_{3(b)}$), 1.84 (s, 3, MesCH$_{3(c)}$), 1.59 (d, 3, CH(CH$_3$)$_2$), 1.52 (d, 3, CH(CH$_3$)$_2$), 1.23 (d, 3, CH(CH$_3$)$_2$), 0.37 (d, 3, CH(CH$_3$)$_2$).

Example 39

Synthesis of M12. M11 (45 mg, 0.054 mmol) was dissolved in 7 mL of pentane. The mixture was cooled to −35° C. Neat AlMe$_3$ (52 μL, 0.54 mmol) was added. A pale yellow oil precipitated which dissolved as the mixture was allowed to warm to room temperature. The mixture was stirred for 1 h and then solvent was removed. The resulting colorless solid was recrystallized from pentane at −35° C. (24 mg, 60%). The identity of the complex was confirmed by $^1$H NMR and x-ray structure determination. $^1$H NMR (δ, tol-d$_8$) 7.70 (m, 4, Ar), 7.0-7.4 (m, 6, Ar), 6.78 (s, 1, Mes Ar), 6.64 (s, 1, Mes Ar), 6.54 (s, 1, thiazole SC—H), 6.45 (s, 1, CHMes), 3.76 (sept., 1, CH(CH$_3$)$_2$), 3.53 (sept., 1, CH(CH$_3$)$_2$), 2.38 (s, 3, MesCH$_{3(a)}$), 2.15 (s, 3, MesCH$_{3(b)}$), 1.86 (s, 3, MesCH$_{3(c)}$), 1.46 (d, 3, CH(CH$_3$)$_2$), 1.42 (d, 3, CH(CH$_3$)$_2$), 0.92 (d, 3, CH(CH$_3$)$_2$), 0.35 (d, 3, CH(CH$_3$)$_2$), 0.28 (s, 9, Hf(CH$_3$)$_3$).

Example 40

Synthesis of M13. M12 (25 mg, 0.034 mmol) was dissolved in 1 mL of toluene-d$_8$ in an NMR tube. The mixture was heated to 100° C. for 2 hours, at which time all of the starting material had reacted. A major and a minor component were observed in a 80/20 ratio. Solvent was removed and the resulting colorless solid was recrystallized from pentane at −35 C. $^1$H NMR (δ, tol-d$_8$, major isomer) 8.50 (d, 1, Ar), 7.93 (d, 1, Ar) 6.5-7.3 (m, 11, Ar+thiazole), 6.48 (s, 1, CHMes), 3.73 (sept., 1, CH(CH$_3$)$_2$), 3.37 (sept., 1, CH(CH$_3$)$_2$), 2.05 (s, 3, MesCH$_{3(a)}$), 2.03 (s, 3, MesCH$_{3(b)}$), 1.71 (s, 3, MesCH$_{3(c)}$), 1.42 (d, 3, CH(CH$_3$)$_2$), 1.34 (d, 3, CH(CH$_3$)$_2$), 1.18 (d, 3, CH(CH$_3$)$_2$), 0.90 (s, 3, Hf(CH$_3$)$_a$), 0.65 (s, 3, Hf(CH$_3$)$_b$), 0.30 (d, 3, CH(CH$_3$)$_2$). The minor component is proposed to be the dimethyl species resulting from metallation of napthyl at the 8-position.

Example 41

Synthesis of M14. Solid A42 (36 mg, 0.073 mmol) and Hf(NMe$_2$)$_4$ (28 mg, 0.08 mmol) were combined and 2 mL benzene was added. The mixture was stirred for 1 h at room temperature. Solvent was removed and the resulting solid was recrystallized from pentane at −35° C. (37 mg, 60%) $^1$H NMR (δ, C$_6$D$_6$) 6.9-7.5 (m, 12, Ar), 6.31 (s, 1, thiazole SC—H), 6.10 (s, 1, CHPh), 3.69 (sept., 1, CH(CH$_3$)$_2$), 3.33 (sept., 1, CH(CH$_3$)$_2$), 2.7 (br s, 18, NMe$_2$), 2.32 (s, 3, benzothiophene CH$_3$), 1.62 (d, 3, CH(CH$_3$)$_2$), 1.48 (d, 3, CH(CH$_3$)$_2$), 1.27 (d, 3, CH(CH$_3$)$_2$), 0.24 (d, 3, CH(CH$_3$)$_2$).

Example 42

Synthesis of M15. Solid A42 (27 mg, 0.054 mmol) and Zr(NMe$_2$)$_4$ (17 mg, 0.063 mmol) were combined and 2 mL benzene was added. The mixture was heated to 50 C for 1 h. Solvent was removed and the resulting solid was recrystallized from pentane at −35° C. (15 mg, 39%) $^1$H NMR (δ, C$_6$D$_6$) 6.9-7.5 (m, 12, Ar), 6.31 (s, 1, thiazole SC—H), 5.98 (s, 1, CHPh), 3.69 (sept., 1, CH(CH$_3$)$_2$), 3.30 (sept., 1, CH(CH$_3$)$_2$), 2.68 (br s, 18, NMe$_2$), 2.31 (s, 3, benzothiophene CH$_3$)1.61 (d, 3, CH(CH$_3$)$_2$), 1.48 (d, 3, CH(CH$_3$)$_2$), 1.25 (d, 3, CH(CH$_3$)$_2$), 0.26 (d, 3, CH(CH$_3$)$_2$).

Example 43

Synthesis of M16. M14 (62 mg, 0.077 mmol) was dissolved in 7 mL of pentane. The mixture was cooled to −35° C. Neat AlMe$_3$ (75 μL, 0.75 mmol) was added. A pale yellow oil precipitated which dissolved as the mixture was allowed to warm to room temperature. The mixture was stirred for 1 h and then solvent was removed. The resulting white solid was precipitated from pentane at −35° C. (28 mg, 51%). $^1$H NMR (δ, tol-d$_8$) 6.9-7.5 (m, 12, Ar), 6.27 (s, 1, thiazole SC—H), 5.97 (s, 1, CHPh), 3.6 (overlapping sept., 2, CH(CH$_3$)$_2$), 2.30 (br s, 3, benzothiophene CH$_3$), 1.48 (d, 3, CH(CH$_3$)$_2$), 1.35 (d, 3, CH(CH$_3$)$_2$), 1.29 (d, 3, CH(CH$_3$)$_2$), 0.23 (overlapping s+d, 12 total, CH(CH$_3$)$_2$+Hf(CH$_3$)$_3$).

Example 44

Synthesis of M17. M16 (11 mg, 0.015 mmol) was dissolved in 1 mL of toluene-d$_8$ in a NMR tube. The solution was heated to 75 C for 3 h, at which time $^1$H NMR revealed that the reaction was complete. Solvent was removed and the resulting off-white solid was dried in vacuo (11 mg, 100%). $^1$H NMR was consistent with the proposed structure.

Example 45

Synthesis of M18. Solid A45 (54 mg, 0.11 mmol) and Hf(NMe$_2$)$_4$ (49 mg, 0.14 mmol) were combined and 2 mL benzene was added. The mixture was heated to 70° C. for 3 h. Solvent was removed and the resulting solid was recrystallized from pentane at −35° C. (69 mg, 76%) $^1$H NMR (δ, C$_6$D$_6$) 6.7-7.7 (m, 11, Ar), 6.29 (s, 1, thiazole SC—H), 6.25 (s, 1, CHAr), 3.75 (sept., 1, CH(CH$_3$)$_2$), 3.35 (sept., 1, CH(CH$_3$)$_2$), 2.73 (br s, 18, NMe$_2$), 2.36 (s, 3, benzothiophene CH$_3$), 1.84 (s, 3, ArCH$_3$), 1.60 (d, 3, CH (CH$_3$)$_2$), 1.45 (d, 3, CH(CH$_3$)$_2$), 1.25 (d, 3, CH(CH$_3$)$_2$), 0.32 (d, 3, CH(CH$_3$)$_2$).

Example 46

Synthesis of M19. Solid A46 (41 mg, 0.07 mmol) and Hf(NMe$_2$)$_4$ (28 mg, 0.08 mmol) were combined and 2 mL benzene was added. The mixture was heated to 70° C. for 4 h. Solvent was removed and the resulting solid was precipitated from pentane at −35° C. $^1$H NMR (δ, C$_6$D$_6$) 7.9 (d, 1, Ar) 6.8-7.6 (m, 15, Ar), 6.23 (s, 1, thiazole SC—H), 5.87 (s, 1, CHAr), 3.51 (sept., 1, CH(CH$_3$)$_2$), 3.37 (sept., 1, CH(CH$_3$)$_2$), 2.70 (br s, 18, NMe$_2$), 2.36 (s, 3, benzothiophene CH$_3$), 1.32 (d, 3, CH(CH$_3$)$_2$), 1.28 (d, 3, CH(CH$_3$)$_2$), 0.68 (d, 3, CH(CH$_3$)$_2$), 0.44 (d, 3, CH(CH$_3$)$_2$).

Example 47

Synthesis of M20. Solid A47 (36 mg, 0.06 mmol) and Hf(NMe$_2$)$_4$ (22 mg, 0.06 mmol) were combined and 2 mL benzene was added. The mixture was heated to 70° C. for 1 h. Solvent was removed and the resulting solid was recrystallized from hexane at −35° C. (34 mg, 63%) $^1$H NMR (δ, C$_6$D$_6$) 7.0-7.7 (m, 11, Ar), 6.38 (s, 1, thiazole SC—H), 6.22 (s, 1, CHAr), 3.80 (sept., 1, CH(CH$_3$)$_2$), 3.32 (sept., 1, CH(CH$_3$)$_2$), 2.74 (br s, 18, NMe$_2$), 2.37 (s, 3, benzothiophene CH$_3$), 1.72 (d, 3, CH(CH$_3$)$_2$), 1.44 (d, 3, CH(CH$_3$)$_2$), 1.20 (d, 3, CH(CH$_3$)$_2$), 1.1-1.9 (m, 11, Cy), 0.29 (d, 3, CH(CH$_3$)$_2$).

Example 48

Synthesis of M21. Solid A43 (200 mg, 0.37 mmol) and HfCl$_4$ (120 mg, 0.38 mmol) were combined and 15 mL diethylether was added. The mixture was overnight at ambient temperature. A beige-pink precipitate formed. The mixture was then cooled to −35° C. A 3.0 M solution of CH$_3$MgBr in ether (510 μL, 1.53 mmol, 4.1 eq.) was added and the mixture was allowed to warm to room temperature. Gas evolution was observed and the mix was stirred for 1.5 h. Solvent was removed and the resulting solid was extracted with 5 mL toluene and filtered. The volume of the filtrate was reduced to 0.5 mL and 1 mL of pentane was layered on top of the solution. Colorless microcrystals formed at −35° C. overnight. The product was collected, washed with pentane, and dried. (152 mg, 54%) $^1$H NMR (δ, C$_6$D$_5$Cl, 60° C.) 7.75 (d, 1, Ar) 7.0-7.5 (m, 11, Ar), 6.90 (s, 1, thiazole SC—H), 6.69 (s, 1, CHMes), 3.83 (sept., 1, CH(CH$_3$)$_2$), 3.52 (sept., 1, CH(CH$_3$)$_2$), 2.51 (s, 3, Mes CH$_3$ or benzothiophene CH$_3$), 2.44 (s, 3, Mes CH$_3$ or benzothiophene CH$_3$), 2.27 (s, 3, Mes CH$_3$ or benzothiophene CH$_3$), 1.94 (s, 3, Mes CH$_3$ or benzothiophene CH$_3$), 1.60 (d, 3, CH(CH$_3$)$_2$), 1.52 (d, 3, CH(CH$_3$)$_2$), 1.33 (d, 3, CH(CH$_3$)$_2$), 0.38 (d, 3, CH(CH$_3$)$_2$), 0.27 (s, 9, Hf(CH$_3$)$_3$.

Example 49

Synthesis of M22. Solid A49 (41 mg, 0.07 mmol) and Hf(NMe$_2$)$_4$ (28 mg, 0.08 mmol) were combined and 2 mL benzene was added. The mixture was heated to 50° C. for 2 h. Solvent was removed and the resulting solid was recrystallized from pentane at −35° C. 1H NMR revealed that the metallated bis(amide) complex was isolated. $^1$H NMR (δ, C$_6$D$_6$) 7.82 (d, 1, Ar), 7.73 (d, 1, Ar) 6.8-7.5 (m, 11, Ar), d, 6.10 (d, 1, thiazole CH) 5.96 (s, 1, CHPh), 3.45 (sept., 1, CH(CH$_3$)$_2$), 3.38 (sept., 1, CH(CH$_3$)$_2$), 3.10 (s, 6, NMe$_2$), 2.76 (s, 6, NMe$_2$), 1.42 (d, 3, CH(CH$_3$)$_2$), 1.21(d, 3, CH(CH$_3$)$_2$), 1.07 (s, 3, CH(CH$_3$)$_2$), 0.31 (d, 3, CH(CH$_3$)$_2$).

Example 50

Synthesis of M23. Solid A50 (38 mg, 0.08 mmol) and Hf(NMe$_2$)$_4$ (34 mg, 0.10 mmol) were combined and 2 mL benzene was added. The mixture was heated to 60° C. for 2 h. Solvent was removed and the resulting solid was recrystallized from pentane at −35° C. $^1$H NMR (δ, C$_6$D$_6$) 7.95 (d, 1, Ar) 6.8-7.5 (m, 11, Ar+thiazole), d, 6.57 (d, 1, indole CH) 6.49 (m, 1, indole CH), 6.23 (s, 1, CHPh), 3.70 (sept., 1, CH(CH$_3$)$_2$), 3.38 (sept., 1, CH(CH$_3$)$_2$), 2.94 (s, 3, indole NMe) 2.7-3.1 (br overlapping s, 18, NMe$_2$), 1.57 (d, 3, CH(CH$_3$)$_2$), 1.51(d, 3, CH(CH$_3$)$_2$), 1.33 (s, 3, CH(CH$_3$)$_2$), 0.26 (d, 3, CH(CH$_3$)$_2$).

Example 51

Synthesis of M24. Solid A48 (38 mg, 0.08 mmol) and Hf(NMe$_2$)$_4$ (29 mg, 0.08 mmol) were combined and 2 mL benzene was added. The mixture was heated to 50° C. for 2 h. Solvent was removed and the resulting solid was recrystallized from pentane at −35° C. (40 mg, 63%) $^1$H NMR (δ, C$_6$D$_6$) 7.42 (overlapping d, 2, Ar) 6.8-7.3 (m, 10, Ar), 6.37 (s, 1, thiazole SC—H), 6.12 (s, 1, CHPh), 3.70 (sept., 1, CH(CH$_3$)$_2$), 3.35 (sept., 1, CH(CH$_3$)$_2$), 2.7 (br s, 20, NMe$_2$+CH$_2$CH$_3$), 1.62 (d, 3, CH(CH$_3$)$_2$), 1.51 (d, 3, CH(CH$_3$)$_2$), 1.25 (m, 6, overlapping CH(CH$_3$)$_2$+CH$_2$CH$_3$), 0.26 (d, 3, CH(CH$_3$)$_2$).

Example 52

Synthesis of M25. Solid A52 (47 mg, 0.08 mmol) and Hf(NMe$_2$)$_4$ (33 mg, 0.09 mmol) were combined and 4 mL benzene was added. The mixture was heated to 70° C. for 3 h. Solvent was removed and the resulting yellow solid was washed with pentane and dried. (54 mg, 70%) $^1$H NMR (δ, C$_6$D$_6$) 7.96 (d, 1, Ar) 6.8-7.5 (m, 15, Ar), 6.30 (s, 1, thiazole SC—H), 5.87 (s, 1, CHBiPh), 3.52 (sept., 1, CH(CH$_3$)$_2$), 3.35 (sept., 1, CH(CH$_3$)$_2$), 2.77 (br s, 20, NMe$_2$+CH$_2$CH$_3$), 1.34 (d, 3, CH(CH$_3$)$_2$), 1.31 (d, 3, CH(CH$_3$)$_2$), 1.22 (t, 3, CH$_2$CH$_3$), 0.69 (d, 3, CH(CH$_3$)$_2$), 0.44 (d, 3, CH(CH$_3$)$_2$).

Example 53

Synthesis of M26. Solid A2 (48 mg, 0.11 mmol) and Zr(CH$_2$Ph)$_4$ (50 mg, 0.11 mmol) were combined and 2 mL benzene was added. The mixture was heated to 75° C. for 4 h. Solvent was removed and the resulting solid was dissolved in hot hexane and filtered. The volume was reduced to 1 mL and cooled to −35° C. A yellow precipitate formed which was collected and dried. (52 mg, 58%) $^1$H NMR (δ, C$_6$D$_6$) 7.94 (d, 2, Ar), 6.3-7.3 (m, 19, Ar+thiazole), 6.01 (s, 1, CHPh), 3.35 (s, 3, OMe) 3.32 (overlapping sept., 2, CH(CH$_3$)$_2$), 2.80 (d, 1, CH$_2$Ph), 2.50 (s, 2, CH$_2$Ph), 2.34 (d, 1, CH$_2$Ph), 1.37 (d, 3, CH(CH$_3$)$_2$), 1.28 (d, 3, CH(CH$_3$)$_2$), 1.18 (d, 3, CH(CH$_3$)$_2$), 0.04 (d, 3, CH(CH$_3$)$_2$).

Example 54

Synthesis of M27. Solid A2 (27 mg, 0.06 mmol), Zr(CH$_2$Ph)$_4$ (28 mg, 0.06 mmol), and B(C$_6$F$_5$)$_3$ (32 mg, 0.06 mmol) were combined and 2 mL toluene was added. The mixture was stirred at room temperature for 30 minutes, yielding an orange solution. 3 mL pentane was added and the total volume was reduced to 2 mL. The mixture was cooled to −35° C. A yellow-orange oil precipitated. The oil was collected, washed with pentane, and dried, yielding an orange-yellow solid. (54 mg, 68%) 5.8-7.5 (m, 29, Ar+thiazole+CHPh), 3.78 (sept., 1, CH(CH$_3$)$_2$), 3.39 (s, 3, OMe), 3.36 (br s, 2, BCH$_2$Ph), 3.20 (sept., 1, CH(CH$_3$)$_2$), 2.92 (sept., 1, CH(CH$_3$)$_2$), 2.60 (d, 1, CH$_2$Ph), 2.43 (s, 2, CH$_2$Ph), 1.57 (overlapping d, 2, CH$_2$Ph), 1.85 (d, 1, CH$_2$Ph), 1.42 (d, 3, CH(CH$_3$)$_2$), 1.18 (d, 3, CH(CH$_3$)$_2$), 1.13 (d, 3, CH(CH$_3$)$_2$), 0.07 (d, 3, CH(CH$_3$)$_2$).

Example 55

Synthesis of M28. A34 (75 mg, 0.17 mmol) was dissolved in 2 mL benzene. Zr(CH$_2$Ph)$_4$ (81 mg, 0.18 mmol) was dissolved in 2 mL benzene and this solution was added to the ligand solution with stirring. The mixture was stirred at room temperature for 1 h and then solvent was removed. The resulting solid was recrystallized from pentane at −35 C. $^1$H NMR (δ, $C_6D_6$) 6.5-7.5 (m, 19, Ar+thiazole), 5.89 (s, 1, CHPh), 3.58 (sept., 1, $CH(CH_3)_2$), 3.10 (sept., 1, CH $(CH_3)_2$), 2.90 (d, 1, $CH_2Ph$), 1.8-2.1 (overlapping d, 3, $CH_2Ph$), 1.45 (d, 3, $CH(CH_3)_2$), 1.33 (d, 3, $CH(CH_3)_2$), 1.18 (d, 3, $CH(CH_3)_2$), 0.10 (d, 3, $CH(CH_3)_2$).

Example 56

Synthesis of M29. A34 (50 mg, 0.11 mmol) was dissolved in 2 mL benzene. $Hf(CH_2Ph)_4$ (68 mg, 0.13 mmol) was dissolved in 2 mL benzene and this solution was added to the ligand solution with stirring. The mixture was stirred at room temperature for 2 h and then solvent was removed. The resulting off-white solid was precipitated from pentane and dried. $^1$H NMR was consistent with the proposed structure.

Example 57

Synthesis of M30. A36 (20 mg, 0.04 mmol) was dissolved in 1 mL benzene. $Zr(NMe_2)_4$ (12 mg, 0.04 mmol) was dissolved in 1 mL benzene and this solution was added to the ligand solution. The mixture was heated to 65° C. for 1 h, at which time $^1$H NMR revealed that the reaction was complete. Solvent was removed and the resulting off-white solid was recrystallized from pentane. (14 mg, 53%) $^1$H NMR (δ, $C_6D_6$) 6.75-7.4 (m, 7, Ar), 6.73 (s, 1, Mes Ar), 6.55 (s, 1, Mes Ar), 6.52 (s, 1, thiazole SC—H), 6.20 (s, 1, CHMes), 3.69 (sept., 1, $CH(CH_3)_2$), 3.09 (sept., 1, $CH(CH_3)_2$), 2.95 (s, 6, $NMe_2$), 2.79 (s, 6, $NMe_2$), 2.20 (s, 3, $MesCH_{3(a)}$), 2.06 (s, 3, $MesCH_{3(b)}$), 1.73 (s, 3, $MesCH_{3(c)}$), 1.34 (d, 3, $CH(CH_3)_2$), 1.27 (d, 3, $CH(CH_3)_2$), 1.14 (d, 3, $CH(CH_3)_2$), 0.39 (d, 3, $CH(CH_3)_2$).

Example 58

Synthesis of M31. A36 (21 mg, 0.04 mmol) was dissolved in 1 mL benzene. $Hf(NMe_2)_4$ (17 mg, 0.05 mmol) was dissolved in 1 mL benzene and this solution was added to the ligand solution. The mixture was heated to 65° C. for 22 h, at which time $^1$H NMR revealed that the reaction was complete. Solvent was removed and the resulting off-white solid was recrystallized from pentane. The structure of the complex was confirmed by $^1$H NMR and X-ray crystallography. $^1$H NMR (δ, $C_6D_6$) 6.7-7.4 (m, 7, Ar), 6.71 (s, 1, Mes Ar), 6.53 (s, 1, Mes Ar), 6.51 (s, 1, thiazole SC—H), 6.34 (s, 1, CHMes), 3.69 (sept., 1, $CH(CH_3)_2$), 3.15 (sept., 1, $CH(CH_3)_2$), 2.98 (s, 6, $NMe_2$), 2.85 (s, 6, $NMe_2$), 2.19 (s, 3, $MesCH_{3(a)}$), 2.10 (s, 3, $MesCH_{3(b)}$), 1.72 (s, 3, $MesCH_{3(c)}$), 1.33 (d, 3, $CH(CH_3)_2$), 1.27 (d, 3, $CH(CH_3)_2$), 1.19 (d, 3, $CH(CH_3)_2$), 0.38 (d, 3, $CH(CH_3)_2$).

Example 59

Synthesis of M32. B1 (101 mg, 0.24 mmol) and $Hf(NMe_2)_4$ (92 mg, 0.26 mmol) were combined and 2 mL benzene was added. The mixture was heated to 75° C. for 2 h. Solvent was removed and the resulting yellow solid was recrystallized from hexane at −35 C. (151 mg, 85%) $^1$H NMR (δ, $C_6D_6$) 7.91 (d, 2, Ar), 6.9-7.3 (m, 11, Ar), 6.00 (s, 1, thiazole SC—H), 5.88 (s, 1, CHPh), 3.68 (sept., 1, $CH(CH_3)_2$), 3.32 (sept., 1, $CH(CH_3)_2$), 2.86 (br s, 18, $NMe_2$), 1.60 (d, 3, $CH(CH_3)_2$), 1.54 (d, 3, $CH(CH_3)_2$), 1.34 (d, 3, $CH(CH_3)_2$), 0.29 (d, 3, $CH(CH_3)_2$).

Example 60

Synthesis of M33. Solid C15 (63 mg, 0.13 mmol) and $Hf(NMe_2)_4$ (55 mg, 0.15 mmol) were combined and 2 mL benzene was added. The mixture was heated to 50° C. for 1 h. Solvent was removed and the resulting colorless solid was precipitated from pentane at −35° C. $^1$H NMR (δ, $C_6D_6$) 7.96 (d, 2, Ar), 7.37 (t, 2, Ar) 6.9-7.3 (m, 7, Ar), 6.73 (m, 4, Ar), 6.65 (d, 2, Ar), 6.48 (br s, 1 Ar or imidazole), 5.90 (br s, 1 Ar or imidazole), 5.59 (s, 1, CHPh), 3.68 (sept., 1, $CH(CH_3)_2$), 3.33 (sept., 1, $CH(CH_3)_2$), 3.26 (s, 6, $N(CH_3)_2$), 3.05 (s, 6, $N(CH_3)_2$), 2.89 (s, 6, $N(CH_3)_2$), 1.57 (d, 3, $CH(CH_3)_2$), 1.52 (d, 3, $CH(CH_3)_2$), 1.35 (d, 3, $CH(CH_3)_2$), 0.17 (d, 3, $CH(CH_3)_2$).

Example 61

Synthesis of M34. Solid C11 (52 mg, 0.12 mmol) and $Hf(NMe_2)_4$ (50 mg, 0.14 mmol) were combined and 2 mL benzene was added. The mixture was heated to 75° C. for overnight. Solvent was removed and the resulting colorless solid was precipitated from pentane at −35° C. $^1$H NMR (δ, $C_6D_6$) 7.89 (d, 2, Ar), 6.8-7.5 (m, 11, Ar), 6.23 (imidazole) 5.55 (s, 1, CHPh), 3.51 (sept., 1, $CH(CH_3)_2$), 3.25 (sept., 1, $CH(CH_3)_2$), 3.17 (br s, 6, $N(CH_3)_2$), 2.98 (br s, 6, $N(CH_3)_2$), 2.87 (br s, 6, $N(CH_3)_2$), 2.17 (s, 3, $NCH_3$), 1.57 (d, 3, $CH(CH_3)_2$), 1.52 (d, 3, $CH(CH_3)_2$), 1.35 (d, 3, $CH(CH_3)_2$), 0.24 (d, 3, $CH(CH_3)_2$).

Example 62

Synthesis of M35. Solid C12 (28 mg, 0.056 mmol) and $Hf(NMe_2)_4$ (27 mg, 0.076 mmol) were combined and 1 mL benzene was added. The mixture was heated to 75° C. overnight. Solvent was removed and the resulting colorless solid was precipitated from pentane at −35° C. $^1$H NMR (δ, $C_6D_6$) 7.66 (d, 2, Ar), 6.8-7.4 (m, 16, Ar), 5.74 (s, 1, CHPh), 3.76 (sept., 1, $CH(CH_3)_2$), 3.40 (sept., 1, $CH(CH_3)_2$), 3.12 (s, 6, $N(CH_3)_2$), 3.04 (s, 6, $N(CH_3)_2$), 2.89 (s, 6, $N(CH_3)_2$), 2.37 (s, 3, $NCH_3$), 1.62 (overlapping d, 6, $CH(CH_3)_2$), 1.37 (d, 3, $CH(CH_3)_2$), 0.28 (d, 3, $CH(CH_3)_2$).

Example 63

Synthesis of M36. Solid C13 (38 mg, 0.08 mmol) and $Hf(NMe_2)_4$ (38 mg, 0.11 mmol) were combined and 2 mL benzene was added. The mixture was heated to 75° C. for 2 h. Solvent was removed and the resulting colorless solid was recrystallized from pentane at −35° C. (47 mg, 76%) $^1$H NMR (δ, $C_6D_6$) 7.91 (d, 2, Ar), 6.9-7.5 (m, 6, Ar), 6.60 (s, 1, Mes Ar), 6.46(s, 1, Mes Ar), 6.19 (s, 1, imidazole), 5.96 (s, 1, CHMes), 3.80 (sept., 1, $CH(CH_3)_2$), 3.42 (sept., 1, $CH(CH_3)_2$), 3.11 (s, 6, $N(CH_3)_2$), 3.02 (s, 6, $N(CH_3)_2$), 2.86 (s, 6, $N(CH_3)_2$), 2.10 (s, 3, $NCH_3$ or Mes $CH_3$), 2.05 (s, 3, $NCH_3$ or Mes $CH_3$), 2.03 (s, 3, $NCH_3$ or Mes $CH_3$), 1.70 (s, 3, $NCH_3$ or Mes $CH_3$), 1.58(d, 6, $CH(CH_3)_2$), 1.28 (d, 3, $CH(CH_3)_2$), 0.32 (d, 3, $CH(CH_3)_2$).

Example 64

Synthesis of M37. Solid C14 (446 mg, 0.82 mmol) and $Hf(NMe_2)_4$ (352 mg, 0.99 mmol) were combined and 5 mL toluene was added. The mixture was heated to 50° C. for 3 h. Solvent was removed and the resulting colorless solid was recrystallized from pentane at −35° C. (635 mg, 90%) $^1$H NMR (δ, $C_6D_6$) 7.53 (d, 2, Ar), 6.8-7.3 (m, 11, Ar), 6.72 (s, 1, Mes Ar), 6.47 (s, 1, Mes Ar), 6.11 (s, 1, CHMes), 3.92

(sept., 1, CH(CH$_3$)$_2$), 3.40 (sept., 1, CH(CH$_3$)$_2$), 3.21 (br s, 6, N(CH$_3$)$_2$), 2.90 (br s, 6, N(CH$_3$)$_2$), 2.86 (br s, 6, N(CH$_3$)$_2$), 2.28 (s, 3, NCH$_3$ or Mes CH$_3$), 2.20 (s, 3, NCH$_3$ or Mes CH$_3$), 2.05 (s, 3, NCH$_3$ or Mes CH$_3$), 1.72 (s, 3, NCH$_3$ or Mes CH$_3$),1.64 (d, 6, CH(CH$_3$)$_2$), 1.31 (d, 3, CH(CH$_3$)$_2$), 0.37 (d, 3, CH(CH$_3$)$_2$).

Example 65

Synthesis of M38. M37 (510 mg, 0.60 mmol) was dissolved in 15 mL of a toluene/pentane mixture (1:1 v:v). The mixture was cooled to −35° C. Neat AlMe$_3$ (600 µL, 6.0 mmol) was added. A yellow oil precipitated which dissolved as the mixture was allowed to warm to room temperature. The mixture was stirred for 1 h and then solvent was removed, yielding an off-white solid which was recrystallized from hot pentane. $^1$H NMR (δ, C$_6$D$_6$) 7.58 (d, 2, Ar), 6.7-7.2 (m, 12, Ar), 6.47 (s, 1, Mes Ar), 6.19 (s, 1, CHMes), 3.86 (sept., 1, CH(CH$_3$)$_2$), 3.65 (sept., 1, CH(CH$_3$)$_2$), 2.35 (s, 3, NCH$_3$ or Mes CH$_3$), 2.33 (s, 3, NCH$_3$ or Mes CH$_3$), 2.05 (s, 3, Mes), 1.73 (s, 3, Mes),1.47 (overlapping d, 9, CH(CH$_3$)$_2$), 0.62 (s, 9, Hf(CH$_3$)$_3$), 0.40 (d, 3, CH(CH$_3$)$_2$).

Example 66

Synthesis of M39. Solid C14 (54 mg, 0.10 mmol) and Zr(NMe$_2$)$_4$ (30 mg, 0.11 mmol) were combined and 2 mL benzene was added. The mixture was heated to 40° C. for 1 h. Solvent was removed and the resulting colorless solid was recrystallized from pentane at −35° C. (65 mg, 86%) $^1$H NMR (δ, C$_6$D$_6$) 7.53 (d, 2, Ar), 6.8-7.3 (m, 11, Ar), 6.71 (s, 1, Mes), 6.46 (s, 1, Mes), 6.11 (s, 1, CHMes), 3.91 (sept., 1, CH(CH$_3$)$_2$), 3.43 (sept., 1, CH(CH$_3$)$_2$), 3.22 (br s, 6, N(CH$_3$)$_2$), 2.90 (br s, 6, N(CH$_3$)$_2$), 2.86 (br s, 6, N(CH$_3$)$_2$), 2.28 (s, 3, NCH$_3$), 2.20 (s, 3, Mes CH$_3$), 2.06 (s, 3, Mes CH$_3$), 1.72 (s, 3, Mes CH$_3$), 1.63 (d, 6, CH(CH$_3$)$_2$), 1.31 (d, 3, CH(CH$_3$)$_2$), 0.37 (d, 3, CH(CH$_3$)$_2$).

Example 67

Synthesis of M40. M39 (252 mg, 0.33 mmol) was dissolved in 4 mL of a toluene/pentane mixture (1:1 v:v). The mixture was cooled to −35° C. Neat AlMe$_3$ (340 µL, 3.3 mmol) was added. A yellow oil precipitated which dissolved as the mixture was allowed to warm to room temperature. The mixture was stirred for 1 h and then solvent was removed, yielding an off-white solid which was washed with pentane. (162 mg, 73%) $^1$H NMR (δ, C$_6$D$_6$) 7.58 (d, 2, Ar), 6.7-7.2 (m, 12, Ar), 6.48 (s, 1, Mes Ar), 6.16 (s, 1, CHMes), 3.88 (sept., 1, CH(CH$_3$)$_2$), 3.67 (sept., 1, CH(CH$_3$)$_2$), 2.37 (s, 3, NCH$_3$ or Mes CH$_3$), 2.33 (s, 3, NCH$_3$ or Mes CH$_3$), 2.05 (s, 3, Mes), 1.75 (s, 3, Mes), 1.45 (overlapping d, 9, CH(CH$_3$)$_2$), 0.88 (s, 9, Zr(CH$_3$)$_3$), 0.41 (d, 3, CH(CH$_3$)$_2$).

Example 68

Synthesis of M41. Solid C17 (16 mg, 0.03 mmol) and Hf(NMe$_2$)$_4$ (12 mg, 0.03 mmol) were combined and 3 mL benzene was added. The mixture was heated to 50° C. for 1 h. Solvent was removed and the resulting colorless solid was recrystallized from pentane at −35° C. $^1$H NMR data was consistent with the proposed structure.

Example 69

Synthesis of M42. Solid C16 (182 mg, 0.29 mmol) and Hf(NMe$_2$)$_4$ (119 mg, 0.34 mmol) were combined and 5 mL toluene was added. The mixture was heated to 50° C. for 3 h. Solvent was removed and the resulting colorless solid $^1$H recrystallized from pentane at −35° C. (234 mg, 87%) $^1$H NMR (δ, C$_6$D$_6$) 7.62 (m, 2, Ar), 6.85-7.3 (m, 13, Ar), 6.35 (s, 1, CHTRIP), 3.91 (sept., 1, CH(CH$_3$)$_2$), 3.74 (sept., 1, CH(CH$_3$)$_2$), 3.61 (sept., 1, CH(CH$_3$)$_2$), 3.13 (s, 6, NMe$_2$), 2.91 (s, 6, NMe$_2$), 2.82 (s, 6, NMe$_2$), 2.73 (sept., 1, CH(CH$_3$)$_2$), 2.35 (s, 3, imidazole NCH$_3$), 1.65 (d, 3, CH(CH$_3$)$_2$), 1.58 (d, 3, CH(CH$_3$)$_2$), 1.42 (d, 3, CH(CH$_3$)$_2$), 1.31 (d, 3, CH(CH$_3$)$_2$), 1.19 (overlapping d, 6, CH(CH$_3$)$_2$), 1.06 (d, 3, CH(CH$_3$)$_2$), 0.78 (d, 3, CH(CH$_3$)$_2$), 0.51 (d, 3, CH(CH$_3$)$_2$), 0.24 (d, 3, CH(CH$_3$)$_2$).

Example 70

Synthesis of M43. M42 (161 mg, 0.170 mmol) was dissolved in 4 mL of a toluene/pentane mixture (1:1 v:v). The mixture was cooled to −35° C. Neat AlMe$_3$ (165 µL, 1.6 mmol) was added. A yellow oil precipitated which dissolved as the mixture was allowed to warm to room temperature. The mixture was stirred for 1 h and then solvent was removed, yielding an off-white solid. The solid was extracted with 8 mL of warm pentane, filtered, and the volume of the filtrate was reduced to 2 mL. Upon cooling to −35° C. overnight, colorless prisms formed. The crystals were collected, washed with cold pentane and dried (128 mg, 88%). $^1$H NMR (δ, C$_6$D$_6$) 7.61 (d, 2, Ar), 6.7-7.2 (m, 13, Ar), 6.41 (s, 1, CHTRIP), 4.39 (sept., 1, CH(CH$_3$)$_2$), 3.82 (sept., 1, CH(CH$_3$)$_2$), 3.72 (sept., 1, CH(CH$_3$)$_2$), 3.04 (sept., 1, CH(CH$_3$)$_2$), 2.72 (sept., 1, CH(CH$_3$)$_2$), 2.44 (s, 3, NCH$_3$), 1.54 (d, 3, CH(CH$_3$)$_2$), 1.45 (overlapping d, 6, CH(CH$_3$)$_2$), 1.18 (overlapping d, 6, CH(CH$_3$)$_2$), 1.10 (d, 3, CH(CH$_3$)$_2$), 0.72 (d, 3, CH(CH$_3$)$_2$), 0.57 (s, 9, Hf(CH$_3$)$_3$), 0.55 (d, 3, CH(CH$_3$)$_2$), 0.30 (d, 3, CH(CH$_3$)$_2$).

Example 71

Synthesis of M44. Solid C16 (57 mg, 0.09 mmol) and Zr(NMe$_2$)$_4$ (28 mg, 0.10 mmol) were combined and 2 mL benzene was added. The mixture was heated to 40° C. for 1 h. Solvent was removed and the resulting colorless solid was recrystallized from pentane at −35° C. (68 mg, 89%)$^1$H NMR (δ, C$_6$D$_6$) 7.62 (m, 2, Ar), 6.85-7.3 (m, 13, Ar), 6.29 (s, 1, CHTRIP), 3.97 (sept., 1, CH(CH$_3$)$_2$), 3.70 (sept., 1, CH(CH$_3$)$_2$), 3.61 (sept., 1, CH(CH$_3$)$_2$), 3.13 (sept., 1, CH(CH$_3$)$_2$), 3.05 (s, 6, NMe$_2$), 2.95 (s, 6, NMe$_2$), 2.72 (overlapping s+sept, 7, NMe$_2$+CH(CH$_3$)$_2$), 2.35 (s, 3, imidazole NCH$_3$), 1.65 (d, 3, CH(CH$_3$)$_2$), 1.58 (d, 3, CH(CH$_3$)$_2$), 1.42 (d, 3, CH(CH$_3$)$_2$), 1.31 (d, 3, CH(CH$_3$)$_2$), 1.19 (overlapping d, 6, CH(CH$_3$)$_2$), 1.08 (d, 3, CH(CH$_3$)$_2$), 0.78 (d, 3, CH(CH$_3$)$_2$), 0.54 (d, 3, CH(CH$_3$)$_2$), 0.24 (d, 3, CH(CH$_3$)$_2$).

Example 72

Synthesis of M45. M44 (139 mg, 0.164 mmol) was dissolved in 3 mL C$_6$D$_6$. TMSCl (65 µL, 0.51 mmol) was added and the mixture was heated to 70° C. overnight. $^1$H NMR of an aliquot revealed that the reaction was complete. The mixture was cooled to room temperature and a 3.0 M solution of MeMgBr in Et$_2$O (175 µL, 0.52 µmol) was added. The mixture was stirred for 2 h at room temperature, and then solvent was removed, yielding a pale yellow-white solid. The solid was extracted with a mixture of toluene/pentane (2:1 v:v) and filtered. Solvent was removed, yielding a crystalline colorless solid which was washed with 1 mL pentane and dried (108 mg, 87%). $^1$H NMR (δ, C$_6$D$_6$)

7.60 (d, 2, Ar), 7.40 (s, 1, Ar) 6.7-7.2 (m, 12, Ar), 6.38 (s, 1, CHAr), 4.32 (sept., 1, CH(CH$_3$)$_2$), 3.85 (sept., 1, CH(CH$_3$)$_2$), 3.71 (sept., 1, CH(CH$_3$)$_2$), 3.06 (sept., 1, CH(CH$_3$)$_2$), 2.72 (sept., 1, CH(CH$_3$)$_2$), 2.45 (s, 3, NCH$_3$), 1.52 (d, 3, CH(CH$_3$)$_2$), 1.40 (overlapping d, 6, CH(CH$_3$)$_2$), 1.18 (overlapping d, 6, CH(CH$_3$)$_2$), 1.10 (d, 3, CH(CH$_3$)$_2$), 0.82 (s, 9, Hf(CH$_3$)$_3$), 0.71 (d, 3, CH(CH$_3$)$_2$), 0.54 (d, 3, CH(CH$_3$)$_2$), 0.30 (d, 3, CH(CH$_3$)$_2$).

Example 73

Synthesis of M46. Solid Hf(NMe$_2$)$_4$ (34 mg, 0.10 mmol) and C27 (50 mg, 0.09 mmol) were combined and dissolved in 2 mL C$_6$D$_6$. The mixture was heated to 70° C. for 2 h. $^1$H NMR of an aliquot revealed that the reaction was complete. Solvent was removed and the resulting beige solid was recrystallized from a toluene/pentane mixture at −35° C. (26 mg, 34%) $^1$H NMR (δ, C$_6$D$_6$) 7.86 (d, 1, Ar), 7.64 (d, 1, Ar), 7.42 (d, 1, Ar) 6.9-7.3 (m, 13, Ar), 6.02 (s, 1 imidazole CH), 5.42 (s, 1, CHBiPh), 3.62 (sept, 1, CH(CH$_3$)$_2$), 3.38 (sept, 1, CH(CH$_3$)$_2$), 2.86 (br s, 20, NMe$_2$+CH$_2$CH$_3$), 2.46 (s, 3, imidazole NCH$_3$), 1.40 (d, 3, CH(CH$_3$)$_2$), 1.34 (m, 6, overlapping CH(CH$_3$)$_2$ and CH$_2$CH$_3$), 0.76 (d, 3, CH(CH$_3$)$_2$), 0.43 (d, 3, CH(CH$_3$)$_2$).

Example 74

Synthesis of M47. Solid Zr(NMe$_2$)$_4$ (38 mg, 0.14 mmol) and C27 (73 mg, 0.13 mmol) were combined and dissolved in 2 mL C$_6$D$_6$. The mixture was heated to 70° C. for 2 h. $^1$H NMR of an aliquot revealed that the reaction was complete. Solvent was removed and the resulting solid was recrystallized from a toluene/pentane mixture at −35° C. $^1$H NMR (δ, C$_6$D$_6$) 7.93 (d, 1, Ar), 7.65 (d, 1, Ar), 7.42 (d, 1, Ar) 6.9-7.3 (m, 13, Ar), 6.06 (s, 1 imidazole CH), 5.32 (s, 1, CHBiPh), 3.63 (sept, 1, CH(CH$_3$)$_2$), 3.35 (sept, 1, CH(CH$_3$)$_2$), 2.82 (br s, 20, NMe$_2$+CH$_2$CH$_3$), 2.49 (s, 3, imidazole NCH$_3$), 1.39 (d, 3, CH(CH$_3$)$_2$), 1.34 (m, 6, overlapping CH(CH$_3$)$_2$ and CH$_2$CH$_3$), 0.77 (d, 3, CH(CH$_3$)$_2$), 0.45 (d, 3, CH(CH$_3$)$_2$).

Example 75

Synthesis of M48. Solid Hf(NMe$_2$)$_4$ (71 mg, 0.20 mmol) and C29 (103 mg, 0.17 mmol) were combined and dissolved in 5 mL toluene. The mixture was heated to 80° C. overnight. $^1$H NMR of an aliquot revealed that the reaction was complete. Solvent was removed and the resulting glassy yellow solid was dissolved in 5 mL pentane, filtered, and solvent was removed, yielding a pale yellow solid containing traces of residual Hf(NMe$_2$)$_4$. The material was recrystallized from pentane at −35° C. (110 mg, 70%). $^1$H NMR (δ, C$_6$D$_6$) 7.58 (d, 1, Ar), 7.41 (d, 1, Ar), 6.9-7.2 (m, 7, Ar), 6.17 (s, 1 imidazole CH), 5.90 (s, 1, CHTRIP), 3.84 (sept., 1, CH(CH$_3$)$_2$), 3.62 (sept., 1, CH(CH$_3$)$_2$), 3.56 (sept., 1, CH(CH$_3$)$_2$), 3.02 (sept., 1, CH(CH$_3$)$_2$), 2.92 (s, 6, NMe$_2$), 2.87 (s, 6, NMe$_2$), 2.69 (sept., 1, CH(CH$_3$)$_2$), 2.64 (s, 6, NMe$_2$), 2.73 (sept., 1, CH(CH$_3$)$_2$), 2.30 (s, 3, imidazole NCH$_3$), 1.55 (d, 6, CH(CH$_3$)$_2$), 1.31 (p, 6, overlapping CH(CH$_3$)$_2$ and CH$_2$CH$_3$), 1.19 (overlapping d, 6, CH(CH$_3$)$_2$), 1.06 (d, 3, CH(CH$_3$)$_2$), 0.71 (d, 3, CH(CH$_3$)$_2$), 0.52 (d, 3, CH(CH$_3$)$_2$), 0.27 (d, 3, CH(CH$_3$)$_2$). Note: The CH$_2$CH$_3$ peaks from the 2-Ethylbenzofuran are obscured by the amide peaks.

Example 76

Synthesis of M49. M48 (82 mg, 0.088 mmol) was dissolved in 5 mL C$_6$D$_6$. TMSCl (40 μL, 0.32 mmol) was added and the mixture was heated to 70° C. for 3 h. $^1$H NMR of an aliquot revealed that the reaction was complete. The mixture was cooled to room temperature and a 3.0 M solution of MeMgBr in Et$_2$O (120 μL, 0.36 μmol) was added. The mixture was stirred for 2 h at room temperature, and then solvent was removed, yielding a beige solid. The solid was extracted with 5 mL toluene and filtered. Solvent was removed, yielding a crystalline colorless solid which was washed with 3 mL pentane and dried (70 mg, 95%). $^1$H NMR (δ, C$_6$D$_6$) 7.66 (d, 1, Ar), 7.42 (d, 1, Ar), 6.9-7.2 (m, 7, Ar), 6.28 (s, 1 imidazole CH), 5.84 (s, 1, CHTRIP), 4.04 (sept., 1, CH(CH$_3$)$_2$), 3.71 (sept., 1, CH(CH$_3$)$_2$), 3.60 (sept., 1, CH(CH$_3$)$_2$), 2.94 (sept., 1, CH(CH$_3$)$_2$), 2.75 (m, 3, CH(CH$_3$)$_2$ and CH$_2$CH$_3$), 2.37 (s, 3, imidazole NCH$_3$), 1.53 (d, 3, CH(CH$_3$)$_2$), 1.47 (d, 3, CH(CH$_3$)$_2$), 1.36 (d, 6, CH(CH$_3$)$_2$), 1.27 (t, 3, CH$_2$CH$_3$) 1.19 (overlapping d, 6, CH(CH$_3$)$_2$), 1.07 (d, 3, CH(CH$_3$)$_2$), 0.79 (d, 3, CH(CH$_3$)$_2$), 0.52 (d, 3, CH(CH$_3$)$_2$), 0.42 (s, 9, Hf(CH$_3$)$_3$) 0.25 (d, 3, CH(CH$_3$)$_2$).

Example 77

Synthesis of M50. Solid Zr(NMe$_2$)$_4$ (24 mg, 0.09 mmol) and C29 (48 mg, 0.08 mmol) were combined and dissolved in 3 mL toluene. The mixture was heated to 80° C. overnight. $^1$H NMR of an aliquot revealed that the reaction was complete. Solvent was removed and the resulting glassy yellow solid was dissolved in 5 mL pentane, filtered, and solvent was removed, yielding a pale yellow solid which was recrystallized from pentane at −35° C. (45 mg, 69%). $^1$H NMR (δ, C$_6$D$_6$) 7.61 (d, 1, Ar), 7.40 (d, 1, Ar), 6.85-7.2 (m, 13, Ar), 6.10 (s, 1, imidazole), 5.96 (s, 1, CHTRIP), 3.95 (sept., 1, CH(CH$_3$)$_2$), 3.58 (sept., 1, CH(CH$_3$)$_2$), 3.48 (sept., 1, CH(CH$_3$)$_2$), 2.96 (s, 6, NMe$_2$), 2.77 (s, 6, NMe$_2$), 2.59 (s, 6, NMe$_2$), 2.34 (s, 3, NMe), 2.35 (s, 3, imidazole NCH$_3$), 1.54 (overlapping d, 6, CH(CH$_3$)$_2$), 1.32 (m, 6, overlapping CH(CH$_3$)$_2$ and CH$_2$CH$_3$), 1.18 (d, 6, CH(CH$_3$)$_2$), 1.08 (d, 3, CH(CH$_3$)$_2$), 0.70 (d, 2, CH(CH$_3$)$_2$), 0.52 (d, 3, CH(CH$_3$)$_2$), 0.27 (d, 3, CH(CH$_3$)$_2$). Note: The CH$_2$CH$_3$ peaks from the 2-Ethylbenzofuran are obscured by the amide peaks.

Example 78

Synthesis of M51. Solid C23 (28 mg, 0.05 mmol) and Hf(NMe$_2$)$_4$ (22 mg, 0.06 mmol) were combined and 2 mL benzene was added. The mixture was heated to 60° C. overnight. The mixture was filtered and solvent was removed. The resulting beige solid was recrystallized from pentane at −35° C. $^1$H NMR was consistent with the proposed structure.

Example 79

Synthesis of M52. Solid D1 (25 mg, 0.06 mmol) and Hf(NMe$_2$)$_4$ (24 mg, 0.07 mmol) were combined and 1 mL benzene was added. The mixture was heated to 50° C. for 1 h. Solvent was removed and the resulting beige solid was recrystallized from pentane at −35° C. $^1$H NMR (δ, tol-d8) 6.9-7.4 (m, 13, Ar), 5.86 (s, 1 imidazole CH), 5.77 (s, 1, CHPh), 3.80 (sept., 1, CH(CH$_3$)$_2$), 3.37 (sept., 1, CH(CH$_3$)$_2$), 2.98 (br s, 6, NMe$_2$), 2.88 (br s, 6, NMe$_2$), 2.78 (br s, 6, NMe$_2$), 2.37 (s, 3, imidazole NCH$_3$), 1.69 (d, 3, CH(CH$_3$)$_2$), 1.58 (d, 3, CH(CH$_3$)$_2$), 1.32 (d, 6, CH(CH$_3$)$_2$), 0.27 (d, 3, CH(CH$_3$)$_2$).

Example 80

Synthesis of M53. Solid D2 (36 mg, 0.08 mmol) and Hf(NMe$_2$)$_4$ (31 mg, 0.09 mmol) were combined and 1 mL benzene was added. The mixture was heated to 50° C. for 1 h. Solvent was removed and the resulting beige solid was recrystallized from pentane at −35° C. (50 mg, 81%) $^1$H NMR (δ, C$_6$D$_6$) 6.9-7.4 (m, 8, Ar), 6.78 (s, 1, Mes), 6.58 (s, 1, Mes), 6.25 (s, 1 imidazole CH), 5.67 (s, 1, CHPh), 3.88 (sept., 1, CH(CH$_3$)$_2$), 3.50 (sept., 1, CH(CH$_3$)$_2$), 3.06 (br s, 6, NMe$_2$), 2.84 (br s, 12, NMe$_2$), 2.49 (s, 3, imidazole NCH$_3$ or Mes), 2.25 (s, 3, imidazole NCH$_3$ or Mes), 2.11 (s, 3, imidazole NCH$_3$ or Mes), 1.93 (s, 3, imidazole NCH$_3$ or Mes), 1.67 (d, 3, CH(CH$_3$)$_2$), 1.61 (d, 3, CH(CH$_3$)$_2$), 1.33 (d, 6, CH(CH$_3$)$_2$), 0.43 (d, 3, CH(CH$_3$)$_2$).

Example 81

Synthesis of M54. Solid Zr(NMe$_2$)$_4$ (16 mg, 0.06 mmol) and C19 (24 mg, 0.05 mmol) were combined and dissolved in 1 mL benzene. The mixture was heated to 50° C. for 2 hours. $^1$H NMR of an aliquot revealed that the reaction was complete. Solvent was removed and the resulting solid was recrystallized from pentane at −35° C. $^1$H NMR (δ, C$_6$D$_6$) 8.30 (s, 2, Ar), 6.9-7.5 (m, 14, Ar), 5.56 (s, 1, CHPh), 3.59 (sept., 1, CH(CH$_3$)$_2$), 3.28 (sept., 1, CH(CH$_3$)$_2$), 3.05 (br s, 18, NMe$_2$), 2.41 (s, 3, NCH$_3$), 1.58 (d, 3, CH(CH$_3$)$_2$), 1.49 (d, 3, CH(CH$_3$)$_2$), 1.30 (d, 3, CH(CH$_3$)$_2$), 0.33 (d, 3, CH(CH$_3$)$_2$).

Example 82

Synthesis of M55. Solid Hf(NMe$_2$)$_4$ (17 mg, 0.05 mmol) and C20 (25 mg, 0.05 mmol) were combined and dissolved in 2 mL benzene. The mixture was heated to 50° C. for 2 hours. $^1$H NMR of an aliquot revealed that the reaction was complete. Solvent was removed and the resulting solid was precipitated from pentane at −35° C. (23 mg, 55%). $^1$H NMR (δ, C$_6$D$_6$) 8.24 (m, 2, Ar), 6.9-7.8 (m, 16, Ar), 5.69 (s, 1, CHPh), 3.61 (sept., 1, CH(CH$_3$)$_2$), 3.31 (sept., 1, CH(CH$_3$)$_2$), 3.03 (br s, 18, NMe$_2$), 2.45 (s, 3, NCH$_3$), 1.60 (d, 3, CH(CH$_3$)$_2$), 1.51 (d, 3, CH(CH$_3$)$_2$), 1.21 (d, 3, CH(CH$_3$)$_2$), 0.31 (d, 3, CH(CH$_3$)$_2$).

Example 83

Synthesis of M56. Solid Hf(NMe$_2$)$_4$ (35 mg, 0.10 mmol) and E1 (43 mg, 0.09 mmol) were combined and dissolved in 2 mL benzene. The mixture was heated to 40° C. for 2 h. Solvent was removed and the resulting pale yellow solid was recrystallized from pentane at −35° C. (62 mg, 90%) $^1$H NMR (δ, C$_6$D$_6$) 7.61 (d, 2, Ar), 6.7-7.4 (m, 16, Ar), 6.04 (s, 1, CHPh), 3.70 (sept., 1, CH(CH$_3$)$_2$), 3.31 (sept., 1, CH(CH$_3$)$_2$), 3.04 (s, 6, NMe$_2$), 2.97 (s, 6, NMe$_2$), 2.80 (s, 6, NMe$_2$), 1.55 (overlapping d, 6, CH(CH$_3$)$_2$), 1.32 (d, 3, CH(CH$_3$)$_2$), 0.26 (d, 3, CH(CH$_3$)$_2$).

Example 84

Synthesis of M57. Solid Hf(NMe$_2$)$_4$ (39 mg, 0.11 mmol) and E2 (49 mg, 0.09 mmol) were combined and dissolved in 2 mL benzene. The mixture was heated to 60° C. overnight. $^1$H NMR of an aliquot revealed that the reaction was complete. Solvent was removed and the resulting colorless solid was recrystallized from pentane at −35° C. (57 mg, 76%) $^1$H NMR (δ, C$_6$D$_6$) 7.68 (d, 2, Ar), 6.7-7.4 (m, 12, Ar), 6.52 (s, 1, Mes) 6.38 (s, 1, CHMes), 3.75 (sept., 1, CH(CH$_3$)$_2$), 3.51 (sept., 1, CH(CH$_3$)$_2$), 3.10 (br s, 6, NMe$_2$), 2.88 (br s, 6, NMe$_2$), 2.75 (br s, 6, NMe$_2$), 2.25 (s, 3, Mes CH$_3$), 2.04 (s, 3, Mes CH$_3$), 1.81 (s, 3, Mes CH$_3$), 1.56 (overlapping d, 6, CH(CH$_3$)$_2$), 1.27 (d, 3, CH(CH$_3$)$_2$), 0.38 (d, 3, CH(CH$_3$)$_2$).

Example 85

Synthesis of M58. Solid Zr(NMe$_2$)$_4$ (66 mg, 0.25 mmol) and E2 (128 mg, 0.24 mmol) were combined and dissolved in 2 mL benzene. The mixture was heated to 60° C. for 2 h. $^1$H NMR of an aliquot revealed that the reaction was complete. Solvent was removed and the resulting yellow solid was recrystallized from pentane at −35° C. $^1$H NMR (δ, C$_6$D$_6$) 7.68 (d, 2, Ar), 6.7-7.4 (m, 12, Ar), 6.52 (s, 1, Mes) 6.27 (s, 1, CHMes), 3.78 (sept., 1, CH(CH$_3$)$_2$), 3.50 (sept., 1, CH(CH$_3$)$_2$), 3.03 (br s, 6, NMe$_2$), 2.92 (br s, 6, NMe$_2$), 2.69 (br s, 6, NMe$_2$), 2.26 (s, 3, Mes CH$_3$), 2.04 (s, 3, Mes CH$_3$), 1.83 (s, 3, Mes CH$_3$), 1.56 (overlapping d, 6, CH(CH$_3$)$_2$), 1.26 (d, 3, CH(CH$_3$)$_2$), 0.40 (d, 3, CH(CH$_3$)$_2$).

Example 86

Synthesis of M59. Solid Hf(NMe$_2$)$_4$ (47 mg, 0.13 mmol) and F1 (55 mg, 0.11 mmol) were combined and dissolved in 2 mL benzene. The mixture was heated to 60° C. for 1 h. Solvent was removed and the resulting yellow powder was washed with pentane and dried. $^1$H NMR (δ, C$_6$D$_6$) 8.27 (s, 1, Ar), 7.86 (m, 3, Ar) 7.0-7.6 (m, 13, Ar), 6.47 (s, 1, Ar) 6.21 (s, 1, CHPh), 3.81 (sept., 1, CH(CH$_3$)$_2$), 3.34 (sept., 1, CH(CH$_3$)$_2$), 2.6 (v. br.s., 12, NMe$_2$), 2.1 (br s, 6, NMe$_2$), 1.67 (d, 3, CH(CH$_3$)$_2$), 1.51 (d, 3, CH(CH$_3$)$_2$), 1.20 (d, 3, CH(CH$_3$)$_2$), 0.24 (d, 3, CH(CH$_3$)$_2$).

Example 87

Synthesis of M60. M35 (80 mg, 0.10 mmol) was dissolved in 4 mL of a pentane/toluene mixture (1:1 v:v). The mixture was cooled to −35 C and 100 uL AlMe$_3$ was added. A colorless precipitate formed which dissolved as the mixture was allowed to warm to room temperature. After 1 hour at room temperature, solvent was removed, yielding a white solid which was precipitated from pentane at −35 C. (61 mg, 84%). $^1$H NMR was consistent with the proposed structure.

II. Polymerization Reactions

Example 88

Propylene Polymerizations Using Metal-Ligand Compositions

A total of 23 separate polymerization reactions (PP 1-PP23) were performed as follows.

Preparation of the Polymerization Reactor Prior to Injection of Catalyst Composition:

Method A: A pre-weighed glass vial insert and disposable stirring paddle were fitted to each reaction vessel of the reactor. The reactor was then closed, 0.200 mL of a 0.05 M solution of Modified Methylaluminoxane 3A (from Azko Chemical Inc., Chicago, Ill.) ("MMAO") in toluene and 3.8 mL of toluene were injected into each pressure reaction vessel through a valve. The temperature was then set to the appropriate setting (with specific temperatures for each polymerization being listed in the tables below), and the stirring speed was set to 800 rpm unless otherwise noted, and the mixture was exposed to propylene at 100 psi pressure. A propylene pressure of 100 psi in the pressure cell and the temperature setting were maintained, using computer control, until the end of the polymerization experiment.

Method B: Method B is similar to method A described above, except that 0.200 mL of a 0.05 M solution of Polymethylaluminoxane-Improved Performance ("PMAO-IP") was used rather than MMAO.

Method C: A pre-weighed glass vial insert and disposable stirring paddle were fitted to each reaction vessel of the reactor. The reactor was then closed, 0.100 mL of a 0.02 M solution of trimethylaluminium ("TMA") in toluene and 3.9 mL of toluene were injected into each pressure reaction vessel through a valve. The temperature was then set to the appropriate setting (with specific temperatures for each polymerization being listed in the tables below), and the stirring speed was set to 800 rpm unless otherwise noted, and the mixture was exposed to propylene at 100 psi pressure. A propylene pressure of 100 psi in the pressure cell and the temperature setting were maintained, using computer control, until the end of the polymerization experiment.

Method D: Method D is similar to method C described above, except that 0.100 mL of a 0.02 M solution of di-isobutylalumiumhydride ("DIBAL") was used rather than TMA.

Method E: Method E is similar to method C described above, except that 0.100 mL of a 0.02 M solution of tri-isobutylalumium ("TIBA") was used rather than TMA.

Method F: Method F is similar to method C described above, except that 0.100 mL of a 0.02 M solution of Polymethylaluminoxane-Improved Performance ("PMAO-IP") was used rather than TMA.

In situ preparation of metal-ligand compositions: The following methods were employed to prepare the metal-ligand compositions as indicated in Tables 5 and 7. Method ZA: 75 µl of the ligand solution (10 mM in toluene) was dispensed in a 1 mL glass vial. To the 1 mL glass vial containing the ligand solution was added an equimolar amount of metal precursor solution (10 mM in toluene) to form the metal-ligand composition solution. The reaction mixture was heated to 80° C. for 3 hours. Method ZB: Similar to Method A except the reaction mixture was heated to 75° C. for 45 min. Method ZC: 120 µl of the ligand solution (10 mM in toluene) was dispensed in a 1 mL glass vial. To the 1 mL glass vial containing the ligand solution was added an equimolar amount of metal precursor solution (5 mM in toluene) to form the metal-ligand composition solution. The reaction mixture was heated to 75° C. for 45 minutes. Method ZD: 110 µl of the ligand solution (10 mM in toluene) was dispensed in a 1 mL glass vial. To the 1 mL glass vial containing the ligand solution was added an equimolar amount of metal precursor solution (10 mM in toluene) to form the metal-ligand composition solution. The reaction mixture was heated to 75° C. for 45 minutes. Method ZE: Similar to Method ZB except that 50 µl of the ligand solution (10 mM in toluene) was dispensed. Method ZF: Similar to Method ZA except that 50 µl of the ligand solution (10 mM in toluene) was dispensed. Method ZG: Similar to method ZE except that the metal precursor solution was 5 mM.

Preparation of the group 13 reagent and activator stock solutions: The "activator solution" is a solution of N,N'-dimethylanilinium tetrakis (pentafluorophenyl) borate ("ABF$_{20}$") in toluene or triphenylmethyl tetrakis (pentafluorophenyl) borate ("TBF20"). The identity and molarity of this solution is indicated in the "activation method" of the individual example described below. The ABF20 solution is heated to approximately 85° C. to dissolve the reagent. The TBF20 is at ambient temperature. The "group 13 reagent" solution is either a solution of trimethylaluminum ("TMA"), triisobutyl aluminium ("TIBA") or a solution of diisobutyl aluminium hydride ("DIBAL") or a solution of Modified Methylaluminoxane 3A (from Azko Chemical Inc., Chicago, Ill.) ("MMAO"), all "group 13 reagent" solutions were solutions in toluene. The molarity of the solutions used is indicated in the "activation method" of the individual example described below.

Activation methods and Injection of solutions into the pressure reactor vessel: The following methods were employed to activate and inject the metal-ligand compositions for the examples in Tables 5 and 7. Method AAAA: To the metal-ligand composition, the appropriate amount of the group 13 reagent solution as a 200 mM solution, containing the indicated equivalents group 13 reagent (per metal precursor) in the specific example, was added to the 1 mL vial. After about 111 minutes, 1.1 mol equivalents (per metal precursor) of the "activator solution" (2.5 mM) was added to the 1 mL vial and the reaction mixture was mixed. About another 30 seconds later, a fraction of the 1 mL vial contents corresponding to the indicated "catalyst amount injected", based on micromoles (umol) of metal precursor, was injected into the prepressurized reaction vessel and was followed immediately by injection of toluene to bring the total volume injected to 0.500 mL. Method BBBB: To the metal-ligand composition, the appropriate amount of the group 13 reagent solution as a 50 mM solution, containing the indicated equivalents group 13 reagent (per metal precursor) in the specific example, was added to the 1 mL vial. After 45 seconds, 1.1 mol equivalents (per metal precursor) of the "activator solution" (2.5 mM) was added to the 1 mL vial and the reaction mixture was mixed. About another 90 seconds later a fraction of the total 1 mL vial contents containing the indicated "catalyst amount injected", based on micromoles (umol) of metal precursor, was injected into the pre-pressurized reaction vessel and was followed immediately by injection of toluene to increase the total volume injected of 0.500 mL. Method CCCC: To the metal-ligand composition, the appropriate amount of the group 13 reagent solution as a 50 mM solution, containing the indicated equivalents group 13 reagent (per metal precursor) in the specific example, was added to the 1 mL vial. After 45 seconds, 1.1 mol equivalents (per metal precursor) of the "activator solution" (5.0 mM) was added to the 1 mL vial and the reaction mixture was mixed. About another 90 seconds later a fraction of the total 1 mL vial contents containing the indicated "catalyst amount injected", based on micromoles (umol) of metal precursor, was injected into the pre-pressurized reaction vessel and was followed immediately by injection of toluene to increase the total volume injected of 1.00 mL. Method DDDD: Similar to method AAAA except that the Group 13 reagent solution was 50 mM (instead of 200 mM). Method EEEE: Similar to Method DDDD except that 0.200 mL toluene was added to the 1 mL vial immediately after activator. Method FFFF: Similar to Method DDDD except that 0.400 mL toluene was added to the 1 mL vial immediately after activator. Method GGGG: Similar to method BBBB except that 0.400 mL toluene was added to the 1 mL vial immediately after activator. Method HHHH: Similar to method AAAA except that 0.400 mL toluene was added to the 1 mL vial immediately after activator.

Polymerization: The polymerization reaction was allowed to continue for 60-1800 seconds, during which time the temperature and pressure were maintained at their pre-set levels by computer control. The specific polymerization times for each polymerization are shown in Table 5. After the reaction time elapsed, the reaction was quenched by addition of an overpressure of carbon dioxide sent to the reactor. The polymerization times were the lesser of the maximum desired polymerization time or the time taken for a predetermined amount of monomer gas to be consumed in the polymerization reaction.

Product work up: Propylene Polymerizations: After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the crystallinity index. The melting point of selected samples was measured by DSC, as described above.

TABLE 5

| Example | Ligand | Metal Precurs. | Complexation method | Reactor prep. Method | Injection method | Polymerization Temp(C.) | Group 13 reagent and mole equivalent alkyl | Activator |
|---|---|---|---|---|---|---|---|---|
| PP1 | A3 | Hf(NMe2)4 | ZA | C | AAAA | 75 | 25 TMA | 1.1 ABF20 |
| PP2 | A3 | Hf(NMe2)4 | ZA | C | AAAA | 110 | 25 TMA | 1.1 ABF20 |
| PP3 | A3 | Zr(NMe2)4 | ZA | C | AAAA | 75 | 25 TMA | 1.1 ABF20 |
| PP4 | A3 | Zr(NMe2)4 | ZA | C | AAAA | 110 | 25 TMA | 1.1 ABF20 |
| PP5 | A6 | Hf(NMe2)4 | ZA | C | AAAA | 75 | 25 TMA | 1.1 ABF20 |
| PP6 | A6 | Hf(NMe2)4 | ZA | C | AAAA | 110 | 25 TMA | 1.1 ABF20 |
| PP7 | A6 | Zr(NMe2)4 | ZA | C | AAAA | 75 | 25 TMA | 1.1 ABF20 |
| PP8 | A6 | Zr(NMe2)4 | ZA | C | AAAA | 110 | 25 TMA | 1.1 ABF20 |
| PP9 | A9 | HfBz4 | ZB | F | BBBB | 75 | 5 PMAO | 1.1 ABF20 |
| PP10 | A9 | ZrBz4 | ZB | F | BBBB | 75 | 5 PMAO | 1.1 ABF20 |
| PP11 | A2 | HfBz3+ | ZC | E | CCCC | 75 | 5 TIBA | 1.1 ABF20 |
| PP12 | A2 | ZrBz3+ | ZC | E | CCCC | 75 | 5 TIBA | 1.1 ABF20 |
| PP13 | A59 | HfBz4 | ZD | F | CCCC | 75 | 5 PMAO | 1.1 TBF20 |
| PP14 | A43 | HfBz3+ | ZE | B | BBBB | 110 | 5 PMAO | 1.1 TBF20 |
| PP15 | A52 | Hf(NMe2)4 | ZF | B | DDDD | 110 | 15 TMA | 1.1 ABF20 |
| PP16 | A52 | Hf(NMe2)4 | ZF | B | DDDD | 130 | 15 TMA | 1.1 ABF20 |
| PP17 | C29 | Hf(NMe2)4 | ZF | B | DDDD | 110 | 15 DIBAL | 1.1 ABF20 |
| PP18 | C29 | Hf(NMe2)4 | ZF | B | DDDD | 130 | 15 DIBAL | 1.1 ABF20 |
| PP18 | G6 | Hf(NMe2)4 | ZF | A | DDDD | 75 | 15 TMA | 1.1 ABF20 |
| PP19 | G15 | Hf(NMe2)4 | ZF | A | DDDD | 75 | 15 TMA | 1.1 ABF20 |
| PP20 | C19 | Hf(NMe2)4 | ZF | B | DDDD | 75 | 15 TMA | 1.1 ABF20 |
| PP21 | C19 | Hf(NMe2)4 | ZF | B | DDDD | 110 | 15 TMA | 1.1 ABF20 |
| PP22 | C22 | Hf(NMe2)4 | ZF | B | DDDD | 75 | 15 TMA | 1.1 ABF20 |
| PP23 | C22 | Hf(NMe2)4 | ZF | B | DDDD | 110 | 15 TMA | 1.1 ABF20 |

| Example | μmol catalyst injected | Polymerization Time (s) | Activity (g Polymer/min * mmol | Mw (/1000) | PDI (Mw/Mn) | Crystallinity index | M.p.(deg. C.) |
|---|---|---|---|---|---|---|---|
| PP1 | 0.06 | 264 | 988 | 664 | 3.5 | 0.42 | n.d. |
| PP2 | 0.1 | 349 | 221 | 316 | 5.3 | 0.34 | n.d. |
| PP3 | 0.1 | 148 | 613 | 249 | 4.5 | 0.31 | n.d |
| PP4 | 0.3 | 1801 | 8 | 52 | 4 | 0.34 | n.d |
| PP5 | 0.06 | 218 | 1505 | 919 | 3.7 | 0.65 | n.d. |
| PP6 | 0.1 | 96 | 1138 | 349 | 2.7 | 0.58 | n.d. |
| PP7 | 0.1 | 133 | 988 | 343 | 2.6 | 0.57 | n.d |
| PP8 | 0.3 | 1801 | 13 | 74 | 3.2 | 0.54 | n.d |
| PP9 | 0.075 | 71 | 4754 | 1510 | 2.5 | 0.77 | 125 |
| PP10 | 0.3 | 221 | 399 | 520 | 1.7 | 0.74 | 112 |
| PP11 | 1 | 734 | 7 | 59 | 2.5 | 0.9 | 151 |
| PP12 | 1 | 693 | 8 | 399 | 2.1 | 0.91 | 153 |
| PP13 | 0.5 | 433 | 34 | 1065 | 3.5 | 0.63 | n.d. |
| PP14 | 0.05 | 217 | 843 | 309 | 2.1 | 0.84 | 145 |
| PP15 | 0.06 | 146 | 1235 | 449 | 1.7 | 0.78 | 118 |
| PP16 | 0.12 | 160 | 553 | 161 | 2.2 | 0.80 | 127 |
| PP17 | 0.06 | 66 | 3577 | 100 | 1.6 | 0.96 | 144 |
| PP18 | 0.12 | 128 | 916 | 36 | 1.8 | 0.94 | 140 |
| PP18 | 0.2 | 111 | 396 | 128 | 1.8 | low iso | n.d |
| PP19 | 0.2 | 95 | 561 | 174 | 2 | 0.21 | n.d |
| PP20 | 0.1 | 383 | 157 | 50 | 2.665 | 0.32 | n.d |
| PP21 | 0.1 | 1801 | 16 | 8 | 2.705 | 0.33 | n.d |
| PP22 | 0.1 | 228 | 296 | 35 | 3.709 | 0.40 | n.d |
| PP23 | 0.1 | 905 | 75 | 5 | 1.881 | 0.50 | n.d |

Example 89

Propylene Polymerizations Using Isolated Complexes

A total of 104 separate polymerization reactions (PP24-PP127) were performed as follows.

Preparation of the polymerization reactor prior to injection of catalyst composition: The polymerization reactor was prepared in the manner described in Example 88.

Preparation of the group 13 reagent and activator stock solutions:

The "activator solution" is either a solution of N,N'-dimethylanilinium tetrakis (pentafluorophenyl) borate ("ABF$_{20}$") in toluene or a solution of trityl tetrakis (pentafluorophenyl) borate ("TBF$_{20}$") in toluene. The "ABF$_{20}$" solution is heated to approximately 85° C. to dissolve the reagent. The molarity is indicated in the "activation method" of the individual example described below. The "group 13 reagent" solution is either a solution of trimethylaluminium ("TMA"), a solution of diisobuthylaluminium hydride ("DIBAL"), or a solution of modified methalumoxane-3A ("MMAO"). All "group 13 reagent" solutions were solutions in toluene. The molarity of the solutions used is indicated in the "activation method" of the individual example described below.

Activation method and Injection of solutions into the pressure reactor vessel: The following methods were employed to activate and inject the isolated complexes as indicated in Table 6. Method AA: 50 µL of a 0.200M solution of the group 13 reagent is dispensed into a 1 mL vial. 80 µL complex solution (5 mM in toluene) containing 0.4 µmol metal complex is added. After about 12 min, 176 µL of the activator solution in toluene (2.5 mM) was added to the 1 mL vial and the content of the 1 mL vial was mixed. About another 70 seconds later a fraction of the total 1 mL vial contents containing the indicated "catalyst amount injected" in Table 6, based on micromoles (µmol) of metal complex, was injected into the pre-pressurized reaction vessel and was followed immediately by injection of toluene to increase the total volume injected of 0.500 mL. Method BB: 62.5 µL of a 0.200M solution of the group 13 reagent is dispensed into a 1 mL vial. 100 µL complex solution (5 mM in toluene) containing 0.5 µmol metal complex is added. After about 12 min, 220 µL of the activator solution in toluene (2.5 mM) was added to the 1 mL vial and the content of the 1 mL vial was mixed. About another 70 seconds later a fraction of the total 1 mL vial contents containing the indicated "catalyst amount injected" in Table 6, based on micromoles (µmol) of metal complex, was injected into the pre-pressurized reaction vessel and was followed immediately by injection of toluene to increase the total volume injected of 0.500 mL. Method CC: Similar to Method AA, except that the activator is added approximately one minute after the alkylator. Method DD: 40 µL of a 0.050M solution of the group 13 reagent is dispensed into a 1 mL vial. 80 µL complex solution (5 mM in toluene) containing 0.4 µmol metal complex is added. After about 1 min, 176 µL of the activator solution in toluene (2.5 mM) was added to the 1 mL vial and the content of the 1 mL vial was mixed. About another 70 seconds later a fraction of the total 1 mL vial contents containing the indicated "catalyst amount injected" in Table 6, based on micromoles (µmol) of metal complex, was injected into the pre-pressurized reaction vessel and was followed immediately by injection of toluene to increase the total volume injected of 0.500 mL. Method EE: Similar to Method DD except that 0.300 mL toluene is added to the 1 mL vial immediately following addition of the activator. Method FF: 100 µL of a 0.050M solution of the group 13 reagent is dispensed into a 1 mL vial. 200 µL complex solution (5 mM in toluene) containing 1.0 µmol metal complex is added. After about 1 min, 220 µL of the activator solution in toluene (5.0 mM) was added to the 1 mL vial and the content of the 1 mL vial was mixed. About another 70 seconds later a fraction of the total 1 mL vial contents containing the indicated "catalyst amount injected" in Table 6, based on micromoles (µmol) of metal complex, was injected into the pre-pressurized reaction vessel and was followed immediately by injection of toluene to increase the total volume injected of 0.800 mL. Method GG: Similar to Method FF except that activator is added approximately 11 minutes after addition of the catalyst. Method HH: 150 µL of a 0.050M solution of the group 13 reagent is dispensed into a 1 mL vial. 100 µL complex solution (5 mM in toluene) containing 0.5 µmol metal complex is added. After about 12 min, 220 µL of the activator solution in toluene (2.5 mM) was added to the 1 mL vial and the content of the 1 mL vial was mixed. About another 70 seconds later a fraction of the total 1 mL vial contents containing the indicated "catalyst amount injected" in Table 6, based on micromoles (µmol) of metal complex, was injected into the pre-pressurized reaction vessel and was followed immediately by injection of toluene to increase the total volume injected of 0.500 mL. Method II Similar to Method HH except that 100 uL (instead of 150 uL) of the group 13 reagent sultion is added. Method JJ: Similar to Method II except that the total injection volume is 800 uL. Method KK: 120 µL of a 0.050M solution of the group 13 reagent is dispensed into a 1 mL vial. 80 µL complex solution (5 mM in toluene) containing 0.4 µmol metal complex is added. After about 12 min, 176 µL of the activator solution in toluene (2.5 mM) was added to the 1 mL vial, and the content of the 1 mL vial was mixed. About another 70 seconds later a fraction of the total 1 mL vial contents containing the indicated "catalyst amount injected" in Table 6, based on micromoles (µmol) of metal complex, was injected into the pre-pressurized reaction vessel and was followed immediately by injection of toluene to increase the total volume injected of 0.500 mL. Method LL: Similar to Method KK except that the total volume injected is 800 uL. Method MM: Similar to method KK except that 200 uL toluene was added to the 1 mL vial immediately after addition of activator. Method NN: 120 µL of a 0.050M solution of the group 13 reagent is dispensed into a 1 mL vial. 80 µL complex solution (5 mM in toluene) containing 0.4 µmol metal complex is added. After about 12 min, 176 µL of the activator solution in toluene (2.5 mM) was added to the 1 mL vial, followed by 0.400 mL toluene and the content of the 1 mL vial was mixed. About another 70 seconds later a fraction of the total 1 mL vial contents containing the indicated "catalyst amount injected" in Table 6, based on micromoles (µmol) of metal complex, was injected into the pre-pressurized reaction vessel and was followed immediately by injection of toluene to increase the total volume injected of 0.800 mL. Method OO: Similar to Method GG except that 125 µL of a 0.200 M Group 13 reagent solution was used (instead of 100 µL of the 0.050 M Group 13 reagent solution). Method PP: Similar to Method KK except that 0.600 toluene was added to the 1 mL vial after the activator.

Polymerization: The polymerization reaction was allowed to continue for 60-1800 seconds, during which time the temperature and pressure were maintained at their pre-set levels by computer control. The specific polymerization times for each polymerization are shown in Table 6. After the reaction time elapsed, the reaction was quenched by addition of an overpressure of carbon dioxide sent to the reactor. The polymerization times were the lesser of the maximum desired polymerization time or the time taken for a predetermined amount of monomer gas to be consumed in the polymerization reaction.

Product work up: Propylene Polymerizations: After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the crystallinity index. The melting point of selected samples was measured by DSC, as described above.

TABLE 6

| Example | Complex # | Scav. Method | Injection Method | Polym. Temp. | Group 13 reagent and mole equivalent | Activator | umol catalyst injected | Polym. time (s) | Activity (g Polymer/ min * mmol) | Crystallinity Index | Mw (/1000) | PDI (mw/Mn) | melting point |
|---|---|---|---|---|---|---|---|---|---|---|---|---|---|
| PP24 | M32 | C | AA | 75 | 25 TMA | 1.1 ABF20 | 0.05 | 205 | 2000 | 0.38 | 750 | 2.2 | n.d. |
| PP25 | M32 | C | AA | 110 | 25 TMA | 1.1 ABF20 | 0.1 | 122 | 820 | 0.36 | 130 | 2.4 | n.d. |
| PP26 | M6 | C | AA | 75 | 25 TMA | 1.1 ABF20 | 0.05 | 417 | 856 | 0.63 | 489 | 3.1 | n.d. |
| PP27 | M6 | C | AA | 110 | 25 TMA | 1.1 ABF20 | 0.05 | 601 | 197 | 0.68 | 511 | 7.5 | n.d. |
| PP28 | M5 | C | AA | 75 | 25 TMA | 1.1 ABF20 | 0.05 | 159 | 1675 | 0.66 | 1706 | 2.9 | n.d |
| PP29 | M5 | C | AA | 110 | 25 TMA | 1.1 ABF20 | 0.05 | 601 | 192 | 0.64 | 883 | 2.3 | n.d |
| PP30 | M1 | C | BB | 75 | 25 TMA | 1.1 ABF20 | 0.05 | 438 | 1226 | 0.52 | 136 | 7.3 | n.d. |
| PP31 | M1 | C | BB | 110 | 25 TMA | 1.1 ABF20 | 0.1 | 100 | 1259 | 0.54 | 123 | 5.4 | n.d. |
| PP32 | M1 | C | BB | 130 | 25 TMA | 1.1 ABF20 | 0.2 | 433 | 125 | 0.63 | 55 | 5.1 | n.d. |
| PP33 | M4 | C | BB | 75 | 25 TMA | 1.1 ABF20 | 0.05 | 601 | 601 | 0.60 | 413 | 9.8 | n.d. |
| PP34 | M4 | C | BB | 110 | 25 TMA | 1.1 ABF20 | 0.1 | 145 | 753 | 0.53 | 172 | 7.8 | n.d. |
| PP35 | M4 | C | BB | 130 | 25 TMA | 1.1 ABF20 | 0.2 | 600 | 60 | 0.53 | 83 | 7.4 | n.d. |
| PP36 | M11 | C | AA | 75 | 25 TMA | 1.1 ABF20 | 0.03 | 185 | 4153 | 0.81 | 960 | 2.2 | 126 |
| PP37 | M11 | C | AA | 110 | 25 TMA | 1.1 ABF20 | 0.05 | 103 | 2078 | 0.76 | 351 | 2.7 | 121 |
| PP38 | M11 | C | AA | 130 | 25 TMA | 1.1 ABF20 | 0.1 | 601 | 113 | 0.73 | 161 | 7.2 | 119 |
| PP39 | M12 | D | CC | 110 | 5 DIBAL | 1.1 ABF20 | 0.05 | 100 | 2414 | 0.81 | 348 | 2.0 | 122 |
| PP40 | M12 | D | CC | 130 | 5 DIBAL | 1.1 ABF20 | 0.2 | 104 | 460 | 0.75 | 104 | 3.9 | 119 |
| PP41 | M13 | A | DD | 75 | 5 DIBAL | 1.1 ABF20 | 0.025 | 325 | 940 | 0.79 | 900 | 2.0 | 137 |
| PP42 | M13 | A | CC | 110 | 5 DIBAL | 1.1 ABF20 | 0.05 | 120 | 1696 | 0.72 | 526 | 1.8 | 123 |
| PP43 | M13 | A | CC | 130 | 5 DIBAL | 1.1 ABF20 | 0.15 | 250 | 197 | 0.65 | 206 | 5.9 | 119 |
| PP44 | M26 | E | GG | 75 | 5 TIBA | 1.1 ABF20 | 0.75 | 241 | 68 | 0.28 | 654 | 2.6 | n.d. |
| PP45 | M27 | E | GG | 75 | 5 TIBA | 1.1 ABF20 | 0.75 | 1233 | 5 | 0.87 | 375 | 1.9 | 155 |
| PP46 | M28 | F | FF | 75 | 5 DIBAL | 1.1 ABF20 | 0.75 | 320 | 33 | 0.89 | 461 | 3.0 | 146 |
| PP47 | M28 | F | FF | 110 | 5 DIBAL | 1.1 ABF20 | 0.75 | 1800 | 4 | 0.90 | 67 | 3.1 | 140 |
| PP49 | M29 | F | FF | 75 | 5 DIBAL | 1.1 ABF20 | 0.75 | 333 | 30 | 0.91 | 204 | 3.3 | 152 |
| PP50 | M29 | F | FF | 110 | 5 TIBA | 1.1 ABF20 | 0.75 | 466 | 4 | 0.96 | 14 | 2.6 | 139 |
| PP51 | M30 | A | OO | 75 | 25 DIBAL | 1.1 ABF20 | 0.75 | 206 | 45 | 0.95 | 90 | 3.5 | 156 |
| PP52 | M30 | A | OO | 110 | 25 DIBAL | 1.1 ABF20 | 0.75 | 1801 | 2 | 0.91 | 23 | 3.1 | 141/150 |
| PP53 | M31 | A | OO | 75 | 25 DIBAL | 1.1 ABF20 | 0.75 | 174 | 45 | 0.93 | 32 | 2.9 | 156/162 |
| PP54 | M31 | A | OO | 110 | 25 DIBAL | 1.1 ABF20 | 0.75 | 1800 | 1 | 0.93 | 75 | 17.3 | 127 |
| PP55 | M8 | A | HH | 75 | 15 TMA | 1.1 ABF20 | 0.05 | 441 | 308 | 0.45 | 283 | 5.6 | 130 |
| PP56 | M8 | A | HH | 110 | 15 TMA | 1.1 ABF20 | 0.1 | 901 | 41 | 0.50 | 222 | 13.2 | 127 |
| PP57 | M10 | B | HH | 75 | 15 TMA | 1.1 ABF20 | 0.05 | 358 | 338 | 0.18 | 32 | 2.8 | n.d |
| PP58 | M10 | B | HH | 110 | 15 TMA | 1.1 ABF20 | 0.1 | 1802 | 20 | 0.28 | 13 | 2 | n.d |
| PP59 | M9 | B | HH | 75 | 15 TMA | 1.1 ABF20 | 0.05 | 236 | 534 | 0.46 | 44 | 3.2 | n.d. |
| PP60 | M9 | B | HH | 110 | 15 TMA | 1.1 ABF20 | 0.1 | 1800 | 19 | 0.30 | 17 | 1.9 | n.d. |
| PP61 | M14 | B | HH | 75 | 15 TMA | 1.1 ABF20 | 0.05 | 219 | 1848 | 0.86 | 953 | 2.4 | 130 |
| PP62 | M14 | B | HH | 75 | 15 TMA | 1.1 TBF20 | 0.05 | 180 | 2228 | 0.79 | 986 | 2.4 | 130 |
| PP63 | M14 | B | HH | 110 | 15 TMA | 1.1 ABF20 | 0.075 | 175 | 811 | 0.90 | 456 | 3.7 | 132 |
| PP64 | M14 | B | HH | 110 | 15 TMA | 1.1 TBF20 | 0.075 | 177 | 829 | 0.88 | 490 | 3.5 | n.d. |
| PP65 | M16 | B | II | 75 | 10 MMAO | 1.1 ABF20 | 0.05 | 415 | 1412 | 0.79 | 987 | 2.1 | 133 |
| PP66 | M16 | B | II | 75 | 10 MMAO | 1.1 TBF20 | 0.05 | 178 | 2461 | 0.74 | 973 | 2.1 | 129 |
| PP67 | M16 | B | II | 110 | 10 MMAO | 1.1 ABF20 | 0.075 | 174 | 931 | 0.94 | 594 | 2.8 | 132 |
| PP68 | M16 | B | II | 110 | 10 MMAO | 1.1 TBF20 | 0.075 | 238 | 694 | 0.92 | 671 | 2.6 | 132 |
| PP69 | M17 | B | II | 75 | 10 MMAO | 1.1 TBF20 | 0.05 | 175 | 2555 | 0.75 | 460 | 2.4 | 129 |
| PP70 | M17 | B | II | 110 | 10 MMAO | 1.1 TBF20 | 0.075 | 124 | 1446 | 0.76 | 214 | 2.5 | 129 |
| PP71 | M17 | B | JJ | 130 | 10 MMAO | 1.1 TBF20 | 0.25 | 146 | 267 | 0.78 | 57 | 3.3 | 127 |
| PP72 | M18 | B | MM | 110 | 15 TMA | 1.1 ABF20 | 0.04 | 900 | 97 | 0.88 | 286 | 3.7 | 138 |
| PP73 | M18 | B | KK | 130 | 15 TMA | 1.1 ABF20 | 0.08 | 901 | 23 | 0.67 | n.d. | n.d. | n.d. |
| PP74 | M20 | B | MM | 110 | 15 TMA | 1.1 ABF20 | 0.04 | 598 | 458 | 0.86 | 352 | 2.8 | 141 |
| PP75 | M20 | B | KK | 130 | 15 TMA | 1.1 TBF20 | 0.08 | 900 | 73 | 0.84 | 199 | 3.6 | 139 |
| PP76 | M19 | B | MM | 110 | 15 TMA | 1.1 TBF20 | 0.06 | 233 | 815 | 0.84 | 330 | 2.3 | 136 |
| PP77 | M19 | B | MM | 130 | 15 TMA | 1.1 TBF20 | 0.08 | 901 | 77 | 0.82 | 116 | 2.9 | 141 |
| PP78 | M21 | A | MM | 75 | 5 PMAO | 1.1 TBF20 | 0.04 | 801 | 202 | 0.88 | 593 | 9.5 | 150 |
| PP79 | M21 | A | MM | 110 | 5 PMAO | 1.1 TBF20 | 0.15 | 138 | 529 | 0.67 | 228 | 5.5 | 143 |
| PP80 | M21 | A | OO | 130 | 5 PMAO | 1.1 TBF20 | 0.3 | 250 | 148 | 0.82 | 80 | 9.1 | 140, 148 |
| PP81 | M22 | A | KK | 110 | 15 TMA | 1.1 TBF20 | 0.15 | 901 | 54 | 0.89 | 341 | 10.9 | 137 |

TABLE 6-continued

| Example | Complex # | Scav. Method | Injection Method | Polym. Temp. | Group 13 reagent and mole equivalent | Activator | umol catalyst injected | Polym. time (s) | Activity (g Polymer/ min * mmol) | Crystal- linity Index | Mw (/1000) | PDI (mw/Mn) | melting point |
|---|---|---|---|---|---|---|---|---|---|---|---|---|---|
| PP82 | M24 | A | KK | 75 | 15 TMA | 1.1 TBF20 | 0.04 | 295 | 2089 | 0.74 | 514 | 11.0 | n.d. |
| PP83 | M24 | A | KK | 110 | 15 TMA | 1.1 TBF20 | 0.06 | 131 | 1497 | 0.94 | 347 | 7.4 | 121, 128 |
| PP84 | M24 | A | KK | 110 | 15 TMA | 1.1 ABF20 | 0.06 | 102 | 2146 | 0.82 | 299 | 7.0 | 123 |
| PP85 | M24 | A | NN | 130 | 15 TMA | 1.1 TBF20 | 0.15 | 901 | 112 | 0.92 | 209 | 12.0 | 108, 121 |
| PP86 | M24 | A | NN | 130 | 15 TMA | 1.1 ABF20 | 0.15 | 194 | 368 | 0.85 | 136 | 9.5 | n.d. |
| PP87 | M23 | B | KK | 75 | 15 TMA | 1.1 TBF20 | 0.12 | 402 | 221 | 0.55 | 638 | 2.9 | n.d. |
| PP88 | M23 | B | KK | 110 | 15 TMA | 1.1 TBF20 | 0.15 | 542 | 118 | 0.62 | 473 | 2.6 | 111 |
| PP89 | M23 | B | LL | 130 | 15 TMA | 1.1 TBF20 | 0.3 | 901 | 28 | 0.61 | 137 | 2.9 | 112 |
| PP90 | M25 | B | KK | 110 | 15 TMA | 1.1 ABF20 | 0.04 | 324 | 679 | 0.79 | 333 | 1.9 | 127 |
| PP91 | M25 | B | KK | 130 | 15 TMA | 1.1 ABF20 | 0.1 | 207 | 554 | 0.82 | 93 | 2.9 | 127 |
| PP92 | M60 | D | DD | 75 | 5 DIBAL | 1.1 ABF20 | 0.1 | 321 | 220 | 0.19 | 526 | 4.8 | n.d. |
| PP93 | M60 | D | DD | 90 | 5 DIBAL | 1.1 ABF20 | 0.1 | 234 | 311 | 0.2 | 241 | 2.3 | n.d |
| PP94 | M60 | D | DD | 110 | 5 DIBAL | 1.1 ABF20 | 0.1 | 270 | 27 | 0.36 | 95 | 3 | n.d |
| PP95 | M33 | A | BB | 75 | 25 TMA | 1.1 ABF20 | 0.05 | 600 | 33 | n.d. | n.d. | n.d. | n.d. |
| PP96 | M33 | A | BB | 110 | 25 TMA | 1.1 ABF20 | 0.1 | 177 | 641 | 0.24 | 247 | 6.2 | n.d. |
| PP97 | M33 | A | BB | 130 | 25 TMA | 1.1 ABF20 | 0.15 | 601 | 52 | 0.34 | 109 | 5 | n.d. |
| PP98 | M36 | C | BB | 75 | 25 TMA | 1.1 ABF20 | 0.05 | 600 | 60 | 0.35 | 60 | 11.1 | n.d. |
| PP99 | M36 | C | BB | 110 | 25 TMA | 1.1 ABF20 | 0.1 | 254 | 299 | 0.86 | 143 | 16.5 | 114 |
| PP100 | M36 | C | BB | 130 | 25 TMA | 1.1 ABF20 | 0.2 | 476 | 100 | 0.66 | 66 | 7.7 | 113 |
| PP101 | M37 | C | BB | 75 | 25 TMA | 1.1 ABF20 | 0.05 | 600 | 182 | 0.8 | 68 | 7.7 | n.d. |
| PP102 | M37 | C | BB | 110 | 25 TMA | 1.1 ABF20 | 0.1 | 378 | 208 | 0.61 | 78 | 8.5 | 112 |
| PP103 | M37 | C | BB | 130 | 25 TMA | 1.1 ABF20 | 0.2 | 330 | 151 | 0.75 | 52 | 5.6 | 112 |
| PP104 | M38 | A | DD | 110 | 5 DIBAL | 1.1 ABF20 | 0.1 | 439 | 340 | 0.6 | 241 | 10.9 | 110 |
| PP105 | M38 | A | DD | 130 | 5 DIBAL | 1.1 ABF20 | 0.15 | 318 | 209 | 0.74 | 113 | 5.6 | 113 |
| PP106 | M42 | A | BB | 75 | 25 TMA | 1.1 ABF20 | 0.05 | 404 | 408 | 0.7 | 704 | 7.6 | 130 |
| PP107 | M42 | A | BB | 110 | 25 TMA | 1.1 ABF20 | 0.1 | 108 | 1126 | 0.65 | 270 | 6.1 | 124 |
| PP108 | M42 | A | BB | 130 | 25 TMA | 1.1 ABF20 | 0.15 | 243 | 358 | 0.73 | 113 | 6.4 | 115 |
| PP109 | M41 | B | HH | 110 | 15 TMA | 1.1 ABF20 | 0.075 | 902 | 81 | 0.64 | 86 | 12.3 | n.d. |
| PP110 | M41 | B | HH | 130 | 15 TMA | 1.1 ABF20 | 0.025 | 900 | 13 | 0.6 | 16 | 9.3 | n.d. |
| PP111 | M51 | B | KK | 75 | 15 TMA | 1.1 TBF20 | 0.06 | 211 | 2875 | 0.79 | 315 | 2.5 | n.d. |
| PP112 | M51 | B | PP | 110 | 15 TMA | 1.1 TBF20 | 0.06 | 231 | 1391 | 0.76 | 109 | 2.3 | 135, 144 |
| PP113 | M51 | B | PP | 130 | 15 TMA | 1.1 TBF20 | 0.15 | 900 | 55 | 0.82 | 85 | 5.4 | 134, 145 |
| PP114 | M48 | B | KK | 110 | 15 TMA | 1.1 ABF20 | 0.04 | 73 | 4477 | 0.95 | 81 | 1.6 | 144 |
| PP115 | M48 | B | KK | 130 | 15 TMA | 1.1 ABF20 | 0.1 | 98 | 1341 | 0.95 | 16 | 2.5 | 138 |
| PP116 | M52 | A | BBB | 75 | 25 TMA | 1.1 ABF20 | 0.05 | 601 | 46 | n.d. | n.d. | n.d. | n.d. |
| PP117 | M52 | A | BBB | 110 | 25 TMA | 1.1 ABF20 | 0.1 | 600 | 38 | 0.31 | 43 | 7.2 | n.d. |
| PP118 | M52 | A | BBB | 130 | 25 TMA | 1.1 ABF20 | 0.15 | 600 | 12 | n.d. | n.d. | n.d. | n.d. |
| PP119 | M53 | A | BBB | 75 | 25 TMA | 1.1 ABF20 | 0.05 | 600 | 50 | 0.51 | 91 | 11.8 | n.d. |
| PP120 | M53 | A | BBB | 110 | 25 TMA | 1.1 ABF20 | 0.1 | 510 | 135 | 0.69 | 65 | 14.2 | 110 |
| PP121 | M53 | A | BBB | 130 | 25 TMA | 1.1 ABF20 | 0.15 | 601 | 41 | 0.53 | 67 | 13.4 | n.d. |
| PP122 | M59 | A | HH | 75 | 15 TMA | 1.1 ABF20 | 0.05 | 900 | 84 | 0.21 | 187 | 5.8 | n.d. |
| PP123 | M59 | A | HH | 110 | 15 TMA | 1.1 ABF20 | 0.1 | 901 | 15 | low | n.d. | n.d. | n.d. |
| PP124 | M56 | A | HH | 75 | 15 TMA | 1.1 ABF20 | 0.05 | 326 | 405 | 0.22 | 252 | 5.3 | n.d. |
| PP125 | M56 | A | HH | 110 | 15 TMA | 1.1 ABF20 | 0.1 | 900 | 37 | 0.26 | 71 | 4.2 | n.d. |
| PP126 | M57 | A | HH | 75 | 15 TMA | 1.1 ABF20 | 0.05 | 138 | 1780 | 0.25 | 225 | 5.1 | n.d. |
| PP127 | M57 | A | HH | 110 | 15 TMA | 1.1 ABF20 | 0.1 | 144 | 622 | 0.43 | 46 | 3.8 | n.d. |

Example 90

Ethylene-1-Octene Copolymerizations Using Metal-Ligand Compositions. A total of 28 separate ethylene-1-octene polymerization reactions (EO1-E028) were performed as follows.

Preparation of the Polymerization Reactor Prior to Injection of Catalyst Composition:

Method G: A pre-weighed glass vial insert and disposable stirring paddle were fitted to each reaction vessel of the reactor. The reactor was then closed, 0.200 mL of a 0.05 M solution of Modified Methylaluminoxane 3A (from Azko Chemical Inc., Chicago, Ill.) ("MMAO") in toluene, 0.400 mL octene and 4.4 mL of toluene were injected into each pressure reaction vessel through a valve. The temperature was then set to the appropriate setting (with specific temperatures for each polymerization being listed in Table 7, below), and the stirring speed was set to 800 rpm unless otherwise noted, and the mixture was exposed to ethylene at 100 psi pressure. A ethylene pressure of 100 psi in the pressure cell and the temperature setting were maintained, using computer control, until the end of the polymerization experiment.

Method H: Method H is similar to method G except that 0.200 mL of a 0.05 M solution of Partially Modified Methalumoxane ("PMAO") in toluene was injected (instead of MMAO).

Preparation of Metal-ligand Compositions: The metal-ligand compositions were prepared as described in Example 88, above.

Activation methods and Injection of solutions into the pressure reactor vessel: The methods used for activating and injecting the catalyst into the reactor are described in Example 88, above.

Polymerization: The polymerization reaction was allowed to continue for 60-900 seconds, during which time the temperature and pressure were maintained at their pre-set levels by computer control. The specific times for each polymerization are shown in Table 7. The polymerization times were the lesser of the maximum desired polymerization time or the time taken for a predetermined amount of monomer gas to be consumed in the polymerization reaction. After the reaction time elapsed, the reaction was quenched by addition of an overpressure of carbon dioxide sent to the reactor.

Product work up: ethylene/1-octene copolymerizations: After the polymerization reaction, the glass vial insert, containing the polymer product and solvent, was removed from the pressure cell and removed from the inert atmosphere dry box, and the volatile components were removed using a centrifuge vacuum evaporator. After substantial evaporation of the volatile components, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and FTIR spectroscopy to determine the comonomer incorporation. Results are presented in Table 7.

pressure cell and the temperature setting were maintained, using computer control, until the end of the polymerization experiment.

Preparation of the group 13 reagent and activator stock solutions: The "activator solution" is either a 2.5 mM solution of N,N'-dimethylanilinium tetrakis (pentafluorophenyl) borate ("$ABF_{20}$") in toluene or a 400 mM solution of Modified Methylaluminoxane-3A (Azko) ("MMAO") in toluene. The "$ABF_{20}$" solution is heated to approximately 85° C. to dissolve the reagent. The group 13 reagent solution is either a solution of trimethylaluminum ("TMA"), diisobutylaluminium hydride ("DIBAL"), or modified methalumoxane-3A ("MMAO") in toluene. The molarity of the group 13 reagent is noted below and the molar equivalents is noted in Table 8.

Activation methods and Injection of solutions into the pressure reactor vessel: Method AAA: 50 μL of a 0.200M solution of the group 13 reagent is dispensed into a 1 mL vial. 80 μL complex solution (5 mM in toluene) containing 0.4 μmol metal complex is added. After about 12 min, 176 μL of the activator solution in toluene (2.5 mM) was added

TABLE 7

| Example | Ligand | Metal Precurs. | Complexation method | Reactor prep. Method | Injection method | Polymerization Temp (C.) | Group 13 reagent and mole equivalent alkyl | Activator | μmol catalyst injected | Polym. Time (s) | Activity (g polymer/ min * mmol) | Mw (/1000) | PDI (Mw/Mn) | mol % Octene by FTIR |
|---|---|---|---|---|---|---|---|---|---|---|---|---|---|---|
| EO1 | A48 | HfBz3+ | ZG | G | GGGG | 100 | 5 PMAO | 1.1 TBF20 | 0.03 | 93 | 4991 | 150 | 3.1 | 19 |
| EO2 | A48 | ZrBz3+ | ZG | G | GGGG | 100 | 5 PMAO | 1.1 TBF21 | 0.03 | 171 | 1137 | 202 | 3.2 | 9 |
| EO3 | A40 | Hf(NMe2)4 | ZF | H | HHHH | 100 | 25 TMA | 1.1 ABF20 | 0.05 | 134 | 1796 | 319 | 2.3 | 17 |
| EO4 | A40 | Zr(NMe2)4 | ZF | H | AAAA | 100 | 25 TMA | 1.1 ABF20 | 0.1 | 110 | 767 | 195 | 4.1 | 11 |
| EO5 | C14 | Hf(NMe2)4 | ZA | H | AAAA | 100 | 25 TMA | 1.1 ABF20 | 0.1 | 61 | 2418 | 46 | 3.4 | 10 |
| EO6 | C14 | Zr(NMe2)4 | ZA | H | AAAA | 100 | 25 TMA | 1.1 ABF20 | 0.1 | 74 | 1334 | 59 | 2.4 | 6 |
| EO7 | C16 | Hf(NMe2)4 | ZA | H | AAAA | 100 | 25 TMA | 1.1 ABF20 | 0.1 | 61 | 2524 | 67 | 3.8 | 17 |
| EO8 | C16 | Zr(NMe2)4 | ZA | H | AAAA | 100 | 25 TMA | 1.1 ABF20 | 0.1 | 76 | 1510 | 67 | 2.5 | 9 |
| EO9 | C27 | Hf(NMe2)4 | ZF | G | FFFF | 100 | 15 TMA | 1.1 ABF20 | 0.025 | 65 | 5978 | 129 | 2.5 | 8 |
| EO10 | C27 | Zr(NMe2)4 | ZF | G | FFFF | 100 | 15 TMA | 1.1 ABF20 | 0.03 | 76 | 3492 | 161 | 3 | 5 |
| EO11 | C29 | HfBz3+ | ZG | G | FFFF | 100 | 5 PMAO | 1.1 TBF20 | 0.03 | 121 | 4379 | 149 | 3.3 | 22 |
| EO12 | C29 | ZrBz3+ | ZG | G | FFFF | 100 | 5 PMAO | 1.1 TBF20 | 0.03 | 122 | 2921 | 195 | 2.5 | 15 |
| EO13 | F1 | Hf(NMe2)4 | ZF | H | HHHH | 100 | 25 TMA | 1.1 ABF20 | 0.05 | 61 | 4014 | 122 | 2.1 | 11 |
| EO14 | F1 | Zr(NMe2)4 | ZF | H | AAAA | 100 | 25 TMA | 1.1 ABF20 | 0.1 | 61 | 1774 | 107 | 1.7 | 8 |
| EO15 | E2 | Hf(NMe2)4 | ZA | H | AAAA | 100 | 25 TMA | 1.1 ABF20 | 0.1 | 105 | 1513 | 114 | 11.5 | 19 |
| EO16 | E2 | Zr(NMe2)4 | ZA | H | AAAA | 100 | 25 TMA | 1.1 ABF20 | 0.1 | 90 | 1149 | 89 | 3.1 | 7 |
| EO17 | G6 | Hf(NMe2)4 | ZF | G | DDDD | 100 | 15 TMA | 1.1 ABF20 | 0.05 | 98 | 1730 | 141 | 2.3 | 7 |
| EO18 | G6 | Zr(NMe2)4 | ZF | G | DDDD | 100 | 15 TMA | 1.1 TBF20 | 0.25 | 252 | 85 | 78 | 3.3 | 5 |
| EO19 | G17 | Hf(NMe2)4 | ZF | G | DDDD | 100 | 15 TMA | 1.1 ABF20 | 0.05 | 95 | 1936 | 123 | 2.4 | 7 |
| EO20 | G17 | Zr(NMe2)4 | ZF | G | DDDD | 100 | 15 TMA | 1.1 TBF25 | 0.25 | 172 | 153 | 78 | 3.2 | 4 |
| EO21 | C19 | Hf(NMe2)4 | ZF | G | EEEE | 100 | 10 TMA | 1.1 ABF20 | 0.03 | 105 | 3834 | 71 | 1.7 | 8 |
| EO22 | C19 | Zr(NMe2)4 | ZF | G | EEEE | 100 | 10 TMA | 1.1 ABF20 | 0.05 | 114 | 1308 | 79 | 1.6 | 3 |
| EO23 | C21 | Hf(NMe2)4 | ZF | G | EEEE | 100 | 10 TMA | 1.1 ABF20 | 0.03 | 72 | 5253 | 55 | 1.8 | 5 |
| EO24 | C21 | Zr(NMe2)4 | ZF | G | EEEE | 100 | 10 TMA | 1.1 ABF20 | 0.05 | 88 | 2122 | 72 | 1.7 | 4 |
| EO25 | C22 | Hf(NMe2)4 | ZF | G | EEEE | 100 | 10 TMA | 1.1 ABF20 | 0.03 | 62 | 6065 | 68 | 2 | 6 |
| EO26 | C22 | Zr(NMe2)4 | ZF | G | EEEE | 100 | 10 TMA | 1.1 ABF20 | 0.05 | 85 | 2296 | 77 | 1.8 | 4 |
| EO27 | C1 | Hf(NMe2)4 | ZF | H | HHHH | 100 | 25 TMA | 1.1 ABF20 | 0.05 | 84 | 2747 | 129 | 1.8 | 12 |
| EO28 | C1 | Zr(NMe2)4 | ZF | H | HHHH | 100 | 25 TMA | 1.1 ABF20 | 0.1 | 75 | 1077 | 129 | 1.5 | 4 |

Example 91

Ethylene-1-Octene Copolymerizations Using Isolated Complexes. A total of 108 separate ethylene-1-octene polymerization reactions (E029-EO136) were performed as follows.

Preparation of the polymerization reactor prior to injection of catalyst composition: The reactor was prepared as described in Method G, above. In some examples hydrogen (as a mixture with nitrogen) was added; the amount added is noted in Table 8. An ethylene pressure of 100 psi in the to the 1 mL vial and the content of the 1 mL vial was mixed. About another 70 seconds later a fraction of the total 1 mL vial contents containing the indicated "catalyst amount injected" in Table 8, based on micromoles (μmol) of metal complex, was injected into the pre-pressurized reaction vessel and was followed immediately by injection of toluene to increase the total volume injected of 0.500 mL. Method BBB: Similar to Method AAA, except that 0.200 mL of toluene was added to the 1 mL vial immediately after addition of the activator solution. Method CCC 40 μL of a 0.05M solution of the group 13 reagent is dispensed into a 1 mL vial. 80 μL complex solution (5 mM in toluene)

containing 0.4 μmol metal complex is added. After about 12 min, 176 μL of the activator solution in toluene (2.5 mM) was added to the 1 mL vial, followed by 0.200 mL of toluene and the content of the 1 mL vial was mixed. About another 70 seconds later a fraction of the total 1 mL vial contents containing the indicated "catalyst amount injected" in Table 8, based on micromoles (Amos) of metal complex, was injected into the pre-pressurized reaction vessel and was followed immediately by injection of toluene to increase the total volume injected of 0.500 mL. Method DDD: 80 μL of a 0.05M solution of the group 13 reagent is dispensed into a 1 mL vial. 80 μL complex solution (5 mM in toluene) containing 0.4 lmol metal complex is added. After about 12 min, 200 μL of the activator solution in toluene (400 mM) was added to the 1 mL vial and the content of the 1 mL vial was mixed. About another 70 seconds later a fraction of the total 1 mL vial contents containing the indicated "catalyst amount injected" in Table 8, based on micromoles (μmos) of metal complex, was injected into the pre-pressurized reaction vessel and was followed immediately by injection of toluene to increase the total volume injected of 0.500 mL. Method EEE: Similar to Method DDD except that 0.300 mL toluene was added to the 1 mL vial immediately after the activator. Method FFF 80 μL of a 0.05M solution of the group 13 reagent is dispensed into a 1 mL vial. 80 μL complex solution (5 mM in toluene) containing 0.4 μmol metal complex is added. After about 12 min, 176 μL of the activator solution in toluene (2.5 mM) was added to the 1 mL vial, followed by 400 uL of toluene and the content of the 1 mL vial was mixed. About another 70 seconds later a fraction of the total 1 mL vial contents containing the indicated "catalyst amount injected" in Table 8, based on micromoles (μmol) of metal complex, was injected into the pre-pressurized reaction vessel and was followed immediately by injection of toluene to increase the total volume injected of 0.500 mL. Method GGG Similar to method FFF except that 200 μL of a 400 mM activator solution was added. Method HHH 200 μL of a 200 mM solution of the group 13 reagent is dispensed into a 1 mL vial. 80 μL complex solution (5 mM in toluene) containing 0.4 μmol metal complex is added. After about 12 min, 200 μL of the activator solution in toluene (200 mM) was added to the 1 mL vial, followed by 0.500 mL of toluene and the content of the 1 mL vial was mixed. About another 70 seconds later a fraction of the total 1 mL vial contents containing the indicated "catalyst amount injected" in Table 8, based on micromoles (μmol) of metal complex, was injected into the pre-pressurized reaction vessel and was followed immediately by injection of toluene to increase the total volume injected of 0.500 mL. Method III: Similar to method HHH except that 0.200 mL (instead of 0.500 mL) was added after the activator. Method JJJ: Similar to Method CCC except that 0.500 mL (instead of 0.200 mL) toluene was added after the activator. Method KKK: Similar to Method DDD except that 0.400 mL toluene was added to the 1 mL vial immediately after the activator. Method LLL: Similar to method HHH except that 0.800 mL toluene (instead of 0.500 mL) is added after the activator. Method MMM: 40 μL of a 0.05M solution of the group 13 reagent is dispensed into a 1 mL vial. 80 μL complex solution (5 mM in toluene) containing 0.4 μmol metal complex is added. After about 12 min, 200 μL of the activator solution in toluene (400 mM) was added to the 1 mL vial, followed by 600 uL toluene and the content of the 1 mL vial was mixed. About another 70 seconds later a fraction of the total 1 mL vial contents containing the indicated "catalyst amount injected" in Table 8, based on micromoles (gmol) of metal complex, was injected into the pre-pressurized reaction vessel and was followed immediately by injection of toluene to increase the total volume injected of 0.500 mL. Method NNN: Similar to method MMM except that 0.300 mL toluene (instead of 0.600 mL) is added immediately after the activator. Method OOO: Similar to Method CCC except that 0.300 mL (instead of 0.200 mL) toluene was added after the activator. Method PPP: Similar to method FFF except that 300 uL toluene (instead of 400) was added immediately after the activator. Method QQQ: 120 μL of a 0.05M solution of the group 13 reagent is dispensed into a 1 mL vial. 80 μL complex solution (5 mM in toluene) containing 0.4 μmol metal complex is added. After about 12 min, 176 μL of the activator solution in toluene (2.5 mM) was added to the 1 mL vial immediately followed by 0.300 mL toluene and the content of the 1 mL vial was mixed. About another 70 seconds later a fraction of the total 1 mL vial contents containing the indicated "catalyst amount injected" in Table 8, based on micromoles (μmol) of metal complex, was injected into the pre-pressurized reaction vessel and was followed immediately by injection of toluene to increase the total volume injected of 0.500 mL. Method RRR: Similar to Method QQQ except that 0.600 mL toluene (instead of 0.300 mL) was added after the activator. Method SSS. 120 μL of a 0.05M solution of the group 13 reagent is dispensed into a 1 mL vial. 80 μL complex solution (5 mM in toluene) containing 0.4 μmol metal complex is added. After about 12 min, 200 μL of the activator solution in toluene (400 mM) was added to the 1 mL vial immediately followed by 0.300 mL toluene and the content of the 1 mL vial was mixed. About another 70 seconds later a fraction of the total 1 mL vial contents containing the indicated "catalyst amount injected" in Table 8, based on micromoles (μmol) of metal complex, was injected into the pre-pressurized reaction vessel and was followed immediately by injection of toluene to increase the total volume injected of 0.500 mL. Method TTT: Similar to Method SSS except that 0.600 mL toluene (instead of 0.300 mL) was added after the activator. Method UUU: Similar to Method FFF except that 0.600 mL toluene (instead of 0.400 mL) was added after the activator. Method VVV: Similar to Method DDD except that 0.800 mL toluene was added immediately after the activator. Method WWW: Similar to Method QQQ except that 0.400 mL toluene (instead of 0.300 mL toluene) was added to the 1 mL vial immediately after the activator. Method XXX: Similar to method SSS except that 0.400 mL toluene (instead of 0.300 mL toluene) was added to the 1 mL vial immediately after the activator.

Polymerization: The polymerization reaction was allowed to continue for 60-900 seconds, during which time the temperature and pressure were maintained at their pre-set levels by computer control. The specific times for each polymerization are shown in Table 8. The polymerization times were the lesser of the maximum desired polymerization time or the time taken for a predetermined amount of monomer gas to be consumed in the polymerization reaction. After the reaction time elapsed, the reaction was quenched by addition of an overpressure of carbon dioxide sent to the reactor.

Product work up: ethylene/1-octene copolymerizations After the polymerization reaction, the glass vial insert, containing the polymer product and solvent, was removed from the pressure cell and removed from the inert atmosphere dry box, and the volatile components were removed using a centrifuge vacuum evaporator. After substantial evaporation of the volatile components, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and FTIR spectroscopy to determine the comonomer incorporation. Results are presented in Table 8.

TABLE 8

| Example # | Complex | Injection Method | Polym. Temp(° C.) | Group 13 reagent and mole equivalent | Activator | μmol catalyst injected | H2 added (psi) | Polym. time (s) | Activity (g polymer/ min * mmol | Mw (k) | PDI (Mw/Mn) | mol % Octene by FTIR |
|---|---|---|---|---|---|---|---|---|---|---|---|---|
| EO29 | M1 | BBB | 100 | 25 TMA | 1.1 ABF20 | 0.04 | 0 | 177 | 1770 | 256 | 6.6 | 11 |
| EO30 | M1 | BBB | 100 | 25 TMA | 1.1 ABF20 | 0.04 | 1 | 154 | 1805 | 189 | 6.4 | 16 |
| EO31 | M1 | AAA | 130 | 25 TMA | 1.1 ABF20 | 0.08 | 0 | 403 | 263 | 112 | 5.5 | 12 |
| EO32 | M1 | AAA | 130 | 25 TMA | 1.1 ABF20 | 0.08 | 1 | 170 | 697 | 111 | 5.3 | 11 |
| EO33 | M1 | BBB | 100 | 25 TMA | 1.1 ABF20 | 0.04 | 4 | 130 | 2451 | 176 | 6.1 | 18 |
| EO34 | M2 | CCC | 100 | 5 DIBAL | 1.1 ABF20 | 0.04 | 0 | 163 | 1477 | 287 | 2.8 | 10 |
| EO35 | M2 | CCC | 100 | 5 MMAO | 1.1 ABF20 | 0.04 | 0 | 133 | 1804 | 224 | 2.6 | 9 |
| EO36 | M2 | CCC | 130 | 5 DIBAL | 1.1 ABF20 | 0.04 | 0 | 901 | 78 | 234 | 2.5 | 14 |
| EO37 | M2 | CCC | 130 | 5 MMAO | 1.1 ABF20 | 0.04 | 0 | 901 | 149 | 251 | 2.4 | 12 |
| EO38 | M2 | CCC | 100 | 5 DIBAL | 1.1 ABF20 | 0.04 | 4 | 187 | 1439 | 213 | 4.3 | 9 |
| EO39 | M2 | CCC | 100 | 5 MMAO | 1.1 ABF20 | 0.04 | 4 | 207 | 930 | 277 | 2.9 | 7 |
| EO40 | M4 | BBB | 100 | 25 TMA | 1.1 ABF20 | 0.04 | 0 | 371 | 487 | 318 | 5.1 | 7 |
| EO41 | M4 | BBB | 100 | 25 TMA | 1.1 ABF20 | 0.04 | 4 | 233 | 1394 | 341 | 6.5 | 17 |
| EO42 | M4 | AAA | 130 | 25 TMA | 1.1 ABF20 | 0.08 | 0 | 230 | 579 | 174 | 5.9 | 12 |
| EO43 | M4 | BBB | 100 | 25 TMA | 1.1 ABF20 | 0.04 | 4 | 382 | 776 | 391 | 7 | 15 |
| EO44 | M11 | BBB | 100 | 25 TMA | 1.1 ABF20 | 0.04 | 0 | 297 | 830 | 475 | 6.7 | 13 |
| EO45 | M11 | BBB | 100 | 25 TMA | 1.1 ABF20 | 0.04 | 1 | 149 | 2561 | 184 | 5.7 | 29 |
| EO46 | M11 | AAA | 130 | 25 TMA | 1.1 ABF20 | 0.08 | 0 | 230 | 545 | 155 | 6.2 | 16 |
| EO47 | M11 | AAA | 130 | 25 TMA | 1.1 ABF20 | 0.08 | 4 | 285 | 495 | 119 | 5 | 17 |
| EO48 | M11 | BBB | 100 | 25 TMA | 1.1 ABF20 | 0.04 | 4 | 125 | 3930 | 155 | 5.7 | 17 |
| EO49 | M14 | EEE | 100 | 10 TMA | 200 MMAO | 0.03 | 0 | 387 | 718 | 225 | 3 | 7 |
| EO50 | M14 | DDD | 100 | 10 TMA | 200 MMAO | 0.06 | 4 | 193 | 591 | 70 | 2.6 | 4 |
| EO51 | M14 | EEE | 130 | 10 TMA | 200 MMAO | 0.1 | 0 | 901 | 98 | 83 | 2.6 | 5 |
| EO52 | M15 | EEE | 100 | 10 TMA | 200 MMAO | 0.03 | 0 | 606 | 422 | 141 | 2.8 | 7 |
| EO53 | M15 | DDD | 100 | 10 TMA | 200 MMAO | 0.06 | 4 | 285 | 502 | 147 | 3.2 | 10 |
| EO54 | M15 | EEE | 130 | 10 TMA | 200 MMAO | 0.1 | 0 | 172 | 189 | 68 | 3 | 11 |
| EO55 | M32 | FFF | 100 | 10TMA | 1.1 ABF20 | 0.03 | 0 | 137 | 2656 | 132 | 3.1 | 13 |
| EO56 | M32 | GGG | 100 | 10TMA | 200 MMAO | 0.03 | 0 | 653 | 334 | 44 | 3.8 | 4 |
| EO57 | M32 | FFF | 130 | 10TMA | 1.1 ABF20 | 0.04 | 0 | 901 | 152 | 143 | 3.1 | 7 |
| EO58 | M32 | GGG | 130 | 10TMA | 200 MMAO | 0.04 | 0 | 900 | 25 | n.d. | n.d. | n.d. |
| EO59 | M32 | FFF | 100 | 10TMA | 1.1 ABF20 | 0.03 | 4 | 199 | 1265 | 118 | 2.9 | 8 |
| EO60 | M32 | GGG | 100 | 10TMA | 200 MMAO | 0.03 | 4 | 900 | 80 | 44 | 5.4 | 5 |
| EO61 | M34 | BBB | 100 | 25 DIBAL | 1.1 ABF20 | 0.04 | 0 | 94 | 2291 | 152 | 2.7 | 4 |
| EO62 | M34 | BBB | 100 | 25 DIBAL | 1.1 ABF20 | 0.04 | 1 | 128 | 1560 | 200 | 2.6 | 4 |
| EO63 | M34 | AAA | 130 | 25 DIBAL | 1.1 ABF20 | 0.06 | 0 | 190 | 629 | 172 | 3.1 | 4 |
| EO64 | M34 | AAA | 130 | 25 DIBAL | 1.1 ABF20 | 0.06 | 1 | 312 | 377 | 158 | 3 | 4 |
| EO65 | M36 | BBB | 100 | 25 DIBAL | 1.1 ABF20 | 0.04 | 0 | 77 | 2916 | 144 | 3 | 3 |
| EO66 | M36 | BBB | 100 | 25 DIBAL | 1.1 ABF20 | 0.04 | 1 | 105 | 1929 | 161 | 3.2 | 3 |
| EO67 | M36 | AAA | 130 | 25 DIBAL | 1.1 ABF20 | 0.06 | 0 | 102 | 1320 | 92 | 3.1 | 3 |
| EO68 | M36 | AAA | 130 | 25 DIBAL | 1.1 ABF20 | 0.06 | 1 | 149 | 1034 | 61 | 3.4 | 6 |
| EO69 | M36 | BBB | 100 | 25 TMA | 1.1 ABF20 | 0.04 | 4 | 106 | 2034 | 162 | 3.3 | 4 |
| EO70 | M35 | BBB | 100 | 25 DIBAL | 1.1 ABF20 | 0.04 | 0 | 96 | 2178 | 211 | 3 | 4 |
| EO71 | M35 | BBB | 100 | 25 DIBAL | 1.1 ABF20 | 0.04 | 1 | 118 | 1996 | 227 | 3.1 | 5 |
| EO72 | M35 | AAA | 130 | 25 DIBAL | 1.1 ABF20 | 0.06 | 0 | 901 | 67 | 137 | 3.3 | 2 |
| EO73 | M35 | AAA | 130 | 25 DIBAL | 1.1 ABF20 | 0.06 | 1 | 243 | 577 | 145 | 3.8 | 6 |
| EO74 | M35 | BBB | 100 | 25 TMA | 1.1 ABF20 | 0.04 | 4 | 152 | 1242 | 243 | 3.6 | 4 |
| EO75 | M37 | BBB | 100 | 25 DIBAL | 1.1 ABF20 | 0.04 | 0 | 78 | 3165 | 157 | 3.2 | 4 |
| EO76 | M37 | BBB | 100 | 25 DIBAL | 1.1 ABF20 | 0.04 | 1 | 118 | 2025 | 184 | 3.8 | 5 |
| EO77 | M37 | AAA | 130 | 25 DIBAL | 1.1 ABF20 | 0.06 | 0 | 87 | 1769 | 101 | 3.3 | 4 |
| EO78 | M37 | AAA | 130 | 25 DIBAL | 1.1 ABF20 | 0.06 | 1 | 136 | 1168 | 91 | 3.6 | 7 |
| EO79 | M37 | BBB | 100 | 25 DIBAL | 1.1 ABF20 | 0.04 | 4 | 125 | 1838 | 171 | 3.5 | 4 |
| EO80 | M38 | JJJ | 100 | 5 DIBAL | 1.1 ABF20 | 0.02 | 0 | 120 | 3225 | 172 | 2.1 | 3 |
| EO81 | M38 | HHH | 100 | 200 MMAO | 200 MMAO | 0.02 | 0 | 71 | 6177 | 66 | 2.4 | 4 |
| EO82 | M38 | CCC | 100 | 5 DIBAL | 1.1 ABF20 | 0.02 | 4 | 167 | 2110 | 173 | 2.1 | 4 |
| EO83 | M38 | III | 100 | 200 MMAO | 200 MMAO | 0.02 | 4 | 414 | 713 | 79 | 2.5 | 3 |
| EO84 | M40 | EEE | 100 | 5 MMAO | 200 MMAO | 0.03 | 0 | 215 | 1676 | 116 | 2.6 | 4 |
| EO85 | M40 | EEE | 130 | 5 MMAO | 200 MMAO | 0.1 | 0 | 201 | 399 | 47 | 2.1 | 3 |
| EO86 | M40 | KKK | 100 | 5 MMAO | 200 MMAO | 0.03 | 4 | 71 | 3612 | 56 | 1.7 | 4 |
| EO87 | M43 | CCC | 100 | 5 MMAO | 1.1 ABF20 | 0.04 | 0 | 61 | 4334 | 74 | 2.9 | 7 |
| EO88 | M43 | LLL | 100 | 200 MMAO | 200 MMAO | 0.02 | 0 | 60 | 8056 | 38 | 2.7 | 5 |
| EO89 | M43 | CCC | 130 | 5 MMAO | 1.1 ABF20 | 0.04 | 0 | 194 | 1041 | 109 | 3 | 5 |
| EO90 | M43 | III | 130 | 200 MMAO | 200 MMAO | 0.04 | 0 | 114 | 2082 | 36 | 3.8 | 6 |
| EO91 | M43 | CCC | 100 | 5 MMAO | 1.1 ABF20 | 0.04 | 4 | 87 | 2604 | 69 | 2.4 | 6 |
| EO92 | M43 | LLL | 100 | 200 MMAO | 200 MMAO | 0.02 | 4 | 86 | 4628 | 50 | 2.4 | 5 |
| EO93 | M45 | JJJ | 100 | 5 MMAO | 1.1 ABF20 | 0.015 | 0 | 149 | 3729 | 238 | 1.7 | 4 |
| EO94 | M45 | MMM | 100 | 5 MMAO | 200 MMAO | 0.015 | 0 | 119 | 4297 | 168 | 1.6 | 4 |
| EO95 | M45 | OOO | 130 | 5 MMAO | 1.1 ABF20 | 0.03 | 0 | 758 | 306 | 204 | 2 | 4 |
| EO96 | M45 | NNN | 130 | 5 MMAO | 200 MMAO | 0.03 | 0 | 276 | 903 | 108 | 1.9 | 4 |

TABLE 8-continued

| Example # | Complex | Injection Method | Polym. Temp(° C.) | Group 13 reagent and mole equivalent | Activator | µmol catalyst injected | H2 added (psi) | Polym. time (s) | Activity (g polymer/ min * mmol | Mw (k) | PDI (Mw/Mn) | mol % Octene by FTIR |
|---|---|---|---|---|---|---|---|---|---|---|---|---|
| EO97 | M45 | JJJ | 100 | 5 MMAO | 1.1 ABF20 | 0.015 | 4 | 106 | 4758 | 79 | 1.7 | 4 |
| EO98 | M45 | MMM | 100 | 5 MMAO | 200 MMAO | 0.015 | 4 | 83 | 6254 | 59 | 1.8 | 5 |
| EO99 | M46 | WWW | 100 | 15 TMA | 1.1 ABF20 | 0.01 | 0 | 140 | 5691 | 262 | 2.2 | 6 |
| EO100 | M46 | RRR | 100 | 15 TMA | 1.1 ABF20 | 0.01 | 4 | 154 | 4375 | 284 | 2.4 | 6 |
| EO101 | M46 | WWW | 130 | 15 TMA | 1.1 ABF20 | 0.02 | 0 | 900 | 258 | 273 | 2.3 | 5 |
| EO102 | M47 | XXX | 100 | 15 TMA | 200 MMAO | 0.01 | 0 | 107 | 5561 | 245 | 2.7 | 4 |
| EO103 | M47 | TTT | 100 | 15 TMA | 200 MMAO | 0.01 | 4 | 105 | 6309 | 132 | 2.5 | 4 |
| EO104 | M47 | XXX | 130 | 15 TMA | 200 MMAO | 0.02 | 0 | 900 | 164 | 181 | 2.9 | 4 |
| EO105 | M49 | WWW | 100 | 15 PMAO | 1.1 ABF20 | 0.01 | 0 | 224 | 3214 | 299 | 2.2 | 6 |
| EO106 | M49 | RRR | 100 | 15 PMAO | 1.1 ABF20 | 0.01 | 4 | 327 | 1930 | 307 | 2.3 | 5 |
| EO107 | M49 | WWW | 130 | 15 PMAO | 1.1 ABF20 | 0.02 | 0 | 901 | 80 | 375 | 2 | 7 |
| EO108 | M50 | XXX | 100 | 15 TMA | 200 MMAO | 0.01 | 0 | 150 | 5772 | 245 | 2.4 | 7 |
| EO109 | M50 | TTT | 100 | 15 TMA | 200 MMAO | 0.01 | 4 | 90 | 9787 | 95 | 3.2 | 7 |
| EO110 | M50 | XXX | 130 | 15 TMA | 200 MMAO | 0.02 | 0 | 323 | 1246 | 174 | 2.4 | 6 |
| EQ111 | M52 | PPP | 100 | 10 TMA | 1.1 ABF20 | 0.02 | 0 | 68 | 6348 | 109 | 1.7 | 4 |
| EO112 | M52 | PPP | 100 | 10 TMA | 1.1 ABF20 | 0.02 | 4 | 89 | 4707 | 112 | 2 | 5 |
| EO113 | M52 | PPP | 130 | 10 TMA | 1.1 ABF20 | 0.03 | 0 | 160 | 1634 | 112 | 2.1 | 3 |
| EO114 | M55 | QQQ | 100 | 15 TMA | 1.1 ABF20 | 0.03 | 0 | 61 | 5028 | 126 | 1.4 | 7 |
| EO115 | M55 | SSS | 100 | 15 TMA | 200 MMAO | 0.03 | 0 | 65 | 3858 | 47 | 1.4 | 4 |
| EO116 | M55 | RRR | 100 | 15 TMA | 1.1 ABF20 | 0.015 | 4 | 365 | 972 | 189 | 1.6 | 5 |
| EO117 | M55 | TTT | 100 | 15 DIBAI | 200 MMAO | 0.015 | 4 | 749 | 414 | 84 | 1.5 | 3 |
| EO118 | M55 | SSS | 130 | 15 TMA | 200 MMAO | 0.03 | 0 | 633 | 330 | 51 | 1.5 | 3 |
| EO119 | M54 | RRR | 100 | 15 DIBAL | 1.1 ABF20 | 0.015 | 0 | 187 | 2336 | 211 | 1.5 | 2 |
| EO120 | M54 | TTT | 100 | 15 DIBAL | 200 MMAO | 0.015 | 0 | 145 | 2842 | 137 | 1.6 | 2 |
| EO121 | M54 | RRR | 100 | 15 DIBAL | 1.1 ABF20 | 0.015 | 4 | 249 | 1462 | 169 | 1.6 | 3 |
| EO122 | M54 | TTT | 100 | 15 DIBAL | 200 MMAO | 0.015 | 4 | 202 | 1658 | 99 | 1.6 | 2 |
| EO123 | M54 | QQQ | 130 | 15 TMA | 1.1 ABF20 | 0.03 | 0 | 901 | 83 | 140 | 2.2 | 2 |
| EO124 | M54 | SSS | 130 | 15 TMA | 200 MMAO | 0.03 | 0 | 900 | 114 | 36 | 2.4 | 2 |
| EO125 | M56 | FFF | 100 | 10TMA | 1.1 ABF20 | 0.03 | 0 | 97 | 4247 | 113 | 2.7 | 11 |
| EO126 | M56 | FFF | 100 | 10TMA | 1.1 ABF20 | 0.03 | 4 | 153 | 2122 | 159 | 3.4 | 7 |
| EO127 | M56 | GGG | 130 | 10TMA | 200 MMAO | 0.04 | 0 | 315 | 564 | 52 | 2.5 | 5 |
| EO128 | M57 | UUU | 100 | 10TMA | 1.1 ABF20 | 0.02 | 0 | 120 | 3989 | 186 | 2.4 | 7 |
| EO129 | M57 | FFF | 100 | 10TMA | 1.1 ABF20 | 0.03 | 4 | 108 | 2896 | 91 | 2.6 | 9 |
| EO130 | M57 | FFF | 130 | 10TMA | 1.1 ABF20 | 0.04 | 0 | 257 | 739 | 185 | 2.1 | 5 |
| EO131 | M58 | VVV | 100 | 10 TMA | 200 MMAO | 0.02 | 0 | 130 | 2882 | 267 | 1.9 | 5 |
| EO132 | M58 | VVV | 100 | 10 TMA | 200 MMAO | 0.02 | 4 | 532 | 453 | 187 | 2.7 | 3 |
| EO133 | M58 | EEE | 130 | 10 TMA | 200 MMAO | 0.04 | 0 | 901 | 118 | 130 | 3.4 | 5 |
| EO134 | M59 | PPP | 100 | 10 TMA | 1.1 ABF20 | 0.03 | 0 | 64 | 6277 | 175 | 1.7 | 8 |
| EO135 | M59 | PPP | 100 | 10 TMA | 1.1 ABF20 | 0.02 | 4 | 184 | 1971 | 280 | 1.7 | 4 |
| EO136 | M59 | PPP | 130 | 10 TMA | 1.1 ABF20 | 0.03 | 0 | 900 | 157 | 365 | 1.7 | 5 |

A number of embodiments of the invention have been described. Nevertheless, it will be understood that various modifications may be made without departing from the spirit and scope of the invention. Accordingly, other embodiments are within the scope of the following claims.

What is claimed is:

1. A metal-ligand complex characterized by the formula:

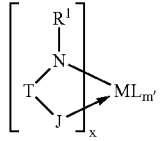

wherein

M is a metal selected from the group consisting of groups 3-6 and lanthanides of the periodic table of elements;

$R^1$ is an optionally substituted hydrocarbyl or heteroatom containing hydrocarbyl;

T is a bridging group of the general formula $-(T'R^2R^3)_n-$, wherein each T' is independently selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, and n is 1 or 2, provided that two or more $R^2$ and/or $R^3$ groups may be joined together to form one or more optionally substituted ring systems, and that one or more T' atoms may be involved in a double bond to a neighboring group and correspondingly be bonded to only a single $R^2$ or $R^3$ substituent;

J is an optionally substituted heterocyclic group containing a five-membered heterocycle, the five-membered heterocycle including at least one but no more than four heteroatoms and including a nitrogen, phosphorus, oxygen, sulfur, or carbene in a ring position adjacent to the ring atom bonded to T, wherein the nitrogen, phosphorus, oxygen, sulfur, or carbene in the ring position adjacent to the ring atom bonded to T is bonded to M via a dative bond, provided that if the five-membered heterocycle includes a nitrogen, phosphorus, oxygen, or sulfur in the ring position adjacent to the bond to T, the five-membered heterocycle contains at least two heteroatoms;

x is 1 or 2;

each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof, provided that optionally, two or more L groups are joined into a ring structure and that one or more of the ligands L may be ionically bonded to the metal M; and m' is 1,2,3, or 4.

2. The complex of claim 1, wherein the five-membered heterocycle includes a nitrogen in the ring position adjacent to the bond to T.

3. The complex of claim 2, wherein the complex is characterized by the formula:

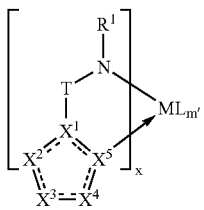

wherein $X^1$ is nitrogen, phosphorus, or —C(R$^4$)$_{n''}$—, $X^2$, $X^3$, and $X^4$ are independently selected from the group consisting of oxygen, sulfur, —C(R$^4$)$_{n'}$—, —N(R$^4$)$_{n''}$—, and —P(R$^4$)$_{n''}$—, and $X^5$ is nitrogen, phosphorus, oxygen, sulfur or a carbene, where each n' is 1 or 2, and each n" is 0 or 1, and each R$^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof; provided that optionally any combination of two or more R$^1$, R$^2$, R$^3$, and/or R$^4$ groups may be joined together to form one or more optionally substituted fused ring systems.

4. The complex of claim 3, wherein $X^4$ is selected from the group consisting of —C(R$^4$)$_{n''}$R$^{4'}$—, —NR$^{4'}$—, and —PR$^{4'}$—, and R$^{4'}$ is optionally substituted cyclic hydrocarbyl or heteroatom-containing hydrocarbyl.

5. The complex of claim 4, wherein R$^{4'}$ is optionally substituted aryl or heteroaryl, and R$^{4'}$ and M are optionally joined to form a metallocycle.

6. The complex of claim 5, wherein the metallocycle is a 5- or 6-membered metallocycle.

7. The complex of claim 3, wherein the complex is characterized by the formula:

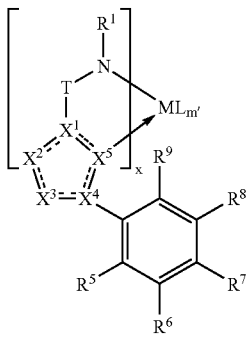

wherein $X^4$ is nitrogen, phosphorus, or —C(R$^4$)$_{n''}$—, and R$^5$, R$^6$, R$^7$, R$^8$ and R$^9$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that optionally, two or more of R$^4$, R$^5$, R$^6$, R$^7$, R$^8$ and R$^9$ may be joined to form one or more optionally substituted fused ring systems.

8. The complex of claim 3, wherein the complex is characterized by the formula:

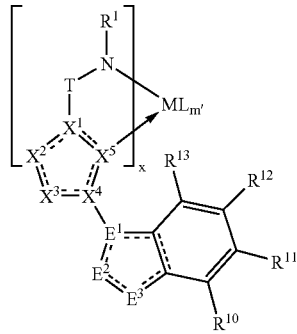

wherein $X^4$ is nitrogen, phosphorus, or —C(R$^4$)$_{n''}$—;

$E^1$ is selected from the group consisting of nitrogen, phosphorus, —C(R$^{14}$)$_{n''}$—, and —Si(R$^{14}$)$_{n''}$—, and $E^2$ and $E^3$ are selected from the group consisting of oxygen, sulfur, —N(R$^{14}$)$_{n''}$—, —C(R$^{14}$)$_{n'}$—, —P(R$^{14}$)$_{n''}$—, and —Si(R$^{14}$)$_{n'}$—, where each n' is 1 or 2 and each n" is 0 or 1; and each R$^{10}$, R$^{11}$, R$^{12}$, R$^{13}$, and R$^{14}$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that if E$^2$ and/or E$^3$ is —N(R$^{14}$)$_{n''}$—, —P(R$^{14}$)$_{n''}$— or —Si(R$^{14}$)$_{n'}$—, the corresponding R$^{14}$ is selected from the group consisting of hydrogen, halogen, and optionally substituted alkyl, heteroalkyl, aryl, heteroaryl, alkoxy, aryloxy, silyl, and provided that optionally, two or more of R$^4$, R$^{10}$, R$^{11}$, R$^{12}$, R$^{13}$, and R$^{14}$ may be joined to form one or more optionally substituted fused ring systems.

9. The complex of claim 3, wherein the complex is characterized by the formula:

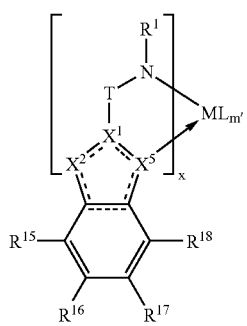

wherein

X$^2$ is oxygen, sulfur, —NR$^4$—, or —PR$^4$—;

R$^{15}$, R$^{16}$, R$^{17}$ and R$^{18}$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that optionally, two or more of R$^4$, R$^{15}$, R$^{16}$, R$^{17}$ and R$^{18}$ may be joined to form one or more optionally substituted fused ring systems.

10. The complex of any of claims 3, 4, 5, 6, 7, 8 or 9, wherein M is selected from the group consisting of Ti, Zr, and Hf, and x is 1.

11. The complex of any of claims 3, 4, 5, 6, 7, 8 or 9, wherein X$^5$ is nitrogen.

12. The complex of claim 11, wherein the five-membered heterocycle is optionally substituted imidazole, oxazole, isoxazole, thiazole, isothiazole, pyrazole, oxadiazole, thiadiazole, indazole, benzimidazole, benzthiazole, triazole, oxadiazole, thiadiazole, tetrazole, and thiatriazole, and isomers thereof.

13. The complex of claim 1, wherein R$^1$ is optionally substituted aryl.

14. The complex of claim 13, wherein R$^1$ is 2,6-disubtituted aryl.

15. The complex of claim 1, wherein R$^2$ is different than R$^3$.

16. A metal-ligand complex characterized by the formula:

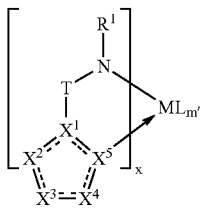

wherein

M is a metal selected from the group consisting of groups 3-6 and lanthanides of the periodic table of elements;

R$^1$ is an optionally substituted hydrocarbyl or heteroatom containing hydrocarbyl;

T is a bridging group;

X$^1$ is nitrogen, phosphorus, or —C(R$^4$)$_{n'}$—, X$^2$ and X$^3$ are independently selected from the group consisting of oxygen, sulfur, —C(R$^4$)$_{n'}$—, —N(R$^4$)$_{n''}$—, and —P(R$^4$)$_{n''}$—, and X$^4$ is —N(R$^{4'}$)—, —P(R$^{4'}$)—, or —C(R$^{4'}$)(R$^4$)$_{n''}$—, where each R$^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and each R$^{4'}$ is selected from the group consisting of optionally substituted aryl and heteroaryl, and X$^{5'}$ is oxygen or sulfur, each n' is 1 or 2, and each n'' is 0 or 1, provided that optionally, two or more R$^1$, R$^2$, R$^3$, R$^4$ or R$^{4'}$ groups may be joined to form one or more optionally substituted fused ring systems;

x is 1 or 2;

each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof, provided that optionally, two or more L groups are joined into a ring structure and that one or more of the ligands L may be ionically bonded to the metal M; and m' is 1, 2, 3, or 4.

17. The complex of claim 16, wherein the bridging group T is represented by the general formula -(T'R$^2$R$^3$)$_n$—, wherein each T' is independently selected from the group consisting of carbon and silicon, R$^2$ and R$^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, and n is 1 or 2, provided that two or more R$^2$ and/or R$^3$ groups may be joined together to form one or more optionally substituted ring systems, and that one or more T' atoms may be involved in a double bond to a neighboring group and correspondingly be bonded to only a single R$^2$ or R$^3$ substituent.

18. The complex of claim 17, wherein the complex is characterized by the formula:

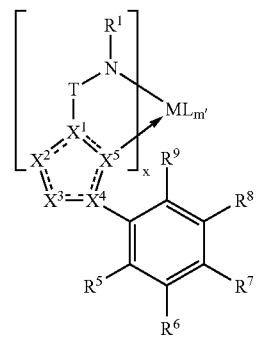

wherein X$^4$ is nitrogen, phosphorus, or —C(R$^4$)$_{n''}$—; and

R$^5$, R$^6$, R$^7$, R$^8$ and R$^9$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that optionally, two or more of R$^1$, R$^2$, R$^3$, R$^4$, R$^5$, R$^6$, R$^7$, R$^8$ and R$^9$ may be joined to form one or more optionally substituted fused ring systems.

19. The complex of claim 17, wherein the complex is characterized by the formula:

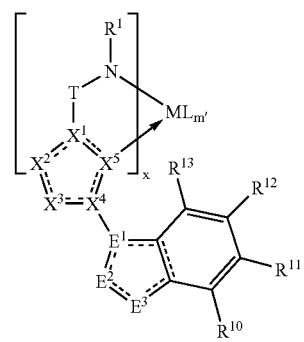

wherein

X$^4$ is nitrogen, phosphorus, or —C(R$^4$)$_{n''}$—;

E$^1$ is selected from the group consisting of nitrogen, phosphorus, —C(R$^{14}$)$_{n''}$—, and —Si(R$^{14}$)$_{n''}$—, and E$^2$ and E$^3$ are selected from the group consisting of oxygen, sulfur, —N(R$^{14}$)$_{n'''}$—, —C(R$^{14}$)$_{n'}$—, —P(R$^{14}$)$_{n'''}$—, and —Si(R$^{14}$)$_{n'}$—, where each n' is 1 or 2 and each n'' is 0 or 1; and each R$^{10}$, R$^{11}$, R$^{12}$, R$^{13}$, and R$^{14}$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that if E$^2$ and/or E$^3$ is —N(R$^{14}$)$_{n'''}$—, —P(R$^{14}$)$_{n'''}$— or —Si(R$^{14}$)$_{n'}$—, the corresponding R$^{14}$ is selected from the group consisting of hydrogen, halogen, and optionally substituted alkyl, heteroalkyl, aryl, heteroaryl, alkoxy, aryloxy, silyl, and provided that optionally, two or more of R$^4$, R$^{10}$, R$^{11}$, R$^{12}$, R$^{13}$, and R$^{14}$ may be joined to form one or more optionally substituted fused ring systems.

20. A metal complex characterized by the formula:

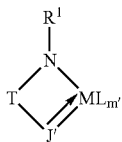

wherein

M is a metal selected from the group consisting of groups 3-6 and lanthanides of the periodic table of elements;

R$^1$ is optionally substituted hydrocarbyl or heteroatom containing hydrocarbyl;

T is a bridging group;

J' is an optionally substituted heterocyclic group containing a five-membered heterocycle, the five-membered heterocycle including at least one but no more than four heteroatoms and including a nitrogen, phosphorus, oxygen, sulfur, or carbene in a ring position adjacent to the ring atom bonded to T, wherein J' includes 2 atoms bonded to the metal M, one of the 2 atoms being the nitrogen, phosphorus, oxygen, sulfur, or carbene in the ring position adjacent to the ring atom bonded to T, and being bonded to M via a dative bond, and the other of the 2-atoms being bonded to the metal M through a covalent bond; and each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof, provided that optionally, two or more L groups are joined into a ring structure and that one or more of the ligands L may be ionically bonded to the metal M, and m' is 1, 2 3, or 4.

21. The complex of claim 20, wherein T is of the general formula -(T'R$^2$R$^3$)$_n$—, wherein each T' is independently selected from the group consisting of carbon and silicon, R$^2$ and R$^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, and n is 1 or 2, provided that two or more R$^2$ and/or R$^3$ groups may be joined together to form one or more optionally substituted ring systems, and that one or more T' atoms may be involved in a double bond to a neighboring group and correspondingly be bonded to only a single R$^2$ or R$^3$ substituent.

22. The complex of claim 21, where the five-membered heterocycle includes a nitrogen in the ring position adjacent to the bond to T.

23. The complex of claim 22, wherein the complex is characterized by the formula:

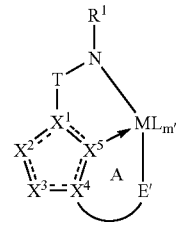

wherein

X$^1$ and X$^4$ are independently selected from the group consisting of nitrogen, phosphorus, or —C(R$^4$)$_{n''}$—, X$^2$ and X$^3$ are independently selected from the group consisting of oxygen, sulfur, —C(R$^4$)$_{n'}$—, —N(R$^4$)$_{n''}$—, and —P(R$^4$)$_{n''}$—, and X$^5$ is nitrogen, phosphorus, oxygen, sulfur or a carbene, where each n' is 1 or 2, each n'' is 0 or 1, and each R$^4$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof; provided that optionally any combination of two or more R$^1$, R$^2$, R$^3$, and/or R$^4$ groups may be joined together to form one or more optionally substituted fused ring systems; and E' is selected from the group consisting of oxygen, sulfur, —N(R$^{21}$)$_{n'''}$—, —C(R$^{21}$)$_{n'}$—, —P(R$^{21}$)$_{n'''}$—, and —Si(R$^{21}$)$_{n'}$—, each R$^{21}$ is independently selected from the group consisting of hydrogen, halogen, and optionally substituted alkyl, heteroalkyl, aryl and heteroaryl, and E' is connected to X$^4$ through an optionally substituted divalent hydrocarbyl or heteroatom-containing hydrocarbyl group to form a metallocycle containing five, six or seven members, including M, provided that R$^{21}$ can be joined to the divalent hydrocarbyl or heteroatom-containing hydrocarbyl group connecting E' to X$^4$ as part of an aromatic ring, each n' is 1 or 2, and each n'' is 0 or 1, depending on the bond order of the adjacent bonds, and provided that optionally two or more R$^4$ and/or R$^{21}$ groups are joined to form one or more optionally substituted ring structures having from 3 to 50 atoms each.

24. The complex of claim 23, wherein the complex is characterized by the formula:

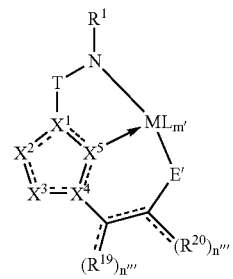

wherein
each $R^{19}$ and $R^{20}$ is independently selected from the group consisting of hydrogen, halogen and optionally substituted alkyl, heteroalkyl, aryl and heteroaryl, and each n''' is 1 or 2, depending on the bond order of the adjacent bonds, provided that optionally two or more $R^4$, $R^{19}$, $R^{20}$ and $R^{21}$ groups are joined to form one or more optionally substituted ring structures having from 3 to 50 atoms each.

25. The complex of claim 23, wherein the complex is characterized by the formula:

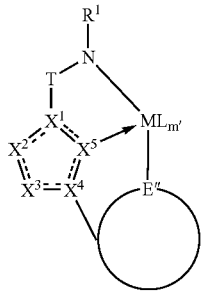

wherein E'' is nitrogen, phosphorus, —C($R^4$)$_{n''}$—, or —Si($R^4$)$_{n''}$—, and is part of an optionally substituted heterocyclic group, where n'' is 0 or 1.

26. The complex of claim 23, wherein the complex is characterized by the formula:

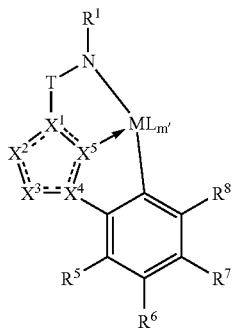

wherein $R^5$, $R^6$, $R^7$, and $R^8$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that optionally, two or more of $R^4$, $R^5$, $R^6$, $R^7$ and $R^8$ may be joined to form one or more optionally substituted fused ring systems.

27. The complex of claim 23, wherein the complex is characterized by the formula:

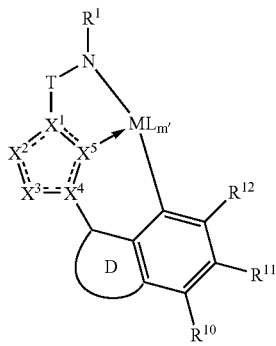

wherein $R^{10}$, $R^{11}$ and $R^{12}$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that optionally, two or more of $R^{10}$, $R^{11}$ and $R^{12}$ may be joined to form one or more optionally substituted fused ring systems; and ring D is a ring selected from the group consisting of optionally substituted aryl and heteroaryl.

28. The complex of claim 23, wherein the complex is characterized by the formula:

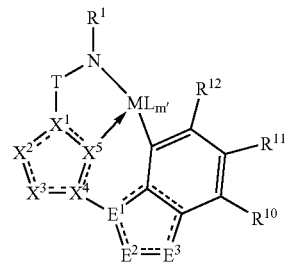

wherein
$E^1$ is selected from the group consisting of nitrogen, phosphorus, —C($R^{14}$)$_{n''}$—, or —Si($R^{14}$)$_{n''}$—, and $E^2$ and $E^3$ are selected from the group consisting of oxygen, sulfur, —N($R^{14}$)$_{n''}$—, —C($R^{14}$)$_{n''}$—, —P($R^{14}$)$_{n''}$—, and —Si($R^{14}$)$_{n''}$—, where each n' is 1 or 2 and each n'' is 0 or 1; and each $R^{10}$, $R^{11}$, $R^{12}$ and $R^{14}$ is independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that if $E^2$ and/or $E^3$ is —N($R^{14}$)$_{n''}$— or —P($R^{14}$)$_{n''}$— or —Si($R^{14}$)$_{n''}$—, the corresponding $R^{14}$ is selected from the group consisting of hydrogen, halogen, and optionally substituted alkyl, heteroalkyl, aryl, heteroaryl, alkoxy, aryloxy, silyl, and provided that optionally, two or more of $R^4$, $R^{10}$, $R^{11}$, $R^{12}$ and $R^{14}$ may be joined to form one or more optionally substituted fused ring systems.

29. The complex of claim 23, wherein the complex is characterized by the formula:

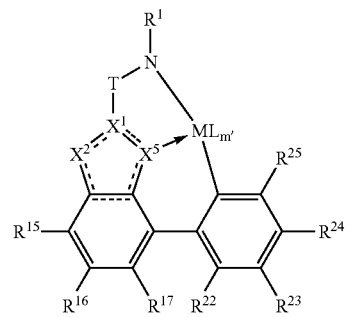

wherein
$X^2$ is oxygen, sulfur, —$NR^4$—, or —$PR^4$—;
$R^{15}$, $R^{16}$, $R^{17}$, $R^{22}$, $R^{23}$, $R^{24}$, and $R^{25}$ are each independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, provided that optionally, two or more of R$^4$, R$^{15}$, R$^{16}$, R$^{17}$, R$^{22}$, R$^{23}$, R$^{24}$, and R$^{25}$ may be joined to form one or more optionally substituted fused ring systems.

30. The complex of any of claims 23, 24, 25, 26, 27, 28, or 29, wherein M is selected from the group consisting of Ti, Zr, and Hf.

31. The complex of claim 22, wherein the five-membered heterocycle is optionally substituted imidazole, oxazole, isoxazole, thiazole, isothiazole, pyrazole, oxadiazole, thiadiazole, indazole, benzimidazole, benzthiazole, triazole, oxadiazole, thiadiazole, tetrazole, and thiatriazole, and isomers thereof.

32. The complex of any of claims 23, 24, 25, 26, 27, 28, or 29, wherein X$^5$ is nitrogen.

33. The complex of claim 32, wherein R' is optionally substituted aryl.

34. A metal-ligand complex characterized by the formula

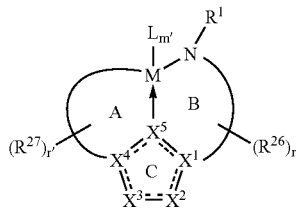

wherein:

M is a metal selected from the group consisting of groups 3-6 and lanthanides of the periodic table of elements;

A is an optionally substituted metallocycle containing five, six or seven atoms in the ring, including M;

B is an optionally substituted metallocycle containing five or six atoms in the ring, including M;

C is an optionally substituted five-membered heterocycle, wherein X$^1$ and X$^4$ are selected from the group consisting of nitrogen, phosphorus, and —C(R$^4$)$_{n'}$—, X$^2$ and X$^3$ are selected from the group consisting of oxygen, sulfur, —C(R$^4$)$_{n'}$—, —N(R$^4$)$_{n''}$—, and —P(R$^4$)$_{n''}$—, and X$^5$ is nitrogen, carbon, oxygen, phosphorus, or sulfur, n' is 1 or 2, and n'' is 0 or 1;

R$^1$ is optionally substituted hydrocarbyl or heteroatom containing hydrocarbyl;

each R$^4$, R$^{26}$ and R$^{27}$ is independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, r is 1, 2, 3 or 4, r' is 1, 2, 3, or 4, provided that optionally any combination of two or more R$^4$, R$^{26}$ and/or R$^{27}$ groups may be joined together to form one or more optionally substituted fused ring systems;

each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof, provided that optionally, two or more L groups are joined into a ring structure and that one or more of the ligands L may be ionically bonded to the metal M, and m' is 1, 2, 3 or 4.

35. The complex of claim 34, wherein one of A or B is a 5-membered ring and the other of A or B is a 6-membered ring; and ring A includes a carbon-metal bond.

36. The complex of claim 34, wherein M is selected from the group consisting of Ti, Zr, and Hf.

* * * * *

UNITED STATES PATENT AND TRADEMARK OFFICE
CERTIFICATE OF CORRECTION

PATENT NO. : 7,256,296 B2
APPLICATION NO. : 11/232982
DATED : August 14, 2007
INVENTOR(S) : Diamond et al.

It is certified that error appears in the above-identified patent and that said Letters Patent is hereby corrected as shown below:

Column 279, claim 20, line 42: "2-atoms" should read -- 2 atoms --.

Column 281, claim 25, line 23: "–C($R^4$)$_{n''}$–," should read -- –C($R^{14}$)$_{n''}$–, --.

Column 281, claim 25, line 24: "–Si($R^4$)$_{n''}$–," should read -- –Si($R^{14}$)$_{n''}$–, --.

Column 283, claim 33, line 14: "R'" should read -- $R^1$ --.

Signed and Sealed this

Ninth Day of September, 2008

JON W. DUDAS
*Director of the United States Patent and Trademark Office*